US010206883B2

(12) United States Patent
Yum et al.

(10) Patent No.: US 10,206,883 B2
(45) Date of Patent: *Feb. 19, 2019

(54) ORAL PHARAMACEUTICAL DOSAGE FORMS

(71) Applicant: DURECT CORPORATION, Cupertino, CA (US)

(72) Inventors: Su Il Yum, Los Altos, CA (US); Wendy Chao, San Jose, CA (US); Huey-Ching Su, San Jose, CA (US); Roger Fu, Saratoga, CA (US); Michael Zamloot, Hillsborough, CA (US)

(73) Assignee: Durect Corporation, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/839,428

(22) Filed: Dec. 12, 2017

(65) Prior Publication Data

US 2018/0193275 A1 Jul. 12, 2018

Related U.S. Application Data

(63) Continuation of application No. 15/486,119, filed on Apr. 12, 2017, which is a continuation of application No. 14/798,263, filed on Jul. 13, 2015, now Pat. No. 9,655,861, which is a continuation of application No. 13/786,218, filed on Mar. 5, 2013, which is a continuation of application No. 12/315,868, filed on Dec. 5, 2008, now Pat. No. 8,425,401.

(60) Provisional application No. 61/198,201, filed on Nov. 3, 2008, provisional application No. 61/005,681, filed on Dec. 6, 2007, provisional application No. 61/005,685, filed on Dec. 6, 2007.

(51) Int. Cl.
| | |
|---|---|
| *A61K 47/00* | (2006.01) |
| *A61K 31/445* | (2006.01) |
| *A61K 9/48* | (2006.01) |
| *A61K 31/137* | (2006.01) |
| *A61K 31/4402* | (2006.01) |
| *A61K 31/485* | (2006.01) |
| *A61K 31/4458* | (2006.01) |

(52) U.S. Cl.
CPC .............. *A61K 9/4866* (2013.01); *A61K 9/48* (2013.01); *A61K 9/4858* (2013.01); *A61K 31/137* (2013.01); *A61K 31/4402* (2013.01); *A61K 31/4458* (2013.01); *A61K 31/485* (2013.01)

(58) Field of Classification Search
USPC .......................... 514/781, 777, 785, 724, 183
See application file for complete search history.

(56) References Cited

U.S. PATENT DOCUMENTS

| | | |
|---|---|---|
| 2,799,241 A | 7/1957 | Wurster |
| 2,931,802 A | 4/1960 | Toney et al. |
| 3,339,546 A | 9/1967 | Chen |
| 3,743,398 A | 7/1973 | Johnson et al. |
| 3,845,770 A | 11/1974 | Theeuwes et al. |
| 3,853,837 A | 12/1974 | Fujino et al. |
| 3,916,889 A | 11/1975 | Russell |
| 3,916,899 A | 11/1975 | Theeuwes et al. |
| 3,952,741 A | 4/1976 | Baker |
| 3,992,365 A | 11/1976 | Beddell et al. |
| 3,995,631 A | 12/1976 | Higuchi et al. |
| 4,008,719 A | 2/1977 | Theeuwes et al. |
| 4,014,334 A | 3/1977 | Theeuwes et al. |
| 4,016,880 A | 4/1977 | Theeuwes et al. |
| 4,024,248 A | 5/1977 | Konig et al. |
| 4,063,064 A | 12/1977 | Saunders et al. |
| 4,088,864 A | 5/1978 | Theeuwes et al. |
| 4,100,274 A | 7/1978 | Dutta et al. |
| 4,111,202 A | 9/1978 | Theeuwes |
| 4,160,020 A | 7/1979 | Ayer et al. |
| 4,327,725 A | 5/1982 | Cortese et al. |
| 4,360,019 A | 11/1982 | Portner et al. |
| 4,395,405 A | 7/1983 | Noda et al. |
| 4,395,495 A | 7/1983 | Cummings |
| 4,411,890 A | 10/1983 | Momany |
| 4,487,603 A | 12/1984 | Harris |
| 4,530,840 A | 7/1985 | Tice et al. |
| 4,578,075 A | 3/1986 | Urquhart et al. |
| 4,622,219 A | 11/1986 | Haynes |
| 4,681,583 A | 7/1987 | Urquhart et al. |
| 4,681,765 A | 7/1987 | Guley |
| 4,689,222 A | 8/1987 | McMichael |
| 4,692,147 A | 9/1987 | Duggan |
| 4,725,442 A | 2/1988 | Haynes |
| 4,725,852 A | 2/1988 | Gamblin et al. |
| 4,767,628 A | 8/1988 | Hutchinson |
| 4,769,372 A | 9/1988 | Kreek |
| 4,795,641 A | 1/1989 | Kashdan |
| 4,834,984 A | 5/1989 | Goldie et al. |
| 4,844,909 A | 7/1989 | Goldie et al. |
| 4,861,598 A | 8/1989 | Oshlack |
| 4,891,225 A | 1/1990 | Langer et al. |
| 4,906,474 A | 3/1990 | Langer et al. |
| 4,931,285 A | 6/1990 | Edgren et al. |

(Continued)

FOREIGN PATENT DOCUMENTS

| | | |
|---|---|---|
| AU | 8374575 | 8/1975 |
| CA | 2222567 | 1/2002 |

(Continued)

OTHER PUBLICATIONS

U.S. Appl. No. 15/826,226, filed Nov. 29, 2017, Yum, et al.

(Continued)

*Primary Examiner* — Shobha Kantamneni
(74) *Attorney, Agent, or Firm* — Carol L. Francis; Michael B. Rubin; Bozicevic, Field & Francis LLP

(57) ABSTRACT

Abuse-resistant oral dosage forms suitable for administration of pharmacologically active agents are provided.

20 Claims, 41 Drawing Sheets

(56) References Cited

U.S. PATENT DOCUMENTS

| | | |
|---|---|---|
| 4,938,763 A | 7/1990 | Dunn et al. |
| 4,957,681 A | 9/1990 | Klimesch et al. |
| 4,957,744 A | 9/1990 | della Valle et al. |
| 4,961,932 A | 10/1990 | Theeuwes |
| 4,970,075 A | 11/1990 | Oshlack |
| 4,990,341 A | 2/1991 | Goldie et al. |
| 5,006,346 A | 4/1991 | Edgren et al. |
| 5,019,397 A | 5/1991 | Wong et al. |
| 5,024,842 A | 6/1991 | Edgren et al. |
| 5,149,543 A | 9/1992 | Cohen et al. |
| 5,156,850 A | 10/1992 | Wong et al. |
| 5,160,743 A | 11/1992 | Edgren et al. |
| 5,188,837 A | 2/1993 | Domb |
| 5,190,765 A | 3/1993 | Jao et al. |
| 5,252,338 A | 10/1993 | Jao et al. |
| 5,266,331 A | 11/1993 | Oshlack et al. |
| 5,273,760 A | 12/1993 | Oshlack et al. |
| 5,278,201 A | 1/1994 | Dunn et al. |
| 5,278,202 A | 1/1994 | Dunn et al. |
| 5,286,493 A | 2/1994 | Oshlack et al. |
| 5,286,496 A | 2/1994 | Stapler et al. |
| 5,324,351 A | 6/1994 | Oshlack et al. |
| 5,324,519 A | 6/1994 | Dunn et al. |
| 5,324,520 A | 6/1994 | Dunn et al. |
| 5,330,835 A | 7/1994 | Kikuchi et al. |
| 5,340,572 A | 8/1994 | Patel et al. |
| 5,340,849 A | 8/1994 | Dunn et al. |
| 5,350,741 A | 9/1994 | Takada |
| 5,352,662 A | 10/1994 | Brooks et al. |
| 5,356,467 A | 10/1994 | Oshlack et al. |
| 5,356,635 A | 10/1994 | Raman et al. |
| 5,366,738 A | 11/1994 | Rork et al. |
| 5,382,424 A | 1/1995 | Stapler et al. |
| 5,391,381 A | 2/1995 | Wong et al. |
| 5,399,363 A | 3/1995 | Liversidge et al. |
| 5,472,712 A | 12/1995 | Oshlack et al. |
| 5,478,577 A | 12/1995 | Sackler et al. |
| 5,487,898 A | 1/1996 | Lu et al. |
| 5,508,042 A | 4/1996 | Oshlack et al. |
| 5,540,912 A | 7/1996 | Roorda et al. |
| 5,545,408 A | 8/1996 | Trigg et al. |
| 5,549,912 A | 8/1996 | Oshlack et al. |
| 5,569,450 A | 10/1996 | Duan et al. |
| 5,580,578 A | 12/1996 | Oshlack et al. |
| 5,599,552 A | 2/1997 | Dunn et al. |
| 5,620,705 A | 4/1997 | Dong et al. |
| 5,633,000 A | 5/1997 | Grossman et al. |
| 5,633,011 A | 5/1997 | Dong et al. |
| 5,639,476 A | 6/1997 | Oshlack et al. |
| 5,656,295 A | 8/1997 | Oshlack et al. |
| 5,672,360 A | 9/1997 | Sackler et al. |
| 5,681,585 A | 10/1997 | Oshlack et al. |
| 5,702,716 A | 12/1997 | Dunn et al. |
| 5,725,841 A | 3/1998 | Duan et al. |
| 5,728,396 A | 3/1998 | Peery et al. |
| 5,733,950 A | 3/1998 | Dunn et al. |
| 5,736,152 A | 4/1998 | Dunn |
| 5,739,176 A | 4/1998 | Dunn et al. |
| 5,744,280 A | 4/1998 | Mooney, III et al. |
| 5,747,051 A | 5/1998 | Granger et al. |
| 5,747,058 A | 5/1998 | Tipton et al. |
| 5,750,100 A | 5/1998 | Yamagata et al. |
| 5,759,563 A | 6/1998 | Yewey et al. |
| 5,777,124 A | 7/1998 | Zavareh et al. |
| 5,780,044 A | 7/1998 | Yewey et al. |
| 5,786,484 A | 7/1998 | Dyer et al. |
| 5,837,284 A | 11/1998 | Mehta et al. |
| 5,840,329 A | 11/1998 | Bai |
| 5,840,731 A | 11/1998 | Mayer et al. |
| 5,879,705 A | 3/1999 | Haefield et al. |
| 5,908,850 A | 6/1999 | Zeitlin et al. |
| 5,919,473 A | 7/1999 | Elkhoury |
| 5,932,597 A | 8/1999 | Brown et al. |
| 5,942,241 A | 8/1999 | Chasin et al. |
| 5,958,446 A | 9/1999 | Miranda et al. |
| 5,958,452 A | 9/1999 | Oshlack et al. |
| 5,965,161 A | 10/1999 | Oshlack et al. |
| 5,968,542 A | 10/1999 | Tipton |
| 5,985,305 A | 11/1999 | Peery et al. |
| 5,994,548 A | 11/1999 | Langston et al. |
| 6,008,355 A | 12/1999 | Huang et al. |
| 6,042,811 A | 3/2000 | Duan et al. |
| 6,051,558 A | 4/2000 | Burns et al. |
| 6,093,419 A | 7/2000 | Rolf |
| 6,126,919 A | 10/2000 | Stefely et al. |
| 6,143,322 A | 11/2000 | Sackler et al. |
| 6,190,680 B1 | 2/2001 | Sakurada et al. |
| 6,203,813 B1 | 3/2001 | Gooberman et al. |
| 6,210,705 B1 | 4/2001 | Mantelle et al. |
| 6,228,398 B1 | 5/2001 | Devane et al. |
| 6,245,351 B1 | 6/2001 | Nara et al. |
| 6,291,013 B1 | 9/2001 | Gibson et al. |
| 6,294,195 B1 | 9/2001 | Oshlack et al. |
| 6,312,717 B1 | 11/2001 | Molinoff et al. |
| 6,344,215 B1 | 2/2002 | Bettman et al. |
| 6,348,211 B1 | 2/2002 | Mantelle et al. |
| 6,355,656 B1 | 3/2002 | Zeitlin et al. |
| 6,375,957 B1 | 4/2002 | Kaiko et al. |
| 6,384,227 B2 | 5/2002 | Dyer et al. |
| 6,403,609 B1 | 6/2002 | Asgharian et al. |
| 6,413,356 B1 | 7/2002 | Chokshi et al. |
| 6,413,536 B1 | 7/2002 | Gibson et al. |
| 6,419,960 B1 | 7/2002 | Krishnamurthy |
| 6,426,339 B1 | 7/2002 | Berde et al. |
| 6,440,493 B1 | 8/2002 | Gibson et al. |
| 6,479,074 B2 | 11/2002 | Murdock et al. |
| 6,486,138 B1 | 11/2002 | Asgharian et al. |
| 6,498,153 B1 | 12/2002 | Cady et al. |
| 6,512,009 B1 | 1/2003 | Daoust et al. |
| 6,514,516 B1 | 2/2003 | Chasin et al. |
| 6,521,259 B1 | 2/2003 | Chasin et al. |
| 6,524,607 B1 | 2/2003 | Goldenheim et al. |
| 6,528,530 B2 | 3/2003 | Zeitlin et al. |
| 6,552,031 B1 | 4/2003 | Burch et al. |
| 6,635,284 B2 | 10/2003 | Mehta et al. |
| 6,699,908 B2 | 3/2004 | Sackler et al. |
| 6,730,325 B2 | 5/2004 | Devane et al. |
| 6,733,783 B2 | 5/2004 | Oshlack et al. |
| 6,919,373 B1 | 7/2005 | Lam et al. |
| 6,921,541 B2 | 7/2005 | Chasin et al. |
| 6,930,129 B2 | 8/2005 | Lam et al. |
| 6,992,065 B2 | 1/2006 | Okumu et al. |
| 7,053,209 B1 | 5/2006 | Gibson et al. |
| 7,431,944 B2 | 10/2008 | Mehta et al. |
| 7,691,880 B2 | 4/2010 | Herman |
| 7,833,543 B2 | 11/2010 | Gibson et al. |
| 7,838,522 B2 | 11/2010 | Esposito et al. |
| 8,124,123 B2 | 2/2012 | Pillai et al. |
| 8,133,507 B2 | 3/2012 | Yum et al. |
| 8,147,870 B2 | 4/2012 | Yum et al. |
| 8,153,152 B2 | 4/2012 | Yum et al. |
| 8,163,798 B2 | 4/2012 | Gupta et al. |
| 8,168,217 B2 | 5/2012 | Yum et al. |
| 8,354,124 B2 | 1/2013 | Yum et al. |
| 8,415,401 B2 | 4/2013 | Yum et al. |
| 8,420,120 B2 | 4/2013 | Yum et al. |
| 8,926,783 B2 | 1/2015 | Akhtar et al. |
| 8,945,614 B2 | 2/2015 | Yum et al. |
| 8,951,556 B2 | 2/2015 | Yum et al. |
| 8,974,821 B2 | 3/2015 | Yum et al. |
| 9,233,160 B2 | 1/2016 | Yum et al. |
| 9,517,271 B2 | 12/2016 | Yum et al. |
| 9,555,113 B2 | 1/2017 | Yum et al. |
| 9,572,885 B2 | 2/2017 | Yum et al. |
| 9,592,204 B2 | 3/2017 | Yum et al. |
| 9,616,055 B2 | 4/2017 | Yum et al. |
| 9,655,861 B2 | 5/2017 | Yum et al. |
| 9,855,333 B2 | 1/2018 | Yum et al. |
| 9,884,056 B2 | 2/2018 | Scicinski et al. |
| 2001/0000522 A1 | 4/2001 | Dyer et al. |
| 2001/0029257 A1 | 10/2001 | Murdock et al. |
| 2001/0047005 A1 | 11/2001 | Farrar et al. |
| 2001/0055613 A1 | 12/2001 | Burnside et al. |
| 2002/0086878 A1 | 7/2002 | Dobrozsi et al. |

(56) References Cited

U.S. PATENT DOCUMENTS

| | | |
|---|---|---|
| 2002/0114835 A1 | 8/2002 | Sackler et al. |
| 2002/0143065 A1 | 10/2002 | Liu et al. |
| 2003/0004177 A1 | 1/2003 | Kao et al. |
| 2003/0045454 A1 | 3/2003 | Okumu et al. |
| 2003/0152637 A1 | 8/2003 | Chasin et al. |
| 2003/0157168 A1 | 8/2003 | Breder et al. |
| 2003/0165562 A1 | 9/2003 | Gutierrez-Rocca et al. |
| 2003/0185873 A1 | 10/2003 | Chasin et al. |
| 2003/0191147 A1 | 10/2003 | Sherman et al. |
| 2004/0001889 A1 | 1/2004 | Chen et al. |
| 2004/0024021 A1 | 2/2004 | Sudo et al. |
| 2004/0052336 A1 | 3/2004 | Langlet et al. |
| 2004/0101557 A1 | 5/2004 | Gibson et al. |
| 2004/0109893 A1 | 6/2004 | Chen et al. |
| 2004/0146562 A1 | 7/2004 | Shah |
| 2004/0161382 A1 | 8/2004 | Yum et al. |
| 2004/0224020 A1 | 11/2004 | Schoenhard |
| 2004/0224903 A1 | 11/2004 | Berry et al. |
| 2005/0042194 A1 | 2/2005 | Ng et al. |
| 2005/0106304 A1 | 5/2005 | Cook et al. |
| 2005/0158382 A1 | 7/2005 | Cruz et al. |
| 2005/0171052 A1 | 8/2005 | Cook et al. |
| 2005/0208132 A1 | 9/2005 | Sathyan et al. |
| 2005/0232876 A1 | 10/2005 | Minga et al. |
| 2005/0244489 A1 | 11/2005 | Paris |
| 2005/0260264 A1 | 11/2005 | Edgren et al. |
| 2005/0266087 A1 | 12/2005 | Junnarkar et al. |
| 2006/0034926 A1 | 2/2006 | Fraatz et al. |
| 2006/0058401 A1 | 3/2006 | Ishikawa et al. |
| 2006/0104909 A1 | 5/2006 | Vaghefi et al. |
| 2006/0115527 A1 | 6/2006 | Hassan et al. |
| 2006/0165800 A1 | 7/2006 | Chen et al. |
| 2006/0210599 A1 | 9/2006 | Gibson et al. |
| 2007/0027105 A1 | 2/2007 | Junnarkar et al. |
| 2007/0031502 A1 | 2/2007 | Pettersson et al. |
| 2007/0104763 A1 | 5/2007 | Jobdevairakkam et al. |
| 2007/0259033 A1 | 11/2007 | Cruz |
| 2008/0023261 A1 | 1/2008 | Kaneko et al. |
| 2008/0026052 A1 | 1/2008 | Schoenhard |
| 2008/0145419 A1 | 6/2008 | Gibson et al. |
| 2008/0152708 A1 | 6/2008 | Gibson et al. |
| 2008/0206321 A1 | 8/2008 | Yum et al. |
| 2009/0023689 A1 | 1/2009 | Yum et al. |
| 2009/0023690 A1 | 1/2009 | Yum et al. |
| 2009/0164240 A1 | 6/2009 | Friedmann et al. |
| 2009/0165578 A1 | 7/2009 | Zamloot et al. |
| 2009/0169631 A1 | 7/2009 | Zamloot et al. |
| 2009/0215808 A1 | 8/2009 | Yum et al. |
| 2009/0298862 A1 | 12/2009 | Yum et al. |
| 2010/0260844 A1 | 10/2010 | Scicinski et al. |
| 2011/0287093 A1 | 11/2011 | Schoenhard |
| 2012/0135072 A1 | 5/2012 | Yum et al. |
| 2012/0135073 A1 | 5/2012 | Yum et al. |
| 2012/0165358 A1 | 6/2012 | Cruz et al. |
| 2013/0281480 A1 | 10/2013 | Yum et al. |
| 2013/0287845 A1 | 10/2013 | Yum et al. |
| 2013/0295168 A1 | 11/2013 | Yum et al. |
| 2013/0309176 A1 | 11/2013 | Port et al. |
| 2013/0317049 A1 | 11/2013 | Yum et al. |
| 2013/0337059 A1 | 12/2013 | Yum et al. |
| 2013/0337060 A1 | 12/2013 | Yum et al. |
| 2014/0275147 A1 | 9/2014 | Yum et al. |
| 2015/0196644 A1 | 7/2015 | Yum et al. |
| 2016/0038592 A1 | 2/2016 | Yum et al. |
| 2016/0058746 A1 | 3/2016 | Scicinski et al. |
| 2016/0136102 A1 | 5/2016 | Yum et al. |
| 2016/0193345 A1 | 7/2016 | Yum et al. |
| 2016/0038479 A1 | 9/2016 | Yum et al. |
| 2017/0165255 A1 | 6/2017 | Yum et al. |
| 2017/0196978 A1 | 7/2017 | Yum et al. |
| 2017/0209581 A1 | 7/2017 | Yum et al. |
| 2017/0319501 A1 | 11/2017 | Yum et al. |

FOREIGN PATENT DOCUMENTS

| | | |
|---|---|---|
| DE | 1569231 | 8/1969 |
| DE | 2213717 | 11/1972 |
| DE | 2321174 | 4/1973 |
| DE | 2438352 | 2/1976 |
| DE | 2720245 | 11/1977 |
| DE | 19714765 | 10/1998 |
| EP | 0244118 | 11/1987 |
| EP | 0535899 | 4/1993 |
| EP | 0539559 | 5/1993 |
| EP | 0539751 | 5/1993 |
| EP | 0544612 | 6/1993 |
| EP | 0621042 | 10/1994 |
| EP | 0290983 | 1/1995 |
| EP | 0640336 | 3/1995 |
| EP | 0773034 | 5/1997 |
| EP | 0778768 | 6/1997 |
| EP | 0537559 | 1/1998 |
| EP | 0711548 | 1/1998 |
| EP | 0635531 | 6/2001 |
| EP | 0782569 | 3/2002 |
| EP | 1010436 | 10/2002 |
| EP | 0804417 | 6/2003 |
| EP | 0788480 | 7/2003 |
| EP | 0788481 | 8/2003 |
| EP | 0999825 | 10/2003 |
| EP | 1348427 | 10/2003 |
| EP | 1032390 | 11/2003 |
| EP | 1548093 | 6/2005 |
| EP | 2510924 | 10/2012 |
| GB | 1088992 | 10/1967 |
| GB | 2238478 | 6/1991 |
| JP | 59210024 | 11/1984 |
| JP | 62000419 | 1/1987 |
| JP | 2096516 | 4/1990 |
| JP | 5194273 | 8/1993 |
| JP | 7053356 | 2/1995 |
| JP | 7112940 | 5/1995 |
| JP | 7115901 | 5/1995 |
| JP | 7124196 | 5/1995 |
| JP | 9502181 | 3/1997 |
| JP | 2003508449 | 3/2003 |
| WO | WO 1990003768 | 4/1990 |
| WO | WO 1990003809 | 4/1990 |
| WO | WO 1991018016 | 11/1991 |
| WO | WO 199214466 | 3/1992 |
| WO | WO 1992017900 | 10/1992 |
| WO | WO 1993003751 | 3/1993 |
| WO | WO 1993007833 | 4/1993 |
| WO | WO 1994005265 | 3/1994 |
| WO | WO 1994015587 | 7/1994 |
| WO | WO 1995009613 | 4/1995 |
| WO | WO 1995017901 | 7/1995 |
| WO | WO 1996009290 | 3/1996 |
| WO | WO 1996012699 | 5/1996 |
| WO | WO 1996012700 | 5/1996 |
| WO | WO 1996022281 | 7/1996 |
| WO | WO 1996039995 | 12/1996 |
| WO | WO 1996041616 | 12/1996 |
| WO | WO 1997015285 | 5/1997 |
| WO | WO 1997027840 | 8/1997 |
| WO | WO 1997049391 | 12/1997 |
| WO | WO 1998027962 | 7/1998 |
| WO | WO 1998027963 | 7/1998 |
| WO | WO 1998034596 | 8/1998 |
| WO | WO 1998044903 | 10/1998 |
| WO | WO 1998051246 | 11/1998 |
| WO | WO 1998053837 | 12/1998 |
| WO | WO 1999006023 | 2/1999 |
| WO | WO 1999013913 | 3/1999 |
| WO | WO 1999025349 | 5/1999 |
| WO | WO 2000000120 | 1/2000 |
| WO | WO 200016750 | 3/2000 |
| WO | WO 2000078335 | 12/2000 |
| WO | WO 2001008661 | 2/2001 |
| WO | WO 2001015734 | 3/2001 |
| WO | WO 2001051024 | 7/2001 |
| WO | WO 2001076599 | 10/2001 |

(56) References Cited

FOREIGN PATENT DOCUMENTS

| | | |
|---|---|---|
| WO | WO 2002010436 | 2/2002 |
| WO | WO 2002053187 | 7/2002 |
| WO | WO 2002087512 | 11/2002 |
| WO | WO 2003000282 | 1/2003 |
| WO | WO 2003013476 | 2/2003 |
| WO | WO 2003055475 | 7/2003 |
| WO | WO 2003086368 | 10/2003 |
| WO | WO 2003101358 | 12/2003 |
| WO | WO 2004026262 | 4/2004 |
| WO | WO 2004037224 | 5/2004 |
| WO | WO 2004037289 | 5/2004 |
| WO | WO 2004052336 | 6/2004 |
| WO | WO 2004056337 | 7/2004 |
| WO | WO 2004056338 | 7/2004 |
| WO | WO 2004082658 | 9/2004 |
| WO | WO 2004101557 | 11/2004 |
| WO | WO 2005009408 | 2/2005 |
| WO | WO 2005048744 | 6/2005 |
| WO | WO 2005105031 | 11/2005 |
| WO | WO 2005112896 | 12/2005 |
| WO | WO 2005115333 | 12/2005 |
| WO | WO 2006008141 | 1/2006 |
| WO | WO 2006069293 | 6/2006 |
| WO | WO 2006084139 | 8/2006 |
| WO | WO 2006134018 | 12/2006 |
| WO | WO 2007058923 | 5/2007 |
| WO | WO 2007070632 | 6/2007 |
| WO | WO 2007135193 | 11/2007 |
| WO | WO 2008023261 | 2/2008 |
| WO | WO 2009076227 | 6/2009 |
| WO | WO 2009076231 | 6/2009 |
| WO | WO 2009076236 | 6/2009 |
| WO | WO 2009088414 | 7/2009 |
| WO | WO 2013142279 | 9/2013 |
| WO | WO 2014144984 | 3/2014 |
| WO | WO 2004054542 | 7/2014 |
| WO | WO 2014144975 | 9/2014 |

OTHER PUBLICATIONS

U.S. Appl. No. 15/872,855, filed Jan. 16, 2018, Yum, et al.
U.S. Appl. No. 15/887,797, filed Feb. 2, 2018, Yum, et al.
"New Drugs/Programs", Current Drug Discovery, Nov. 2004 pp. 7-10.
"Ritalin product monograph"; CPS Compendium of Pharmaceuticals and Specialties, 34th ed.; Gillis, M., Ed. Canadian Pharmacists Association: Ottawa, (1999); pp. 1573-1574.
3M, "3M DDS Announces Development of New HFA-Compatible Exipients: Novel Oligomeric Acids as MDI Suspension Aid and Solubilizers" 3M Delivery Newsletter, Jun. 2000, pp. 9-11, vol. 15, 3M Drug Delivery Systems.
Abdul-Fattah, Ahmad M., et al; "Preparation and in Vitro Evaluation of Solid Dispersions of Halofantrine."; International Journal of Pharmaceutics 235; (2002); pp. 17-33.
Adams EG, et al. "A comparison of the abuse liability of tramadol, NSAIDS, and hydrocodone in patients with chronic pain." Journal of Pain and Symptom Management. 31(5), 465-476 2006.
Ajayaghosh, A., et al., "Solid-Phase Synthesis of N-Methyl- and N-Ethylamides of Peptides Using Photolytically Detachable ((3-Nitro-4 (alkylamino)methyl)benzamido)methyl)polystyrene Resin", J. Org. Chem. 1990, 55, 2826-2829.
Allahham A, et al. "Flow and injection characteristics of pharmaceutical parenteral formulations using a micro-capillary rheometer". Int J Pharm. 2004; 270(1-2):139-48.
Ansel, H.C. et al., Pharmaceutical Dosage Forms and Drug Delivery System , sixth ed., (1995).
Ash Michael and Ash Irene; "Handbook of Pharmaceutical Additives: An International Guide to More Than 6000 Products by Trade Name, Chemical, Function, and Manufacturer" ; Gower (1995); 3 pages.
Aungst, B.J., et al; "Improved Oral Bioavailability of an HIV Protease Inhibitor Using Gelucire 44/14 and Labrasol Vehicles"; Bulletin Technique Gattefosse, No. 87, (1994); pp. 49-54.
Aungst, B.J et al; "Amphiphilic vehicles improve the oral bioavailability of a poorly soluble HIV Protease inhibitor at high doses."; International Journal of Pharmaceutics, vol. 156; (1997); pp. 79-88.
Bansal, Tripta, et al; "Solid Self Nanoemulsifying Delivery Systems as a Platform Technology for Formulation of Poorly Soluble Drugs"; Critical Reviews™ in Therapeutic Drug Carrier Systems, 25(1); (2008); pp. 63-116.
Barakat, N .S.; "Etodolac-Liquid-Filled Dispersion into Hard Gelatin Capsules: An Approach to Improve Dissolution and Stability of Etodolac Formulation."; Drug Pev. Pharm. 32[7]; (2006); pp. 865-876.
Barker, S.A., et al; "An investigation into the structure and bioavailability of α-tocopheroll dispersions in Gelucire 44/14"; Journal of Controlled Release 91; (2003); pp. 477-488.
Barb, R., et al., "Evaluation of the SABER Delivery System for the Controlled Release of Deslorelin: Effect of Dose in Estrogen Primed Ovarectomized Gilts", Proceed. Int'l, Symp. Control. Rel. Bioact. Mater., pp. 1170-1171 (1999) Controlled Release Society, Inc.
Becker & Johnson "Effects of Gonadotropin-Releasing Hormone Infused in a Pulsatile or Continuous Fashion Serum Gonadotropin Concentrations and Ovulation in the Mare", J. Anim. Sci. pp. 1208-1215 vol. 70, 1992.
Bekersky I, et al. "Effect of low- and high-fat meals on tacrolimus absorption following 5 mg single oral doses to healthy human subjects." J Clin Pharmacol 2001; 41 (2):176-82.
Berge et al. "Pharmaceutical salts" J Pharm. Sci. 66(1); Jan. 1977; pp. 1-19.
Betschart, R., et al., "Evaluation of the SABER Delivery System for the Controlled Release of the GnRH Analogue Deslorelin for Advancing Ovulation in Mares: Effect of Gamma Radiation", Proceed. Int'l. Symp. Control. Rel. Bioact. Mater., 25 (1998) pp. 655-656 Controlled Release Society, Inc.
Blachez, P., et al; "Development of immediate release pellets of poorly soluble compounds using Gelucire 44/14 using melt pelletization"; Poster, Oct. 26, 2003. Conference "AAPS Annual Meeting & Exposition", Salt Lake City, Utah, United States.X.
Blažková, A. et al, "Viscosity properties of aqueous solutions of hydroxyethylcellulose"; Chem Papers 44 (3); (1990) pp. 289-301.
Brevard J, et al. "Pain and opioid abuse in a population of substance abuse patients: data from the NAVIPPRO system." Conference paper presented at the 42nd American Pain Society (APS) Annual Scientific Meeting, Washington D.C., 2007.
Bühler, K., GnRH Agonists and Safety, In GnRH Analagoues The State of the Art 1993, A Summary of the 3rd International Symposium on GnRH Analogues in Cancer and Human Reproduction, Geneva, Feb. 1993.
Burns, P. et al., "Pharmacodynamic Evaluation of the Saber.TM. Delivery System for the Controlled Release of the GnRH Analogue Deslorelin Acetate for Advancing Ovulation in Cyclic Mares," Proceed. Int'l. Symp. Control. Rel. Bioact. Mater., 24 (1997), Controlled Release Society, Inc.
"Cab-O-Sil®, Untreated Fumed Silica: Properties & Functions"; Cabot Corporation, Cab-O-Sil Division; (1993); pp. 1-34.
Carraway, et al. (2000) "Drug Delivery From a Controlled Release Aerosol: Effects of Formulation Variables" AAPS J Abstract. Southern BioSystems, Inc. Birmingham AL, USA.
Carraway, et al. (2000) "Drug Release from a Novel Controlled Release Aerosol Based on Sucrose Acetate Isobutyrate" AAPS Midwest Regional Meeting Chicago, IL, May 22, 2000.
Cellulose Acetate Butyrate. In: European pharmacopoeia. 4 edn. Strasbourg Cedex, France: Council of Europe; 2001; p. 853-4.
Chambin, O., et al; "Interest of Multifunctional Lipid Excipients: Case of Gelucire® 44/14"; Drug Development and Industrial Pharmacy, 31; (2005); pp. 527-534.
Chambin, O., et al; "Influence of drug polarity upon the solid-state structure and release properties of self-emulsifying drug delivery systems in relation with water affinity"; Colloids and Surfaces B: Biointerfaces 71 (2009) pp. 73-78.
Chauhan Bhaskar, et al; "Preparation and Characterization of Etoricoxib Solid Dispersions Using Lipid Carriers by Spray Drying Technique"; AAPS PharmSciTech 6 (3), Article 50; (2005); pp. E405-E412; (http://www.aapspharmscitech.org).

(56) References Cited

OTHER PUBLICATIONS

Chauhan, B., et al; "Preparation and evaluation of glibenclamide-polyglycolized glycerides solid dispersions with silicon dioxide by spray drying technique"; *European J. Pharm . . . Sci.* 26[2]; (2005); pp. 219-230.

Chen, X. Q., et al; "Evaluation of Lipid-based Formulations in Dogs and Monkeys for a Highly Lipophilic Compound"; (2007); Conference "Annual Meeting of AAPS", San Diego, CA. poster pages.

Coy, et al., "Solid Phase Synthesis of Lutenizing Hormone-Releasing Hormone and Its Analogs", Methods Enzymol. 37, 416 (1975).

Cuine, Jean F., et al; "Evaluation of the Impact of Surfactant Digestion on the Bioavailability of Danazol after Oral Administration of Lipidic Self-Emulsifying Formulations to Dogs"; *Journal of Pharmaceutical Sciences*, vol. 97, No. 2; Feb. 2008; pp. 995-1012.

Damian, Festo et al; "Physicochemical characterization of solid dispersions of the antiviral agent UC-781 with polyethylene glycol 6000 and Gelucire 44/14"; *European Journal of Pharmaceutical Sciences* 10; (2000); pp. 311-322.

Darling, et al. (2000) "Extended Release of Human Growth Hormone Suspended in SABERTM Formulation Design and in Vitro Assessment" Genentech, Inc., South San Francisco, CA USA and Southern BioSystems, Inc. Birmingham AL, USA. Poster.

DataBase WPI Section Ch, Week 198532 Derwent Publications Ltd., London GB; Class B07, AN 1985-193549 XP002284488 & JP 60120811 A (Sealer, R P KK) Jun. 28, 1985 (Abstract).

Desai et al., "Surface Modification of Polymeric Biomaterials for Reduced Thrombogenicity," Polym. Mater. Sci. Eng., 62:731-735 Jun. 1990.

Dodson, K.M., Et al. "Oral Controlled Release of Antiretrovirals Using the SABER Delivery System Incorporated into Soft Gelatin Capsules", AAPS Meeting, 1999, New Orleans, LA.

Dordunoo, S.K., et al; "Preformulation Studies on Solid Dispersions Containing Triamterene or Temazepam in Polyethylene Glycols or Gelucire® 44/14 for Liquid Filling of Hard Gelatin Capsules."; *Drug Development and Industrial Pharmacy*, vol. 17, No. 12,; (1991); pp. 1685-1713.

Dordunoo, S.K., et al; "Solidification studies of polyethylene glycols, Gelucire® 44/14 or their dispersions with Triamterene or-Temazepam."; *Journal of Pharm. Pharmacology*, vol. 101; (1996); pp. 782-789.

Duan, D.C. et al., "Novel Dispersing Aids for Hydrofluoroalkane-Based Metered Dose Inhalers," 1988 Conference of the American Association of Pharmaceutical Scientists, San Francisco, California, Nov. 1998.

Duan, D.C. et al., "Oligomeric Lactic Acids as Solubilizing Aids for HFA-Based Metered Dose Inhalers," 1998 Conference of the American Association of Pharmaceutical Scientists, San Francisco, California, Nov. 1998.

Dunbar SA, Katz NP "Chronic opioid therapy for nonmalignant pain in patients with a history of substance abuse: report of 20 cases." Journal of Pain and Symptom Management. 11(3), 163-171. 1996.

Edimo, A., et al; "Capacity of Lipophilic Auxiliary Substances to Give Spheres by Extrusion-Spheronization"; *Drug Development and Industrial Pharmacy*, 19(7); (1993); pp. 827-842.

Eliasen, Helle; et al; "Effects of binder rheology on melt agglomeration in a high shear mixer"; *International Journal of Pharmaceutics* 176; (1998) pp. 73-83.

Fernandez, Sylvie, et al; "Lipolysis of the semi-solid self-emulsifying excipient Gelucire® 44/14 by digestive lipases"; *Biochimica et Biophysica Acta* 1781; (2008); pp. 367-375.

Fitzgerald, B. P., et al., "Effect of Constant Administration of a Gonadotropin-Releasing Hormone Agonist on Reproductive Activity in Mares: Preliminary Evidence on Suppression of Ovulation During the Breeding Season", Am. J. Vet. Res., pp. 1746-1751, vol. 54, No. 10, Oct. 1993.

Fleury, J., et al., "Evaluation of the SABER Delivery System for the Controlled Release of Deslorelin for Advancing Ovulation in the Mare: Effects of Formulation & Dose", Proceed. Int'l. Symp. Control. Rel. Bioact. Mater., 25 (1998) Controlled Release Society, Inc. pp. 657-658.

Friedmann N, Klutzaritz V, Webster L; "Efficacy and safety of an extended-release oxycodone (Remoxy) formulation in patients with moderate to severe osteoarthritic pain"; *J Opioid Manag.* 7(3); (2011); pp. 193-202.

Friedmann N, Klutzaritz V, Webster L.; "Long-term safety of Remoxy(R) (extended-release oxycodone) in patients with moderate to severe chronic osteoarthritis or low back pain"; *Pain Med.*, 12(5); (2011); pp. 755-760.

Gad, Shayne C., et al; Nonclinical Vehicle Use in Studies by Multiple Routes in Multiple Species ; *International Journal of Toxicology*, 25; (2006); pp. 1-23.

Gattefossé Corporation (1989); "To Help With Your Impossible Formulations: A Guide to Gattefossé Liquid Excipients"; 6 pages.

Gattefossé (1998); "Oral Route Excipients" 8 pages.

Gelucire 44-14 brochure (1999); "Immediate Release and Enhanced Bioavailability"; pp. 1-16.

Gelucire Technical Dossier (1996); "Answering the Need for Enhanced Bioavailability"; pp. 1-16.

Gelucire® (1996); "Answering the Need for Enhanced Bioavailability"; 5 pages.

"General Characteristics of Polymers"; *Museum of Fine Arts, Boston*; (2007); pp. 1-4.

Gibson, et al. (1999) "Effects of Formulation Variables on Controlled Release of Paclitaxel and other Chemotherapeutic Agents from a Novel Delivery System" AAPS New Orleans, LA. Southern BioSystems, Inc. Birmingham AL, USA.

Gibson, et al. (1999) "In Vitro and in Vivo Evaluation of a Novel in Situ-Forming Pareteral Delivery System" Meeting of Recent Advances in Drug Delivery Systems, Salt Lake City, UT. Southern BioSystems, Inc. Birmingham AL, USA.

Gilderman L., et al. "Remoxy.TM.: A New Opioid Drug With Effective Analgesia and Abuse-Resistance." American Pain Society Annual Meeting, San Antonio, TX, May 2006.

Ginther, O.J, "Follicles", Ultrasonic Imaging and Reproductive Events in the Mare. EquiServices, Chapter 4: 43-72, Cross Plains, WI, 1986.

Ginther, O.J., "Effect of a Synthetic Gonadotropin-Releasing Hormone on Plasma Concentrations of Luteinizing Hormone in Ponies", Am. J. Vet. Res., pp. 79-81 vol. 35, No. x, Jan. 1974.

Ginther, O.J., "Reproductive Efficiency", *Reproductive Biology of the Mare Basic and Applied Aspects*, Second Ed., Chapter 12; (1992); pp. 499-509.

Glajchen, M. "Chronic Pain: Treatment Barriers and Strategies for Clinical Practice." J AM Board Fam Pract. 2001;14(3):178-183.

González et al; "Methylphenidate bioavailability from two extended-release formulations"; *International Journal of Clinical Pharmacology Therapeutics*, vol. 40, No. 4; (2002) pp. 175-184.

Gould Phillip; "Salt selection for basic drugs"; *International Journal of Pharmaceutics*, 33 (1986), pp. 201-217.

Greydanus, D. E.; "Psychopharmacology for ADHD in Adolescents: Quo Vadis?"; *Psychiatric Times* vol. 20, No. 5; May 5, 2003; pp. 1-7.

Handbook of Pharmaceutical Excipients: Sixth Edition; "Medium-chain Triglycerides"; *Pharmaceutical Press and American Pharmacists Association 2009*; pp. 429-431.

Harrison, L.A., et al., "Comparison of HCG, Buserelin and Luprostiol for Induction of Ovulation in Cycling Mares", Equine Veterinary Science, pp. 163-166 vol. 11, No. 3, 1991.

Hatakeyama et al., "Synthesis and physical properties of polyurethanes from saccharide-based polycaprolactones." Macromolecular Symposia, vol. 130, pp. 127-138, 1998.

Hauss, D.J., et al; "Lipid-Based Delivery Systems for Improving the Bioavailability and Lymphatic Transport of a Poorly Water-Soluble LTB$_4$ Inhibitor."; *Journal of Pharmaceutical Sciences*, vol. 87, No. 2; (1998) pp. 164-169.

Hays LR. "A profile of OxyContin addiction. Journal of Addictive Diseases." 23 (4), 1-9. 2004.

(56) References Cited

OTHER PUBLICATIONS

Henry, C. (1995) "Sucrose Acetate Isobutyrate Special Grade for Beverage Applications" *International Food Ingred*. pp. 47-49.
He, Y., et al; "Oral Formulation of a Novel Antiviral Agent, PG301 029, in a Mixture of Gelucire 44/14 and DMA (2:1, wt/wt)"; *AAPS Pharm. Sci. Tech.* 6(1) (2005); pp. E1-E5.
Hoskin PJ, et al. "The bioavailability and pharmacokinetics of morphine after intravenous, oral and buccal administration in healthy volunteers." Br J Clin Pharmacol 1989; 27 (4):499-505.
Hülsmann, S. et al; "Melt extrusion—an alternative method for enhancing the dissolution rate of 17β-estradiol hemihydrate"; *European Journal of Pharmaceutics and Biopharmaceutics* 49; (2000); pp. 237-242.
Hyland, J.H., et al., "Infusion of Gonadotrophin-releasing hormone (GnRH) Induces Ovulation and Fertile Oestrus in Mares During Seasonal Anoestrus", J. Reprod. Fert., Suppl. 35 (1987), 211-220.
Inciardi JA, Surratt HL, Kurtz SP, Cicero TJ. "Mechanisms of prescription drug diversion among drug-involved club- and street-based populations." Pain Medicine. 8(2), 171-183, 2007.
Irvine, "GnRH Clinical Application," in Equine Reproduction, (eds) McKinon, A.O. and Voss, J.L., Chapter 36, pp. 41-45, Lea & Febiger (1993).
Irvine, D.S., "Duration of Oestrus and Time of Ovulation in Mares Treated with Synthetic GnRH (Ay24,031)," J. Reprod. Fert. Supp. 23:279-283 (1975).
Ishida T, Oguri K, et al. "Isolation and identification of urinary metabolites of oxycodone in rabbits." Drug Metab Dispos 1979; 7 (3):162-5.
Ishida T, Oguri K, Yoshimura H. "Determination of oxycodone metabolites in urines and feces of several mammalian species." J Pharmacobiodyn 1982; 5 (7):521-5.
Itoh, K., et al; "Improvement of physiochemical properties of N-4472 part I formulation design by using self-microemulsifying system"; *Int .J. Pharm.*, 238[1-2); (2002); pp. 153-160.
Iwanaga Kazunori, et al; "Disposition of Lipid-Based Formulation in the Intestinal Tract Affects the Absorption of Poorly Water-Soluble Drugs"; *Biol. Pharm. Bull.* vol. 29, No. 3; (2006); pp. 508-512.
Iyakuhin Tenkabutsu Kenkyykai Ed. "Jitsuyo Iyakuhin Tenkabutsu (Practical Medical Additives)" pub. Kagaku Kogyo-sha Mar. 5, 1974, Tokyo.
Jannin, V., et al; "Systemes auto-emulsionnables et emulsions secbes"; *STP Pharma Pratiques*—vol. 15—No. 3—May/Jun. 2005; pp. 247-254.
Jannin, V., et al; "Approaches for the development of solid and semi-solid lipid-based formulations"; *Advanced Drug Delivery Reviews* 60; (2008); pp. 734-746.
Japanese Office Action for Japanese Application No. 2010-537128, dated Jun. 5, 2013.
Jöchle, W., et al., "Control of Ovulation in the Mare with Ovuplant a Short-Term Release Implant (STI) Containing the GnRH Analogue Deslorelin Acetate: Studies from 1990 to 1994.", Journal of Equine Veterinary Science, pp. 632-644, vol. 14m No. 12, 1994.
Johnson, et al. (1999) "Biodegradable Delivery Systems for Estradiol: Comparison Between Poly(DL-Lactide) Microspheres and the Saber Delivery System" Proceed. Int'l Symp. Control. Rel. Bioact. Mater., 26, Controlled Release Society, Inc.
Johnson, R.M., et al. "Applications of Continuous Site-Directed Drug Delivery", Proc. West Pharmacol Soc. vol. 45: 2 19-222 (2002).
Johnston LD, O'Malley PM, Bachman JG, Schulenberg, JE. "Monitoring the future. National results on adolescent drug use: overview of key findings" (NIH Publication No. 05-5726). Bethesda, MD: National Institute on Drug Abuse 2004.
Kaiko (2005) "Pharmacology of Tablets of Oxycontin the Development Process Thereof" *Palliative Care Research* 7(1):3-13.
Kale, A., et al; "Design and Evaluation of Self-Emulsifying Drug Delivery Systems (SEDDS) of Nimodipine"; *AAPS Pharm. Sci. Tech.*, 9(1); (2008); pp. 191-196.

Kamel S., et al; "Pharmaceutical significance of cellulose: A review"; *eXPRESS Polymer Letters* vol. 2, No. 11; (2008); pp. 758-778.
Kane, Anil, et al; "A Statistical Mixture Design Approach Fo Formulating Poorly Soluble Compounds in Liquid Filled Hard Shell Capsules"; *Bulletin Technique Gattefosse* No. 99; (2006); pp. 43-49.
Karatas, A., et al; "Improved solubility and dissolution rate of piroxicam using gelicore 44/14 and labrasol"; *Il Farmaco* 60(9); (2005); pp. 777-782.
Katz NP, et al. "Challenges in the development of prescription opioid abuse-deterrent formulations." Clin J Pain. 2007;23(8):648-60.
Katz NP, et al. "Development and preliminary experience with an ease of extractability rating system for prescription opioids." Drug Development and Industrial Pharmacy. 32(6) 727-746(20). 2006.
Katz NP, et al. "Prescription monitoring of medical and non-medical Schedule II opioid abuse in Massachusetts: 1996-2005." Conference paper presented at the 69th College on Problems of Drug Dependence (CPDD), Quebec, Canada, 2007.
Katz NP, et al. (2003) "Behavioral monitoring and urine toxicology testing in patients receiving long-term opioid therapy" *Anesth Analg*. 97(4):1097-102.
King; "Tablets, Capsules, and Pills" Remington's Pharmaceutical Sciences, Ed. Arthur Osol, Chapter 89, (1980); pp. 1553-1584.
Koga, Kenjiro, et al; "In vitro and in situ evidence for the contribution of Labrasol® and Gelucire 44/14 on transport of cephalexin and cefoperazone by rat intestine"; *European Journal of Pharmaceutics and Biopharmaceutics* 54; (2002); pp. 311-318.
Kulkarni, et al., "Polyactic Acid for Surgical Implants," Arch. Surg. 93:839 (1966).
Lacoste, D., et al., "Reversible Inhibition of Testicular Androgen Secretion by 3-, 5- and 6-Month Controlled-Release Microsphere Formulations of the LH-RH Agonist [D-Trp.sup.6, des-Gly-NH.sub. 2]LH-RH Ethylamide in the Dog", J. Seroid Biochem. vol. 33, No. 5, pp. 1007-1011, 1989.
Laforet, Jean-Pierre, et al; "The Right Mix"; *Gattefosse*, vol. 7, No. 1; (1995); pp. 1-10.
Lalovic B, Kharasch E, Hoffer C et al. Pharmacokinetics and pharmacodynamics of oral oxycodone in healthy human subjects: role of circulating active metabolites. Clin Pharmacol Ther 2006; 79 (5):461-79.
Larsen, A., et al; (2006) "In vitro evaluation of Pharmaceutical surfactants fate during lipolysis and its effects on solubilization of a poorly soluble model compound: Danazol, Conference on When Poor Solubility Becomes an Issue"; From Early Stage to Proof of Principles, Verona (Italy).
Larsen, A., et al; "Pharmaceutical surfactants in biorelevant media: impact on lipolysis and solubility of a poorly soluble model compound" Danazol,. Conference "5$^{th}$ World Meeting on Pharmaceutics Biopharmaceutics and Pharmaceutical Technology", Geneva,Switzerland. (2006) 1-2 pages.
Lopez et al; "Comparative efficacy of two once daily methylphenidate formulations (Ritalin LA and Concerta) and placebo in children with attention deficit hyperactivity disorder across the school day"; *Pediatr Drugs* 5(8); (2003); pp. 545-555.
Lowden, K.; "Filling hard gelatin capsules: experience in a new environment"; *Pharmaceutical Manufacturing Review*, vol. 10, No. 5; (1998); pp. 27 29.
Loy, R.G., et al., "The Effects of Human Chorionic Gonadotrophin on Ovulation, Length of Estrus, and Fertility in the Mare", University of California, Davis, California, Jan. 30, 1965, pp. 41-50.
Malhotra et al. "The pharmacokinetics of oxycodone and its metabolites following single oral doses of Remoxy®, an abuse-deterrent formulation of extended-release oxycodone, in patients with hepatic or renal impairment," Journal of Opioid Mgmt 11(2):157-169 (Mar./Apr. 2015).
Markowitz et al; "Advances in the pharmacotherapy of attention-deficit-hyperactivity disorder: focus on methylphenidate formulations"; *Pharmacotherapy* 23(10); (2003); pp. 1281-1299.
Markowitz et al; "Pharmacokinetics of methylphenidate after oral administration of two modified-release formulations in healthy adults"; *Clin Pharmacokinet* 42(4); (2003); pp. 393-401.

(56) References Cited

OTHER PUBLICATIONS

Material Safety Data Sheet "Eastman: Cellulose Acetate Butyrate CAB-381-2 BP CAB381-20 BP: Coating Chemicals" Eastman Chemical Company, Publication E-296B, Aug. 1994.
Material Safety Data Sheet "Eastman: Cellulose Esters for Pharmaceutical Drug Delivery" Eastman Chemical Company, Publication PCI-105B, Jun. 2004.
Material Safety Data Sheet of Eastman Chemical Products, "SAIB" Sucrose Acetate Isobutyrate, pp. 1-24. Publication GN-311F (Jun. 2004).
Material Safety Data Sheet of Eastman Fine Chemical Pharmaceutical Ingredients, Sucrose Acetate Isobutyrate Special Grade (SAIB-SG), Publication No. EFC-211, (May 1991).
Material Safety Data Sheet of Eastman Products for the Food Industry, "Sucrose Acetate Isbutyrate (SAIB-SB) for Use in Fruit-Flavored Beverages," Publication No. ZM-90, pp. 2-7 (Sep. 1989).
McCabe SE, Cranford JA, Boyd CJ, Teter CJ. "Motives, diversion and routes of administration associated with nonmedical use of prescription opioids." Addictive Behaviors. 32, 562-575. 2007.
McCarthy, P.F., et al., "Management of Stallions on Large Breeding Farms", Veterinary Clinics of North America: Equine Practice, pp. 219-235, vol. 8, No. 1, Apr. 1992.
McKinnon, A.O., et al., "Effect of GnRH Analogue (Ovuplant), hCG and Dexamethasone on Time to Ovulation in Cycling Mares", World Equine Veterinary Review, pp. 16-18 vol. 2: No. 3: 1997.
McKinnon, A.O., et al., "Repeated Use of a GnRH Analogue Deslorelin (Ovuplant) for Hastening Ovulation in the Transitional Mare", Equine Veterinary Journal (1996) 29 (2) 153-155.
McLellan AT, Luborsky L, Woody GE, O'Brien CP. "An improved diagnostic instrument for substance abuse patients." The Addiction Severity Index. J Nerv Ment Dis. 1980;168:26-33.
Mearns, D., "Changing Seasons", The Blood-Horse, Sep. 28, 1996, pp. 4794-4765.
Meehan, E., et al; "Monitoring the stability of excipients used in lipid matrix formulations"; (Poster), 22-7, Conference "*33rd Annual Meeting of the Controlled Release Society*", Vienna, Austria. (2006) 2 pages.
Mehuys, E., et al; . Human bioavailability of propranolol from a matrix-in-cylinder system with a HPMC-Gelucire® core; *Journal of Controlled Release* 107; (2005); pp. 523-536.
Merrifield, Bruce "Solid Phase Synthesis", Science, Apr. 18, 1986, vol. 232, pp. 341-347.
Meyer RJ, Hussain AS. Awareness topic: mitigating the risk of ethanol induced dose dumping from oral sustained/controlled release dosage forms. In: FDA's Advisory Committee for Pharmaceutical Science Meeting, Oct. 2005.
Montovan, S.M., et al. "The Effect of a Potent GnRH Agonist on Gonadal and Sexual Activity in the Horse", Theriogenology, Jun. 1990, vol. 33 No. 6, pp. 1305-1321.
Mumford, E.L., "Use of Deslorelin Short-Term Implants to Induce Ovulation in Cycling Mares During Three Consecutive Estrous Cycles", Animal Reproduction Science, vol. 39, 1995 pp. 129-140.
Murray S, Wooltorton E. Alcohol-associated rapid release of a long-acting opioid. CMAJ 2005;173(7):756.
Nabors, et al. (1994) "Controlled Release of Diclofenac-Na from Cellulose Ester Microspheres" PDD Presentation 7481 at the 1994 Ninth Annual AAPS Meeting in San Diego, CA, Nov. 6-10, 1994.
Nakagaki, Arita, "Seizai Butsuri Kagaku (Physical Chemistry of Medical Preparations)", pub. Asakura Shoten, Nov. 5, 1968, Tokyo.
Nally, J., et al., "Induction of Mucosal IgA Specific for SeMF3 for *Streptococcus equi* with Intranasal Vaccination Using a Sucrose Acetate Isobutyrate Based Delivery System", Proceed. Int'l Symp. Control. Rel. Bioact. Mater., 26 (1999) Controlled Release Society, Inc.
"NATROSOL® Hydroxyethylcellulose A Nonionic Water-Soluble Polymer"; *Hercules Incorporated, Aqualon Division*; (1999); pp. 1-24.

Nett, T.M., et al., "Further Studies on the Radioimmunoassay of Gonadotropin-releasing Hormone: Effect of Radioiodination, Antiserum and Unextracted Serum on Levels of Immunoreactivity in Serum", Endocrinology vol. 101, No. 4, pp. 1135-1144, 1977.
O'Driscoll, Caitriona M.; "Lipid-based formulations for intestinal lymphatic delivery"; *European Journal of Pharmaceutical Sciences* 15; (2002); pp. 405-415.
Okumu, et al. (2000) "Evaluation of SABERTM as a Local Delivery System for rhVEGF-Formulation Design and in Vitro Assessment" Genentech, Inc., South San Francisco, CA USA and Southern BioSystems, Inc. Birmingham AL, USA.
Okumu, et al. (2001) "Evaluation of SABERTM as a Local Delivery System for rhVEGF-Formulation Design and in Vitro Assessment" Genentech, Inc., South San Francisco, CA USA and Southern BioSystems, Inc. Birmingham AL, USA. Poster.
Patel Pranav, et al; "Preparation, Evaluation and Comparison of Lipid Based Drug Delivery Systems of Tacrolimus"; *International Journal of Pharmacy and Pharmaceutical Sciences*, vol. 6 Suppl 2; (2014); pp. 588-591.
Patrick et al; "New methylphenidate formulations for the treatment of attention-deficit/hyperactivity disorder" *Expert Opin Drug Deliv* 2(1); (2005); pp. 121-143.
Pelham et al; "Once-a-day Concerta methylphenidate versus three-times-daily methylphenidate in laboratory and natural settings"; *Pediatrics* vol. 107, No. 6; Jun. 6, 2001; pp. 1-15.
Perissutti, B., et al; "Solid dispersions of carbamazepine with Gelucire 44/14 and 50/13"; *S.T.P. Pharma Sciences* 10 (6); (2000); pp. 479-484.
Pozzi Franco, et al; "Formulations of Ubidecarenone with Improved Bioavailability"; *Eur. J. Pharm. Biopharm*, vol. 37, No. 4; (1991); pp. 243-246.
Pulido et al., "Enzymatic Regioselective Acylation of Hexoses and Pentoses Using Oxime Esters", J. Chem. Soc. Perkin Trans. 1, (21), 2891-2898, 1992.
Rabb et al., "Effects of Active Immunication Against GnRH on LH, FSH and Prolactin Storage, Sectretion and Response to Their Secretagogues in Pony Geldings," J. Anim. Sci., 68:3322-3329 (1990).
Ren, Shan, et al; "In Vitro Metabolic Stability of Moisture-Sensitive Rabeprazole in Human Liver Microsomes and Its Modulation by Pharmaceutical Excipients"; *Arch Pharm Res* vol. 31, No. 3; (2008); pp. 406-413; published online Apr. 13, 2008.
Reynolds, R.C. et al., "Sucrose acetate isobutyrate (SAIB): historical aspects of its use in beverages and a review of toxicity studies prior to 1988," Food Chem. Toxicol., 1998, 36 (2), pp. 81-93.
Reynolds, R.C., "Metabolism and pharmacokinetics of sucrose acetate isobutyrate (SAIB) and sucrose octaisobutyrate (SOIB) in rats, dogs, monkeys or humans: a review," Food Chem. Toxicol,, 1998, 36 (2), pp. 95-99.
Robinson; "Coating of Pharmaceutical Dosage Forms" *Remington's Pharmaceutical Sciences*, Ed. Arthur Osol, Chapter 90; (1980); pp. 1585-1593.
Roser, J.J., et al., "The Development of Antibodies to Human Chorionic Gonadotrpins Following its Repeated Injection in the Cyclic Mare," J. Reprod. Fert Suppl., 173-179 (1979).
Roussin, P. et al; "Gelucire® 44/14: A High-Performance System to Enhance Bioavailability of Poorly Water Soluble Drugs"; *Bulletin Technique Gattefosse*; (1997); pp. 51-58.
Sachs-Barrable, K., et al; "Lipid Excipients Peceol and Gelucire 44/14 decrease P-glycoprotein mediated efflux of Rhodamine 123 partially due to modifying P-glycoprotein expression within Caco-2 Cells."; *J. Pharm. Pharm. Sci.*, 10[3] (2007); pp. 319-331.
Saeio, Kiattisak, et al; "Factors Influencing Drug Dissolution Characteristic From Hydrophilic Polymer Matrix Tablet"; *Scientia Pharmaceutica (Sci. Pharm.)* 75; (2007); pp. 147-163.
Saeki (2005) "Progress of Orally Opiate Analgesics and Non-Steroidal Anti-Flammatory Agent" *Drug Deliv Syst* 20(5):521-529.
Santus et al.; "Osmotic Drug Delivery: A Review of the Patent Liter" *J. Control Release* 35(1); (1995); pp. 1-21.
Schamp Karen, et al; "Development of an in vitro/in vivo correlation for lipid formulations of EMD 50733, a poorly soluble, lipophilic drug substance"; *European Journal of Pharmaceutics and Biopharmaceutics* 62; (2006); pp. 227-234.

(56) References Cited

OTHER PUBLICATIONS

Serajuddin, A.T.M., et al; "Effect of vehicle amphiphilicity on the dissolution and bioavailability of a poorly water-soluble drug from solid dispersions."; *Journal of Pharmaceutical Sciences*, vol. 77, No. 5, (1988); pp. 414-417.

Serajuddin, A.T.M., et al; "Water Migration from Soft Gelatin Capsule Shell to Fill Material and Its Effect on Drug Solubility"; *Journal of Pharmaceutical Sciences*, vol. 75, No. 1; (1986); pp. 62-64.

Selimovic, Seila, and Hu Yue; "Aging Effects in Suspensions of Silica Particles"; *Mat. Res. Soc. Symp. Proc.*, vol. 790 Materials Research Society; (2004) pp. P7.11.1-P7.11.6.

Sethia Sundeep, et al; "Physicochemical Characterization of Solid Dispersions of Carbamazepine Formulated by Supercritical Carbon Dioxide and Conventional Solvent Evaporation Method"; *Journal of Pharmaceutical Sciences*, vol. 91, No. 9; Sep. 2002; pp. 1948-1957.

Sethia Sundeep, et al; "In Vitro-In Vivo Evaluation of Supercritical Processed Solid Dispersions: Permeability and Viability Assessment in Caco-2 Cells"; *Journal of Pharmaceutical Sciences*, vol. 93, No. 12; Dec. 2004; pp. 2985-2993.

Setnik B, Roland CL, Cleveland JM, Webster L.; "The abuse potential of Remoxy®, an extended-release formulation of oxycodone, compared with immediate- and extended-release oxycodone"; Pain Med. 2011; 12(4):618-631.

Shah N. H; et al; "Self-Emulsifying Drug Delivery Systems (SEDDS) for Improving In Vitro Dissolution and Oral Absorption of Lipophilic Drugs"; *Bulletin Technique*. Gattefossé Report No. 85; (1992/93); pp. 45-54.

Sheen, P.C., et al; "Bioavallabiltty of a poorly water soluble drug from tablet and solid dispersion in humans."; *Journal of Pharmaceutical Sciences*,, vol. 80, No. 7, (1991); pp. 712·714.

Shevipi Shyam, et al; "Preparation and Evaluation of Diltiazem Hydrochloride-Gelucire 43/01 Floating Granules Prepared by Melt Granulation"; *AAPS PharmSciTech* 5(3), Article 43; (2004); pp. 1-6; (http://www.aapspharmscitech.org).

Smith & Tipton (1996) "A Novel Parental Delivery System" AAPS Seattle, WA, Presentaion PDD 7270, 1996 Annual Meeting.

Soliman M. S., et al; "Preparation and in vitro characterization of a semi-solid dispersion of flurbiprofen with Gelucire 44/14 and Labrasol"; *Pharmazie* 60(4); (2005); pp. 288-293.

Srinivas et al.; "Enantioselective pharmacokinetics and pharmacodynamics of dl-threo-methylphenidate in children with attention deficit hyperactivity disorder"; *Clin Pharmacal Ther* 52(5); (1992); pp. 561-568.

Stegemann. S., et al; "When Poor Solubility Becomes an Issue: From Early Stage to Proof of Concept"; European Journal of Pharmaceutical Sciences 31; (2007); pp. 249-261.

Strickley, Robert G; "An Overview of Lipid Excipients Currently Available: Strengths, Weaknesses and Opportunity gaps: The Options for the Formulator"; *Bulletin Technique Gattefosse*, No. 100; (2007); pp. 31-37.

Strickley, Robert G.; "Solubilizing Excipients in Oral and Injectable Formulations"; *Pharmaceutical Research*, vol. 21, No. 2; Feb. 2004; pp. 201-230.

Subramanian Ramaswamy, et al; "Effect of Lipid Excipients on In Vitro Pancreatic Lipase Activity"; *Drug Development and Industrial Pharmacy*, vol. 29, No. 8; (2003); pp. 885-890.

Sucrose Acetate Isobutyrate, 21 CFR 172.831 (1999).

Sullivan, et al. (1997) "Delivery of Taxol®. and other Antineoplastic Agents from a Novel System Based on Sucrose Acetate Isobutyrate" AAPS Boston, MA. Southern BioSystems, Inc. Birmingham AL, USA.

Sullivan, et al. (1998) "Sustained Release of Bupivacaine from the SABER TM Delivery System" AAPS, San Francisco, CA. Southern BioSystems, Inc. Birmingham AL, USA.

Sullivan, et al. (1998) "Sustained Release of Progesterone and Estradiol from the SABERTM Delivery System: In Vitro and In Vivo Release Rates" CRS Las Vegas, NV. Southern BioSystems, Inc. Birmingham AL, USA.

Sullivan, et al. (1999) "Sustained Release of Lysozyme from the SABER™ Delivery System" AAPS, New Orleans, LA. Southern BioSystems, Inc. Birmingham AL, USA.

Sullivan, et al. (2000) "Incorporation of Polymer Microparticles Into Sucrose Acetate Isobutyrate Reduces Burst and Extends Release"; Proceed. Int'l Symp. Control. Rel. Bioact. Mater., 27, Controlled Release Society, Inc. Paris, France, Jul. 7-13, 2000.

Sullivan, et al., "Sustained Release of Orally Administered Active Using SABER Delivery System Incorporated into Soft Gelatin Capsules" *Int'l. Control. Rel. Bioact. Mater. Controlled Release Society*, vol. 25 pp. 918-919, Jun. 1998, Las Vegas NV.

Sullivan, J. J., et al., "Duration of Estrus and Ovulation Time in Nonlactating Mares Given Human Chorionic Gonadotropin During Three Successive Estrous Periods", J.A.V.M.A., pp. 895-898, vol. 162, No. x, May 15, 1973.

Svensson, a., et al; Hydration of an amphiphillic excipient 44/14; *Int.J. Pharm.*, 281(1-2); (2004); pp. 107-118.

Swanson et al; "Objective and subjective measures of the pharmacodynamic effects of Adderall in the treatment of children with ADHD in a controlled laboratory classroom setting"; *Psychopharmacol Bull* 34(1); (1998); pp. 55-60.

Swanson et al; "Acute tolerance to methylphenidate in the treatment of attention deficit hyperactivity disorder in children" *Clin Pharmacal Ther* 66(3); (1999); pp. 295-305.

Swanson et al. Ritalin: Theory and Practice. 2nd Edition, Greenhill & Osman Ed., Mary Ann Liebert, Larchmont, NY; (1999) pp. 405-430.

Swanson et al; "Efficacy of a new pattern of delivery of methylphenidate for the treatment of ADHD: effects on activity level in the classroom and on the playground" *J Am Acad Child Adolesc Psychiatry* 41(11); (2002); pp. 1306-1314.

Swanson et al; "Pharmacokinetic and pharmacodynamic properties of stimulants: implications for the design of new treatments for ADHD"; *Behav Brain Res* 130(1-2); (2002); pp. 73-78.

Swanson et al; "Development of a new once-a-day formulation of methylphenidate for the treatment of attention-deficit/hyperactivity disorder: proof-of-concept and proof-of-product studies"; *Arch Gen Psychiatry* 60(2); (2003); pp. 204-211.

Swanson et al; "Serum and brain concentrations of methylphenidate: implications for use and abuse"; *Neurosci Biobehav Rev* 27(7); (2003); pp. 615-621.

Swanson et al; "A comparison of once-daily extended-release methylphenidate formulations in children with attention-deficit/ hyperactivity disorder in the laboratory school (the Comacs Study)"; *Pediatrics* 113(3 Pt. 1); (2004); pp. e206-e216.

Swiderski et al., "Application of 14C Isotope in Studies on the Lability of Sugar Substituents" Nuklconika, Supl., vol. 10, pp. 347-352, 1966.

Tashtoush Bassam M.; et al; "In Vitro and In Vivo Evaluation of Glibenclamide in Solid Dispersion Systems"; *Drug Development and Industrial Pharmacy*, vol. 30, No. 6; (2004); pp. 601-607.

Thompson, D. L., et al., "Effects of Melatonin and Thyrotropin Releasing Hormone on Mares During the Nonbreeding Season", Journal of Animal Science, pp. 668-677, vol. 56, No. 3, 1983.

Thompson, D. L., et al., "Testosterone Effects on Mares During Synchronization with Altrenogest: FHS, LH, Estrous Duration and Pregnancy Rate", Journal of Animal Science, pp. 678-686, vol. 56, No. 3, 1983.

Tipton (1999) "Peptide Delivery from an in Situ Gelling System Based 1on Sucrose Acetate Isobutyrate" AAPS J Abstract. Southern BioSystems, Inc. Birmingham AL, USA.

Tipton (2000) "In Situ Gelling Systems" Sustained-Release Injectable Products, Ed. Senior & Radomsky, Interpharm Press, Denver, CO, pp. 258-259.

Tipton, et al. (2000) "Local Delivery from a Novel Biodegradable in Situ Delivery System" Sixth World Biomaterials Congress, Kamuela, HI, May 15-20, 2000. Southern BioSystems, Inc. Birmingham AL, USA.

Tran Thao Truong-Dinh; et al; "Dissolution-modulating mechanism of alkalizers and polymers in a nanoemulsifying solid dispersion containing ionizable and poorly water-soluble drug"; *European Journal of Pharmaceutics and Biopharmaceutics* 72; (2009); pp. 83-90.

(56) References Cited

OTHER PUBLICATIONS

Trescot AM, et al. "Opioid Guidelines in the Management of Chronic Non-Cancer Pain." Pain Physician. 2006;9:1-40.

U.S. Department of Health and Human Services "Guidance for Industry: Food-Effect Bioavailability and Fed Bioequivalence Studies" FDA, Center for Drug Evaluation and Research (CDER), Dec. 2002.

U.S. Appl. No. 12/754,486, filed Apr. 5, 2010, 103 pages; with Preliminary Amendment filed Nov. 23, 2010, 13 pages.

U.S. Appl. No. 60/434,839, filed Dec. 18, 2002, 111 pages.

Vega-Rios A, Villalobos H, Mata-Segreda JF. "Acid-catalyzed hydrolysis of triacylglycerols obeys monoexponential kinetics." Int J Chem Kinet. 1992;24:887-94.

Venkatesan, N. et al; "Gelucire® 44/14 and Labrasol® in Enhancing Oral Absorption of Poorly Absorbable Drugs"; *Bulletin Technique Gattefosse*, No. 99; (2006); pp. 79-88.

Vila, Jato J.L., et al; "Influence of melting point and HLB on the release of amoxicillin from granulates containing Geludre® as excipients"; *S.T.P. Pharma*, vol. 6, No. 5 (1990); pp. 287-292.

Voss, J.L., et al., "The Effect of HCG on Duration of Oestrus, Ovulation Time and Fertility in Mares", Journal of Reprod. Fert., Suppl. 23 (1975), 297-301.

Volkow et al; "Relationship between psychostimulant-induced "high" and dopamine transporter occupancy"; *Proc Natl Acad Sci USA* 93(19); (1996); pp. 10388-10392.

Volkow et al. "Temporal relationships between the pharmacokinetics of methylphenidate in the human brain and its behavioral and cardiovascular effects"; *Psychopharmacology* 123; (1996) pp. 26-33.

Volkow et al; "Methylphenidate and cocaine have a similar in vivo potency to block dopamine transporters in the human brain"; *Life Sciences* vol. 65, No. 1; (1999); PL7-PL12.

Volkow et al; "Relationship between blockade of dopamine transporters by oral methylphenidate and the increases in extracellular dopamine: therapeutic implications"; *Synapse* 43(3); (2002); pp. 181-187.

Volkow, et al; "Dopamine transporter occupancies in the human brain induced by therapeutic doses of oral methylphenidate"; *Am J Psychiatry* 155(10); (1998); pp. 1325-1331.

Wigal et al; "Reliability and validity of the Skamp rating scale in a laboratory school setting" *Psychopharmacol Bulletin*, vol. 34, No. 1; (1998); pp. 47-53.

Wigal et al; "Selection of the Optimal Dose Ratio for a Controlled-Delivery Formulation of Methylphenidate"; *The Journal of Applied Research* 3; (2003); pp. 46-63.

Wightman et al; "Transient changes in mesolimbic dopamine and their association with 'reward'"*Journal of Neurochemistry* 82(4); (2002); pp. 721-735.

Wolraich et al; "Randomized, controlled trial of oros methylphenidate once a day in children with attention-deficit/hyperactivity disorder"; *Pediatrics* 108(4); (2001); pp. 883-892.

Yüksel, Nilüfer, et al; "Enhanced bioavailability of piroxicam using Gelucire 44/14 and Labrasol: in vitro and in vivo evaluation"; *European Journal of Pharmaceutics and Biopharmaceutics* 56; (2003); pp. 453-459.

Webster LR. PTI-821: sustained-release oxycodone using gel-cap technology. Expert Opin Investig Drugs. 2007; 16(3):359-366.

Zamloot M, Chao W, Kang L, Ross L, Fu R. Remoxy®: a novel formulation of extended-release oxycodone release oxycodone developed using the ORADUR® technology. J Appl Res. 2010; 10(3):88-96.

R= Acetate

R= Isobutyrate

ORAL PHARAMACEUTICAL DOSAGE FORMS

CROSS REFERENCE TO RELATED APPLICATIONS

This application is a continuation of U.S. application Ser. No. 15/486,119, filed Apr. 12, 2017, which application is a continuation of U.S. application Ser. No. 14/798,263, filed Jul. 13, 2015, now U.S. Pat. No. 9,655,861, issued May 23, 2017, which application is a continuation of U.S. application Ser. No. 13/786,218, filed Mar. 5, 2013, now abandoned, which application is a continuation of U.S. application Ser. No. 12/315,868, filed Dec. 5, 2008, now U.S. Pat. No. 8,415,401, issued Apr. 9, 2013, which application claims the benefit of U.S. Provisional Application Ser. No. 61/005,681 filed Dec. 6, 2007, U.S. Provisional Application Ser. No. 61/005,685 filed Dec. 6, 2007, and U.S. Provisional Application Ser. No. 61/198,201, filed Nov. 3, 2008, all of which applications are fully incorporated herein by reference.

FIELD OF THE INVENTION

The invention relates to oral pharmaceutical dosage forms and the use thereof. More specifically, this invention relates to abuse-resistant oral pharmaceutical dosage forms and their use to deliver pharmacologically active agents.

BACKGROUND

Techniques and compositions for drug delivery of pharmaceuticals, including oral delivery, are well known. For example antihistamines, decongestants and antacids are all commonly delivered in solid tablet form. Analgesics have been delivered orally in tablet form for many years, for example salicylic acid, morphine, Demerol™ (meperidine), codeine and Percocet™ (oxycodone). Controlled release and sustained release pharmaceutical compositions have also been available for many years; for example the Contac 400 Time Capsule™ (Phenylpropanolamine Hydrochloride and Chlorpheniramine Maleate), antipsychotics, melatonin formulations provide release of an active agent over several hours. Analgesics are of particular interest for controlled release formulations, and common controlled release formulations for analgesics include the OxyContin® (oxycodone), MS Contin™ (morphine), CS Contin™ (codeine).

Formulation of drugs for delivery, particularly oral delivery, poses certain challenges. One challenge is to produce an oral controlled-release dosage form that provides for a relatively steady dose of drug over the approximately eight hours during which the dosage form passes through the gastrointestinal tract. Sustained release is often achieved by providing the tablet with a coating that delays release, or by formulating the tablet in such a way that it disintegrates relatively slowly, releasing drug as it does so. A tablet, however, once ingested, is subject to considerable mechanical and chemical stresses as it passes through the esophagus, stomach, duodenum, jejunum, ileum, large intestine and colon, thus providing a significant challenge in maintaining controlled release of the drug formulation. Acids, enzymes and peristalsis can cause the tablet to break apart, resulting in exposure of the inside of the tablet and an increase in surface area of the tablet material. This will tend to increase the delivery rate of the drug or otherwise adversely affect the controlled release properties of the dosage form.

Another challenge, is to produce a dosage form, including an oral dosage form, that reduces the potential for drug abuse. In particular, opioids, CNS-depressants, and stimulants are commonly abused. According to a 1999 study by the National Institute on Drug Abuse (NIDA), an estimated 4 million people, about 2 percent of the population age 12 and older, were (at the time of the study) using prescription drugs "non-medically." Of these, 2.6 million misused pain relievers, 1.3 million misused sedatives and tranquilizers, and 0.9 million misused stimulants.

While many prescription drugs can be abused, the most common classes of abused drugs are: (1) Opioids—often prescribed to treat pain, (2) CNS Depressants—used to treat anxiety and sleep disorders, and (3) Stimulants—prescribed to treat narcolepsy and attention deficit/hyperactivity disorder.

Opioids are a class of potent narcotics that includes, for example, morphine, codeine, oxycodone and fentanyl and related drugs. Morphine is often used to alleviate severe pain. Codeine is used for milder pain. Other examples of opioids that can be prescribed to alleviate pain include oxycodone (e.g. OxyContin®—an oral, controlled release form of the drug); propoxyphene (e.g. Darvon™); hydrocodone (e.g. Vicodin™); hydromorphone (e.g. Dilaudid™); and meperidine (e.g. Demerol™).

In addition to relieving pain, opioids can also produce a sensation of euphoria, and when taken in large doses, can cause severe respiratory depression which can be fatal.

CNS depressants slow down normal brain function by increasing GABA activity, thereby producing a drowsy or calming effect. In higher doses, some CNS depressants can become general anesthetics, and in very high doses may cause respiratory failure and death. CNS depressants are frequently abused, and often the abuse of CNS depressants occurs in conjunction with the abuse of another substance or drug, such as alcohol or cocaine. Many deaths occur yearly through such drug abuse. CNS depressants can be divided into two groups, based on their chemistry and pharmacology: (1) Barbiturates, such as mephobarbital (e.g. Mebaral™) and pentobarbital sodium (e.g. Nembutal™), which are used to treat anxiety, tension, and sleep disorders. (2) Benzodiazepines, such as diazepam (e.g. Valium™) chlordiazepoxide HCl (e.g. Librium™), and alprazolam (e.g. Xanax™), which can be prescribed to treat anxiety, acute stress reactions, and panic attacks. Benzodiazepines that have a more sedating effect, such as triazolam (e.g. Halcion™) and estazolam (e.g. ProSom™) can be prescribed for short-term treatment of sleep disorders.

Stimulants are a class of drugs that enhance brain activity—they cause an increase in alertness, attention, and energy that is accompanied by increases in blood pressure, heart rate, and respiration. Stimulants are frequently prescribed for treating narcolepsy, attention-deficit hyperactivity disorder (ADHD), and depression. Stimulants may also be used for short-term treatment of obesity, and for patients with asthma. Stimulants such as dextroamphetamine (Dexedrine™) and methylphenidate (Ritalin™) have chemical structures that are similar to key brain neurotransmitters called monoamines, which include norepinephrine and dopamine. Stimulants increase the levels of these chemicals in the brain and body. This, in turn, increases blood pressure and heart rate, constricts blood vessels, increases blood glucose, and opens up the pathways of the respiratory system. In addition, the increase in dopamine is associated with a sense of euphoria that can accompany the use of these drugs.

Taking high doses of a stimulant can result in an irregular heartbeat, dangerously high body temperatures, and/or the potential for cardiovascular failure or lethal seizures. Taking high doses of some stimulants repeatedly over a short period of time can lead to hostility or feelings of paranoia in some individuals.

A common and particularly dangerous cocktail of drugs is produced when stimulants are mixed with antidepressants or over-the-counter cold medicines containing decongestants. Anti-depressants may enhance the effects of a stimulant, and stimulants in combination with decongestants may cause blood pressure to become dangerously high or lead to irregular heart rhythms, which in extreme cases may be fatal.

Solid dosage forms are particularly susceptible to abuse. For example, tablets for oral drug delivery can be ground down into a powder. Drug addicts and abusers grind down the tablet in order to nasally inhale the drug. Addicts also grind the tablet to extract the drug into alcohol or water to make a concentrated injectable drug solution. Administration of various abused drugs in this way produces a sudden high dose of drug into the blood stream making the user euphoric. These well-known techniques for drug abuse have been used for many years with all manner of drugs.

One particularly important example of a highly addictive drug that is commonly abused by crushing (for nasal inhalation), and/or alcohol or water extraction (for intravenous injection) is Oxycodone. Oxycodone is a powerful analgesic that is available in an extended release tablet form (Oxy-Contin®, Purdue Pharmaceuticals) and is manufactured in 10 mg, 20 mg, 40 mg, and 80 mg tablet strengths (the 160 mg tablet strength has been withdrawn from the US market due to prevalence of abuse of this particular product strength and the associated hazard from abuse of such a high dose of oxycodone. The OxyContin® tablets are formulated as time-release tablets (about 12 hours of release), but of course crushing and grinding the tablet destroys its controlled-release properties. In 2004, oxycodone abuse resulted in 36,600 visits to US emergency rooms, 20,000 of which are known to stem from abuse of sustained-release oxycodone formulations (e.g., OxyContin® tablets). Intentional abuse of oxycodone has reached epidemic proportions in the US, where, according to a 2004 National Survey on Drug Use and Health, 3.1 million Americans have used sustained-release oxycodone for non-medical purposes. Furthermore, unintentional overdose deaths from opioid analgesics have increased over 18% per year from 1990 to 2002, at which time opioid analgesic poisoning was listed in 5528 death certificates, more than either heroin or cocaine. Chewing/snorting a crushed 40 mg OxyContin® is like taking eight Percocet™ at once or an 80 mg OxyContin® is like taking 16 Percocet™ all at once. Overdose produces small pupils, slow breathing, dizziness, weakness, seizures, loss of consciousness, coma, and sometimes death.

SUMMARY OF THE INVENTION

Abuse-resistant oral pharmaceutical dosage forms that include a pharmacologically active agent and a controlled release carrier system are provided. It is thus an object of the present invention to provide an oral pharmaceutical dosage form that includes a pharmacologically active agent and a controlled release carrier system, where the controlled release carrier system includes a High Viscosity Liquid Carrier Material ("HVLCM"), a network former, a rheology modifier, a hydrophilic agent and a solvent. It is also an object of the present invention to provide the above-described dosage forms wherein the in vivo absorption of the active agent from the dosage form is enhanced upon administration of the dosage form with food, or, conversely, wherein in vivo release of the active agent from the controlled release carrier system is substantially free from food effect. It is a related object of the invention to provide the above-described dosage forms where the controlled release carrier system further provides a decreased risk of misuse or abuse, for example where such decreased risk of misuse or abuse is characterized by a low in vitro solvent extractability value of the active agent from the dosage form and/or by the absence of any significant effect on absorption of the active agent from the dosage form upon co-ingestion of the dosage form and alcohol by a subject. In each of the above-described related objects of the invention, the controlled release carrier system can be further characterized by a unique set of pharmaceutical excipients including certain combinations of solvents, viscosity enhancing agents, and the like. The controlled release carrier system provides abuse-resistant properties to the dosage form. It is accordingly a related object of the invention to provide the above-described dosage form wherein the controlled release carrier system also includes one or more of the following additional components: a viscosity enhancing agent; and a stabilizing agent. In particular embodiments, the HVLCM can comprise sucrose acetate isobutyrate ("SAIB"); the network former can comprise cellulose acetate butyrate ("CAB"), cellulose acetate phthalate, ethyl cellulose, hydroxypropylmethyl cellulose or cellulose triacetate; the rheology modifier can comprise isopropyl myristate ("IPM"), caprylic/capric triglyceride, ethyl oleate, triethyl citrate, dimethyl phthalate or benzyl benzoate; the hydrophilic agent can comprise hydroxyethylcellulose ("HEC"), hydroxypropylcellulose, caboxymethylcellulose, polyethylene glycol or polyvinylpyrrolidone; and the solvent can comprise triacetin, N-methyl-2-pyrrolidone, 2-pyrrolidone, dimethylsulfoxide, ethyl lactate, propylene carbonate or glycofurol. In addition, the viscosity enhancing agent can comprise a silicon dioxide, and the stabilizer can comprise butylhydroxyl toluene ("BHT"). In certain preferred embodiments, the active agent can be an opioid, CNS-depressant, or CNS-stimulant that has a particularly high potential for abuse, diversion or other misuse. Preferably, the active agent can comprise an opioid, an amphetamine, or a methylphenidate, in each case either as a salt or as a free base.

It is another object of the invention to provide an oral pharmaceutical dosage form that includes a pharmacologically active agent and a controlled release carrier system. The controlled release carrier system includes a High Viscosity Liquid Carrier Material ("HVLCM"), a network former and at least one viscosity enhancing agent, a hydrophilic colvent, and a hydrophobic solvent. It is also an object of the present invention to provide the above-described dosage forms wherein the in vivo absorption of the active agent from the dosage form is enhanced upon administration of the dosage form with food, or, conversely, wherein in vivo release of the active agent from the controlled release carrier system is substantially free from food effect. It is a related object of the invention to provide the above-described dosage forms where the controlled release carrier system further provides a decreased risk of misuse or abuse, for example where such decreased risk of misuse or abuse is characterized by a low in vitro solvent extractability value of the active agent from the dosage form and/or by the absence of any significant effect on absorption of the active agent from the dosage form upon co-ingestion of the dosage form and alcohol by a subject. In each of the above-described related objects of the invention, the controlled release carrier system can be further characterized by a unique set of pharmaceutical excipients including certain combinations of solvents, viscosity enhancing agents, and the like. The controlled release carrier system provides abuse-resistant properties to the dosage form. In certain preferred embodiments, the network former can comprise CAB, cellulose acetate phthalate, ethyl cellulose, hydroxypropylmethyl cellulose or cellulose triacetate; the first viscosity enhancing agent can comprise HEC, hydroxypropylcellulose, carboxymethylcellulose, polyethylene glycol or polyvinylpyrrolidone; the hydrophilic solvent can comprise triacetin, N-methyl-2-pyrrolidone, 2-pyrrolidone, dimethylsulfoxide, ethyl lactate, propylene carbonate or glycofurol; and the hydrophobic solvent can comprise IPM. In addition, the active agent can be an opioid, CNS-depressant, or CNS-stimulant that has a particularly high potential for abuse, diversion or other misuse. Preferably, the active agent can comprise an opioid, an amphetamine, or a methylphenidate, in each case either as a salt or as a free base.

It is another object of the invention to provide a process for the preparation of an oral pharmaceutical dosage form that includes a pharmacologically active agent and a controlled release carrier system, where the controlled release carrier system includes a High Viscosity Liquid Carrier Material ("HVLCM"), a network former, a rheology modifier, a hydrophilic agent and a solvent. The manufacturing or compounding process includes the steps of: preheating the HVLCM; mixing the solvent with the preheated HVLCM to form a uniform solution of the HVLCM in the solvent; dispersing the network former in the solution to dissolve the network former in the solution; mixing from 5 to 30% of the rheology modifier or, optionally, a solution of a stabilising agent and from 5 to 30% of the rheology modifier with the formulation; add and mixing the pharmacologically active agent; adding and mixing the hydrophilic agent; and, optionally, adding and mixing a viscosity enhancing agent, and adding and the balance of the rheology modifier. Furthermore, the process can include the step of filling capsules with the formulation obtained in the process and, optionally, packaging the filled capsules into unit dose blisters or multidose plastic bottles. It is a related object of the invention to provide a process for the preparation of an oral pharmaceutical dosage form that includes a pharmacologically active agent and a controlled release carrier system, where the controlled release carrier system includes a HVLCM, a network former, a rheology modifier, a hydrophilic agent and a solvent. The manufacturing or compounding process includes the steps of: preheating the HVLCM; mixing the solvent with the preheated HVLCM to form a uniform solution of the HVLCM in the solvent; optionally, mixing a solution of a stabilising agent and from 5 to 30% of the rheology modifier with the solution obtained in preceeding step; adding and mixing the rheology modifier or, if step the balance of the rheology modifier with the solution obtained in the earlier step; optionally, adding and mixing a viscosity enhancing agent with the formulation obtained in the preceeding step; adding and dispersing the network former into the solution thus obtained, thereby dissolving the network former in the solution; adding and mixing the pharmacologically active agent with the formulation obtained in the previous step; adding and mixing the hydrophilic agent. Furthermore, the process can include the step of filling capsules with the formulation obtained in the process and, optionally, packaging the filled capsules into unit dose blisters or multidose plastic bottles. It is a related object of the present invention to provide an oral pharmaceutical dosage form that is obtainable by the above manufacturing or compounding processes.

It is another object of the invention to provide a process for the preparation of an oral pharmaceutical dosage form that includes a pharmacologically active agent and a controlled release carrier system, where the controlled release carrier system includes a HVLCM, a network former, a first viscosity enhancing agent, a hydrophilic solvent and a hydrophobic solvent. The manufacturing or compounding process includes the steps of: preheating the HVLCM; mixing the solvent with the preheated HVLCM to form a uniform solution of the HVLCM in the solvent; dispersing the network former in the solution to dissolve the network former in the solution; mixing from 5 to 30% of the rheology modifier or, optionally, a solution of a stabilising agent and from 5 to 30% of the rheology modifier with the formulation; add and mixing the pharmacologically active agent; adding and mixing the hydrophilic agent; and, optionally, adding and mixing a viscosity enhancing agent, and adding and the balance of the rheology modifier. Furthermore, the process can include the step of filling capsules with the formulation obtained in the process and, optionally, packaging the filled capsules into unit dose blisters or multidose plastic bottles. It is a related object of the invention to provide a process for the preparation of an oral pharmaceutical dosage form that includes a pharmacologically active agent and a controlled release carrier system, where the controlled release carrier system includes a HVLCM, a network former, a first viscosity enhancing agent, a hydrophilic solvent and a hydrophobic solvent. The manufacturing or compounding process includes the steps of: preheating the HVLCM; mixing the solvent with the preheated HVLCM to form a uniform solution of the HVLCM in the solvent; optionally, mixing a solution of a stabilising agent and from 5 to 30% of the rheology modifier with the solution obtained in preceeding step; adding and mixing the rheology modifier or, if step the balance of the rheology modifier with the solution obtained in the earlier step; optionally, adding and mixing a viscosity enhancing agent with the formulation obtained in the preceeding step; adding and dispersing the network former into the solution thus obtained, thereby dissolving the network former in the solution; adding and mixing the pharmacologically active agent with the formulation obtained in the previous step; adding and mixing the hydrophilic agent. Furthermore, the process can include the step of filling capsules with the formulation obtained in the process and, optionally, packaging the filled capsules into unit dose blisters or multidose plastic bottles. It is a related object of the present invention to provide an oral pharmaceutical dosage form that is obtainable by the above manufacturing or compounding processes.

It is a further object of the invention to provide an abuse-resistant oral pharmaceutical dosage form that includes a pharmacologically active agent and a controlled release carrier system. The controlled release carrier system provides for controlled in vivo release of the agent characterized in that the individual steady state $C_{min}/C_{max}$ variance within an interdose interval is less than or equal to the Therapeutic Index of the active agent. It is also an object of the present invention to provide an abuse-resistant oral pharmaceutical dosage form that includes a pharmacologically active agent and a controlled release carrier system, where the dosage form is suitable for use in a BID-dosing regimen. It is a related object of the invention to provide the above-described dosage forms where the in vivo pharmacological performance is characterized by having individual $C_{min}/C_{max}$ variance at steady state is less than or equal to about 2 to 3 when dosed at the therapeutically effective dose or AUC. It is also a related object of the invention to provide the above-described dosage forms where the controlled release carrier system further provides a decreased risk of misuse or abuse, for example where such decreased risk of misuse or abuse is characterized by a low in vitro solvent extractability value of the active agent from the dosage form and/or by the absence of any significant effect on absorption of the active agent from the dosage form upon co-ingestion of the dosage form and alcohol by a subject. In each of the above-described related objects of the invention, the controlled release carrier system can be further characterized by a unique set of pharmaceutical excipients including solvents, carrier materials, and viscosity enhancing agents. In certain preferred embodiments, the active agent can be an opioid, CNS-depressant, or CNS-stimulant that has a particularly high potential for abuse, diversion or other misuse. Preferably, the active agent can comprise an opioid, an amphetamine, or a methylphenidate, in each case either as a salt or as a free base.

It is a further object of the present invention to provide an abuse-resistant oral pharmaceutical dosage form that includes a pharmacologically active agent and a controlled release carrier system. The controlled release carrier system provides for controlled in vivo release of the agent characterized in that the individual steady state $C_{min}/C_{max}$ variance within an interdose interval is less than or equal to the Therapeutic Index of the active agent, and the in vivo absorption of the active agent from the dosage form is enhanced upon administration of the dosage form with food, however, the dosage form is still safe even if taken in an un-prescribed manner, for example, without food. It is also an object of the present invention to provide an abuse-resistant oral pharmaceutical dosage form that includes a pharmacologically active agent and a controlled release carrier system, where the dosage form is suitable for use in a BID-dosing regimen, and further where the in vivo absorption of the active agent from the dosage form is enhanced upon administration of the dosage form with food. It is a related object of the invention to provide the above-described dosage forms where the in vivo pharmacological performance is characterized by having individual $C_{min}/C_{max}$ variance at steady state that is less than or equal to about 2 to 3. It is also a related object of the invention to provide the above-described dosage forms where the controlled release carrier system further provides a decreased risk of misuse or abuse, for example where such decreased risk of misuse or abuse is characterized by a low in vitro solvent extractability value of the active agent from the dosage form and/or by the absence of any significant effect on absorption of the active agent from the dosage form upon co-ingestion of the dosage form and alcohol by a subject. In each of the above-described related objects of the invention, the controlled release carrier system can be further characterized by a unique set of pharmaceutical excipients including solvents, carrier materials, network formers and viscosity enhancing agents. In certain preferred embodiments, the active agent can be an opioid, CNS-depressant, or CNS-stimulant that has a particularly high potential for abuse, diversion or other misuse. Preferably, the active agent can comprise an opioid, an amphetamine, or a methylphenidate, in each case either as a salt or as a free base.

It is yet a further object of the present invention to provide an abuse-resistant oral pharmaceutical dosage form that includes an opioid analgesic agent and a controlled release carrier system. The controlled release carrier system provides for controlled in vivo release of the agent characterized in that the individual steady state $C_{min}/C_{max}$ variance within an interdose interval is less than or equal to the Therapeutic Index of the active agent, and the pharmacokinetic in vivo release performance of the opioid analgesic agent from the controlled release carrier system is characterized by a $T_{max}$ of at least about 4 hours after ingestion by the subject. It is also an object of the present invention to provide an abuse-resistant oral pharmaceutical dosage form that includes an opioid analgesic agent and a controlled release carrier system, where the dosage form is suitable for use in a BID-dosing regimen, and further wherein the pharmacokinetic in vivo release performance of the opioid analgesic agent from the controlled release carrier system is characterized by a $T_{max}$ of at least about 4 hours after ingestion by the subject. It is a related object of the invention to provide the above-described dosage forms wherein the in vivo absorption of the opioid analgesic agent from the dosage form is enhanced upon administration of the dosage form with food, or, conversely, wherein in vivo release of the opioid analgesic agent from the controlled release carrier system is substantially free from food effect. It is a further related object of the invention to provide the above-described dosage forms where the in vivo pharmacological performance is characterized by having individual $C_{min}/C_{max}$ variance at steady state is less than or equal to about 2 to 3. It is also a related object of the invention to provide the above-described dosage forms where the controlled release carrier system further provides a decreased risk of misuse or abuse, for example where such decreased risk of misuse or abuse is characterized by a low in vitro solvent extractability value of the opioid analgesic agent from the dosage form and/or by the absence of any significant effect on absorption of the opioid analgesic agent from the dosage form upon co-ingestion of the dosage form and alcohol by a subject. In each of the above-described related objects of the invention, the controlled release carrier system can be further characterized by a unique set of pharmaceutical excipients including solvents, carrier materials, network formers and viscosity enhancing agents.

It is a yet even further object of the present invention to provide an abuse-resistant oral pharmaceutical dosage form that includes a pharmacologically active agent and a controlled release carrier system. The controlled release carrier system provides for controlled in vivo release of the agent characterized in that the individual steady state $C_{min}/C_{max}$ variance within an interdose interval is less than or equal to the Therapeutic Index of the active agent, and the carrier system includes a High Viscosity Liquid Carrier Material ("HVLCM"), a network former and at least one viscosity enhancing agent. It is also an object of the present invention to provide an abuse-resistant oral pharmaceutical dosage form that includes a pharmacologically active agent and a controlled release carrier system, where the dosage form is suitable for use in a BID-dosing regimen, and further where the controlled release carrier system includes a High Viscosity Liquid Carrier Material ("HVLCM"), a network former and at least one viscosity enhancing agent. It is a related object of the invention to provide the above-described dosage forms wherein the in vivo absorption of the active agent from the dosage form is enhanced upon administration of the dosage form with food, or, conversely, wherein in vivo release of the active agent from the controlled release carrier system is substantially free from food effect. It is a related object of the invention to provide the above-described dosage forms where the in vivo pharmacological performance is characterized by having individual $C_{min}/C_{max}$ variance at steady state is less than or equal to about 2 to 3. It is also a related object of the invention to provide the above-described dosage forms where the controlled release carrier system further provides a decreased risk of misuse or abuse, for example where such decreased risk of misuse or abuse is characterized by a low in vitro solvent extractability value of the active agent from the dosage form and/or by the absence of any significant effect on absorption of the active agent from the dosage form upon co-ingestion of the dosage form and alcohol by a subject. In each of the above-described related objects of the invention, the controlled release carrier system can be further characterized by a unique set of pharmaceutical excipients including certain combinations of solvents, viscosity enhancing agents, and the like. In certain preferred embodiments, the active agent can be an opioid, CNS-depressant, or CNS-stimulant that has a particularly high potential for abuse, diversion or other misuse. Preferably, the active agent can comprise an opioid, an amphetamine, or a methylphenidate, in each case either as a salt or as a free base.

It is also an object of the present invention to provide an abuse-resistant oral pharmaceutical dosage form that includes a pharmacologically active agent and a controlled release carrier system. The controlled release carrier system provides for controlled in vivo release of the agent characterized in that the individual steady state $C_{min}/C_{max}$ variance within an interdose interval is less than or equal to the Therapeutic Index of the active agent, more particularly, the individual $C_{min}/C_{max}$ variance at steady state is less than or equal to about 2 to 3. It is also an object of the present invention to provide an abuse-resistant oral pharmaceutical dosage form that includes a pharmacologically active agent and a controlled release carrier system, where the dosage form is suitable for use in a BID-dosing regimen, and further where the pharmacokinetic in vivo release performance of the active agent from the controlled release carrier system is characterized by a $T_{max}$ of at least about 4 hours after ingestion by the subject. It is a related object of the invention to provide the above-described dosage forms wherein the in vivo absorption of the active agent from the dosage form is enhanced upon administration of the dosage form with food, or, conversely, wherein in vivo release of the active agent from the controlled release carrier system is substantially free from food effect. It is a related object of the invention to provide the above-described dosage forms where the controlled release carrier system further provides a decreased risk of misuse or abuse, for example where such decreased risk of misuse or abuse is characterized by a low in vitro solvent extractability value of the active agent from the dosage form and/or by the absence of any significant effect on absorption of the active agent from the dosage form upon co-ingestion of the dosage form and alcohol by a subject. In each of the above-described related objects of the invention, the controlled release carrier system can be further characterized by a unique set of pharmaceutical excipients including certain combinations of solvents, viscosity enhancing agents, and the like. In certain preferred embodiments, the active agent can be an opioid, CNS-depressant, or CNS-stimulant that has a particularly high potential for abuse, diversion or other misuse. Preferably, the active agent can comprise an opioid, an amphetamine, or a methylphenidate, in each case either as a salt or as a free base.

It is a further object of the present invention to provide an abuse-resistant oral pharmaceutical dosage form that includes a pharmacologically active agent and a controlled release carrier system. The controlled release carrier system includes a High Viscosity Liquid Carrier Material ("HVLCM"), a network former and at least one viscosity enhancing agent. It is also an object of the present invention to provide the above-described dosage forms wherein the in vivo absorption of the active agent from the dosage form is enhanced upon administration of the dosage form with food, or, conversely, wherein in vivo release of the active agent from the controlled release carrier system is substantially free from food effect. It is a related object of the invention to provide the above-described dosage forms where the controlled release carrier system further provides a decreased risk of misuse or abuse, for example where such decreased risk of misuse or abuse is characterized by a low in vitro solvent extractability value of the active agent from the dosage form and/or by the absence of any significant effect on absorption of the active agent from the dosage form upon co-ingestion of the dosage form and alcohol by a subject. In each of the above-described related objects of the invention, the controlled release carrier system can be further characterized by a unique set of pharmaceutical excipients including certain combinations of solvents, viscosity enhancing agents, and the like. In certain preferred embodiments, the active agent can be an opioid, CNS-depressant, or CNS-stimulant that has a particularly high potential for abuse, diversion or other misuse. Preferably, the active agent can comprise an opioid, an amphetamine, or a methylphenidate, in each case either as a salt or as a free base.

It is yet a further object of the invention to provide an abuse-resistant oral pharmaceutical dosage form including a pharmacologically active agent and a controlled release carrier system, wherein the carrier system provides at least 8 hours of substantially constant in vitro release of the active agent when tested in an USP Type II Dissolution Apparatus with a stationary basket assembly using a paddle speed of 100 rpm and 0.1N HCl dissolution media containing surfactant; and 20% or less of the active agent is extractable from the dosage form in an in vitro solvent extraction test using EtOH (100 proof) as the extraction solvent, at ambient temperature (RT), for 1 hour. It is a related object of the invention to provide an abuse-resistant oral pharmaceutical dosage form including a pharmacologically active agent and a controlled release carrier system, wherein the carrier system provides at least 8 hours of substantially constant in vitro release of the active agent when tested in an USP Type II Dissolution Apparatus with a stationary basket assembly using a paddle speed of 100 rpm and 0.1N HCl dissolution media containing surfactant; and 30% or less of the active agent is extractable from said dosage form in an in vitro solvent extraction test using a panel of extraction solvents at ambient temperature (RT), for 1 hour.

It is a further object of the invention to provide an oral pharmaceutical dosage form that includes a pharmacologically active agent and a controlled release carrier system, where the controlled release carrier system includes an HVLCM, a network former, a rheology modifier and a hydrophilic agent, and the dosage form is abuse-resistant. It is a related object of the invention to provide the above-described dosage form wherein the controlled release carrier system also includes one or more of the following additional components: a viscosity enhancing agent; a solvent; and a stabilizer agent. In particular embodiments, the HVLCM can comprise sucrose acetate isobutyrate ("SAM"), the network former can comprise cellulose acetate butyrate ("CAB"), the rheology modifier can comprise isopropyl myristate ("IPM"), the hydrophilic agent can comprise hydroxyethyl cellulose ("HEC") and therefore also serve as a viscosity enhancing agent, the viscosity enhancing agent can also be a silicon dioxide, the stabilizer can comprise butylhydroxyl toluene ("BHT"), and the active agent can comprise an opioid, either as a salt or as a free base.

It is another object of the invention to provide a controlled release oral pharmaceutical dosage form that includes an opioid active agent, where the dosage form provides effective analgesia to a subject when dosed on a twice per day (BID) dosing schedule, and further where the dosage form has one or more of the following abuse-resistant performance features (which may be assessed using the methodology of Example 4): (a) when exposed to extraction in 100 proof ethanol at room temperature for 5 minutes, the dosage form releases less than about 5% of the opioid, preferably less than about 2% of the opioid; (b) when exposed to extraction in vinegar at room temperature for 5 minutes, the dosage form releases less than about 5% of the opioid, preferably less than about 2% of the opioid; (c) when exposed to extraction in saturated baking soda solution at room temperature for 5 minutes, the dosage form releases less than about 5% of the opioid, preferably less than about 2% of the opioid; (d) when exposed to extraction in a cola soft drink at room temperature for 5 minutes, the dosage form releases less than about 10% of the opioid, preferably less than about 5% of the opioid; (e) when exposed to extraction in 100 proof ethanol at room temperature for 60 minutes, the dosage form releases less than about 20% of the opioid, preferably less than about 11% of the opioid; (f) when exposed to extraction in vinegar at room temperature for 60 minutes, the dosage form releases less than about 20% of the opioid, preferably less than about 12% of the opioid; (g) when exposed to extraction in saturated baking soda solution at room temperature for 60 minutes, the dosage form releases less than about 20% of the opioid, preferably less than about 12% of the opioid; (h) when exposed to extraction in a cola soft drink at room temperature for 60 minutes, the dosage form releases less than about 30% of the opioid, preferably less than about 22% of the opioid; (i) when exposed to extraction in 100 proof ethanol at 60° C. for 5 minutes, the dosage form releases less than about 15% of the opioid, preferably less than about 11% of the opioid; (j) when exposed to extraction in vinegar at 60° C. for 5 minutes, the dosage form releases less than about 15% of the opioid, preferably less than about 11% of the opioid; (k) when exposed to extraction in saturated baking soda solution at 60° C. for 5 minutes, the dosage form releases less than about 15% of the opioid, preferably less than about 11% of the opioid; (l) when exposed to extraction in a cola soft drink at 60° C. for 5 minutes, the dosage form releases less than about 45% of the opioid, preferably less than about 30% of the opioid; (m) when exposed to extraction in 100 proof ethanol at 60° C. for 60 minutes, the dosage form releases less than about 33% of the opioid, preferably less than about 26% of the opioid; (n) when exposed to extraction in vinegar at 60° C. for 60 minutes, the dosage form releases less than about 33% of the opioid, preferably less than about 20% of the opioid; (o) when exposed to extraction in saturated baking soda solution at 60° C. for 60 minutes, the dosage form releases less than about 33% of the opioid, preferably less than about 23% of the opioid; (p) when exposed to extraction in a cola soft drink at 60° C. for 60 minutes, the dosage form releases less than about 60% of the opioid, preferably less than about 45% of the opioid; (q) when exposed to extraction in a panel of extraction solvents including vinegar, hot tea, saturated baking soda and a cola soft drink, each at 25° C. for 60 minutes, releases less than about 20% of the opioid, preferably less than about 15% of the opioid; (r) when exposed to extraction in a panel of aqueous buffer extraction solutions ranging from pH 1 to pH 12, each at 25° C. for 60 minutes, releases less than about 15% of the opioid, preferably less than about 12% of the opioid; (s) when physically disrupted by crushing the dosage form and exposed to extraction in a panel of aqueous extraction solutions including water at 25° C., water at 60-70° C., 0.1N HCL at 25° C., and 100 proof ethanol at 25° C., each for 60 minutes, releases less than about 40% of the opioid, preferably less than about 35% of the opioid; and/or (t) when physically disrupted by microwaving the dosage form and then exposed to extraction in a panel of aqueous extraction solutions including water, 0.1N HCL, and 100 proof ethanol, each at 25° C. for 60 minutes, releases less than about 25% of said opioid, preferably less than about 20% of the opioid. In particular embodiments, the opioid is oxycodone, oxymorphone, hydrocodone, or hydromorphone and can be present in either salt or free base form. In one preferred embodiment, the opioid is oxycodone.

It is still a further object of the invention to provide safer methods of treatment (including palliative care) to a patient in need of such treatment. The methods entail administration of the abuse-resistant oral pharmaceutical dosage forms of the present invention. More particularly, it is an object of the invention to provide a method for establishing and maintaining analgesia in a subject by repetitive administration of an oral analgesic dosage form, wherein the dosage form is abuse-resistant therefore providing a safer method of treatment. The dosage form that is used in the instant method includes a controlled release carrier system and an analgesic agent, and the controlled release carrier system provides for controlled in vivo release of the analgesic agent characterized in that the individual steady state $C_{min}/C_{max}$ variance within an interdose interval is less than or equal to the Therapeutic Index of the analgesic agent. It is also an object of the present invention to provide a method for establishing and maintaining analgesia in a subject by repetitive administration of an oral analgesic dosage form, wherein the dosage form is abuse-resistant and is suitable for use in a BID-dosing regimen. It is a related object of the invention to provide methods wherein the in vivo pharmacological performance of the dosage forms is characterized by having individual $C_{min}/C_{max}$ variance at steady state is less than or equal to about 2 to 3. It is also a related object of the invention to provide the above methods using dosage forms where the controlled release carrier system further provides a decreased risk of misuse or abuse, for example where such decreased risk of misuse or abuse is characterized by a low in vitro solvent extractability value of the analgesic agent from the dosage form and/or by the absence of any significant effect on absorption of the analgesic agent from the dosage form upon co-ingestion of the dosage form and alcohol by a subject. It is a still further related object of the invention to provide a method for establishing and maintaining analgesia in a subject by repetitive administration of an abuse-resistant oral analgesic dosage form, where the bioavailability of the analgesic agent is enhanced (e.g., the in vivo absorption of the agent from the dosage form is increased) upon co-administration of the dosage form with food. In particular embodiments, the methods entail repetitive administration of the above dosage forms where the analgesic agent is an opioid, and in a preferred embodiment, the opioid is present in the dosage form in its free base form.

It is another object of the invention to provide a method for establishing and maintaining analgesia in a subject by repetitive administration of an oral analgesic dosage form, wherein the dosage form includes a controlled release carrier system and an analgesic agent, and the controlled release carrier system includes an HVLCM, a network former and at least one viscosity enhancing agent. In a related object of the invention, the dosage form is abuse-resistant, therefore providing a safer method of treatment. It is another related object to provide a method for establishing and maintaining analgesia in a subject by repetitive administration of an oral analgesic dosage form, wherein the dosage form includes the above-described controlled release carrier system that further provides for controlled in vivo release of the analgesic agent characterized in that the individual steady state $C_{min}/C_{max}$ variance within an interdose interval is less than or equal to the Therapeutic Index of the analgesic agent. It is also an object of the present invention to provide a method for establishing and maintaining analgesia in a subject by repetitive administration of an oral analgesic dosage form, wherein the dosage form is suitable for use in a BID-dosing regimen. It is a related object of the invention to provide methods wherein the in vivo pharmacological performance of the dosage forms is characterized by having individual $C_{min}/C_{max}$ variance at steady state is less than or equal to about 2 to 3. It is also a related object of the invention to provide the above methods using dosage forms where the controlled release carrier system further provides a decreased risk of misuse or abuse, for example where such decreased risk of misuse or abuse is characterized by a low in vitro solvent extractability value of the analgesic agent from the dosage form and/or by the absence of any significant effect on absorption of the analgesic agent from the dosage form upon co-ingestion of the dosage form and alcohol by a subject. It is a still further related object of the invention to provide a method for establishing and maintaining analgesia in a subject by repetitive administration of an abuse-resistant oral analgesic dosage form, where the bioavailability of the analgesic agent is enhanced (e.g., the in vivo absorption of the agent from the dosage form is increased) upon co-administration of the dosage form with food. In particular embodiments, the methods entail repetitive administration of the above dosage forms where the analgesic agent is an opioid, and in a preferred embodiment, the opioid is present in the dosage form in its free base form.

It is an advantage of the present invention that the abuse-resistant oral dosage forms are able to provide enhanced safety features and/or abuse-resistance properties in addition to enhanced in vivo pharmacological performance as compared with prior dosage forms. It is a further advantage of the invention that the inventive dosage forms can be readily constructed and used to provide a wide range of safer and more efficacious pharmacological solutions to the medical field.

These and other objects, aspects and advantages of the present invention will readily occur to the skilled person upon reading the instant disclosure and specification.

POINTS OF THE INVENTION

1. An oral pharmaceutical dosage form comprising a pharmacologically active agent and a controlled release carrier system which comprises:
   a high viscosity liquid carrier material (HVLCM);
   a network former;
   a rheology modifier;
   a hydrophilic agent; and
   a solvent.
2. The dosage form of point 1, wherein the pharmacologically active agent is an opioid, a central nervous system (CNS) depressant or a CNS stimulant.
3. The dosage form of point 2, wherein the pharmacologically active agent is selected from oxycodone, oxymorphone, hydrocodone, hydromorphone, either in the free base form or a pharmaceutically acceptable salt form thereof.

4. The dosage form of point 2, wherein the pharmacologically active agent is selected from amphetamine, methylphenidate, and pharmaceutically acceptable salts thereof.
5. The dosage form of any one of the preceding points, wherein:
   the HVLCM is sucrose acetate isobutyrate (SAIB);
   the network former is selected from cellulose acetate butyrate (CAB), cellulose acetate phthalate, ethyl cellulose, hydroxypropylmethyl cellulose and cellulose triacetate;
   the rheology modifier is selected from isopropyl myristate (IPM), caprylic/capric triglyceride, ethyl oleate, triethyl citrate, dimethyl phthalate and benzyl benzoate;
   the hydrophilic agent is selected from hydroxyethylcellulose (HEC), hydroxypropylcellulose, caboxymethylcellulose, polyethylene glycol and polyvinylpyrrolidone; and
   the solvent is selected from triacetin, N-methyl-2-pyrrolidone, 2-pyrrolidone, dimethylsulfoxide, ethyl lactate, propylene carbonate and glycofurol.
6. The dosage form of point 5, wherein (a) the HVLCM is SAIB, (b) the network former is CAB, (c) the rheology modifier is IPM, (d) the hydrophilic agent is HEC, and (e) the solvent is triacetin.
7. The dosage form of any one of the preceding points, which comprises (a) from 1.3 to 35 wt % of the pharmacologically active agent, (b) from 2 to 10 wt % of the network former, (c) from 0.1 to 20 wt % of the rheology modifier, (d) from 1 to 8 wt % of the hydrophilic agent, (e) from 10 to 40 wt % of the solvent, and (f) from 30 to 60 wt % of the HVLCM.
8. The dosage form of any one of the preceding points, wherein the controlled release carrier system further comprises a viscosity enhancing agent.
9. The dosage form of point 8, wherein the viscosity enhancing agent is a silicon dioxide.
10. An oral pharmaceutical dosage form comprising a pharmacologically active agent and a controlled release carrier system which comprises:
    a HVLCM;
    a network former;
    a first viscosity enhancing agent;
    a hydrophilic solvent; and
    a hydrophobic solvent.
11. The dosage form of point 10, wherein the pharmacologically active agent is an opioid, a central nervous system (CNS) depressant or a CNS stimulant.
12. The dosage form of point 11, wherein the pharmacologically active agent is selected from oxycodone, oxymorphone, hydrocodone, hydromorphone, either in the free base form or a pharmaceutically acceptable salt form thereof.
13. The dosage form of point 11, wherein the pharmacologically active agent is selected from amphetamine, methylphenidate, and pharmaceutically acceptable salts thereof.
14. The dosage form of any one of points 10 to 13, wherein:
    the HVLCM is SAIB;
    the network former is selected from CAB, cellulose acetate phthalate, ethyl cellulose, hydroxypropylmethyl cellulose and cellulose triacetate;
    the first viscosity enhancing agent is HEC, hydroxypropylcellulose, carboxymethylcellulose, polyethylene glycol and polyvinylpyrrolidone;
    the hydrophilic solvent is selected from triacetin, N-methyl-2-pyrrolidone, 2-pyrrolidone, dimethylsulfoxide, ethyl lactate, propylene carbonate and glycofurol; and the hydrophobic solvent is IPM.

15. The dosage form of point 14, wherein (a) the HVLCM is SAIB, (b) the network former is CAB, (c) the first viscosity enhancing agent is HEC, (d) the hydrophilic solvent is triacetin, and (e) the hydrophobic solvent is IPM.

16. The dosage form of any one of the points 10 to 15, which comprises (a) from 1.3 to 35 wt % of the pharmacologically active agent, (b) from 2 to 10 wt % of the network former, (c) from 1 to 8 wt % of the first viscosity enhancing agent, (d) from 10 to 40 wt % of the hydrophilic solvent, (e) from 0.1 to 20 wt % of the hydrophobic solvent, and (f) from 30 to 60 wt % of the HVLCM.

17. The dosage form of any one of points 10 to 16, which further comprises a second viscosity enhancing agent.

18. The dosage form of point 17, wherein the second viscosity enhancing agent is silicone dioxide.

19. The dosage form of any one of the preceding points further comprising a stabilizer agent.

20. The dosage form of point 19, wherein the stabilizer agent is butylhydroxyl toluene (BHT).

21. The dosage form of any one of the preceding points, which provides at least 8 hours of substantially constant in vitro release of the active agent when tested in an USP Type II Dissolution Apparatus with a stainless steel stationary basket assembly using a paddle speed of 100 rpm and 0.1N HCl dissolution media containing 0.5% sodium lauryl sulfate; and 20% or less of said active agent is extracted from said dosage form after 1 hour of extraction in 100 proof ethanol (EtOH) at ambient temperature.

22. The dosage form of any one of the preceding points, wherein less than 20% of the active agent is extracted after 60 minutes of extraction in 100 proof EtOH at ambient temperature and less than 30% is extracted after 60 minutes of extraction in 100 proof EtOH at 60° C.

23. The dosage form of any one of the preceding points, wherein the formulation of the active agent and the carrier system is encapsulated within a capsule.

24. The dosage form of point 23, wherein the capsule comprises gelatin, hydroxyethylcellulose or hydroxypropylmethylcellulose.

25. The dosage form of point 23 or 24, wherein the capsule is packaged in unit dose blisters or multidose plastic bottles.

26. A process for the preparation of an oral pharmaceutical dosage form as defined in point 1, which process comprises:
  (i) preheating the HVLCM;
  (ii) mixing the solvent with the preheated HVLCM, thereby forming a uniform solution of the HVLCM in the solvent;
  (iii) dispersing the network former in the solution, thereby dissolving the network former in the solution;
  (iv) mixing from 5 to 30% of the rheology modifier or, optionally, a solution of a stabilising agent and from 5 to 30% of the rheology modifier with the formulation obtained in step (iii);
  (v) mixing the pharmacologically active agent with the formulation obtained in step (iv);
  (vi) mixing the hydrophilic agent with the formulation obtained in step (v);
  (vii) optionally, mixing a viscosity enhancing agent with the formulation obtained in step (vi);
  (viii) mixing the balance of the rheology modifier with the formulation obtained in step (vi) or, if step (vii) is effected, step (vii);
  (ix) optionally, filling capsules with the formulation obtained in step (viii); and
  (x) optionally, packaging the filled capsules into unit dose blisters or multidose plastic bottles.

27. A process for the preparation of an oral pharmaceutical dosage form as defined in point 1, which process comprises:
  (i) preheating the HVLCM;
  (ii) mixing the solvent with the preheated HVLCM, thereby forming a uniform solution of the HVLCM in the solvent;
  (iii) optionally, mixing a solution of a stabilising agent and from 5 to 30% of the rheology modifier with the solution obtained in step (ii);
  (iv) mixing the rheology modifier or, if step (iii) is effected, the balance of the rheology modifier with the solution obtained in step (ii) or (iii);
  (v) optionally, mixing a viscosity enhancing agent with the formulation obtained in step (iv);
  (vi) dispersing the network former in the solution obtained in step (iv) or, if step (v) is effected, step (v), thereby dissolving the network former in the solution;
  (vii) mixing the pharmacologically active agent with the formulation obtained in step (vi);
  (viii) mixing the hydrophilic agent with the formulation obtained in step (vii);
  (ix) optionally, filling capsules with the formulation obtained in step (viii); and
  (x) optionally, packaging the filled capsules into unit dose blisters or multidose plastic bottles.

28. A process for the preparation of an oral pharmaceutical dosage form as defined in point 10, which process comprises:
  (i) preheating the HVLCM;
  (ii) mixing the hydrophilic solvent with the preheated HVLCM, thereby forming a uniform solution of the HVLCM in the solvent;
  (iii) dispersing the network former in the solution, thereby dissolving the network former in the solution;
  (iv) mixing from 5 to 30% of the hydrophobic solvent or, optionally, a solution of a stabilising agent and from 5 to 30% of the hydrophobic solvent with the formulation obtained in step (iii);
  (v) mixing the pharmacologically active agent with the formulation obtained in step (iv);
  (vi) mixing the first viscosity enhancing agent with the formulation obtained in step (v);
  (vii) optionally, mixing a second viscosity enhancing agent with the formulation obtained in step (vi);
  (viii) mixing the balance of the hydrophobic solvent with the formulation obtained in step (vi) or, if step (vii) is effected, step (vii);
  (ix) optionally, filling capsules with the formulation obtained in step (viii); and
  (x) optionally, packaging the filled capsules into unit dose blisters or multidose plastic bottles.

29. A process for the preparation of an oral pharmaceutical dosage form as defined in point 10, which process comprises:
  (i) preheating the HVLCM;
  (ii) mixing the hydrophilic solvent with the preheated HVLCM, thereby forming a uniform solution of the HVLCM in the solvent;
  (iii) optionally, mixing a solution of a stabilising agent and from 5 to 30% of the hydrophobic solvent with the solution obtained in step (ii);
  (iv) mixing the hydrophobic solvent or, if step (iii) is effected, the balance of the hydrophobic solvent with the solution obtained in step (ii) or (iii);

(v) optionally, mixing a second viscosity enhancing agent with the formulation obtained in step (iv);

(vi) dispersing the network former in the solution obtained in step (iv) or, if step (v) is effected, step (v), thereby dissolving the network former in the solution;

(vii) mixing the pharmacologically active agent with the formulation obtained in step (vi);

(viii) mixing the first viscosity enhancing agent with the formulation obtained in step (vii);

(ix) optionally, filling capsules with the formulation obtained in step (viii); and (x) optionally, packaging the filled capsules into unit dose blisters or multidose plastic bottles.

30. An oral pharmaceutical dosage form obtainable by a process as defined in any one points 26 to 29.

31. An oral pharmaceutical dosage form comprising a pharmacologically active agent and a controlled release carrier system, wherein:

said pharmaceutical dosage form is abuse-resistant; and
said controlled release carrier system provides for controlled in vivo release of the agent characterized in that the individual steady state $C_{min}/C_{max}$ variance within an interdose interval is less than or equal to the Therapeutic Index of said active agent.

32. The dosage form of point 31, wherein the active agent is suspended within the controlled release carrier system.

33. The dosage form of point 31, wherein the individual $C_{min}/C_{max}$ variance at steady state is less than or equal to about 2 to 3.

34. The dosage form of point 31 suitable for use in a BID-dosing regimen.

35. The dosage form of point 31, wherein the active agent is an opioid.

36. The dosage form of point 31, wherein the active agent is in salt form.

37. The dosage form of point 31, wherein the controlled release carrier system comprises an HVLCM and a network former.

38. The dosage form of point 37, wherein the controlled release carrier system further comprises a plurality of hydrophilic excipients.

39. The dosage form of point 37, wherein the controlled release carrier system further comprises a plurality of viscosity enhancing agents.

40. The dosage form of point 37, wherein the controlled release carrier system further comprises a plurality of solvents.

41. The dosage form of point 40, wherein the solvents comprise a hydrophobic solvent and a hydrophilic solvent.

42. The dosage form of point 31, wherein the controlled release carrier system further provides a decreased risk of misuse or abuse.

43. The dosage form of point 42, wherein said decreased risk of misuse or abuse is characterized by a low in vitro solvent extractability value of the active agent from the dosage form.

44. The dosage form of point 42, wherein said decreased risk of misuse or abuse is characterized by the absence of any significant effect on absorption of the active agent from the dosage form upon co-ingestion of the dosage form and alcohol by a subject.

45. The dosage form of point 43, wherein said decreased risk of misuse or abuse is further characterized by the absence of any significant effect on absorption of the active agent from the dosage form upon co-ingestion of the dosage form and alcohol by a subject.

46. An oral pharmaceutical dosage form comprising a pharmacologically active agent and a controlled release carrier system, wherein:

said pharmaceutical dosage form is abuse-resistant;
said controlled release carrier system provides for controlled in vivo release of the agent characterized in that the individual steady state $C_{min}/C_{max}$ variance within an interdose interval is less than or equal to the Therapeutic Index of said active agent; and
the in vivo absorption of said active agent from the dosage form is enhanced upon administration of the dosage form with food.

47. The dosage form of point 46, wherein the active agent is suspended within the controlled release carrier system.

48. The dosage form of point 46, wherein the individual $C_{min}/C_{max}$ variance at steady state is less than or equal to about 2 to 3.

49. The dosage form of point 46 suitable for use in a BID-dosing regimen.

50. The dosage form of point 46, wherein the active agent is an opioid.

51. The dosage form of point 46, wherein the active agent is in the form of a free base.

52. The dosage form of point 46, wherein the controlled release carrier system comprises an HVLCM and a network former.

53. The dosage form of point 52, wherein the controlled release carrier system further comprises a plurality of hydrophilic excipients.

54. The dosage form of point 52, wherein the controlled release carrier system further comprises a plurality of viscosity enhancing agents.

55. The dosage form of point 52, wherein the controlled release carrier system further comprises a plurality of solvents.

56. The dosage form of point 55, wherein the solvents comprise a hydrophobic solvent and a hydrophilic solvent.

57. The dosage form of point 46, wherein the controlled release carrier system further provides a decreased risk of misuse or abuse.

58. The dosage form of point 57, wherein said decreased risk of misuse or abuse is characterized by a low in vitro solvent extractability value of the active agent from the dosage form.

59. The dosage form of point 57, wherein said decreased risk of misuse or abuse is characterized by the absence of any significant effect on absorption of the active agent from the dosage form upon co-ingestion of the dosage form and alcohol by a subject.

60. The dosage form of point 59, wherein said decreased risk of misuse or abuse is further characterized by the absence of any significant effect on absorption of the active agent from the dosage form upon co-ingestion of the dosage form and alcohol by a subject.

61. A method of increasing the oral bioavailability of an active agent to a subject receiving therapy with the active agent, said method comprising orally administering to the subject the dosage form of point 46 with food.

62. A method of increasing the extent of absorption of an active agent from an oral dosage form, said method comprising orally administering to the subject the dosage form of point 46 with food.

63. An oral pharmaceutical dosage form comprising an opioid analgesic agent and a controlled release carrier system, wherein:

said pharmaceutical dosage form is abuse-resistant;

said controlled release carrier system provides for controlled in vivo release of the agent characterized in that the individual steady state $C_{min}/C_{max}$ variance within an interdose interval is less than or equal to the Therapeutic Index of said active agent; and the pharmacokinetic in vivo release performance of said opioid analgesic agent from the controlled release carrier system is characterized by a $T_{max}$ of at least about 4 hours after ingestion by the subject.

64. The dosage form of point 63, wherein the opioid analgesic agent is suspended within the carrier system.

65. The dosage form of point 63, wherein the individual $C_{min}/C_{max}$ variance at steady state is less than or equal to about 2 to 3.

66. The dosage form of point 63 suitable for use in a BID dosing regimen.

67. The dosage form of point 63, wherein the opioid analgesic agent is in salt form.

68. The dosage form of point 63, wherein the opioid analgesic agent is in the form of a free base.

69. The dosage form of point 63, wherein the controlled release carrier system comprises HVLCM and network former.

70. The dosage form of point 69, wherein the controlled release carrier system further comprises a plurality of hydrophilic excipients.

71. The dosage form of point 69, wherein the controlled release carrier system further comprises a plurality of viscosity enhancing agents.

72. The dosage form of point 69, wherein the controlled release carrier system further comprises a plurality of solvents.

73. The dosage form of point 72, wherein the solvents comprise a hydrophobic solvent and a hydrophilic solvent.

74. The dosage form of point 63, wherein the in vivo release of said opioid analgesic agent from the controlled release carrier system is substantially free from food effect.

75. The dosage form of point 63, wherein the controlled release carrier system further provides enhanced in vivo absorption of said opioid analgesic agent from the dosage form upon administration of the dosage form with food.

76. The dosage form of point 63, wherein the controlled release carrier system further provides a decreased risk of misuse or abuse.

77. The dosage form of point 76, wherein said decreased risk of misuse or abuse is characterized by a low in vitro solvent extractability value of the opioid analgesic agent from the dosage form.

78. The dosage form of point 76, wherein said decreased risk of misuse or abuse is characterized by the absence of any significant effect on absorption of the opioid analgesic agent from the dosage form upon co-ingestion of the dosage form and alcohol by a subject.

79. The dosage form of point 78, wherein said decreased risk of misuse or abuse is further characterized by the absence of any significant effect on absorption of the opioid analgesic agent from the dosage form upon co-ingestion of the dosage form and alcohol by a subject.

80. An oral pharmaceutical dosage form comprising a pharmacologically active agent and a controlled release carrier system, wherein:

said oral pharmaceutical dosage form is abuse-resistant;
said controlled release carrier system provides for controlled in vivo release of the agent characterized in that the individual steady state $C_{min}/C_{max}$ variance within an interdose interval is less than or equal to the Therapeutic Index of said active agent; and
said controlled release carrier system comprises an HVLCM, a network former, and at least one viscosity enhancing agent.

81. The dosage form of point 80, wherein the active agent is suspended within the controlled release carrier system.

82. The dosage form of point 80, wherein the individual $C_{min}/C_{max}$ variance at steady state is less than or equal to about 2 to 3.

83. The dosage form of point 80 suitable for use in a BID dosing regimen.

84. The dosage form of point 80, wherein the active agent is an opioid.

85. The dosage form of point 80, wherein the active agent is in salt form.

86. The dosage form of point 80, wherein the active agent is in the form of a free base.

87. The dosage form of point 80, wherein the controlled release carrier system further comprises a surfactant.

88. The dosage form of point 80, wherein the controlled release carrier system comprises a plurality of hydrophilic excipients.

89. The dosage form of point 80, wherein the controlled release carrier system further comprises a second viscosity enhancing agent.

90. The dosage form of point 80, wherein the controlled release carrier system comprises a plurality of solvents.

91. The dosage form of point 90, wherein the solvents comprise a hydrophobic solvent and a hydrophilic solvent.

92. The dosage form of point 80, wherein the in vivo release of said active agent from the controlled release carrier system is substantially free from food effect.

93. The dosage form of point 80, wherein the controlled release carrier system further provides enhanced in vivo absorption of said active agent from the dosage form upon administration of the dosage form with food.

94. The dosage form of point 80, wherein the controlled release carrier system further provides a decreased risk of misuse or abuse.

95. The dosage form of point 94, wherein said decreased risk of misuse or abuse is characterized by a low in vitro solvent extractability value of the active agent from the dosage form.

96. The dosage form of point 94, wherein said decreased risk of misuse or abuse is characterized by the absence of any significant effect on absorption of the active agent from the dosage form upon co-ingestion of the dosage form and alcohol by a subject.

97. The dosage form of point 96, wherein said decreased risk of misuse or abuse is further characterized by the absence of any significant effect on absorption of the active agent from the dosage form upon co-ingestion of the dosage form and alcohol by a subject.

98. An oral pharmaceutical dosage form comprising a pharmacologically active agent and a controlled release carrier system, wherein:

said oral pharmaceutical dosage form is abuse-resistant;
said controlled release carrier system provides for controlled in vivo release of the agent characterized in that the individual steady state $C_{min}/C_{max}$ variance within an interdose interval is less than or equal to the Therapeutic Index of said active agent; and
said individual $C_{min}/C_{max}$ variance at steady state is less than or equal to about 2 to 3.

99. The dosage form of point 98 suitable for use in a BID dosing regimen.

100. The dosage form of point 98, wherein the pharmacokinetic in vivo release performance of said active agent from the controlled release carrier system is characterized by a $T_{max}$ of at least about 4 hours after ingestion by the subject.

101. The dosage form of point 98, wherein said controlled release carrier system comprises an HVLCM, a network former, and at least one viscosity enhancing agent.

102. The dosage form of point 98, wherein the active agent is an opioid.

103. The dosage form of point 98, wherein the active agent is in salt form.

104. The dosage form of point 98, wherein the active agent is in the form of a free base.

105. The dosage form of point 101, wherein the controlled release carrier system further comprises a surfactant.

106. The dosage form of point 101, wherein the controlled release carrier system further comprises a plurality of hydrophilic excipients.

107. The dosage form of point 101, wherein the controlled release carrier system further comprises a second viscosity enhancing agent.

108. The dosage form of point 101, wherein the controlled release carrier system further comprises a plurality of solvents.

109. The dosage form of point 108, wherein the solvents comprise a hydrophobic solvent and a hydrophilic solvent.

110. The dosage form of point 98, wherein the in vivo release of said active agent from the controlled release carrier system is substantially free from food effect.

111. The dosage form of point 98, wherein the controlled release carrier system further provides enhanced in vivo absorption of said active agent from the dosage form upon administration of the dosage form with food.

112. The dosage form of point 98, wherein the controlled release carrier system further provides a decreased risk of misuse or abuse.

113. The dosage form of point 112, wherein said decreased risk of misuse or abuse is characterized by a low in vitro solvent extractability value of the active agent from the dosage form.

114. The dosage form of point 112, wherein said decreased risk of misuse or abuse is characterized by the absence of any significant effect on absorption of the active agent from the dosage form upon co-ingestion of the dosage form and alcohol by a subject.

115. The dosage form of point 114, wherein said decreased risk of misuse or abuse is further characterized by the absence of any significant effect on absorption of the active agent from the dosage form upon co-ingestion of the dosage form and alcohol by a subject.

116. An abuse-resistant oral pharmaceutical dosage form comprising a pharmacologically active agent and a controlled release carrier system, wherein:
  said controlled release carrier system comprises an HVLCM, a network former, and at least one viscosity enhancing agent.

117. The dosage form of point 116, wherein the viscosity enhancing agent is a synthetic polymer.

118. The dosage form of point 117, wherein the synthetic polymer is a cellulose derivative.

119. The dosage form of point 116, wherein the active agent is an opioid.

120. The dosage form of point 116, wherein the active agent is in salt form.

121. The dosage form of point 116, wherein the active agent is in the form of a free base.

122. The dosage form of point 116, wherein the controlled release carrier system further comprises a surfactant.

123. The dosage form of point 116, wherein the controlled release carrier system further comprises a plurality of hydrophilic excipients.

124. The dosage form of point 116, wherein the controlled release carrier system further comprises a second viscosity enhancing agent.

125. The dosage form of point 124, wherein the second viscosity enhancing agent comprises a stiffening agent.

126. The dosage form of point 125, wherein the second viscosity enhancing agent comprises a $SiO_2$.

127. The dosage form of point 116, wherein the controlled release carrier system further comprises a plurality of solvents.

128. The dosage form of point 127, wherein the solvents comprise a hydrophobic solvent and a hydrophilic solvent.

129. The dosage form of point 116, wherein the in vivo release of said active agent from the controlled release carrier system is substantially free from food effect.

130. The dosage form of point 116, wherein the controlled release carrier system further provides enhanced in vivo absorption of said active agent from the dosage form upon administration of the dosage form with food.

131. The dosage form of point 116, wherein the controlled release carrier system further provides a decreased risk of misuse or abuse.

132. The dosage form of point 131, wherein said decreased risk of misuse or abuse is characterized by a low in vitro solvent extractability value of the active agent from the dosage form.

133. The dosage form of point 131, wherein said decreased risk of misuse or abuse is characterized by the absence of any significant effect on absorption of the active agent from the dosage form upon co-ingestion of the dosage form and alcohol by a subject.

134. The dosage form of point 133, wherein said decreased risk of misuse or abuse is further characterized by the absence of any significant effect on absorption of the active agent from the dosage form upon co-ingestion of the dosage form and alcohol by a subject.

135. An abuse-resistant oral pharmaceutical dosage form comprising a pharmacologically active agent and a controlled release carrier system, wherein:
  said controlled release carrier system provides at least 8 hours of substantially constant in vitro release of the active agent when tested in an USP Type II Dissolution Apparatus with a stationary basket assembly using a paddle speed of 100 rpm and 0.1N HCl dissolution media containing surfactant; and
  20% or less of said active agent is extractable from said dosage form in an in vitro solvent extraction test using EtOH (100 proof) as the extraction solvent, at RT, for 1 hour.

136. An abuse-resistant oral pharmaceutical dosage form comprising a pharmacologically active agent and a controlled release carrier system, wherein:
  said controlled release carrier system provides at least 8 hours of substantially constant in vitro release of the active agent when tested in an USP Type II Dissolution Apparatus with a stationary basket assembly using a paddle speed of 100 rpm and 0.1N HCl dissolution media containing surfactant; and
  30% or less of said active agent is extractable from said dosage form in an in vitro solvent extraction test using a panel of extraction solvents at RT, for 1 hour.

137. An oral pharmaceutical dosage form comprising a pharmacologically active agent and a controlled release carrier system, wherein:
said controlled release carrier system comprises an HVLCM, a network former, a rheology modifier and a hydrophilic agent; and
said dosage form is abuse-resistant.

138. The dosage form of point 137, wherein the controlled release carrier system further comprises a viscosity enhancing agent.

139. The dosage form of point 138, wherein the hydrophilic agent also serves as a second viscosity enhancing agent.

140. The dosage form of any one of points 137 to 139, wherein the hydrophilic agent is hydroxyethyl cellulose (HEC).

141. The dosage form of any one of points 137 to 140, wherein the HVLCM is sucrose acetate isobutyrate (SAIB).

142. The dosage form of any one of points 137 to 141 further comprising a solvent.

143. The dosage form of point 142, wherein the solvent is triacetin.

144. The dosage form of point 138, wherein the viscosity enhancing agent is a silicon dioxide.

145. The dosage form of any one of points 137 to 144, wherein the network former is cellulose acetate butyrate (CAB).

146. The dosage form of any one of points 137 to 145, wherein the rheology modifier is isopropyl myristate (IPM).

147. The dosage form of any one of points 137 to 146, wherein the active agent is an opioid.

148. The dosage form of point 147, wherein the opioid is oxycodone, oxymorphone, hydrocodone, or hydromorphone.

149. The dosage form of point 148, wherein the opioid is oxycodone.

150. The dosage form of any one of points 147-149, wherein the opioid is present in the form of a free base.

151. The dosage form of any one of points 147-149, wherein the opioid is present in the form of a salt.

152. The dosage form of any one of points 137 to 151 further comprising a stabilizer agent.

153. The dosage form of point 152, wherein the stabilizer agent is butylhydroxyl toluene (BHT).

154. The dosage form of any one of points 137 to 153, wherein the active agent is micronized.

155. A method for establishing and maintaining analgesia in a subject by repetitive administration of an oral analgesic dosage form, wherein:
said dosage form is abuse-resistant;
said dosage form comprises a controlled release carrier system and an analgesic agent; and
said controlled release carrier system provides for controlled in vivo release of the analgesic agent characterized in that the individual steady state $C_{min}/C_{max}$ variance within an interdose interval is less than or equal to the Therapeutic Index of said analgesic agent.

156. The method of point 155, wherein the individual $C_{min}/C_{max}$ variance at steady state is less than or equal to about 2 to 3.

157. The method of point 155, wherein said repetitive administration comprises a BID-dosing regimen.

158. The method of point 155, wherein the controlled release carrier system further provides a decreased risk of misuse or abuse.

159. The method of point 158, wherein said decreased risk of misuse or abuse is characterized by a low in vitro solvent extractability value of the analgesic agent from the dosage form.

160. The method of point 158, wherein said decreased risk of misuse or abuse is characterized by the absence of any significant effect on absorption of the analgesic agent from the dosage form upon co-ingestion of the dosage form and alcohol by a subject.

161. The method of point 159, wherein said decreased risk of misuse or abuse is further characterized by the absence of any significant effect on absorption of the analgesic agent from the dosage form upon co-ingestion of the dosage form and alcohol by a subject.

162. The method of point 155, wherein the in vivo absorption of said analgesic agent from the dosage form is enhanced upon administration of the dosage form with food.

163. The method of point 155, wherein the analgesic agent comprises an opioid.

164. The method of point 163, wherein the opioid is present in the dosage form as a free base.

165. A method for establishing and maintaining analgesia in a subject by repetitive administration of an oral analgesic dosage form, wherein:
said dosage form comprises a controlled release carrier system and an analgesic agent, and further wherein said controlled release carrier system comprises an HVLCM, a network former, and at least one viscosity enhancing agent.

166. The method of point 165, wherein the dosage form is abuse-resistant.

167. The method of point 165, wherein said controlled release carrier system provides for controlled in vivo release of the analgesic agent characterized in that the individual steady state $C_{min}/C_{max}$ variance within an interdose interval is less than or equal to the Therapeutic Index of said analgesic agent.

168. The method of point 167, wherein the individual $C_{min}/C_{max}$ variance at steady state is less than or equal to about 2 to 3.

169. The method of point 165, wherein said repetitive administration comprises a BID-dosing regimen.

170. The method of point 165, wherein the controlled release carrier system further provides a decreased risk of misuse or abuse.

171. The method of point 170, wherein said decreased risk of misuse or abuse is characterized by a low in vitro solvent extractability value of the analgesic agent from the dosage form.

172. The method of point 170, wherein said decreased risk of misuse or abuse is characterized by the absence of any significant effect on absorption of the analgesic agent from the dosage form upon co-ingestion of the dosage form and alcohol by a subject.

173. The method of point 171, wherein said decreased risk of misuse or abuse is further characterized by the absence of any significant effect on absorption of the analgesic agent from the dosage form upon co-ingestion of the dosage form and alcohol by a subject.

174. The method of point 165, wherein the in vivo absorption of said analgesic agent from the dosage form is enhanced upon administration of the dosage form with food.

175. The method of point 165, wherein the analgesic agent comprises an opioid.

176. The method of point 175, wherein the opioid is present in the dosage form as a free base.

177. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in 100 proof ethanol at room temperature for 5 minutes releases less than about 2% of said opioid.

178. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in vinegar at room temperature for 5 minutes releases less than about 2% of said opioid.

179. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a saturated baking soda solution at room temperature for 5 minutes releases less than about 2% of said opioid.

180. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a cola soft drink at room temperature for 5 minutes releases less than about 5% of said opioid.

181. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in 100 proof ethanol at room temperature for 60 minutes releases less than about 11% of said opioid.

182. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in vinegar at room temperature for 60 minutes releases less than about 12% of said opioid.

183. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a saturated baking soda solution at room temperature for 60 minutes releases less than about 12% of said opioid.

184. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a cola soft drink at room temperature for 60 minutes releases less than about 22% of said opioid.

185. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in 100 proof ethanol at room temperature for 5 minutes releases less than about 5% of said opioid.

186. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in vinegar at room temperature for 5 minutes releases less than about 5% of said opioid.

187. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a saturated baking soda solution at room temperature for 5 minutes releases less than about 5% of said opioid.

188. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a cola soft drink at room temperature for 5 minutes releases less than about 10% of said opioid.

189. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in 100 proof ethanol at room temperature for 60 minutes releases less than about 20% of said opioid.

190. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in vinegar at room temperature for 60 minutes releases less than about 20% of said opioid.

191. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a saturated baking soda solution at room temperature for 60 minutes releases less than about 20% of said opioid.

192. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a cola soft drink at room temperature for 60 minutes releases less than about 30% of said opioid.

193. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in 100 proof ethanol at 60° C. for 5 minutes releases less than about 11% of said opioid.

194. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in vinegar at 60° C. for 5 minutes releases less than about 11% of said opioid.

195. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a saturated baking soda solution at 60° C. for 5 minutes releases less than about 11% of said opioid.

196. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a cola soft drink at 60° C. for 5 minutes releases less than about 30% of said opioid.

197. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in 100 proof ethanol at 60° C. for 60 minutes releases less than about 26% of said opioid.

198. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in vinegar at 60° C. for 60 minutes releases less than about 20% of said opioid.

199. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a saturated baking soda solution at 60° C. for 60 minutes releases less than about 23% of said opioid.

200. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a cola soft drink at 60° C. for 60 minutes releases less than about 45% of said opioid.

201. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in 100 proof ethanol at 60° C. for 5 minutes releases less than about 15% of said opioid.

202. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in vinegar at 60° C. for 5 minutes releases less than about 15% of said opioid.

203. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a saturated baking soda solution at 60° C. for 5 minutes releases less than about 15% of said opioid.

204. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a cola soft drink at 60° C. for 5 minutes releases less than about 45% of said opioid.

205. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in 100 proof ethanol at 60° C. for 60 minutes releases less than about 33% of said opioid.

206. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in vinegar at 60° C. for 60 minutes releases less than about 33% of said opioid.

207. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a saturated baking soda solution at 60° C. for 60 minutes releases less than about 33% of said opioid.

208. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a cola soft drink at 60° C. for 60 minutes releases less than about 60% of said opioid.

209. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a panel of extraction solvents including vinegar, hot tea, saturated baking soda and a cola soft drink, each at 25° C. for 60 minutes, releases less than about 20% of said opioid.

210. A controlled release oral pharmaceutical dosage form comprising an opioid active agent, wherein said dosage form provides effective analgesia to a subject when dosed on a twice per day (BID) dosing schedule and further wherein said dosage form, when exposed to extraction in a panel of aqueous buffer extraction solutions ranging from pH 1 to pH 12, each at 25° C. for 60 minutes, releases less than about 15% of said opioid.

211. A controlled release oral pharmaceutical dosage form comprising an opioid active agent, wherein said dosage form provides effective analgesia to a subject when dosed on a twice per day (BID) dosing schedule and further wherein said dosage form, when physically disrupted by crushing said dosage form and exposed to extraction in a panel of aqueous extraction solutions including water at 25° C., water at 60-70° C., 0.1N HCL at 25° C., and 100 proof ethanol at 25° C., each for 60 minutes, releases less than about 40% of said opioid.

212. A controlled release oral pharmaceutical dosage form comprising an opioid active agent, wherein said dosage form provides effective analgesia to a subject when dosed on a twice per day (BID) dosing schedule and further wherein said dosage form, when physically disrupted by microwaving said dosage form and then exposed to extraction in a panel of aqueous extraction solutions including water, 0.1N HCL, and 100 proof ethanol, each at 25° C. for 60 minutes, releases less than about 25% of said opioid.

213. The dosage form of any one of points 177 to 212, wherein the opioid is oxycodone, oxymorphone, hydrocodone, or hydromorphone.

214. The dosage form of point 213, wherein the opioid is oxycodone.

215. The dosage form of any one of points 177-214, wherein the opioid is present in the form of a free base.

216. The dosage form of any one of points 177-214, wherein the opioid is present in the form of a salt.

217. An oral pharmaceutical dosage form comprising a pharmacologically active agent and a controlled release carrier system, wherein:
said pharmaceutical dosage form is abuse-resistant; and
said dosage form is suitable for twice per day (BID) dosing.

218. An oral pharmaceutical dosage form comprising an opioid active agent and a controlled release carrier system, wherein said pharmaceutical dosage form is abuse-resistant and formulated for BID administration.

219. An oral pharmaceutical dosage form comprising an opioid active agent and a controlled release carrier system, wherein said pharmaceutical dosage form is abuse-resistant and provides effective pain relief for at least 12 hours.

220. The dosage form of any one of points 217 to 219, wherein the active agent is oxycodone, oxymorphone, hydrocodone, or hydromorphone.

221. The dosage form of point 220, wherein the opioid is oxycodone.

222. The dosage form of any one of points 217 to 221, wherein the active agent is present in the form of a free base.

223. The dosage form of any one of points 217 to 221, wherein the active agent is present in the form of a salt.

224. The dosage form of any one of points 217 to 223, wherein the controlled release carrier system further provides a decreased risk of misuse or abuse.

225. The dosage form of point 224, wherein said decreased risk of misuse or abuse is characterized by a low in vitro solvent extractability value of the active agent from the dosage form.

226. The dosage form of point 224, wherein said decreased risk of misuse or abuse is characterized by the absence of any significant effect on absorption of the active agent from the dosage form upon co-ingestion of the dosage form and alcohol by a subject.

227. The dosage form of point 225, wherein said decreased risk of misuse or abuse is further characterized by the absence of any significant effect on absorption of the active agent from the dosage form upon co-ingestion of the dosage form and alcohol by a subject.

228. The dosage form of any one of points 217 to 227, wherein the in vivo absorption of the active agent from the dosage form is enhanced upon administration of the dosage form with food.

229. An oral pharmaceutical dosage form comprising oxycodone and a controlled release carrier system, wherein said pharmaceutical dosage form is abuse-resistant and, when dosed on a twice per day (BID) dosing schedule for a dosing interval of 5 days, provides a percent fluctuation (PF) ranging between about 85% and 115%.

230. The dosage form of point 229, wherein the PF ranges between about 95% and 100%.

231. The dosage form of any of points 229 or 230, wherein the dosage form provides effective pain relief for at least 12 hours.

232. The dosage form of any of points 229 to 231, wherein the dosage form is further characterized by the absence of any significant effect on absorption of the oxycodone from the dosage form upon co-ingestion of the dosage form and alcohol by a subject.

233. The dosage form of any of points 229 to 232, wherein the dosage form is further characterized by a low injectability potential.

234. The dosage form of any of points 229 to 233, wherein the dosage form is not susceptible to common forms of abuse comprising injection, inhalation (crushing and sniffing) and volatilization (smoking).

235. An oral pharmaceutical dosage form comprising oxycodone and a controlled release carrier system, wherein said pharmaceutical dosage form is abuse-resistant and exhibits an Abuse Quotient (AQ) value of less than 10 when taken intact and with water as intended.

236. An oral pharmaceutical dosage form comprising oxycodone and a controlled release carrier system, wherein said pharmaceutical dosage form is abuse-resistant and exhibits an Abuse Quotient (AQ) value of less than 30 when taken after physical crushing and with 80 proof alcohol.

237. An oral pharmaceutical dosage form comprising oxycodone and a controlled release carrier system, wherein said pharmaceutical dosage form is abuse-resistant and exhibits an Abuse Quotient (AQ) value of less than about 25 when taken intact and after holding the dosage form in the buccal cavity for 10 minutes before swallowing.

238. An oral pharmaceutical dosage form comprising oxycodone and a controlled release carrier system, wherein said pharmaceutical dosage form is abuse-resistant and exhibits an Abuse Quotient (AQ) value of less than 35 when taken after vigorous chewing prior to swallowing.

239. The dosage form of any of points 235 or 238, wherein the dosage form provides effective pain relief for at least 12 hours.

240. The dosage form of any of points 235 to 239, wherein the dosage form is further characterized by a low injectability potential.

241. The dosage form of any of points 235 to 240, wherein the dosage form is not susceptible to common forms of abuse comprising injection, inhalation (crushing and sniffing) and volatilization (smoking).

242. An oral pharmaceutical dosage form comprising a pharmacologically active agent, wherein the agent is an opioid, a central nervous system (CNS) depressant or a CNS stimulant, and a controlled release carrier system which comprises:
(a) a high viscosity liquid carrier material (HVLCM),
(b) a network former,
(c) a rheology modifier,
(d) a hydrophilic agent; and
(e) a solvent;
wherein: the HVLCM is sucrose acetate isobutyrate (SAIB); the network former is selected from cellulose acetate butyrate (CAB), cellulose acetate phthalate, ethyl cellulose, hydroxypropylmethyl cellulose and cellulose triacetate; the rheology modifier is selected from isopropyl myristrate (IPM), caprylic/capric triglyceride, ethyl oleate, triethyl citrate, dimethyl phthalate and benzyl benzoate; the hydrophilic agent is selected from hydroxyethylcellulose (HEC), hydroxypropylcellulose, carboxymethylcellulose, polyethylene glycol and polyvinylpyrrolidone; and the solvent is selected from triacetin, N-methyl-2-pyrrolidone, 2-pyrrolidone, dimethylsulfoxide, ethyl lactate, propylene carbonate and glycofurol.

243. The dosage form of point 242, wherein the pharmacologically active agent is selected from oxycodone, oxymorphone, hydrocodone, hydromorphone, as free base or as pharmaceutically acceptable salts thereof.

244. The dosage form of point 243, wherein (a) the HVLCM is SAIB, (b) the network former is CAB, (c) the rheology modifier is IPM, (d) the hydrophilic agent is HEC, and (e) the solvent is triacetin.

245. The dosage form of any one of points 242 to 244, which comprises (a) from 1.3 to 35 wt % of the pharmacologically active agent, (b) from 2 to 10 wt % of the network former, (c) from 0.1 to 20 wt % of the rheology modifier, (d) from 1 to 8 wt % of the hydrophilic agent, (e) from 10 to 40 wt % of the solvent, and (f) from 30 to 60 wt % of the HVLCM.

246. The dosage form of any one of points 242 to 245, wherein the controlled release carrier system further comprises a viscosity enhancing agent.

247. The dosage form of point 246, wherein the viscosity enhancing agent is a silicon dioxide.

248. The dosage form of any one of points 242 to 247 further comprising a stabilizer agent.

249. The dosage form of point 248, wherein the stabilizer agent is butylhydroxyl toluene (BHT).

250. The dosage form of any one points 242 to 249, which provides at least 8 hours of substantially constant in vitro release of the active agent when tested in an USP Type II Dissolution Apparatus modified with a stainless steel stationary basket assembly using a paddle speed of 100 rpm and 0.1N HCl dissolution media containing 0.5% sodium lauryl sulfate; and 20% or less of said active agent is extracted from said dosage form after 1 hour at ambient temperature using EtOH (100 proof) as the extraction solvent.

251. The dosage form of any one of points 242 to 250, wherein less than 20% of the active agent is extracted after 60 minutes of extraction in ethanol (100 proof) at ambient temperature and less than 30% is extracted after 60 minutes of extraction in ethanol (100 proof) at 60° C.

252. The dosage form of any one of points 242 to 251, wherein the formulation of the active agent and the carrier system is encapsulated within a biodegradable capsule.

253. The dosage form of point 252, wherein the capsule comprises gelatin, hydroxyethylcellulose or hydroxypropylmethylcellulose.

254. The dosage form of point 251 or 252, wherein the capsules are packaged in unit dose blisters or multidose plastic bottles.

255. A process for the preparation of an oral pharmaceutical dosage form as defined in point 242, which process comprises:
(i) preheating the HVLCM;
(ii) mixing the solvent with the preheated HVLCM, thereby forming a uniform solution of the HVLCM in the solvent;
(iii) dispersing the network former in the solution, thereby dissolving the network former in the solution;
(iv) mixing from 5 to 30% of the rheology modifier or, optionally, a solution of a stabilising agent and from 5 to 30% of the rheology modifier with the formulation obtained in step (iii);
(v) mixing the pharmacologically active agent with the formulation obtained in step (iv);
(vi) mixing the hydrophilic agent with the formulation obtained in step (v);
(vii) optionally, mixing a viscosity enhancing agent with the formulation obtained in step (vi);
(viii) mixing the balance of the rheology modifier with the formulation obtained in step (vi) or, if step (vii) is effected, step (vii);
(ix) optionally, filling capsules with the formulation obtained in step (viii); and
(x) optionally, packaging the filled capsules into unit dose blisters or multidose plastic bottles.

256. A process for the preparation of an oral pharmaceutical dosage form as defined in point 242, which process comprises:
(i) preheating the HVLCM;
(ii) mixing the solvent with the preheated HVLCM, thereby forming a uniform solution of the HVLCM in the solvent;
(iii) optionally, mixing a solution of a stabilising agent and from 5 to 30% of the rheology modifier with the solution obtained in step (ii);
(iv) mixing the rheology modifier or, if step (iii) is effected, the balance of the rheology modifier with the solution obtained in step (ii) or (iii);
(v) optionally, mixing a viscosity enhancing agent with the formulation obtained in step (iv);
(vi) dispersing the network former in the solution obtained in step (iv) or, if step (v) is effected, step (v), thereby dissolving the network former in the solution;
(vii) mixing the pharmacologically active agent with the formulation obtained in step (vi);
(viii) mixing the hydrophilic agent with the formulation obtained in step (vii);
(ix) optionally, filling capsules with the formulation obtained in step (viii); and
(x) optionally, packaging the filled capsules into unit dose blisters or multidose plastic bottles.

257. An oral pharmaceutical dosage form obtainable by a process as defined in point 255 or 256.

BRIEF DESCRIPTION OF THE FIGURES

FIG. 4 shows the in vitro release performance of Test Capsules at 10, 20 and 40 mg strength as described in Example 3a.

FIG. 13 shows the overall kinetics of active agent extraction from Test Capsules and Control tablets in a panel of household solvents at ambient temperature (RT) in the in vitro abuse-resistance tests described in Example 4a.

FIG. 14 shows the overall kinetics of active agent extraction from Test Capsules and Control tablets in a panel of household solvents at elevated temperature (60° C.) in the in vitro abuse-resistance tests described in Example 4a.

FIG. 20 shows the mean linear plasma concentration-time curves of active agent in the clinical trial study described in Example 7a.

FIGS. 27 and 28 show the results of the in vivo abuse-resistance test comparing 40 mg Test Capsules against a SR Control tablet containing 40 mg oxycodone and an immediate release oxycodone dosage form as described in Example 8a.

DETAILED DESCRIPTION

Figure 1A:
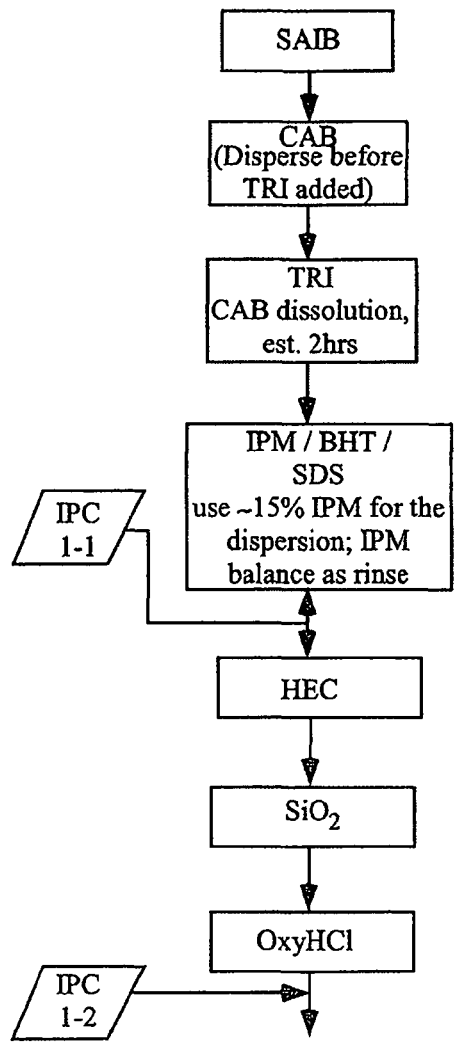
FIGS. 1A-1C depict the lab-scale manufacturing processes (Process Schemes 1-3) described in Example 1.

Before describing the present invention in detail, it is to be understood that this invention is not limited to particularly exemplified carrier materials or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, for example, reference to "a non-polymeric carrier material" includes a mixture of two or more such carrier materials, reference to "a solvent" includes a mixture of two or more such solvents, reference to "an active agent" includes mixtures of two or more such agents, and the like.

In our earlier U.S. Patent Application, Publication No. US 2004/0161382, "Oral Drug Delivery System", hereinafter referred to as the "382 Publication", we describe certain pharmaceutical dosage forms and drug-delivery devices suitable for oral delivery of pharmacologically active agents. These novel dosage forms and devices feature a unique combination of pharmaceutical excipients including an HVLCM, a network former, and an optional rheology modifier and/or a solvent that together provide a controlled release carrier system. The controlled release carrier system is loaded with an active agent of interest, and will release the same over a period of time when in an aqueous environment, and in particular, an environment similar to that of the GI tract of a mammal. The controlled release carrier system can further provide the added benefit of enhanced abuse-resistance, wherein the carrier system resists various physical disruption and other in vitro extraction techniques (e.g., extraction into ethanol, water or other common solvents) that could be employed by someone wishing to disable the controlled release function of the system to access substantially all or most of the sequestered active agent in an immediate release form that can be ingested, inhaled or injected to provide a euphoric effect. The 382 Publication therefore describes a number of controlled release carrier systems that can be used to produce oral dosage forms or delivery devices that provide desirable controlled release kinetics and/or abuse-resistance characteristics.

It is a primary object of the present invention to provide for improved pharmaceutical dosage forms and drug-delivery devices suitable for oral delivery of pharmacologically active agents, where such improved dosage forms and delivery devices are based upon the controlled release carrier systems described in the 382 Publication. In this regard, there has remained a need in the art to provide a controlled release carrier system that provides all of the benefits of those described in the 382 Publication as well as providing enhanced safety features and/or abuse-resistance properties in addition to enhanced in vivo pharmacological performance. One of the key hindrances facing the skilled person desiring to provide such a controlled release carrier system resides in the very nature of the carrier system itself.

More particularly, the unique controlled release carrier system is responsible for in vivo pharmacological performance, where the active agent must be delivered from the system by diffusion from the system as it transits the GI tract. This same controlled release carrier system is also responsible for the in vitro abuse-resistance and in vivo safety performance, that is, the carrier system must prevent active agent from leaving the system when contacted with very efficient aqueous solvents and/or prolonged exposure to aqueous environments having a low or high pH. Thus, manipulations that can be made to the controlled release system in order to, for example, increase overall delivery efficiency (AUC) or to provide for extended release rates (manipulations designed to increase release of the active agent from the controlled release carrier system) typically will frustrate the in vitro abuse-resistance and in vivo safety performance of that same system. This is because, generally, formulation manipulations that increase $C_{max}$ or decrease $T_{max}$ can frustrate abuse-resistance by allowing more/faster extractability (e.g., changes designed to increase rate/extent of in vivo drug release also increase rate/extent of in vitro drug release when attempts are made to defeat the controlled release mechanism of a dosage form). The term "AUC" means the area under the curve obtained from an in vivo assay in a subject by plotting blood plasma concentration of the active agent in the subject against time, as measured from the time of administration, to a time "T" after administration. The time T will correspond to the delivery period of the active agent to a subject. In like manner, manipulations that can be made to the controlled release system in order to enhance in vitro abuse-resistance and in vivo safety performance (manipulations designed to decrease release of active agent from the controlled release carrier system) typically will frustrate the in vivo pharmacological performance of that same system. As used throughout this specification and the attached claims, the terms "abuse-resistance" and abuse-resistant" are completely interchangeable with the related terms "abuse-deterrence" and "abuse-deterrent", as well as "tamper-resistance" and "tamper-resistant", and "extraction-resistance" and "extraction-resistant" and thus mean exactly the same thing.

Accordingly, in one aspect of the invention, an abuse-resistant oral pharmaceutical dosage form is provided that comprises a pharmacologically active agent in a controlled release carrier system. The subject dosage form is characterized in that the controlled release carrier system provides for controlled in vivo release of the agent characterized in that the individual steady state $C_{min}/C_{max}$ variance within an interdose interval is less than or equal to the Therapeutic Index of the subject active agent. By "abuse-resistant", herein, it is meant that the dosage form is resistant to extraction in ethanol (80 or 100 proof) such that: less than about 20%, preferably less than about 15% and more preferably less than about 10 to 11% of the active agent is extracted after 60 minutes of extraction in 100 proof ethanol at ambient temperature (RT); less than about 30%, more preferably less than about 28% and more preferably less than about 25 to 27% of the active agent is extracted after 60 minutes of extraction in 100 proof ethanol at 60° C.; less than about 20%, preferably less than about 15% and more preferably less than about 12 to 13% of the active agent is extracted after 60 minutes of extraction in 80 proof ethanol at ambient temperature (RT); and less than about 40%, preferably less than about 35% and more preferably less than about 30 to 32% of the active agent is extracted after 180 minutes of extraction in 80 proof ethanol at ambient temperature (RT). By the term "ambient temperature", used interchangeably herein with "room temperature" and/or "RT", is meant the normal temperature of a working area or laboratory and ranges from about 18 to 25° C., and is more particularly used herein to denote a normal temperature of 25° C. Suitable in vitro test methodology, techniques, apparatus and equipment to determine if a dosage form is properly resistant to extraction in ethanol are described below in Example 4.

In certain preferred embodiments, the "abuse-resistant" dosage form is also resistant to extraction in a panel of common household solvents, that is, the dosage form is further resistant to extraction in one or more of the following: (a) resistant to extraction in cola soft drinks (pH about 2.5) such that less than 30%, preferably less than about 25% and more preferably less than about 22 to 23% of the active agent is extracted after 60 minutes of extraction in the cola soda at ambient temperature (RT) and/or less than about 50%, preferably less than about 48%, and more preferably less than about 42 to 46% is extracted after 60 minutes of extraction in the cola soda at 60° C.; (b) resistant to extraction in household vinegar (pH about 2.5) such that less than 20%, preferably less than about 15% and more preferably less than about 11 to 13% of the active agent is extracted after 60 minutes of extraction in the vinegar at ambient temperature (RT) and/or less than about 25%, preferably less than about 23%, and more preferably less than about 18 to 21% is extracted after 60 minutes of extraction in the vinegar at 60° C.; or (c) resistant to extraction in a saturated baking soda solution (pH about 8.5) such that less than 20%, preferably less than about 15% and more preferably less than about 10 to 14% of the active agent is extracted after 60 minutes of extraction in the saturated baking soda solution at ambient temperature (RT) and/or less than about 27%, preferably less than about 25%, and more preferably less than about 20 to 24% of the active agent is extracted after 60 minutes of extraction in the saturated baking soda solution at 60° C. Here again, suitable in vitro tests to determine if a dosage form is properly resistant to extraction in these additional household solvents are described below in Example 4.

In certain other preferred embodiments, the "abuse-resistant" dosage form is also characterized by having a low injectability potential. Injectability potential of a dosage form can be assessed using standard testing methods, and in particular using the testing methods described in Example 4c below, wherein both "syringeability" and "injectability" of a test formulations are determined. In this regard, the characteristics of an injectable suspension are defined as syringeability and injectability. Syringeability pertains to the ability of a suspension to be drawn into an empty syringe through a hypodermic needle, while injectability address the ability of a suspension to be pushed from a pre-filled syringe through a hypodermic needle. Both characteristics depend upon the viscosity and physical characteristics of a test formulation. A formulation or dosage form containing that formulation will have a "low injectability potential" if the syringeability and/or injectability of that formulation is low. In related embodiments, the "abuse-resistant" dosage form is also characterized by not being susceptible to common forms of abuse comprising injection, inhalation (crushing and sniffing) and volatilization (smoking). Standard tests for assessing the susceptibility of a particular dosage form to these forms of abuse are known in the art including, for example, the tests described in Examples 4 and 8 below. In still further related embodiments, the "abuse-resistant" dosage form is also characterized by having: an Abuse Quotient (AQ) value of less than 10 when taken intact and with water as intended; an AQ value of less than 30 when taken after physical crushing and with 80 proof alcohol; an AQ value of less than about 25 when taken intact and after holding the dosage form in the buccal cavity for 10 minutes before swallowing; and/or an AQ value of less than 35 when taken after vigorous chewing prior to swallowing. The Abuse Quotient (AQ) can be used as a method to express the attractiveness for abuse of a formulation/dosage form. The AQ takes into account the observation that increasing $C_{max}$ and decreasing $T_{max}$ increases the attractiveness of a particular dosage form for abuse. Represented as a formula, $AQ=C_{max}/T_{max}$ AQ is a dose dependent metric as $C_{max}$ varies with dose. The AQ for any dosage form under normal or under abuse-conditions can be assessed using standard testing methods known to the skilled person including, for example, the test methods described below in Example 8.

By "provides for controlled in vivo release of the agent characterized in that the individual steady state $C_{min}/C_{max}$ variance within an interdose interval is less than or equal to the Therapeutic Index of the active agent", it is meant herein that, at steady state, the controlled release carrier system provides for optimum therapy in methods of treatment that use repetitive administration of the dosage forms of the present invention. An "interdose interval;" refers to the period of time between a single administration of dosage form(s) and the next subsequent administration in a repetitive administration regimen (e.g., if given every 24 hours (QD), the interdose interval would be the 24 hours between dosing, if given every 12 hours (BID), it would be the 12 hours between dosing, and the like). In this regard, to assess optimum dosing for a particular active agent of interest, a "Therapeutic Index" can be defined in terms of plasma concentration (systemic concentration) such that the Therapeutic Index equals the ratio of $C^*_{max}/C^*_{min}$, where "$C^*_{max}$" and "$C^*_{min}$" are the maximum and minimum desired plasma concentrations, respectively, that is, the maximum desired plasma concentration being the point above which the active agent would have toxic affect, and the minimum desired plasma concentration being the point below which the active agent no longer provides the desired pharmacological effect. See Theeuwes et al. (1977) *Journal of Pharmaceutical Sciences* 66(10):1388-1392. These maximal and minimal plasma concentration ranges of course relate to the dose at the repeat dosage amount, wherein an effective dose is generally the effective AUC (at steady state). The Therapeutic Index for any particular active agent of interest can be readily ascertained by the skilled person. It is understood that the Therapeutic Index may vary from person to person and may vary in one person over time as the disease progresses or conditions of treatment change. In general for opioids, patients become more tolerant to the drug as the level of pain increases and higher doses are needed. Physicians will therefore adjust the dose over time. It is, however, very desirable to have a dosage form with fluctuation index=$C_{max}/C_{min}$ that is consistent and reproducible such that only the dose which gives rise to the average plasma level or AUC at steady needs to be adjusted to achieve optimum treatment.

For the dosage forms of the present invention, the controlled release carrier system provides for consistent and reproducible controlled release of the active agent such that the variance (ratio) of the measured maximum and minimum plasma concentration extremes at steady state ($C_{max}$ and $C_{min}$), that is, individual steady state $C_{min}/C_{max}$ variance, will be less than or equal to the Therapeutic Index for that particular active agent when dosed at the therapeutically effective dose. In some cases, the individual steady state $C_{min}/C_{max}$ variance within an interdose interval is particularly low, that is, less than or equal to about 2 to 3. In preferred embodiments, the individual steady state $C_{min}/C_{max}$ variance within an interdose interval is about 2 or less. In other cases, for example where the Therapeutic Index for the active agent is substantially larger, the individual steady state $C_{min}/C_{max}$ variance within an interdose interval may be larger, for example about 5 to 6, or even greater; however, release from the dosage forms of the present invention is preferably much better controlled and thus provide for particularly low variance regardless of the size of the Therapeutic Index. The ability of a controlled release carrier system to provide for controlled in vivo release of the agent characterized in that the individual steady state $C_{min}/C_{max}$ variance within an interdose interval is less than or equal to the Therapeutic Index of the active agent can be readily determined by the skilled person by using standard in vitro dissolution testing, particularly the in vitro dissolution methods set forth in Example 4 below, and then applying an IVIVC transformation function such as those set forth in Example 6 below to determine anticipated in vivo variability over the duration of controlled release for that dosage form. In addition to these in vitro testing methods, the ability of a controlled release carrier system to provide for controlled in vivo release of the agent characterized in that the individual steady state $C_{min}/C_{max}$ variance within an interdose interval is less than or equal to the Therapeutic Index of the active agent can be readily determined by the skilled person by using standard in vivo pharmacological testing methods such as those described below in Examples 7 and 9-11.

As an alternative, the controlled release carrier systems of the present invention can provide for consistent and reproducible controlled release of the active agent characterized by having a low degree of fluctuation at steady state. Accordingly, in certain preferred embodiments of the invention, the abuse-resistant oral pharmaceutical dosage forms of the present invention comprise a controlled release carrier system that provides enhanced in vivo pharmacokinetic performance, such as when the dosage form is continuously administered on, e.g., a BID (twice daily) dosing schedule over a dosing interval sufficient to reach steady state (e.g., 5 days), the percent fluctuation (PF) will range from about 85% to 115%, preferably, between about 95% and 100%. The PF value can be obtained using standard pharmacokinetic analysis of plasma concentration/time data obtained in a steady state testing format, wherein $PF=100\times(C_{min}-C_{max})$ $C_{average}=100\times(C_{min}-C_{max})/(AUC_{0-\tau}/\tau$, wherein $\tau$=time. By "$C_{max}$" is meant the maximum concentration of an active agent in the blood plasma of a subject, generally expressed as mass per unit volume, typically nanograms per milliliter. "$C_{min}$" is meant the minimum concentration of an active agent in the blood plasma of a subject, generally expressed as mass per unit volume, typically nanograms per milliliter. $AUC_{0-\tau}$ is the area under the plasma concentration-time curve from time=0 throughout a dosing interval ($\tau$); calculated using the linear trapezoidal rule.

In certain other preferred embodiments of the invention, the abuse-resistant oral pharmaceutical dosage forms comprise a controlled release carrier system that can provide enhanced in vivo pharmacokinetic performance such as wherein the in vivo release of the active agent from the carrier system is substantially free from food effect, or wherein the carrier system has a food effect such that the in vivo absorption of the active agent from the carrier system is actually enhanced when administered in the presence of food. In this regard, the physiological behavior of the stomach is usually determined by whether it contains food (fed state) or is empty (fasted state). In the fed state, food is mixed and partially digested in the distal stomach as the stomach undergoes contractions, helping to move materials into the main part of the stomach for further digestion. At the end of a digestive period, the stomach enters the fasting stage and begins a cycle called the interdigestive myoelectric motor cycle. These changes in physiological behavior, as well as certain concomitant chemical changes (e.g., pH) as the stomach switches between fed and fasted states may give rise to variability in the rate and/or amount of delivery of an active agent from an oral dosage form. More particularly, a variety of formulation-dependent food-induced absorption changes (hereinafter "food effect") can occur with controlled release compositions. These changes can include decreases in the rate and/or extent, increases in the rate and/or extent when taken in fed or fasted states, and erratic or variable absorption of active agent from a controlled release composition such as differences in absorption when the composition is taken with low-fat or high-fat meals. In extreme cases, a controlled release composition can have a significant food effect such that when the composition is taken with food, or with different kinds of food (high fat versus low fat meals), there can be a significant increase in absorption (dose dumping) that, with a highly potent active agent and/or an active agent with significant side effect potential, can cause a dosage form to be unsafe. In these cases, that is, where a formulation exhibits a pronounced food effect, the dosing relative to meal intake may be made part of the product labeling to assure consistent and safe absorption. If the difference in both the rate and extent of absorption of an active agent from an oral dosage form varies significantly when it is administered in a fed versus a fasted state, the dosage form is characterized as having a food effect. In some cases, a dosage form can have a food effect wherein administration of the dosage form with food will enhance the bioavailability of the active agent. On the other hand, if there is not a significant difference in both the rate and extent of absorption of an active agent from an oral dosage form as between fed and fasted states, the dosage form is characterized as being substantially free from a food effect (e.g., co-administration with food may still have an effect on the maximal plasma concentration of the active agent).

The controlled release carrier systems of the present invention can be provided such that they are characterized: as having a food effect (administration of the dosage form with food will have a significant effect on both the rate and extent of absorption of an active agent, i.e., the rate of absorption is decreased and the extent of absorption is increased); as having a consistent food effect (administration of the dosage form with food will effect both the rate and extent of absorption of an active agent, however, there is not a significant difference or variability in this food effect as between different types of meals or diets); or as being substantially free from a food effect (administration of the dosage form with or without food does not significantly effect both the rate to maximal plasma concentration, or $T_{max}$, and the extent of absorption of the active agent, or AUC, although co-administration with food may still have an effect on the maximal plasma concentration, or $C_{max}$, of the active agent). Accordingly, as used herein, "absence from food effect" means that the ratio of mean AUC fed/fasted is within the accepted 80% to 125% bioequivalence limits for pharmaceutical dosage forms, and the ratio of mean $T_{max}$ fed/fasted is likewise within the accepted 80% to 125% bioequivalence limits. In addition, as used herein, "enhanced in vivo absorption" means that the ratio of mean AUC fed/fasted is at least greater than the 125% upper bioequivalence limit and the ratio of mean $T_{max}$ fed/fasted is greater than the 125% upper bioequivalence limit. As used herein, a "consistent food effect" means that there is enhanced in vivo absorption and the ratio of mean AUC fed high-fat/fed low-fat is within the accepted 80% to 125% bioequivalence limits for pharmaceutical dosage forms, and the ratio of mean $T_{max}$ fed/fasted is likewise within the accepted 80% to 125% bioequivalence limits. By "C" is meant the concentration of an active agent in the blood plasma of a subject, generally expressed as mass per unit volume, typically nanograms per milliliter. By "$C_{max}$" is meant the maximum concentration of an active agent in the blood plasma of a subject, generally expressed as mass per unit volume, typically nanograms per milliliter, within a specified time interval "T" after administration of the active agent to a subject, or "$T_{max}$". As used herein, "fasted" means that, under a clinical trial setting, a dosage form is administered to a subject that has fasted overnight for at least 10 hours, fasted for an additional 4 hours after dosage administration, and then received a standardized high-fat (breakfast) meal. As used herein, "fed" means that, under a clinical trial setting, a dosage form is administered to a subject immediately after having ingested a high-fat or low-fat standardized meal. A "high-fat" standardized meal consists of 2 slices of toasted white bread spread with butter, two eggs fried in butter, two slices of bacon, 2 oz hash-browned potatoes, and 8 oz whole milk (approximately 33 g protein, 58 to 75 g fat, 58 g carbohydrate, 870 to 1020 calories). A "low-fat" standardized meal consists of one slice of toasted white bread spread with butter or jelly, 1 oz dry cereal (corn flakes), 8 oz skim milk, 6 oz orange juice, and one banana (approximately 17 g protein, 8 g fat, 103 g carbohydrate, 583 calories). All of the above-described pharmacokinetic values can be readily determined by the skilled person using established in vivo clinical trail procedures such as those described below in Example 7. Reference may also be made to "Guidance for Industry", Food-Effect Bioavailability and Fed Bioequivalence Studies, US Dept Health and Human Services, FDA, Center for Drug Evaluation and Research (CDER), December 2002.

Accordingly, in one particularly preferred embodiment of the invention, an abuse-resistant oral pharmaceutical dosage form is provided that includes a pharmacologically active agent and a controlled release carrier system. The controlled release carrier system provides for controlled in vivo release of the agent characterized in that the individual steady state $C_{min}/C_{max}$ variance within an interdose interval is less than or equal to the Therapeutic Index of the active agent, and the in vivo release of the active agent from the controlled release carrier system is substantially free from food effect. In one aspect of the invention, the pharmacologically active agent is present in the dosage form as a salt. In another aspect of the invention, the active agent is an opioid salt. In another particularly preferred embodiment of the invention, an abuse-resistant oral pharmaceutical dosage form is provided that includes a pharmacologically active agent and a controlled release carrier system. The controlled release carrier system provides for controlled in vivo release of the agent characterized in that the individual steady state $C_{min}/C_{max}$ variance within an interdose interval is less than or equal to the Therapeutic Index of the active agent, and the extent of the in vivo absorption of the active agent from the controlled release carrier system is enhanced upon administration of the dosage form with food. In one aspect of the invention, the dosage form is characterized as having a consistent food effect, such that the extent of in vivo absorption of the active agent from the controlled release carrier system is enhanced upon administration of the dosage form with food but there is not a significant difference between various diets or meal intakes (fed high-fat and fed, low-fat states). In this regard, this particular embodiment of the invention is believed to be a safer and more effective dosage form, since the bioavailability of active agent from the dosage form is enhanced by the food effect and yet this food effect is consistent over a range of reasonable diets, has a low sensitivity to the particular food actually ingested, and does not dose-dump on administration concomitant with a heavy, high-fat meal. In certain preferred embodiments, the active agent can be an opioid, CNS-depressant, or CNS-stimulant that has a particularly high potential for abuse, diversion or other misuse. Preferably, the active agent can comprise an opioid, an amphetamine, or a methylphenidate, in each case either as a salt or as a free base. In one aspect of the invention, the active agent is an opioid free base, particularly oxycodone free base.

The ability to manipulate a controlled release carrier system produced according to the invention in order to provide different food-effect performance was assessed as follows. An exemplary controlled release formulation comprised of 40.1 wt % SAIB; 29.7 wt % Triacetin; 17 wt % IPM; 6 wt % HEC; 5.25 wt % CAB; 2 wt % $SiO_2$ and 0.02 wt % BHT was prepared and filled into a size 00 gelatin capsule. A dissolution test (Method 1 of Example 3, below) was set up using a modified USP Type II dissolution apparatus, paddle speed of 100 rpm and temperature controlled at 37° C. and a dissolution medium of 0.1N HCl and 0.5% SDS. Sample formulations were added and the entire mass removed at: 3, 6, 8, 10, 12, 18, 24 and 36 hours. Morphology and weight changes in the samples were evaluated (n=2) to assess ingress of water into the formulation over time. It was found that there was significant weight change as a function of time, wherein significant weight loss was observed over the first 6 hours, and then weight gain occurring between 8 and 10 hours. Next, the egress of the solvent (triacetin) over time was assessed. Using the same testing parameters and sampling the dissolution medium over time, the results of the study indicated that elution of Triacetin takes place within the first 3 hours during the time in which water uptake into the formulation is slow. However, after the 3 hour point, water uptake is significantly increased. These results indicate that factors such as solubility of the active agent in the selected solvent and in water can have an effect on the release kinetics of the agent from the formulation, wherein an active agent with high solubility in the solvent and low water solubility would be expected to display a quick onset (e.g., burst) of release during the first 6 to 8 hours of delivery, followed by a leveling off or tapering of release at around 12 hours; whereas an active agent with high water solubility and low solubility in the solvent would like follow zero-order dissolution profile (substantially constant) over the delivery period. In order to assess this expectation, the sample controlled release formulation was used to produce oral dosage forms containing oxycodone free base (high solubility in Triacetin, low water solubility) and oxycodone in salt form (HCl, low solubility in Triacetin, high solubility in water), and the exemplary formulations were assessed using the above-described dissolution testing methodologies. The results of the study demonstrated that the formulation containing the free base form of the active agent showed strong initial release performance, with about 60 to 70% of the total active agent being released within the first twelve hours. In contrast, the formulation containing the salt form of the active agent showed a substantially constant release performance over the entire test duration, with a much slower onset of action and only about 20 to 30% of the total active agent being released within the first twelve hours. Accordingly, matching active agent solubility parameters with the controlled release formulation constituents can be used to speed up or delay onset of action, and to enhance or decrease the total amount of active agent that will be absorbed from the dosage form over the dosing interval.

In certain other preferred embodiments of the invention, the abuse-resistant oral pharmaceutical dosage forms comprise a controlled release carrier system that can provide enhanced in vivo pharmacokinetic performance such as wherein the in vivo release of the active agent from the carrier system is sufficient to provide for an individual $C_{min}/C_{max}$ variance at steady state is less than or equal to about 2 or 3. By "steady state" is meant the condition in which the amount of an active agent present in the blood plasma of a subject does not vary significantly over a prolonged period of time. By "C" is meant the concentration of an active agent in the blood plasma of a subject, generally expressed as mass per unit volume, typically nanograms per milliliter. By "$C_{max}$" is meant the maximum concentration of an active agent in the blood plasma of a subject, generally expressed as mass per unit volume, typically nanograms per milliliter, within a specified time interval "T" after administration of the active agent to a subject, or "$T_{max}$". By "$C_{min}$" is meant the minimum concentration of drug in the blood plasma of a subject, generally expressed as mass per unit volume, typically nanograms per milliliter, within a specified time interval after administration of the active agent to a subject. Here again, each of these pharmacokinetic values can be readily determined by the skilled person using established in vivo clinical trail procedures such as those described below in Example 7.

In still further preferred embodiments of the invention, the abuse-resistant oral pharmaceutical dosage forms include a controlled release carrier system that can provide enhanced in vivo pharmacokinetic performance such as wherein the in vivo release of an opioid analgesic agent from the carrier system is characterized by a $T_{max}$ of at least about 4 hours after ingestion by the subject. In one aspect of the invention, the opioid analgesic agent is present in the dosage form as a free base. In another aspect of the invention, the opioid analgesic active agent is oxycodone in free base form. This enhanced in vivo pharmacokinetic performance can be readily assessed by the skilled person using established in vivo clinical trial procedures such as those described below in Example 7.

In certain other preferred embodiments of the invention, the abuse-resistant oral pharmaceutical dosage forms comprise a controlled release carrier system that can provide a decreased risk of misuse or abuse. An important advantage of the dosage forms disclosed herein is that they have abuse-resistant characteristics and/or reduced risk of diversion. In this regard, the formulation contained within the dosage form (the controlled release carrier system and the active agent) is neither susceptible to common crushing, pulverization or attrition techniques, nor susceptible to extraction using common household solvents such as ethanol. In addition, the formulation contained within the dosage form (the controlled release carrier system and the active agent) is also not susceptible to common heat extraction techniques (e.g., microwaving), vaporization techniques (e.g., volatilization or smoking), nor injection techniques due to very poor syringeability and/or injectability properties of the formulation. Specifically, since an HVLCM is a highly viscous liquid, formulations containing HVLCMs avoid the possibility of crushing for the purpose of inhalation. However, in a particular aspect of the invention, enhanced safety features can further be provided by the controlled release carrier system. In this regard, the subject dosage forms are characterized as having either one or both of the following enhanced safety features: the controlled release carrier system is characterized by a low in vitro solvent extractability value of the active agent from the dosage form; and/or the carrier system is characterized by the absence of any significant effect on absorption of the active agent from the dosage form upon co-ingestion of the dosage form with ethanol by a subject, or upon chewing (masticating) or holding the tablet within the mouth (buccal cavity) instead of swallowing the dosage form whole as intended. This second feature, so-called "dose-dumping" is of critical concern to regulatory agencies concerned with the safety of potent analgesic agents such as opioids. This is because, unlike the standard concerns about intentional abuse, a patient may inadvertently take a controlled release dosage form containing a high potency opioid with a glass of wine, or a cocktail, or a child may find a dropped capsule and chew the same. If this activity is enough to defeat the controlled release system, a potentially lethal dose of the opioid analgesic may be inadvertently administered. In this regard, recently the Palladone® brand controlled release hydromorphone product was withdrawn from the US market for this safety reason.

Accordingly, in certain particularly preferred embodiments of the invention, an abuse-resistant oral pharmaceutical dosage form is provided that comprises a controlled release carrier system that can provide a decreased risk of misuse or abuse, wherein the carrier system is characterized by the absence of any significant effect on absorption of the pharmacologically active agent from the dosage form upon co-ingestion of the dosage form with ethanol by a subject. The ability of a dosage form to avoid this dose-dumping effect can be assessed using carefully controlled in vivo human clinical trial methods such as those described below in Example 8. By "no significant effect", it is meant that both the $C_{max}$ ratio and the AUC ratio of absorption of the active agent from the dosage form when taken with water, or with 4%, 20% or 40% ethanol is within a range of about 0.8 to 1.2. In certain preferred embodiments, the active agent can be an opioid, CNS-depressant, or CNS-stimulant that has a particularly high potential for abuse, diversion or other misuse. Preferably, the active agent can comprise an opioid, an amphetamine, or a methylphenidate. In one aspect of the invention, the pharmacologically active agent is present in the dosage form as a free base. In another aspect of the invention, the active agent is an opioid free base, particularly oxycodone in free base form.

In another particularly preferred embodiment of the invention, an abuse-resistant oral pharmaceutical dosage form is provided that comprises a controlled release carrier system that can provide a decreased risk of misuse or abuse, wherein the carrier system is characterized by a low in vitro solvent extractability value of the active agent from the dosage form. Suitable in vitro test methodology, techniques and apparatus to determine if a dosage form is properly characterized as having "a low in vitro solvent extractability value" are described below in Example 4. In summary, a test dosage form can be placed within a suitable amount of a liquid that my be readily obtained, for example water, alcohol (ethanol), soft drinks, vinegar, baking soda solutions, and the like. After a suitable time (and, for example, with suitable agitation or application of heat), the liquid "extraction solvent" can be tested for the presence of extracted active agent. Any number of such liquids can be assembled into a "panel" of extraction solvents for the purposes of such testing. Accordingly, in these preferred embodiments, the "abuse-resistant" dosage form is resistant to extraction across a panel of common household solvents, that is, less than 30% of the starting active agent is extracted from the dosage form after extraction in all the following solvents for 60 minutes at ambient (RT) temperature: cola soft drinks (pH about 2.5); household vinegar (pH about 2.5); a saturated baking soda solution (pH about 8.5); and ethanol (100 proof). In certain preferred embodiments, the active agent can be an opioid, CNS-depressant, or CNS-stimulant that has a particularly high potential for abuse, diversion or other misuse. Preferably, the active agent can comprise an opioid, an amphetamine, or a methylphenidate. In one aspect of the invention, the pharmacologically active agent is present in the dosage form as a free base. In another aspect of the invention, the active agent is an opioid free base, particularly oxycodone in free base form. In a particularly preferred embodiment of the invention, the carrier system is further characterized by the absence of any significant effect on absorption of the pharmacologically active agent from the dosage form upon co-ingestion of the dosage form with ethanol by a subject.

In another particularly preferred embodiment of the invention, a controlled release oral pharmaceutical dosage form is provided that includes an opioid active agent, where the dosage form provides effective analgesia to a subject when dosed on a twice per day (BID) dosing schedule, and further where the dosage form has one or more abuse-resistant performance features (that may be assessed, for example, using the methodology of Examples 4 and 8). As used herein, the term "controlled release" is used in its broadest sense to include any physical and/or chemical association of a dosage form (containing, including or consisting of a pharmaceutical formulation) with one or more active agents that provides for a controlled release (e.g., extended release, delayed release or a release performance that is in any other way attenuated or altered from immediate release) of the active agent to become pharmacologically available in the system of a recipient. In addition, a dosage form provides "effective analgesia" to a subject when dosed on a twice per day (BID) dosing schedule when administration of such dosage form elicits alleviation (e.g., amelioration, attenuation, reduction, diminishment, blockage, inhibition or prevention) of at least one sign or symptom of a pain symptom, including symptoms of acute or chronic pain. The ability of a dosage form to provide for effective analgesia can be readily assessed by the skilled person using standard clinical trial techniques including those employed in Example 7f.

In particular embodiments, the controlled release dosage forms provide for one or more of the following abuse-resistant performance features: (a) when exposed to extraction in 100 proof ethanol at room temperature for 5 minutes, the dosage form releases less than about 5% of the opioid, preferably less than about 2% of the opioid; (b) when exposed to extraction in vinegar at room temperature for 5 minutes, the dosage form releases less than about 5% of the opioid, preferably less than about 2% of the opioid; (c) when exposed to extraction in saturated baking soda solution at room temperature for 5 minutes, the dosage form releases less than about 5% of the opioid, preferably less than about 2% of the opioid; (d) when exposed to extraction in a cola soft drink at room temperature for 5 minutes, the dosage form releases less than about 10% of the opioid, preferably less than about 5% of the opioid; (e) when exposed to extraction in 100 proof ethanol at room temperature for 60 minutes, the dosage form releases less than about 20% of the opioid, preferably less than about 11% of the opioid; (f) when exposed to extraction in vinegar at room temperature for 60 minutes, the dosage form releases less than about 20% of the opioid, preferably less than about 12% of the opioid; (g) when exposed to extraction in saturated baking soda solution at room temperature for 60 minutes, the dosage form releases less than about 20% of the opioid, preferably less than about 12% of the opioid; (h) when exposed to extraction in a cola soft drink at room temperature for 60 minutes, the dosage form releases less than about 30% of the opioid, preferably less than about 22% of the opioid; (i) when exposed to extraction in 100 proof ethanol at 60° C. for 5 minutes, the dosage form releases less than about 15% of the opioid, preferably less than about 11% of the opioid; (j) when exposed to extraction in vinegar at 60° C. for 5 minutes, the dosage form releases less than about 15% of the opioid, preferably less than about 11% of the opioid; (k) when exposed to extraction in saturated baking soda solution at 60° C. for 5 minutes, the dosage form releases less than about 15% of the opioid, preferably less than about 11% of the opioid; (l) when exposed to extraction in a cola soft drink at 60° C. for 5 minutes, the dosage form releases less than about 45% of the opioid, preferably less than about 30% of the opioid; (m) when exposed to extraction in 100 proof ethanol at 60° C. for 60 minutes, the dosage form releases less than about 33% of the opioid, preferably less than about 26% of the opioid; (n) when exposed to extraction in vinegar at 60° C. for 60 minutes, the dosage form releases less than about 33% of the opioid, preferably less than about 20% of the opioid; (o) when exposed to extraction in saturated baking soda solution at 60° C. for 60 minutes, the dosage form releases less than about 33% of the opioid, preferably less than about 23% of the opioid; (p) when exposed to extraction in a cola soft drink at 60° C. for 60 minutes, the dosage form releases less than about 60% of the opioid, preferably less than about 45% of the opioid; (q) when exposed to extraction in a panel of extraction solvents including vinegar, hot tea, saturated baking soda and a cola soft drink, each at 25° C. for 60 minutes, releases less than about 20% of the opioid, preferably less than about 15% of the opioid; (r) when exposed to extraction in a panel of aqueous buffer extraction solutions ranging from pH 1 to pH 12, each at 25° C. for 60 minutes, releases less than about 15% of the opioid, preferably less than about 12% of the opioid; (s) when physically disrupted by crushing the dosage form and exposed to extraction in a panel of aqueous extraction solutions including water at 25° C., water at 60-70° C., 0.1N HCL at 25° C., and 100 proof ethanol at 25° C., each for 60 minutes, releases less than about 40% of the opioid, preferably less than about 35% of the opioid; and/or (t) when physically disrupted by microwaving the dosage form and then exposed to extraction in a panel of aqueous extraction solutions including water, 0.1N HCL, and 100 proof ethanol, each at 25° C. for 60 minutes, releases less than about 25% of said opioid, preferably less than about 20% of the opioid. All of these abuse-resistant performance features can be readily assessed using standard techniques, such as the techniques described in Example 4. Alternatively, or in addition, the above-described controlled release dosage forms may provide one or more of the following abuse-resistant performance features: (a) the dosage form is not subject to dose dumping as a result of physical disruption of the controlled release formulation by chewing, holding in the buccal cavity, or co-ingestion of alcohol (e.g., 4% ethanol (beer), 20% ethanol (fortified wine), or 40% ethanol (spirits)); (b) the dosage form is not subject to inhalation abuse techniques (e.g., vaporization or smoking, or crushing and snorting); and/or (c) the dosage form is not subject to injection abuse techniques (e.g., the formulation in the dosage form is not syringeable and/or injectable). All of these abuse-resistant performance features can be readily assessed using standard techniques, such as the techniques described in Example 8.

In certain preferred embodiments, the opioid is oxycodone, oxymorphone, hydrocodone, or hydromorphone and can be present in either salt or free base form. In one particularly preferred embodiment, the opioid is oxycodone.

The pharmacologically active agents that are included in the abuse-resistant oral pharmaceutical dosage forms of the present invention may include any type of biologically active compound or composition of matter which, when administered to an organism (human or animal subject) induces a desired pharmacologic and/or physiologic effect by local and/or systemic action. The term therefore encompasses and can be used interchangeably with those compounds or chemicals traditionally regarded as drugs, biopharmaceuticals (including molecules such as peptides, proteins, nucleic acids), and vaccines. The term further encompasses those compounds or chemicals traditionally regarded as diagnostic agents.

Accordingly, examples of such biologically active compounds or compositions of matter useful in the practice of the invention include opioids, CNS depressants and stimulants, as well as proteins, hormones, chemotherapeutic agents, anti-nausea medication, antibiotics, antivirals and other agents. One class of biologically active compounds that is of particular interest herein is the opioids class, which includes alfentanil, allylprodine, alphaprodine, anileridine, apomorphine, apocodeine, benzylmorphine, bezitramide, buprenorphine, butorphanol, clonitazene, codeine, cyclazocine, cyclorphen, cyprenorphine, desomorphine, dextromoramide, dextromethorphan, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, levomethorphan, lofentanil, meperidine, meptazinol, metazocine, methadone, methylmorphine, metopon, morphine, myrophine, nalbuphine, narceine, nicomorphine, norlevorphanol, normethadone, nalorphine, normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, propheptazine, promedol, profadol, properidine, propiram, propoxyphene, remifentanyl, sufentanyl, tramadol, tilidine, naltrexone, naloxone, nalmefene, methylnaltrexone, naloxone methiodide, nalorphine, naloxonazine, nalide, nalmexone, nalbuphine, nalorphine dinicotinate, naltrindole (NTI), naltrindole isothiocyanate, (NTII), naltriben (NTB), nor-binaltorphimine (nor-BNI), tapentadol, beta-funaltrexamine (b-FNA), BNTX, cyprodime, ICI-174,864, LY117413, MR2266, etorphine, DAMGO, CTOP, diprenorphine, naloxone benzoylhydrazone, bremazocine, ethylketocyclazocine, U50,488, U69,593, spiradoline, DPDPE, [D-Ala2,Glu4] deltorphin, DSLET, Met-enkephalin, Leu-enkephalin, ß-endorphin, dynorphin A, dynorphin B, a-neoendorphin, or an opioid having the same pentacyclic nucleus as nalmefene, naltrexone, buprenorphine, levorphanol, meptazinol, pentazocine, dezocine, or their pharmacologically effective esters or salts. Preferred opioids for use in the practice of the present invention include morphine, hydrocodone, oxycodone, codeine, fentanyl (and its relatives), hydromorphone, meperidine, methadone, oxymorphone, propoxyphene or tramadol, or mixtures thereof. More preferred opioids include oxycodone, oxymorphone, hydrocodone and hydromorphone. In regard to the preferred opioid oxycodone, it may be beneficial to provide formulations that have a reduced level of peroxide degradation products such as alpha beta unsaturated ketones (ABUK). In such cases, the controlled release carrier system can be subjected to peroxide contaminant reduction and/or removal techniques in accordance with known methods.

Other biologically active compounds or compositions of matter useful in the practice of the invention include prochlorperazine edisylate, ferrous sulfate, aminocaproic acid, potassium chloride, mecamylamine, procainamide, amphetamine (all forms including dexamphetamine, dextroamphetamine, d-S-amphetamine, and levoamphetamine), benzphetamine, isoproternol, methamphetamine, dexmethamphetamine, phenmetrazine, bethanechol, metacholine, pilocarpine, atropine, methascopolamine, isopropamide, tridihexethyl, phenformin, methylphenidate (all forms including dexmethylphenidate, d-threo methylphenidate, and dl-threo methylphenidate), oxprenolol, metroprolol, cimetidine, diphenidol, meclizine, prochlorperazine, phenoxybenzamine, thiethylperazine, anisindone, diphenadione erythrityl, digoxin, isofurophate, reserpine, acetazolamide, methazolamide, bendroflumethiazide, chlorpropamide, tolazamide, chlormadinone, phenaglycodol, allopurinol, aluminum aspirin, methotrexate, acetyl sulfisoxazole, erythromycin, progestins, estrogenic progrestational, corticosteroids, hydrocortisone, hydrocorticosterone acetate, cortisone acetate, triamcinolone, methyltesterone, 17 beta.-estradiol, ethinyl estradiol, ethinyl estradiol 3-methyl ether, prednisolone, 17-hydroxyprogesterone acetate, 19-nor-progesterone, norgestrel, orethindone, norethiderone, progesterone, norgestrone, norethynodrel, aspirin, indomethacin, naproxen, fenoprofen, sulindac, diclofenac, indoprofen, nitroglycerin, propranolol, metroprolol, sodium valproate, valproic acid, taxanes such as paclitaxel, camptothecins such as 9-aminocamptothecin, oxprenolol, timolol, atenolol, alprenolol, cimetidine, clonidine, imipramine, levodopa, chloropropmazine, resperine, methyldopa, dihydroxyphenylalanine, pivaloyloxyethyl ester of .alpha.-methyldopa hydrochloride, theophylline, calcium gluconate ferrous lactate, ketoprofen, ibuprofen, cephalexin, haloperiodol, zomepirac, vincamine, diazepam, phenoxybenzamine, .beta.-blocking agents, calcium-channel blocking drugs such as nifedipine, diltiazen, verapamil, lisinopril, captopril, ramipril, fosimopril, benazepril, libenzapril, cilazapril cilazaprilat, perindopril, zofenopril, enalapril, indalapril, qumapril, and the like.

Still other biologically active compounds or compositions of matter useful in the practice of the invention include immunosuppressants, antioxidants, anesthetics, chemotherapeutic agents, steroids (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds, antipsychotics, and radiation absorbers, including UV-absorbers, chemotherapeutic agents, anti-nausea medication, and the like. Thus, anti-infectives such as nitrofurazone, sodium propionate, antibiotics, including penicillin, tetracycline, oxytetracycline, chlorotetracycline, bacitracin, nystatin, streptomycin, neomycin, polymyxin, gramicidin, chloramphenicol, erythromycin, and azithromycin; sulfonamides, including sulfacetamide, sulfamethizole, sulfamethazine, sulfadiazine, sulfamerazine, and sulfisoxazole, and anti-virals including idoxuridine; antiallergenics such as antazoline, methapyritene, chlorpheniramine, pyrilamine prophenpyridamine, hydrocortisone, cortisone, hydrocortisone acetate, dexamethasone, dexamethasone 21-phosphate, fluocinolone, triamcinolone, medrysone, prednisolone, prednisolone 21-sodium succinate, and prednisolone acetate; desensitizing agents such as ragweed pollen antigens, hay fever pollen antigens, dust antigen and milk antigen; vaccines such as smallpox, yellow fever, distemper, hog cholera, chicken pox, antivenom, scarlet fever, dyptheria toxoid, tetanus toxoid, pigeon pox, whooping cough, influenzae rabies, mumps, measles, poliomyelitic, and Newcastle disease; decongestants such as phenylephrine, naphazoline, and tetrahydrazoline; miotics and anticholinesterases such as pilocarpine, esperine salicylate, carbachol, diisopropyl fluorophosphate, phospholine iodide, and demecarium bromide; parasympatholytics such as atropine sulfate, cyclopentolate, homatropine, scopolamine, tropicamide, eucatropine, and hydroxyamphetamine; sympathomimetics such as epinephrine; sedatives and hypnotics such as pentobarbital sodium, phenobarbital, secobarbital sodium, codeine, (a-bromoisovaleryl) urea, carbromal; psychic energizers such as 3-(2-aminopropyl) indole acetate and 3-(2-aminobutyl) indole acetate; tranquilizers such as reserpine, chlorpromayline, and thiopropazate; androgenic steroids such as methyl-testosterone and fluorymesterone; estrogens such as estrone, 17-.beta.-estradiol, ethinyl estradiol, and diethyl stilbestrol; progestational agents such as progesterone, megestrol, melengestrol, chlormadinone, ethisterone, norethynodrel, 19-norprogesterone, norethindrone, medroxyprogesterone and 17-.beta.-hydroxy-progesterone; humoral agents such as the prostaglandins, for example $PGE_1$, $PGE_2$ and $PGF_2$; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine, antihistamines such as diphenhydramine, dimenhydrinate, tripelennamine, perphenazine, and chlorphenazine; cardioactive agents such as dibenzhydroflume thiazide, flumethiazide, chlorothiazide, and aminotrate; nutritional agents such as vitamins, natural and synthetic bioactive peptides and proteins, including growth factors, cell adhesion factors, cytokines, and biological response modifiers are all suitable for use herein as the active agent. These and other active agents are readily available to those of ordinary skill in the art and are described in detail by references such as: *Pharmaceutical Sciences*, by Remington, 14th Ed., 1979, published by Mack Publishing Co., Easton, Pa.; *Medical Chemistry*, 3rd Ed., Vol. 1 and 2, by Burger, published by Wiley-Interscience, New York; and, *Physician's Desk Reference*, 56th Ed., 2002, published by Medical Economics Co., New Jersey.

The active agent can be present in the formulations used to make the dosage forms of the present invention in a neutral form, as a free base form, or in the form of a pharmaceutically acceptable salt. The term "pharmaceutically acceptable salt," as used herein, intends those salts that retain the biological effectiveness and properties of neutral active agents and are not otherwise unacceptable for pharmaceutical use. Pharmaceutically acceptable salts include salts of acidic or basic groups, which groups may be present in the active agents. Those active agents that are basic in nature are capable of forming a wide variety of salts with various inorganic and organic acids. Pharmaceutically acceptable acid addition salts of basic active agents suitable for use herein are those that form non-toxic acid addition salts, i.e., salts comprising pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Active agents that include an amino moiety may form pharmaceutically acceptable salts with various amino acids, in addition to the acids mentioned above. Suitable base salts can be formed from bases which form non-toxic salts, for example, aluminium, calcium, lithium, magnesium, potassium, sodium, zinc and diethanolamine salts. See, e.g., Berge et al. (1977) *J. Pharm. Sci.* 66:1-19.

In the abuse-resistant oral pharmaceutical dosage forms of the present invention, the pharmacologically active agent will be dissolved (fully or partially) or dispersed within the controlled release carrier system. The phrase "dissolved or dispersed" is intended to encompass all means of establishing a presence of the active agent in the subject controlled release carrier system and includes dissolution, dispersion, partial dissolution and dispersion, and/or suspension and the like. In addition, in certain embodiments of the invention wherein the active agent is in a solid particulate form suspended within the controlled release carrier system, the active agent particulate may be pre-treated with a micronization process such as those described in Examples 1 and 2 below to provide a particle population having a substantially homogeneous particle size the bulk of which fall within the micron (μm) range.

The pharmacologically active agent, which can include one or more suitable active agent, will be present in the formulation used to make the present dosage forms in an amount of from about 95 to about 0.1 percent by weight relative to the total weight of the formulation (wt %), in an amount of from about 40 to 1 wt %, in an amount of from about 35 to 1.3 wt %, or in an amount of about 30 to 5 wt %, depending upon the identity of the active agent, the desired dose required for the dosage form, and the intended use thereof. In certain preferred embodiments, the active agent is present in the formulation in an amount of about 1 to about 10 wt %, and can thus be loaded into a suitable dosage form to provide single dosages ranging from about 0.01 mg to 1000 mg, or from about 0.1 mg to 500 mg, or from about 2 mg to 250 mg, or from about 2 mg to 250 mg, or from about 2 mg to 150 mg, or from about 5 mg to 100 mg, or from about 5 mg to 80 mg. For certain preferred embodiments that include an opioid active agent, exemplary single dosages include, but are not limited to, 1, 2, 3, 5, 10, 15, 20, 30, 40, 60, 80 100, and 160 mg. In other preferred embodiments that include a CNS depressant or CNS stimulant, exemplary single dosages include, but are not limited to, 5, 10, 15, 18, 20, 25, 27, 30, 36, 40, 50, 54, 60, 70, 80 and 100 mg. The precise amount of active agent desired can be determined by routine methods well known to pharmacological arts, and will depend on the type of agent, and the pharmacokinetics and pharmacodynamics of that agent.

The controlled release carrier systems that are employed in the abuse-resistant oral pharmaceutical dosage forms disclosed and claimed herein are formed by the combination of a High Viscosity Liquid Carrier Material ("HVLCM"), a network former, and a rheology modifier. An HVLCM is a non-polymeric, non-water soluble liquid material having a viscosity of at least 5,000 cP at 37° C. that will not crystallize neat under ambient or physiological conditions. The term "non-water soluble" refers to a material that is soluble in water to a degree of less than one percent by weight under ambient conditions. The term "non-polymeric" refers to esters or mixed esters having essentially no repeating units in the acid moiety of the ester, as well as esters or mixed esters having acid moieties wherein functional units in the acid moiety are repeated a small number of times (i.e., oligomers). Generally, materials having more than five identical and adjacent repeating units or mers in the acid moiety of the ester are excluded by the term "non-polymeric" as used herein, but materials containing dimers, trimers, tetramers, or pentamers are included within the scope of this term. When the ester is formed from hydroxy-containing carboxylic acid moieties that can further esterify, such as lactic acid or glycolic acid, the number of repeat units is calculated based upon the number of lactide or glycolide moieties, rather than upon the number of lactic acid or glycolic acid moieties, where a lactide repeat unit contains two lactic acid moieties esterified by their respective hydroxy and carboxy moieties, and where a glycolide repeat unit contains two glycolic acid moieties esterified by their respective hydroxy and carboxy moieties. Esters having 1 to about 20 etherified polyols in the alcohol moiety thereof, or 1 to about 10 glycerol moieties in the alcohol moiety thereof, are considered non-polymeric as that term is used herein. HVLCMs may be carbohydrate-based, and may include one or more cyclic carbohydrates chemically combined with one or more carboxylic acids. HVLCMs also include non-polymeric esters or mixed esters of one or more carboxylic acids, having a viscosity of at least 5,000 cP at 37° C., that do not crystallize neat under ambient or physiological conditions, wherein when the ester contains an alcohol moiety (e.g., glycerol). The ester may, for example comprise from about 2 to about 20 hydroxy acid moieties. Various HVLCMs used with the present controlled release carrier systems are described in U.S. Pat. Nos. 5,747,058; 5,968,542; and 6,413,536. The present invention may employ any HVLCM described in these patents but is not limited to any specifically described materials. The HVLCM is typically present in a dosage form according to the invention in an amount of from 30 to 60%, for example from 35 to 45%, by weight.

Figure 34:
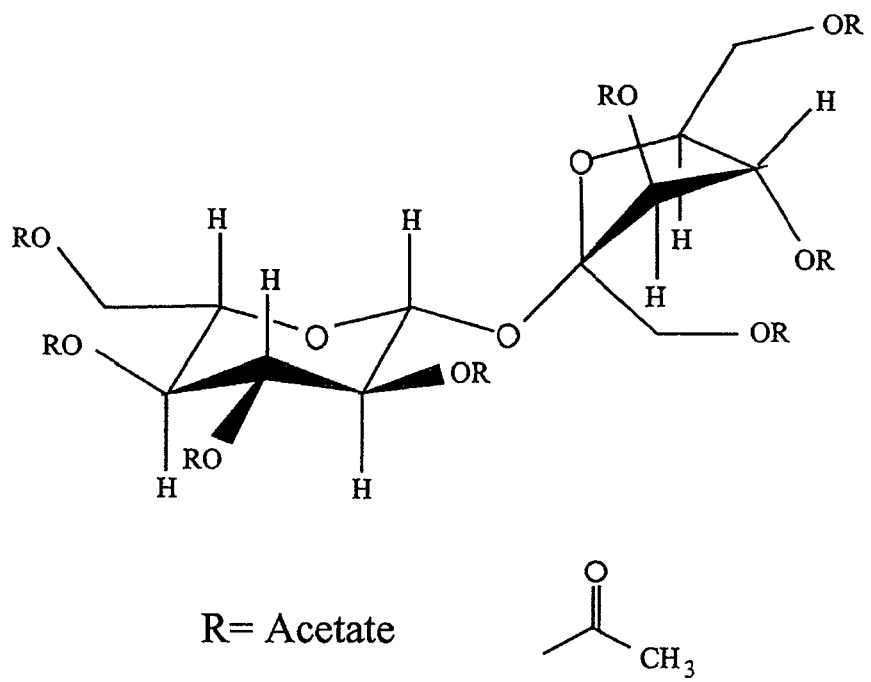
FIG. 34 depicts the chemical structure of sucrose acetate isobutyrate (SAM).

In certain preferred embodiments of the invention, the controlled release carrier system comprises Sucrose Acetate Isobutyrate ("SAIB") as the HVLCM. SAIB is a non-polymeric highly viscous liquid at temperatures ranging from −80° C. to over 100° C., it is a fully esterified sucrose derivative, at a nominal ratio of six isobutyrates to two acetates. The chemical structure of SAIB is depicted herein as FIG. 34. The SAIB material is available from a variety of commercial sources including Eastman Chemical Company, where it is available as a mixed ester that does not crystallize but exists as a very highly viscous liquid. It is a hydrophobic, non-crystalline, low molecular weight molecule that is water insoluble and has a viscosity that varies with temperature. For example, pure SAIB exhibits a viscosity of approximately 2,000,000 centipoise (cP) at ambient temperature (RT) and approximately 600 cP at 80° C. The SAIB material has unique solution-viscosity relationship in that a SAIB solution established in a number of organic solvents has a significantly lower viscosity value than the pure SAIB material, and therefore the SAIB-organic solvent solutions render themselves capable of processing using conventional equipment such as mixers, liquid pumps and capsule production machines. SAIB also has applications in drug formulation and delivery, for example as described in U.S. Pat. Nos. 5,747,058; 5,968,542; 6,413,536; and 6,498,153. In the present invention, SAIB may be used as the HVLCM and may be present in quantities that vary significantly. For example, quantities of at least about 30, 35, 40, 50, 60, or from 61 to 99.9 percent by weight of the HVLCM, which can include one or more suitable HVLCM, relative to the total weight of the formulation (wt %) used to make the dosage form can be used. Typically, SAIB is present in a dosage form according to the invention in an amount of from 30 to 60% by weight, for example from 35 to 45% by weight.

In certain circumstances, it may be beneficial to provide a SAIB carrier material having a lower peroxide level to avoid peroxide-based degradation of various components of the controlled release carrier system and/or active agent. See, e.g., U.S. Patent Application Publication Number US 2007/0027105, "Peroxide Removal From Drug Delivery Vehicle". Various specific pharmaceutical formulations containing SAIB at about 40 wt % that are used to produce suitable dosage forms are discussed in the examples.

A "rheology modifier", as used herein, refers to a substance that possesses both a hydrophobic and a hydrophilic moiety. Rheology modifiers used in the practice of the invention generally have a logarithm of octanol-water partition coefficient ("Log P") of between about −7 and +15, preferably between −5 and +10, more preferable between −1 and +7. In addition, the rheology modifier will typically have a molecular weight of around 1,000 daltons or less. Rheology refers to the property of deformation and/or flow of a liquid material, and rheology modifiers are used to modify (lower) viscosity and (increase) flowability of the HVLCM and other constituents used in the controlled release carrier system, that is, to plasticize the HVLCM and other constituents. The rheology modifier may thus be a plasticizer, typically a plasticizer for the HVLCM. Rheology modifiers that are useful herein include, for example, caprylic/capric triglyceride (Migliol 810), isopropyl myristate ("IPM"), ethyl oleate, triethyl citrate, dimethyl phthalate, labrafil, labrasol, Gelucires, and benzyl benzoate. In certain preferred embodiments of the invention, the rheology modifier is IPM. The IPM material is a pharmaceutically acceptable hydrophobic solvent. The rheology modifier, which can include one or more suitable rheology modifier material, can be present in the formulations at from about 0.1 to about 20 percent by weight relative to the total weight of the formulation (wt %) used to produce the dosage forms of the present invention, preferably at from about 1 to about 18 wt %, and more preferably at from about 2 to about 15 wt %.

A "network former" refers to a material or compound that forms a network structure when introduced into a liquid medium (such as a HVLCM or a controlled release carrier system comprising an HVLCM). Network formers may be added to the liquid formulation such that, upon exposure to an aqueous environment, they form a three dimensional network within the formulation. While not wishing to be bound by any particular theory, it is believed that the network former allows the formation of a micro-network within the formulation upon exposure to an aqueous environment. This micro-network formation appears to be due, at least in part, to a phase inversion (e.g., a change in glass transition temperature, $T_g$) of the network former. The result is believed to be a skin or surface layer of precipitated network former at the interface between the dosage form and the aqueous environment of the GI tract, as well as the formation of a three-dimensional micro-network of precipitated network former within the dosage form. The network former is selected so as to have good solubility in the selected solvent used in the formulations, for example a solubility of between about 0.1 and 20 wt %. Additionally, good network formers will typically have a Log P between about −1 to 7. Suitable network formers include, for example, cellulose acetate butyrate ("CAB"), carbohydrate polymers, organic acids of carbohydrate polymers and other polymers, hydrogels, cellulose acetate phthalate, ethyl cellulose, Pluronic, Eudragit, Carbomer, hydroxyl propyl methyl cellulose, other cellulose acetates such as cellulose triacetate, PMMA, as well as any other material capable of associating, aligning or congealing to form three-dimensional networks in an aqueous environment. A particularly preferred network former for use in the practice of the invention is cellulose acetate butyrate grade 381-20 BP ("CAB 381-20" available from Eastman Chemicals). CAB 381-20 is a non-biodegradable polymer material that has the following chemical and physical characteristics: butyryl content of 36%, acetyl content of 15.5%, hydroxy content of 0.8%, a melting point of 185-196° C., glass transition temperature of 128° C., and a molecular weight number average of 66,000 to 83,000. Preferably, if a CAB material is used in the present formulations, it should be subjected to an ethanol washing step (and subsequent drying step) prior to addition to the formulation in order to remove potential contaminants therefrom. The network former, which can include one or more suitable network former materials, can be present in the formulations at from about 0.1 to about 20 percent by weight relative to the total weight of the formulation (wt %), preferably at from about 1 to about 18 wt %, more preferably at from about 2 to about 10 wt %, and even more preferably at from about 4 to about 6 wt %.

In addition to the combination of the HVLCM, network former and rheology modifier materials discussed above, the controlled release carrier systems that are employed in the abuse-resistant oral pharmaceutical dosage forms disclosed and claimed herein can further include a number additional excipient materials including solvents, viscosity enhancing agents, hydrophilic agents, surfactants, and stabilizing agents.

The term "solvent", as used herein, refers to any substance that dissolves another substance (solute). Solvents may be used in the controlled release carrier systems of the present invention to dissolve one or more of the following constituents: HVCLMs; active agents; network formers; rheology modifiers; viscosity enhancing agents; hydrophilic agents; surfactants; and stabilizing agents. Preferably, the solvent can dissolve both the HVLCM and the network former. In addition, materials that can serve as rheology modifiers in certain controlled release carrier systems can also serve the function as a solvent to one or more constituent (e.g., the HVLCM, or the active agent), or serve solely as a solvent in other carrier systems. One example of such a solvent is IPM, which is a hydrophobic solvent. In one embodiment of the invention, therefore, a dosage form may comprise both a hydrophilic solvent and a hydrophobic solvent. Organic solvents suitable for use with the present invention include, but are not limited to: substituted heterocyclic compounds such as N-methyl-2-pyrrolidone (NMP) and 2-pyrrolidone (2-pyrol); triacetin; esters of carbonic acid and alkyl alcohols such as propylene carbonate, ethylene carbonate and dimethyl carbonate; fatty acids such as acetic acid, lactic acid and heptanoic acid; alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, isopropyl myristate (IPM), dimethyl adipate, dimethyl succinate, dimethyl oxalate, dimethyl citrate, triethyl citrate, acetyl tributyl citrate, glyceryl triacetate; alkyl ketones such as acetone and methyl ethyl ketone; ether alcohols such as 2-ethoxyethanol, ethylene glycol dimethyl ether, glycofurol and glycerol formal; alcohols such as benzyl alcohol, ethanol and propanol; polyhydroxy alcohols such as propylene glycol, polyethylene glycol (PEG), glycerin (glycerol), 1,3-butyleneglycol, and isopropylidene glycol (2,2-dimethyl-1,3-dioxolone-4-methanol); Solketal; dialkylamides such as dimethylformamide, dimethylacetamide; dimethylsulfoxide (DMSO) and dimethylsulfone; tetrahydrofuran; lactones such as ε-caprolactone and butyrolactone; cyclic alkyl amides such as caprolactam; aromatic amides such as N,N-dimethyl-m-toluamide, and 1-dodecylazacycloheptan-2-one; and the like; and mixtures and combinations thereof. Preferred solvents include triacetin, N-methyl-2-pyrrolidone, 2-pyrrolidone, dimethylsulfoxide, ethyl lactate, propylene carbonate, and glycofurol. In one particular preferred embodiment, the solvent is triacetin which is a hydrophilic solvent. The hydrophilic triacetin solvent can preferably be combined with the IPM rheology modifier which is a hydrophobic solvent to provide a solvent hydrophobic/hydrophilic solvent system within the controlled release carrier system. The solvent, which can include one or more suitable solvent materials, can be present in the formulations at from about 0.1 to about 40 percent by weight relative to the total weight of the formulation (wt %), preferably at from about 1 to about 35 wt %, more preferably at from about 10 to about 30 wt %, and even more preferably at from about 15 to about 28 wt %.

A "viscosity enhancing agent" or "second viscosity enhancing agent" is a material that can be added to the controlled release carrier system in order to increase the viscosity of the resulting carrier system. Viscosity enhancing agents can be selected to have good hydrogen bonding capability, such as a bonding capability greater than or equal to one per molecule. In certain cases, the viscosity enhancing agent has very low to no significant solubility in the formulation. If the agent is soluble, then preferably the solubility is less than 50 wt %. For inorganic or mineral viscosity enhancing agents, it is preferable if the material has a specific surface area greater than or equal to about 100 m2/g. For those skilled in the use of pharmaceutical systems using an HVLCM, particularly SAIB, it is generally known that as the viscosity of the controlled release system increases, e.g., as a solvent for the HVLCM leaves the system or by addition of a polymer material, release of the active agent from that carrier system will typically slow down since the HVLCM carrier matrix material has become more resistant to diffusion of the agent from the matrix material. Accordingly, it may be counter-intuitive for the skilled person to purposefully enhance (increase) the overall viscosity of the present controlled release carrier systems when it is desired to enhance the in vivo pharmacological performance of such systems to, for example, extend and/or increase the release performance to increase bioavailability of an active agent. However, it has been found that in certain dosage forms of the present invention, the addition of a viscosity enhancing agent can be used to provide dosage forms having enhanced in vivo pharmacological performance as well as enhanced safety features and/or abuse-resistance properties as required herein. Suitable viscosity enhancing agents include biodegradable and non-biodegradable polymer materials. Non-limiting examples of suitable biodegradable polymers and oligomers include: poly(lactide), poly(lactide-co-glycolide), poly(glycolide), poly(caprolactone), polyamides, polyanhydrides, polyamino acids, polyorthoesters, polycyanoacrylates, poly(phosphazines), poly(phosphoesters), polyesteramides, polydioxanones, polyacetals, polyketals, polycarbonates, polyorthocarbonates, degradable polyurethanes, polyhydroxybutyrates, polyhydroxyvalerates, polyalkylene oxalates, polyalkylene succinates, poly(malic acid), chitin, chitosan, and copolymers, terpolymers, oxidized cellulose, hydroxyethyl cellulose, or combinations or mixtures of the above materials. Suitable non-biodegradable polymers include: polyacrylates, ethylene-vinyl acetate polymers, cellulose and cellulose derivatives, acyl substituted cellulose acetates and derivatives thereof including cellulose acetate butyrate (CAB), which is also used herein as a network former, non-erodible polyurethanes, polystyrenes, polyvinyl chloride, polyvinyl fluoride, polyvinyl (imidazole), chlorosulphonated polyolefins, polyethylene oxide, and polyethylene. Other suitable viscosity enhancing materials include stiffening agents such as clay compounds, including, talc, bentonite and kaolin, and metal oxides including silicon dioxide, zinc oxide, magnesium oxide, titanium oxide, and calcium oxide. In one preferred embodiment of the invention, a colloidal silicon dioxide (Cab-O-Sil) is used as a viscosity enhancing agent in a controlled release carrier system that further contains CAB as a network former. The colloidal silicon dioxide may further be characterized as a thixtropic agent since it is thought to enhance viscosity at resting conditions, which may be useful for product stability purposes, while also serving as viscosity thinning agent under conditions of mechanical stress which may be useful for controlled release performance. The viscosity enhancing agent, which can include one or more suitable viscosity enhancing material, can be present in the formulations at from about 0.01 to about 10 percent by weight relative to the total weight of the formulation (wt %) used to produce the dosage forms of the present invention, preferably at from about 0.1 to about 6 wt %, and more preferably at from about 1 to about 2 wt %.

Materials that can be used as "hydrophilic agents" in the practice of the invention include those that have natural affinity for aqueous systems. A material may be regarded as a hydrophilic agent for the purposes of this invention if the material displays a water sorption between about 10 to 100% (w/w). Hydrophilic agents will have a low Log P value. As discussed herein above, there are a number of constituents used to produce the controlled release carrier systems of the present invention that can be classed as a hydrophilic material (e.g., a hydrophilic solvent), or at least a material having a hydrophilic portion (e.g., a rheology modifier). Since the HVLCM material used in the present carrier systems is hydrophobic, it may be useful to include other materials in the carrier system that are hydrophilic in order to provide a carrier system that is balanced to have both hydrophobic and hydrophilic characteristics. For example, it is believed that the inclusion of one or more hydrophilic agent in the controlled release carrier systems of the present invention may participate in the control of active agent diffusion from the carrier system. Accordingly, suitable hydrophilic agents include, but are not limited to, sugars such as sorbitol, lactose, mannitol, fructose, sucrose and dextrose, salts such as sodium chloride and sodium carbonate, starches, hyaluronic acid, glycine, fibrin, collagen, polymers such as hydroxylpropylcellulose ("HPC"), carboxymethylcellulose, hydroxyethyl cellulose ("HEC"); polyethylene glycol and polyvinylpyrrolidone, and the like. In a particularly preferred embodiment, a controlled release carrier system is provided that includes HEC as a hydrophilic agent. The hydrophilic agent, which can include one or more suitable hydrophilic agent material, can be present in the formulations at from about 0.1 to about 10 percent by weight relative to the total weight of the formulation (wt %) used to produce the dosage forms of the present invention, preferably at from about 1 to about 8 wt %, and more preferably at from about 3 to about 6 wt %. The hydrophilic agent may alternatively constitute the "first viscosity enhancing agent" of an embodiment of the invention.

Materials that can be used as "surfactants" in the practice of the invention include neutral and/or anionic/cationic excipients. Accordingly, suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics); polyoxyethylenesorbitans, e.g., TWEEN® surfactants (Atlas Chemical Industries); polysorbates; polyoxyethylene ethers, e.g. Brij; pharmaceutically acceptable fatty acid esters, e.g., lauryl sulfate and salts thereof; ampiphilic surfactants (glycerides, etc.); Gelucires (saturated polyglycolized glyceride (e.g., Gattefosse brand); and like materials. Surfactants, which can include one or more suitable surfactant material, can be present in the formulations at from about 0.01 to about 5 percent by weight relative to the total weight of the formulation (wt %) used to produce the dosage forms of the present invention, preferably at from about 0.1 to about 5 wt %, and more preferably at from about 0.1 to about 3 wt %.

Materials that can be used as stabilizing agents in the practice of the invention include any material or substance that can inhibit or reduce degradation (e.g., by chemical reactions) of other substances or substances in the controlled release carrier system with which the stabilizer is mixed. Exemplary stabilizers typically are antioxidants that prevent oxidative damage and degradation, e.g., sodium citrate, ascorbyl plamitate, vitamin A, and propyl gallate and/or reducing agents. Other examples include ascorbic acid, vitamin E, sodium bisulfite, butylhydroxyl toluene ("BHT"), BHA, acetylcysteine, monothioglycerol, phenyl-alpha-napthylamine, lecithin, and EDTA. These stabilizing materials, which can include one or more suitable such materials, can be present in the formulations at from about 0.001 to about 2 percent by weight relative to the total weight of the formulation (wt %) used to produce the dosage forms of the present invention, preferably at from about 0.01 to about 0.1 wt %, and more preferably at from about 0.01 to about 0.02 wt %.

An oral pharmaceutical dosage form produced according to the invention and comprising a pharmacologically active agent and a controlled release carrier system which comprises a HVLCM, a network former, a rheology modifier, a hydrophilic agent and a solvent can thus contain: (a) from 1.3 to 35 wt % such as 5 to 10 wt % of the pharmacologically active agent; (b) from 2 to 10 wt % such as 4 to 6 wt % of the network former; (c) from 0.1 to 20 wt % for example 2 to 15 wt % of the rheology modifier; (d) from 1 to 8 wt % for example 3 to 6 wt % of the hydrophilic agent; (e) from 10 to 40 wt % for example from 10 to 30 wt % of the solvent; and (f) from 30 to 60 wt % such as 35 to 45 wt % of the HVLCM. Typically, the HVLCM is sucrose acetate isobutyrate (SAIB); the network former is selected from cellulose acetate butyrate (CAB), cellulose acetate phthalate, ethyl cellulose, hydroxypropylmethyl cellulose and cellulose triacetate; the rheology modifier is selected from isopropyl myristate (IPM), caprylic/capric triglyceride, ethyl oleate, triethyl citrate, dimethyl phthalate and benzyl benzoate; the hydrophilic agent is selected from hydroxyethylcellulose (HEC), hydroxypropylcellulose, caboxymethylcellulose, polyethylene glycol and polyvinylpyrrolidone; and the solvent is selected from triacetin, N-methyl-2-pyrrolidone, 2-pyrrolidone, dimethylsulfoxide, ethyl lactate, propylene carbonate and glycofurol. Preferably, the HVLCM is SAIB, the network former is CAB, the rheology modifier is IPM, the hydrophilic agent is HEC, and the solvent is triacetin.

The controlled release carrier system can further comprise a viscosity enhancing agent such as silicon dioxide. The viscosity enhancing agent is typically present in an amount from 0.1 to 6 wt % such as 1 to 2 wt %.

In an alternative embodiment, an oral pharmaceutical dosage form produced according to the invention and comprising a pharmacologically active agent and a controlled release carrier system which comprises a HVLCM, a network former, a first viscosity enhancing agent, a hydrophilic solvent and a hydrophobic solvent, can contain: (a) from 1.3 to 35 wt % such as 5 to 10 wt % of the pharmacologically active agent; (b) from 2 to 10 wt % such as 4 to 6 wt % of the network former; (c) from 1 to 8 wt % for example 3 to 6 wt % of the first viscosity enhancing agent; (d) from 10 to 40 wt % for example 10 to 30 wt % of the hydrophilic solvent; (e) from 0.1 to 20 wt % for example from 2 to 15 wt % of the hydrophobic solvent; and (f) from 30 to 60 wt % such as 35 to 45 wt % of the HVLCM. Typically in this embodiment the HVLCM is SAIB; the network former is selected from CAB, cellulose acetate phthalate, ethyl cellulose, hydroxypropylmethyl cellulose and cellulose triacetate; the first viscosity enhancing agent is HEC, hydroxypropylcellulose, carboxymethylcellulose, polyethylene glycol and polyvinylpyrrolidone; the hydrophilic solvent is selected from triacetin, N-methyl-2-pyrrolidone, 2-pyrrolidone, dimethylsulfoxide, ethyl lactate, propylene carbonate and glycofurol; and the hydrophobic solvent is IPM. Preferably, the HVLCM is SAIB, the network former is CAB, the first viscosity enhancing agent is HEC, the hydrophilic solvent is triacetin, and the hydrophobic solvent is IPM.

The controlled release system can further comprise a second viscosity enhancing agent such as silicone dioxide. The second viscosity enhancing agent is typically present in an amount from 0.1 to 6 wt % such as 1 to 2 wt %.

Once all of the constituents have been selected to produce a controlled release carrier system in accordance with the present invention, a liquid pharmaceutical formulation can be prepared by simply mixing, for example a HVLCM, a rheology modifier, a network former, the active agent, a solvent and any additional additives. The formulations of the present invention are produced as liquid mixtures, and have a number of excipient ingredients that are in solution, suspension, or in partial solution within the final formulation. Suitable methods for compounding or manufacturing the formulations make use of typical pharmaceutical/chemical mixing and handling apparatus and techniques. Since the liquid formulations of the invention are formed from a number of highly viscous liquids and solids, they will tend to have exceptionally high final viscosities. Accordingly, the specific equipment and techniques employed in the manufacture of such formulations are preferably selected so as to accommodate such material demands. In particular, various excipients such as network formers, are typically added to the formulation mixture in the solid or semi-solid state, and as such they may be screened or otherwise size-reduced prior to addition to a formulation mixing apparatus. Other solid excipients may require melting prior to addition to the liquid mixture. The HVLCM materials are very high viscosity liquid materials, however they tend to exhibit a dramatic reduction in viscosity with increases in heat, and as such the mixing apparatus may be heated to accommodate the addition of the HVLCM material or other similar materials. However, the mixing and processing conditions must take into account the final integrity of the formulation and the mixing conditions are thus preferably selected so as to have a low-sheer effect on the formulation, and/or to avoid any extended or pronounced excursions into high or low heat conditions. Once the formulation has been properly combined, an appropriate amount of the resulting liquid mixture can be placed into a suitable capsule, such as a gelatin capsule or the like to provide an oral pharmaceutical dosage form. Alternative liquid formulations may include emulsifying the mixture in water, and introducing this emulsion into a capsule.

With regard to a formulation that is formed from the mixture of a pharmacologically active agent, a HVLCM, a network former, a rheology modifier, a hydrophilic agent and a solvent, one suitable manufacturing or compounding process includes the steps of: (1) preheating the HVLCM; (ii) mixing the solvent with the preheated HVLCM to form a uniform solution of the HVLCM in the solvent; (iii) dispersing the network former in the solution to dissolve the network former in the solution; mixing from 5 to 30%, for example 10 to 20%, of the rheology modifier or, optionally, a solution of a stabilising agent and from 5 to 30%, for example 10 to 20%, of the rheology modifier with the formulation; (iv) adding and mixing the pharmacologically active agent;

adding and mixing the hydrophilic agent; (v) optionally, adding and mixing a viscosity enhancing agent; and (vi) adding and mixing the balance of the rheology modifier. The process may further include the step of filling capsules with the formulation thus obtained and, optionally, packaging the filled capsules into unit dose blisters or multidose plastic bottles.

Step (i) is carried out to reduce the viscosity of the HVLCM so that it readily flows and other components can be easily mixed into it. Step (i) may be carried out at, for example, from 50 to 65° C. or 50 to 60° C. or 55 to 65°. Typically, steps (ii) to (vi) are each carried out at such a temperature.

With regard to a formulation that is formed from the mixture of a pharmacologically active agent, a HVLCM, a network former, a rheology modifier, a hydrophilic agent and a solvent, a suitable manufacturing or compounding process may include the steps of: (i) preheating the HVLCM; (ii) mixing the solvent with the preheated HVLCM to form a uniform solution of the HVLCM in the solvent; (iii) optionally, mixing a solution of a stabilising agent and from 5 to 30%, for example 10 to 20%, of the rheology modifier with the solution obtained in preceding step; (iv) adding and mixing the rheology modifier or, if step (iii) is effected, the balance of the rheology modifier with the solution obtained in step (ii) or (iii); (v) optionally, adding and mixing a viscosity enhancing agent with the formulation obtained in the preceding step; (vi) adding and dispersing the network former into the solution obtained in step (iv) or, if step (v) is effected, step (v) thereby dissolving the network former in the solution; (vii) adding and mixing the pharmacologically active agent with the formulation obtained in the previous step; and (viii) adding and mixing the hydrophilic agent with the formulation obtained in step (vii).

Furthermore, the process can further include the step of filling capsules with the formulation thus obtained and, optionally, packaging the filled capsules into unit dose blisters or multidose plastic bottles.

Again, step (i) is carried out to reduce the viscosity of the HVLCM so that it readily flows and other components can be easily mixed into it. Step (i) may be carried out at, for example, from 50 to 65° C. or 50 to 60° C. or 55 to 65°. Typically, steps (ii) to (viii) are each carried out at such a temperature. In this process, though, lower temperatures can be maintained in steps (ii) to (viii). Each of these steps may therefore be conducted at, for example, 35 to 65° C. such as 35 to 60° C. or 40 to 60°.

With regard to a formulation that is formed from the mixture of a pharmacologically active agent, a HVLCM, a network former, a first viscosity enhancing agent, a hydrophilic solvent and a hydrophobic solvent, a suitable manufacturing or compounding process may include the steps of:
(i) preheating the HVLCM;
mixing the hydrophilic solvent with the preheated HVLCM to form a uniform solution of the HVLCM in the solvent; (ii) dispersing the network former in the solution to dissolve the network former in the solution; (iii) mixing from 5 to 30%, for example from 10 to 20%, of the hydrophobic solvent or, optionally, a solution of a stabilising agent and from 5 to 30%, for example from 10 to 20%, of the hydrophobic solvent with the formulation; (iv) adding and mixing the pharmacologically active agent; (v) adding and mixing the first viscosity enhancing agent; (vi) optionally, adding and mixing a second viscosity enhancing agent; and (vii) adding and mixing the balance of the hydrophobic solvent.

Furthermore, the process can further include the step of filling capsules with the formulation thus obtained and, optionally, packaging the filled capsules into unit dose blisters or multidose plastic bottles.

Step (i) is carried out to reduce the viscosity of the HVLCM so that it readily flows and other components can be easily mixed into it. Step (i) may be carried out at, for example, from 50 to 65° C. or 50 to 60° C. or 55 to 65°. Typically, steps (ii) to (viii) are each carried out at such a temperature.

Also with regard to a formulation that is formed from the mixture of a pharmacologically active agent, a HVLCM, a network former, a first viscosity enhancing agent, a hydrophilic solvent and a hydrophobic solvent, a suitable manufacturing or compounding process may include the steps of: (i) preheating the HVLCM; (ii) mixing the hydrophilic solvent with the preheated HVLCM to form a uniform solution of the HVLCM in the solvent; (iii) optionally, mixing a solution of a stabilising agent and from 5 to 30%, for example 10 to 20%, of the hydrophobic solvent with the solution obtained in preceding step; (iv) adding and mixing the hydrophobic solvent or, if step (iii) is effected, the balance of the hydrophobic solvent with the solution obtained in step (ii) or (iii); (v) optionally, adding and mixing a second viscosity enhancing agent with the formulation obtained in the preceding step; (vi) adding and dispersing the network former into the solution obtained in step (iv) or, if step (v) is effected, step (v) thereby dissolving the network former in the solution; (vii) adding and mixing the pharmacologically active agent with the formulation obtained in the previous step; and (viii) adding and mixing the first viscosity enhancing agent with the formulation obtained in step (vii). The process may further include the step of filling capsules with the formulation obtained in the process and, optionally, packaging the filled capsules into unit dose blisters or multidose plastic bottles.

In this process embodiment, step (i) is carried out to reduce the viscosity of the HVLCM so that it readily flows and other components can be easily mixed into it. Step (i)

may be carried out at, for example, from 50 to 65° C. or 50 to 60° C. or 55 to 65°. Typically, steps (ii) to (viii) are each carried out at such a temperature. In this process, though, lower temperatures can be maintained in steps (ii) to (viii). Each of these steps may therefore be conducted at, for example, 35 to 65° C. such as 35 to 60° C. or 40 to 60°.

With regard to a formulation that is formed from the mixture of a pharmacologically active agent, a HVLCM, a network former, a rheology modifier, a hydrophilic agent and a solvent, one suitable manufacturing or compounding process would include the steps of: preheating the HVLCM; mixing the solvent with the preheated HVLCM to form a uniform solution of the HVLCM in the solvent; dispersing the network former in the solution to dissolve the network former in the solution; mixing from 5 to 30% of the rheology modifier or, optionally, a solution of a stabilising agent and from 5 to 30% of the rheology modifier with the formulation; add and mixing the pharmacologically active agent; adding and mixing the hydrophilic agent; and, optionally, adding and mixing a viscosity enhancing agent, and adding and the balance of the rheology modifier. Furthermore, the process can include the step of filling capsules with the formulation obtained in the process and, optionally, packaging the filled capsules into unit dose blisters or multidose plastic bottles.

With regard to a formulation that is formed from the mixture of a pharmacologically active agent, a HVLCM, a network former, a rheology modifier, a hydrophilic agent and a solvent, a suitable manufacturing or compounding process may include the steps of: preheating the HVLCM to a first temperature range; mixing the solvent with the preheated HVLCM to form a uniform solution of the HVLCM in the solvent; optionally, mixing a solution of a stabilising agent and from 5 to 30% of the rheology modifier with the solution obtained in preceeding step at a temperature in a second range; adding and mixing the rheology modifier or, if step the balance of the rheology modifier with the solution obtained in the earlier step whilst maintaining the temperature in the second range; optionally, adding and mixing a viscosity enhancing agent with the formulation obtained in the preceeding step whilst maintaining the temperature in the second range; adding and dispersing the network former into the solution thus obtained or, whilst maintaining the temperature of the solution in the second range, thereby dissolving the network former in the solution; adding and mixing the pharmacologically active agent with the formulation obtained in the previous step whilst maintaining the temperature in the second range; adding and mixing the hydrophilic agent whilst maintaining the temperature in the second range. Furthermore, the process can include the step of filling capsules with the formulation obtained in the process and, optionally, packaging the filled capsules into unit dose blisters or multidose plastic bottles.

With regard to a formulation that is formed from the mixture of a pharmacologically active agent, a HVLCM, a network former, a first viscosity enhancing agent, a hydrophilic solvent and a hydrophobic solvent, a suitable manufacturing or compounding process may include the steps of: preheating the HVLCM; mixing the solvent with the preheated HVLCM to form a uniform solution of the HVLCM in the solvent; dispersing the network former in the solution to dissolve the network former in the solution; mixing from 5 to 30% of the rheology modifier or, optionally, a solution of a stabilising agent and from 5 to 30% of the rheology modifier with the formulation; adding and mixing the pharmacologically active agent; adding and mixing the hydrophilic agent; and, optionally, adding and mixing a viscosity enhancing agent, and adding and the balance of the rheology modifier. Furthermore, the process can include the step of filling capsules with the formulation obtained in the process and, optionally, packaging the filled capsules into unit dose blisters or multidose plastic bottles.

With regard to a formulation that is formed from the mixture of a pharmacologically active agent, a HVLCM, a network former, a first viscosity enhancing agent, a hydrophilic solvent and a hydrophobic solvent, a suitable manufacturing or compounding process may include the steps of: preheating the HVLCM to a first temperature range; mixing the solvent with the preheated HVLCM to form a uniform solution of the HVLCM in the solvent; optionally, mixing a solution of a stabilising agent and from 5 to 30% of the rheology modifier with the solution obtained in preceeding step at a temperature in a second range; adding and mixing the rheology modifier or, if step the balance of the rheology modifier with the solution obtained in the earlier step whilst maintaining the temperature in the second range; optionally, adding and mixing a viscosity enhancing agent with the formulation obtained in the preceeding step whilst maintaining the temperature in the second range; adding and dispersing the network former into the solution thus obtained or, whilst maintaining the temperature of the solution in the second range, thereby dissolving the network former in the solution; adding and mixing the pharmacologically active agent with the formulation obtained in the previous step whilst maintaining the temperature in the second range; adding and mixing the hydrophilic agent whilst maintaining the temperature in the second range. Furthermore, the process can include the step of filling capsules with the formulation obtained in the process and, optionally, packaging the filled capsules into unit dose blisters or multidose plastic bottles.

A number of other suitable lab-scale, GMP and commercial manufacturing methods for producing the abuse-resistant dosage forms and formulations of the present invention are described in Examples 1 and 2 below.

In certain preferred embodiments, the oral dosage form is composed of a liquid formulation containing the active agent and the controlled release carrier system encapsulated within an enclosure or capsule, preferably biodegradable, such as a capsule or a gelatin capsule ("gelcap"), wherein the capsule is made of a substance that degrades or otherwise dissociates when exposed to conditions present in the gastro-intestinal tract of a mammal. Capsules and gelcaps are well known in drug delivery technology and one of skill could select such a capsule as appropriate for delivery of a particular active agent. Once the capsule has dissolved or dissociated from the formulation, the formulation of the invention generally remains intact, especially for hydrophobic formulations, and passes through the GI tract without emulsification or fragmentation.

In certain more specific embodiments the invention encompasses an oral dosage form comprising a liquid formulation contained within a biodegradable capsule, wherein the formulation comprises an active agent and a HVLCM, and wherein the capsule is made of a substance that degrades when exposed to conditions present in the gastro-intestinal tract of a mammal. In certain embodiments the capsule comprises gelatin or synthetic polymers such as hydroxyl ethyl cellulose and hydroxyl propylmethyl cellulose. Gelcaps can be of the hard or soft variety, including, for example, polysaccharide or hypromellose acetate succinate based caps (e.g., Vegicaps brand, available from Catalent). The capsule can also be coated with an enteric coating matereial such as AQIAT (Shin-Etsu) to delay release Gelatin capsules are well suited for delivering liquid formulations such as vitamin E and cod-liver oil. Gelatin capsules are stable in storage, but once in the acid environment of the stomach (low pH less than about pH 4-5), the gelcap dissolves over a 1-15 minute period.

In certain embodiments, the abuse-resistant oral pharmaceutical dosage forms may be formulated so as to produce particular controlled plasma levels of an active agent over a particular period. This is obviously of great importance in maintaining a plasma level within an appropriate therapeutic range. An appropriate therapeutic range will vary depending on the active agent, but can range from femtogram/mL levels up to above microgram/mL levels for a desired period of time. For example, a single dose of a dosage form disclosed herein may result in maintenance of plasma levels of greater than 5 ng/mL for a period of greater than 8 hours. In other embodiments, the plasma level achieved using a single dose may be greater than 5 ng/mL for a period of greater than 10 hours, greater than 12 hours, greater than 14 hours, greater than 16 hours, greater than 18 hours, or greater than 20 hours. In yet other embodiments, the plasma level achieved using a single dose may be greater than 5 ng/mL, greater than 10 ng/mL, greater than 15 ng/mL, greater than 20 ng/mL, greater than 30 ng/mL, greater than 40 ng/mL, or greater than 50 ng/mL for a period of 4, 8, 10, 12, 14, 16, 18, 20 or 24 hours. The maximum plasma concentration of an active agent may be reached at a time following administration from between 0.1 hr to about 24 hr, or from about 0.25 hr to 10 hr, or from about 0.25 hr to 8 hr, or from about 0.5 hr to 6 hr, or from about 0.5 hr to 4 hr, or from about 0.5 hr to 2 hr, or from about 0.5 hr to 1 hr. The time to maximum plasma concentration may be adjusted by adjusting various components of the controlled release carrier system as taught herein.

The plasma levels obtained may be adjusted by adjusting the dose of the active agent, and/or by adjusting the formulation and other components of the controlled release carrier system, and desirable plasma levels will depend on the therapeutic range or its index for any particular active agent. It is readily within the skill of one in the art to determine the desired therapeutic index.

The rate of active agent release from the dosage form may be varied depending on the agent used and the dosage required. Release rates may be different in different parts of the GI tract, and release rates may be averaged over the time of transit through the GI tract (approximately 8-24 hrs). Typical average release rates may vary substantially. For many active agents, they may range from about 0.01 to 500 mg/hr, from 0.5 to 250 mg/hr, 0.75 to 100 mg/hr, 1.0 to 100 mg/hr, 2.0 to 100 mg/hr, 5 to 100 mg/hr, 10 to 100 mg/hr, 10 to 80 mg/hr, 20 to 50 mg/hr, or about 20 to 40 mg/hr.

Dosage regimens for a particular active agent of interest may be determined by the physician in accordance with standard practices. Once per day (QD) or twice per day (BID) dosing may be used to maintain a sufficient clinical effect, e.g., to maintain pain relief.

EXAMPLES

Please note that the examples described herein are illustrative only and in no way limit the scope of the invention.

Example 1: Preparation of Formulations (Lab-Scale Manufacturing Processes)

Three different lab-scale manufacturing processes for the dosage forms of the present invention were developed and carried out as follows. The following raw materials were used to create formulations used in the processes: Oxycodone HCl, micronized ("OXY"); Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); Sodium Lauryl Sulfate NF ("SDS"); and Labrafil M2125 CS ("LAB"). The specific details for the five different formulations produced using the three lab-scale manufacturing processes of this Example 1 are disclosed below in Table 1. The batch size for the various formulations ranged between 900 g and 1 kg.

TABLE 1

| No. | Process Scheme | OXY (wt %) | SAIB (wt %) | TA (wt %) | CAB (wt %) | IPM (wt %) | EC (wt %) | $SiO_2$ (wt %) | BHT (wt %) | SDS (wt %) | LAB (wt %) |
|---|---|---|---|---|---|---|---|---|---|---|---|
| 1 | 1, 2, 3 | 7.27 | 39.96 | 29.64 | 4.64 | 13.91 | 5.56 | 1.85 | 0.02 | 1.4 | — |
| 2 | 1, 2, 3 | 7.27 | 38.38 | 25.59 | 4.64 | 13.91 | 5.56 | 1.85 | 0.02 | — | 2.78 |
| 3 | 2 | 7.27 | 37.27 | 27.61 | 5.56 | 14.84 | 5.56 | 1.85 | 0.02 | — | — |
| 4 | 2 | 7.27 | 37.54 | 27.81 | 5.1 | 14.84 | 5.56 | 1.85 | 0.02 | — | — |
| 5 | 2 | 7.27 | 36.64 | 30.33 | 5.56 | 12.98 | 5.56 | 1.85 | 0.02 | — | — |

The primary mixing apparatus used in each of the lab-scale manufacturing processes was a Ross Model No. HSM 100 LCI, equipped with propeller type impeller (4 blade) with a diameter of 2.25 inches. The mixing container that was used was a 2 liter Glass Jar with an internal Diameter (mixing area) of 4.181 inches. A Silverson Mixer (Model No. L4RT) was used in each process for homogenization after addition of the $SiO_2$, where homogenization was carried out for 10 minutes, and the rotor speed was kept at 6000 rpm. During the homogenization process, the temperature of the bulk materials was constantly monitored and was kept below 75° C. During each of the other steps of the manufacturing processes, the bulk temperature was maintained around 60° C. throughout using a water bath, and the mixing speed for the mixing apparatus was kept constant at 1500 rpm throughout (with the exception that during addition of any solid materials, mixing speed was increased for a short time to create an efficient vortex to disperse the solid material within the bulk material). Mixing times were kept at 30 minutes after addition of each material except after addition of CAB. In each process, it took about 2 hours for the CAB material to go into solution. After each manufacturing process was completed, the resulting formulations were reheated and injected into soft gel caps using a standard needle and syringe to provide 10 mg and 40 mg oxycodone gel cap dosage forms.

All of the raw materials were used as obtained from the various manufactures with the following exceptions. The active agent (oxycodone HCL) raw material was found to have a variety of different particle sizes and was further subject to agglomeration upon standing at ambient conditions. Accordingly, the oxycodone material was subjected to a jet milling process in order to micronize the solid material into a substantially homogenous particle size. The jet mill apparatus was a Model No. 00 Jet-O-Mizer Jetmill (Fluid Energy). The processing conditions used to process batch sizes of around 80 g, were as follows: nitrogen gas ($N_2$) was used instead of compressed air, with the pusher nozzle set at 100 psi, and the grinding nozzles (Nozzle #1 and #2) set at 90 psi. Processing time was around 2 hours. After collection from the jet mill apparatus, the micronized oxycodone was passed through a 20-mesh stainless steel screen and weighed. This micronization process was carried out just prior to each manufacturing process in order to avoid any possible agglomeration of the processed material. The CAB raw material was washed using ethanol (EtOH) and then dried to remove possible contaminants.

In the first lab-scale manufacturing process (Process Scheme 1), the order of addition of the various material constituents was adjusted such that the active agent (oxycodone) was added at the end of the process. In earlier lab scale processes, the CAB/triacetin solution was added to carrier material SAIB at beginning of the process. In this Process Scheme 1, the CAB material was dispersed in the SAIB material at the beginning of the process, prior to addition of the triacetin. The flow chart for Process Scheme 1 is depicted in FIG. 1A. Process temperatures were maintained at 60° C.±5° C. throughout the process run. CAB dissolution after addition of the triacetin took approximately 2 hours and was confirmed by visual observation of a clear thick liquid that was free from any solid aggregates. About 15% of the IPM was added with the BHT and SDS (where used), with the balance being added as a rinse. In addition, the homogenizer was used for 10 minutes after addition of the $SiO_2$ into the vortex created by the impeller.

Figure 1B:
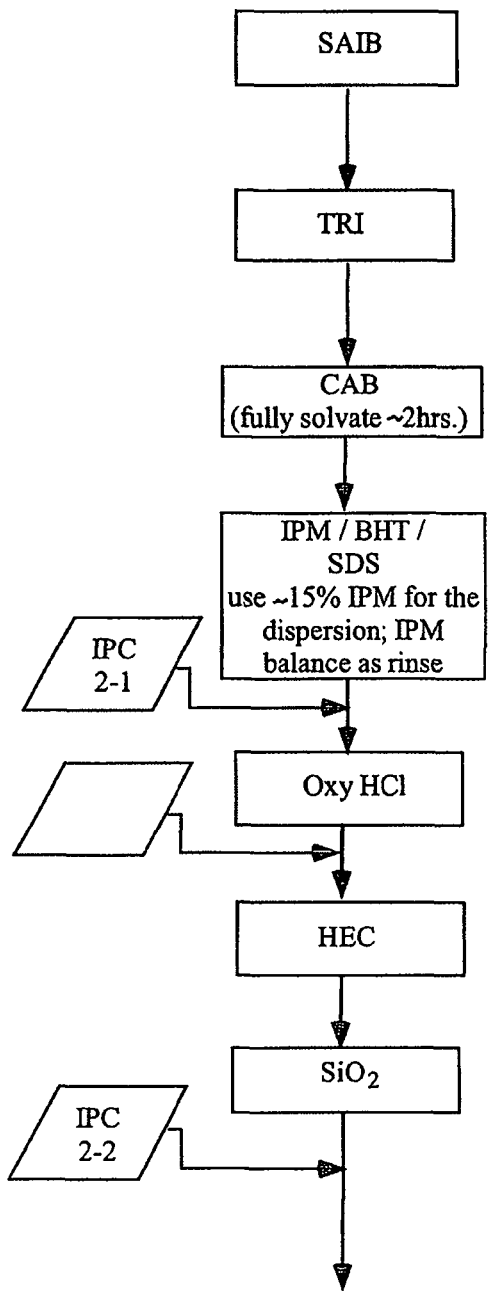

In the second lab-scale manufacturing process (Process Scheme 2), the oxycodone active agent was added prior to addition of the HEC and $SiO_2$ materials. The flow chart for Process Scheme 2 is depicted in FIG. 1B. Here again, process temperatures were maintained at 60° C.±5° C. throughout the process run. CAB dissolution took approximately 2 hours and was confirmed by visual observation of a clear thick liquid that was free from any solid aggregates, and about 15% of the IPM was added with the BHT and SDS (where used), with the balance being added as a rinse. In addition, the homogenizer was used for 10 minutes after addition of the $SiO_2$ into the vortex created by the impeller.

Figure 1C:
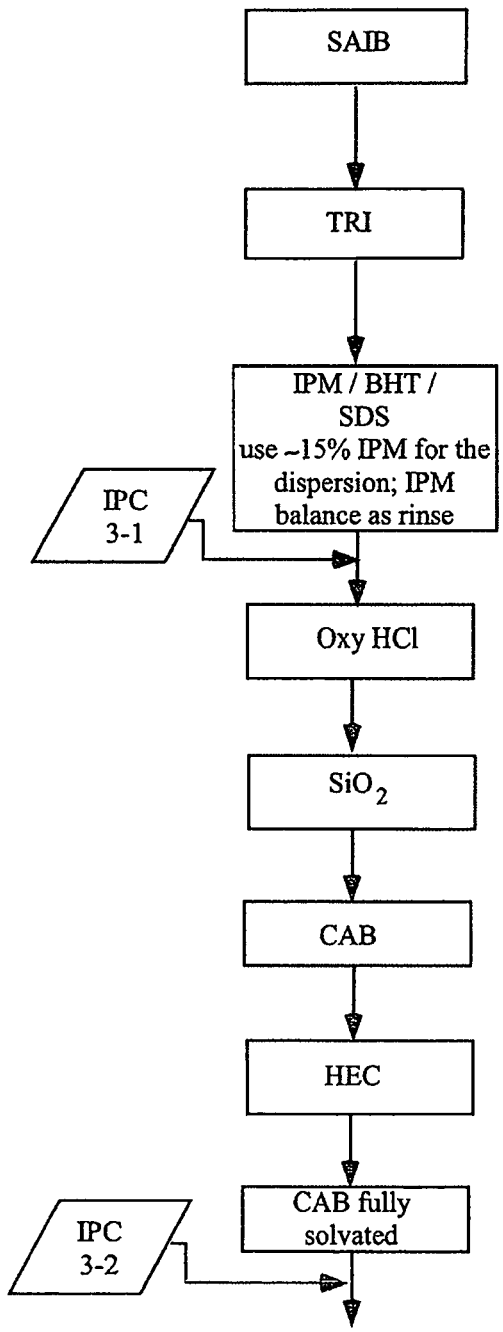

In the third lab-scale manufacturing process (Process Scheme 3), the process was developed such that viscosity of the formulation is ramped up (from low to high viscosity, low shear mixing method) during successive steps of the process to provide for a low-shear process that would be suitable for manufacturing scale-up. In addition, the oxycodone active agent was dispersed in the formulation prior to addition of the CAB and HEC materials. The flow chart for Process Scheme 3 is depicted in FIG. 1C. Process temperatures were maintained at 60° C.±5° C. throughout the process run; however, unlike Process Schemes 1 and 2, the complete CAB component was added much later in the process, immediately prior to final addition of HEC. After addition of the HEC material, mixing was continued until the CAB material went into solution (to provide a clear thick liquid that was free from any solid aggregates, as confirmed by visual observation) which took about 2 hours. In addition, the homogenizer was used for 10 minutes after addition of the $SiO_2$ into the vortex created by the impeller.

After manufacture of the various formulations using the above-described lab-scale manufacturing processes, product performance of the dosage forms was assessed to determine if the sequence of addition of the raw materials had any impact on the controlled release (dissolution) and abuse-resistant (extraction) properties of dosage forms. In addition, viscosity measurements for the formulations were taken at a range of temperatures (25, 37 and 60° C.) using a standard Brookfield viscometer (Digital Rheometer Model Nos. JPII, Model HBDV-III+CP with Programmable/Digital Controller Model 9112; or WI, Model LVDV-III+CP, Immersion Circulator Model 1122S LV DV III, both with CPE Spindle 52) to assess whether or not there was an appreciable difference in the resultant viscosities of formulations produced using the low shear (Process Scheme 3) method relative to the higher shear methods. As a result of this initial viscosity assessment, it was found that the low-shear (Process Scheme 3) manufacturing method produced formulations that had approximately 2 times greater viscosity than those same formulations produced using the high-shear methods. This two-fold viscosity difference was found throughout the temperature range that was tested, suggesting that the low-shear method can produce formulations having a significantly higher final viscosity.

The controlled release performance of the various formulations manufactured in this Example 1 was tested using the in vitro dissolution technique described herein below in Example 3. The abuse-resistance performance of the various formulations manufactured in this Example 1 was tested using the in vitro alcohol extraction technique described herein below in Example 4. With regard to the controlled release performance testing, it was found that the formulation containing SDS (Formulation No. 1) had a slower cumulative release profile (reduced controlled release performance) when manufactured using Process Scheme 1, compared with the same formulations that were manufactured using either Process Scheme 2 or 3. From these observations, it is possible that a change in the sequence of addition of the raw materials may have an effect upon release kinetics in formulations containing the SDS ingredient (in Process Scheme 1, the oxycodone is added at the very last step, whereas in Process Schemes 2 and 3, it is added much earlier in the process). However, this difference in controlled release performance was not noted in the formulations that do not contain the SDS ingredient (Formulation Nos. 2-5). The formulation containing LAB (Formulation No. 2), and the remaining formulations without both SDS and LAB (Formulation Nos. 3-5) showed no substantial difference in controlled release performance regardless of the manufacturing process that was used to produce the subject formulations.

With regard to abuse-resistance performance, the formulation that includes SDS (Formulation No. 1), showed an improved abuse resistance performance between formulation prepared using Process Scheme 1 when compared with formulation prepared using Process Scheme 2, again suggesting a possible sequence of addition effect that could be consistent with the reduction in controlled release performance as noted above. There was no substantial difference observed in the abuse resistance performance for the other formulations (Formulation Nos. 2-5) regardless of manufacturing process.

Example 1a

A GMP manufacturing process for the dosage forms of the present invention was developed and carried out as follows. The following raw materials were used to create the formulations: d-Amphetamine Sulfate (Cambrex) ("AMP"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAM"); Triacetin USP ("TA"); Cellulose Acetate Butyrate, grade 381-20 BP, ethanol washed (Eastman Chemicals) ("CAB"); Caprylocaproyl Polyoxyglycerides (Gattefosse) ("CPG"); Gelucire 50/13 (Gattefosse) ("GEL"); and Polyethylene Glycol 8000 (Dow Chemical) ("PEG 8000"). The specific details for the three different formulations produced using the GMP manufacturing processes of this Example 1a are disclosed below in Table 2a. The batch sizes were up to 500 g.

TABLE 2a

| No. | AMP (wt %) | SAIB (wt %) | TA (wt %) | BHT (wt %) | CAB (wt %) | IPM (wt %) | HEC (wt %) | SiO$_2$ (wt %) | CPG (wt %) | GEL (wt %) | PEG 8000 (wt %) |
|---|---|---|---|---|---|---|---|---|---|---|---|
| 1 | 5.45 | 35.16 | 26.04 | 0.02 | 4.96 | 16.07 | 5.67 | 1.89 | — | 4.73 | — |
| 2 | 7.50 | 36.52 | 27.05 | 0.02 | 4.86 | 15.73 | 5.55 | 1.85 | 0.93 | — | — |
| 3 | 5.45 | 36.24 | 26.85 | 0.02 | 4.96 | 16.07 | 5.67 | 1.89 | — | — | 2.84 |

Figure 1D:
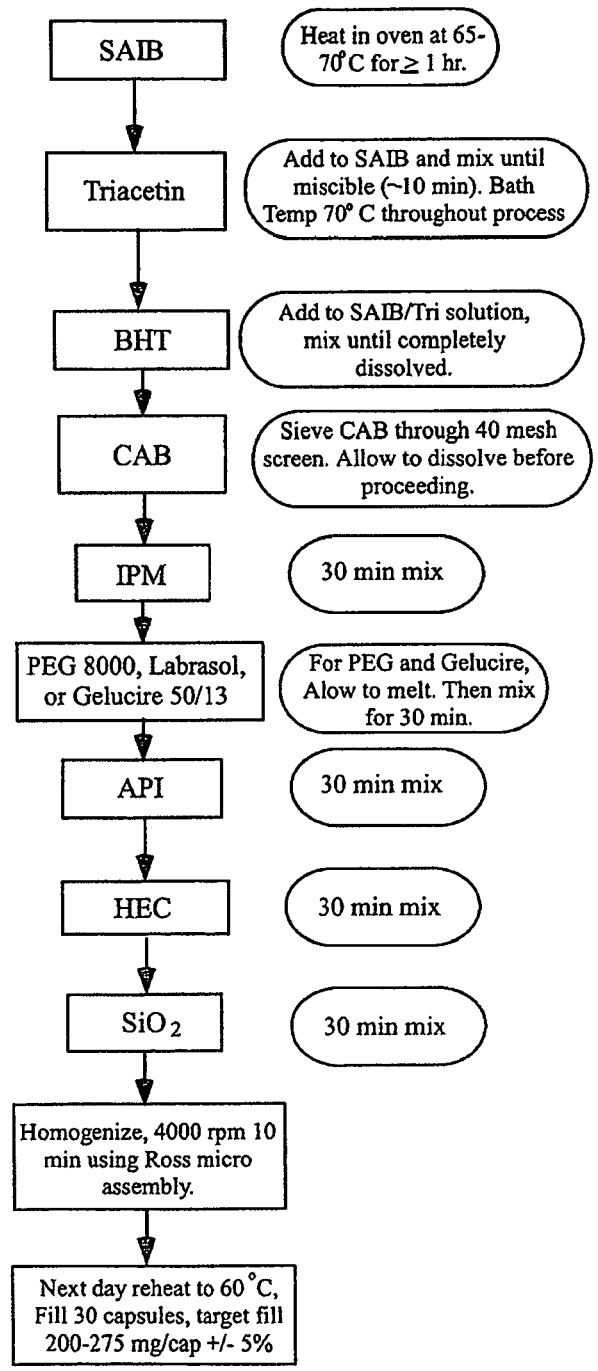
FIG. 1D depicts the GMP manufacturing process (Process Scheme 6) described in Example 1a, FIG. 1E depicts the GMP manufacturing process (Process Scheme 7) described in Example 1b.

The primary mixing apparatus used in the GMP manufacturing process was a Ross Model No. HSM 100 LCI, equipped with propeller type impeller (4 blade) with a diameter of 2.25 inches. The mixing container that was used was a 2 liter Glass Jar with an internal Diameter (mixing area) of 4.181 inches. Temperature control was carried out using a VWR immersion circulator and a VWR gravity convection oven model 1320. A micro mixer homogenizing assembly for the Ross mixer was used for the final homogenization step. After the final mixing step, bulk formulations were allowed to cool to room temperature for a minimum of 16 hours (overnight) prior to filling into capsules. The flow chart for the instant GMP manufacturing process (Process Scheme 6) is depicted in FIG. 1D. The specific process conditions used for Formulations 1-3 are as follows.

For Formula 1, the final homogenization was carried out at 4000 rpm for 5 minutes. The final product temperature was 51.3° C.

| (Formula 1) | SAIB | TA | BHT | CAB | IPM | GEL | AMP | HEC | SiO$_2$ |
|---|---|---|---|---|---|---|---|---|---|
| Mixing speed (rpm) | — | 500 | 500 | 800-1200 | 1200 | 1200 | 1200-1500 | 1750 | 1880-2000 |
| Mixing time (min) | — | 11 | 20 | 91 | 30 | 39 | 34 | 35 | 30 |
| Formula temp. (° C.) | — | 62.3 | 66.7 | 68.4 | 68 | 62.5 | — | — | 69.5 |
| Bath temp. (° C.) | — | 65.3 | 68.1 | 70.0 | 70.0 | 68.2 | 70.0 | 70.0 | 70.0 |

For Formula 2, the homogenization was carried out at 4000 rpm for 10 minutes. The initial product temperature was 69.1° C., and the final product temperature was 63.6° C.

| (Formula 2) | SAIB | TA | BHT | CAB | IPM | CPG | AMP | HEC | SiO$_2$ |
|---|---|---|---|---|---|---|---|---|---|
| Mixing speed (rpm) | — | 500 | 500 | 1000-1250 | 1250 | 1400 | 2000 | 2150 | 1400 |
| Mixing time (min) | — | 11 | 22 | 85 | 32 | 39 | 34 | 41 | 30 |
| Formula temp. (° C.) | — | 68.8 | 69.5 | 70.3 | 68.5 | 70.1 | — | — | 72.5 |
| Bath temp. (° C.) | — | 70.0 | 70.0 | 70.0 | 70.0 | 70.0 | 70.0 | 70.0 | 70.0 |

For Formula 3, the final homogenization was carried out at 4000 rpm for 10 minutes. The initial product temperature was 71.5° C., and the final product temperature was 63.1° C.

| (Formula 3) | SAIB | TA | BHT | CAB | IPM | PEG 8000 | AMP | HEC | SiO$_2$ |
|---|---|---|---|---|---|---|---|---|---|
| Mixing speed (rpm) | — | 500 | 500 | 800-1200 | 1250 | 1400 | 1400-1600 | 1600 | 1200 |
| Mixing time (min) | — | 11 | 19 | 102 | 39 | 49 | 34 | 43 | 30 |
| Formula temp. (° C.) | — | 68.8 | 69.5 | 70.3 | 68.5 | 70.1 | — | — | 72.5 |
| Bath temp. (° C.) | — | 70.0 | 70.0 | 70.0 | 70.0 | 70.0 | 70.0 | 70.0 | 70.0 |

Example 1b

Figure 1E:
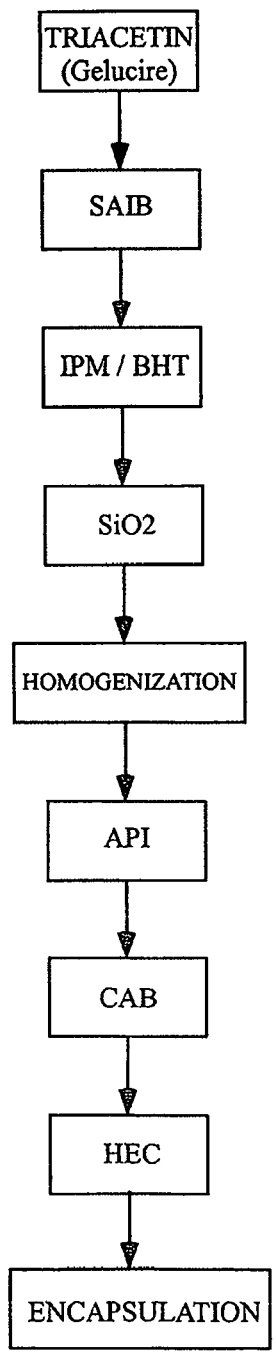
FIGS. 1F and 1G depict the GMP manufacturing processes (Process Schemes 8 and 9) described in Example 1c.

A GMP manufacturing process for the dosage forms of the present invention was developed and carried out as follows. The flow chart for the instant GMP manufacturing process (Process Scheme 7) is depicted in FIG. 1E. Process temperatures were maintained at 55 to 70° C. throughout the process run. Mixing of the IPM/BHT mixture into the compounding mixture was carried out with a 4 inch impeller at 1,500 rpm for 15 minutes. The $SiO_2$ induction step was carried out an additional 2 minutes using a rotor stator at 3,000 rpm. The homogenization step was carried out with a 2.5 inch rotor and slotted stator for 40 minutes after addition of the $SiO_2$. The abuse-resistant oxycodone oral dosage forms used in this Example 1b were prepared using the following raw materials: Oxycodone base, micronized ("OXY"); Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Sodium Lauryl Sulfate ("SLS"); Labrafil M2125 CS ("LAB"); Gelucire 44/14 (Gattefosse) ("GEL"); and Cellulose Acetate Butyrate, grade 381-20 BP, ethanol washed (Eastman Chemicals) ("CAB"). The formulations were then filled into size #00 hard gelatin cap shells to produce 80 mg dosage forms that were used as Test Capsules. The details of the formulations and the dosage forms containing the formulations of this Example 1b are disclosed below in Table 2b.

Example 1c

A GMP manufacturing process for the dosage forms of the present invention was developed and carried out as follows. The following raw materials were used to create the formulations: Hydromorphone HCl ("HMH"); Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Labrafil M2125 CS ("LAB"); and Cellulose Acetate Butyrate, grade 381-20 BP, ethanol washed (Eastman Chemicals) ("CAB"). The formulations were filled into either size #1 (HMH1) or #2 (HMH2-4) gel cap shells. The specific details for the three different formulations produced using the GMP manufacturing processes of this Example 1c are disclosed below in Table 2c. The batch sizes were up to 500 g.

TABLE 2c

| Formula # | HMH | SAIB | TA | CAB | IPM | HEC | $SiO_2$ | BHT | LAB | Total | |
|---|---|---|---|---|---|---|---|---|---|---|---|
| HMH1 | 16.0 | 108.6 | 80.4 | 15.5 | 41.4 | 7.8 | 5.2 | 0.1 | — | 275.0 | (mg) |
|  | 5.82 | 39.49 | 29.5 | 5.65 | 15.07 | 5.65 | 1.88 | 0.02 | — |  | (wt %) |
| HMH2 | 16.0 | 104.1 | 77.1 | 15.5 | 41.4 | 15.5 | 5.2 | 0.1 | — | 275.0 | (mg) |
|  | 5.82 | 37.86 | 28.05 | 5.65 | 15.07 | 5.65 | 1.88 | 0.02 | — |  | (wt %) |
| HMH3 | 16.0 | 101.1 | 74.9 | 15.5 | 38.9 | 15.5 | 5.2 | 0.1 | 7.8 | 275.0 | (mg) |
|  | 5.82 | 36.78 | 27.24 | 5.65 | 14.13 | 5.65 | 1.88 | 0.02 | 2.83 |  | (wt %) |
| HMH4 | 8.0 | 29.8 | 19.9 | 3.6 | 10.8 | 4.3 | 1.4 | 0.1 | 2.2 | 80.0 | (mg) |
|  | 10.00 | 37.25 | 24.83 | 4.50 | 13.50 | 5.40 | 1.80 | 0.02 | 2.70 |  | (wt %) |

Figure 1F:
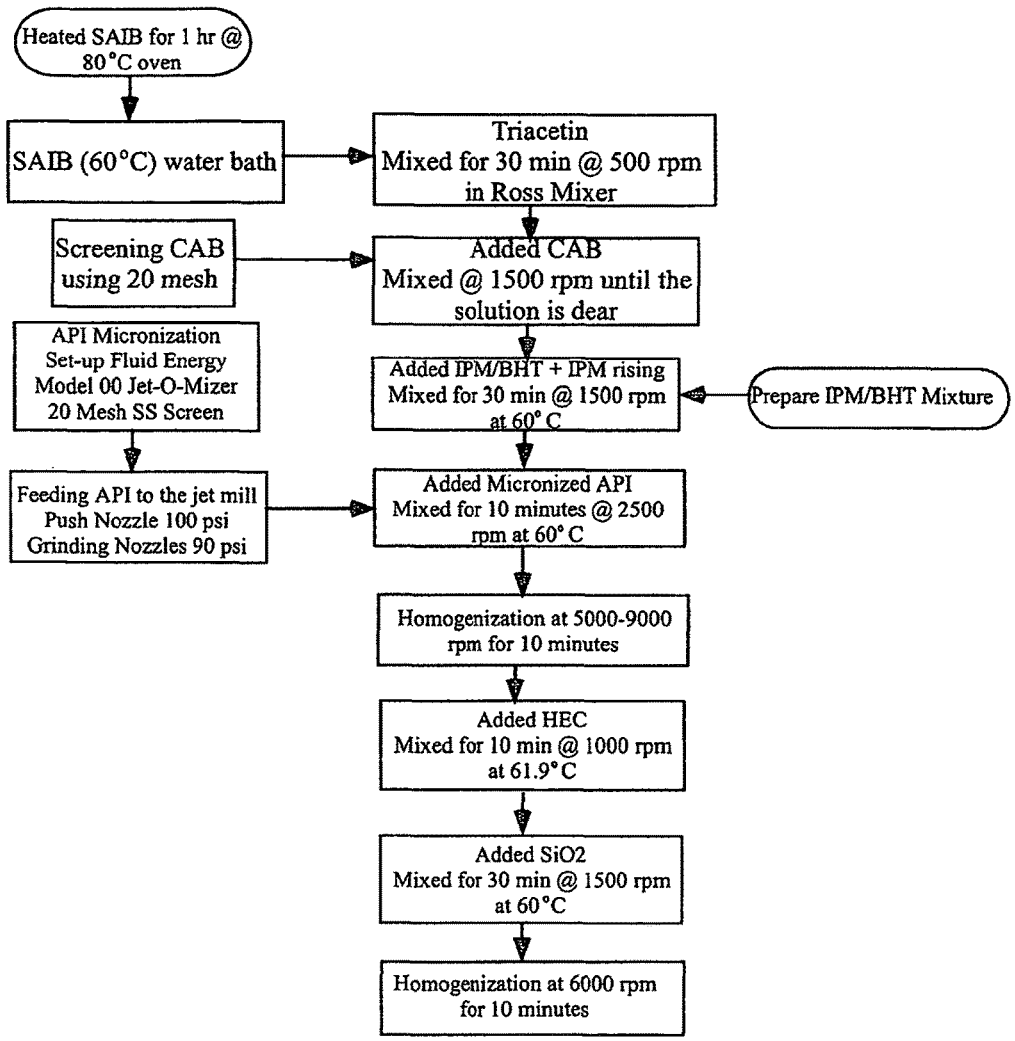

The flow chart for the instant GMP manufacturing process (Process Scheme 8) is depicted in FIG. 1F. The process was carried out as follows. Prior to compounding, the hydromorphone active pharmaceutical ingredient (API) was milled using a Fluid Energy Jet-0-Mizer Jet mill to reduce the API particle size. The formulation was manufactured using a Ross HSM-100LCI overhead mixer fitted with a 2¼ inch, 4-blade, 45° mixing blade. The compounding jar was held in a water bath maintained at 55-65° C. throughout the compounding cycle.

The pre-heated SAIB was added to the compounding jar followed by the triacetin solvent. The contents of the jar were mixed for a minimum of 30 minutes at approximately 500 rpm. The pre-sieved network former (CAB) was slowly added to the compounding jar and mixed at 1500 to 1800 rpm until no granules of CAB were observed. The preservative (BHT), dissolved in a portion of the rheology modifier (IPM), was added to the compounding jar. The remaining IPM was used to rinse the IPM/BHT container and the rinse was added to the compounding jar. The contents of the jar were mixed for a minimum of 30 minutes at approxi- TABLE 2b

|  | OXY | SAIB | TA | CAB | IPM | HEC | $SiO_2$ | BHT | SLS | LAB | GEL | (Total) | |
|---|---|---|---|---|---|---|---|---|---|---|---|---|---|
| OXY1 | 80.0 | 281.4 | 208.4 | 42.0 | 112.0 | 42.0 | 14.0 | 0.2 | — | — | — | 780 | (mg) |
|  | 10.26 | 36.08 | 26.72 | 5.38 | 14.36 | 5.38 | 1.79 | 0.02 | — | — | — |  | (wt %) |
| OXY2 | 80.0 | 297.5 | 198.4 | 42.0 | 105.0 | 42.0 | 14.0 | 0.2 | 1.0 | — | — | 780 | (mg) |
|  | 10.26 | 38.14 | 25.43 | 5.38 | 13.46 | 5.38 | 1.79 | 0.02 | 0.13 | — | — |  | (wt %) |
| OXY3 | 80.0 | 285.5 | 190.3 | 42.0 | 105.0 | 42.0 | 14.0 | 0.2 | — | 21.0 | — | 780 | (mg) |
|  | 10.26 | 36.60 | 24.40 | 5.38 | 13.46 | 5.38 | 1.79 | 0.02 | — | 2.69 | — |  | (wt %) |
| OXY4 | 80.0 | 280.4 | 207.7 | 36.7 | 119.0 | 42.0 | 14.0 | 0.2 | — | — | — | 780 | (mg) |
|  | 10.26 | 35.95 | 26.63 | 4.71 | 15.26 | 5.38 | 1.79 | 0.02 | — | — | — |  | (wt %) |
| OXY5 | 80.0 | 281.0 | 200.8 | 42.0 | 119.0 | 42.0 | 14.0 | 0.2 | 1.0 | — | — | 780 | (mg) |
|  | 10.26 | 36.03 | 25.74 | 5.38 | 15.26 | 5.38 | 1.79 | 0.02 | 0.13 | — | — |  | (wt %) |
| OXY6 | 80.0 | 286.6 | 191.0 | 36.7 | 112.0 | 42.0 | 14.0 | 0.2 | — | 17.5 | — | 780 | (mg) |
|  | 10.26 | 36.74 | 24.49 | 4.71 | 14.36 | 5.38 | 1.79 | 0.02 | — | 2.24 | — |  | (wt %) |
| OXY7 | 80.0 | 284.4 | 210.7 | 42.0 | 112.0 | 21.0 | 15.8 | 0.2 | — | — | 14.0 | 780 | (mg) |
|  | 10.26 | 36.46 | 27.01 | 5.38 | 14.36 | 2.69 | 2.02 | 0.02 | — | — | 1.79 |  | (wt %) |
| OXY8 | 80.0 | 282.4 | 209.2 | 38.5 | 112.0 | 42.0 | 15.8 | 0.2 | — | — | — | 780 | (mg) |
|  | 10.26 | 36.21 | 26.82 | 4.94 | 14.36 | 5.38 | 2.02 | 0.02 | — | — | — |  | (wt %) |
| OXY9 | 80.0 | 285.9 | 204.3 | 38.5 | 112.0 | 42.0 | 15.8 | 0.2 | 1.4 | — | — | 780 | (mg) |
|  | 10.26 | 36.66 | 26.19 | 4.94 | 14.36 | 5.38 | 2.02 | 0.02 | 0.18 | — | — |  | (wt %) | mately 1500 rpm. The milled hydromorphone API was then added to the compounding jar and mixed for a minimum of 10 minutes at 2500-3500 rpm. The compounding mass was then homogenized using a Silverson L4RT Homogenizer with a square hole rotor stator between 5000 and 9000 rpm for 10 minutes. The temperature of the compounding mass was maintained below 75° C. during the homogenizing step. A hydrophilic agent (HEC) was then to the compounding jar and mixed for a minimum of 30 minutes at 2500-3000 rpm. A viscosity enhancing agent (SiO$_2$) was then added and the mass was allowed to mix for a minimum of 30 minutes at approximately 1500 rpm. The compounding mass was then homogenized again using a Silverson L4RT Homogenizer with a square hole rotor stator at approximately 6000 rpm for 10 minutes. The temperature of the compounding mass was maintained below 75° C. during this second homogenizing step.

The compounded mass was reheated in an oven prior to the filling operation. The compounded mass was filled into hard gelatin capsules and sealed using a Capsugel CFS-1000 and a 50% ethanol solution for sealing. The capsules were packaged into plastic bottles with child-resistant caps with induction-sealed liners.

Example 1d

A GMP manufacturing process for the dosage forms of the present invention was developed and carried out as follows. The following raw materials were used to create the formulations: Hydrocodone Bitartrate ("HCB"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAM"); Triacetin USP ("TA"); Gelucire 44/14 (Gattefosse) ("GEL"); and Cellulose Acetate Butyrate, grade 381-20 BP, ethanol washed (Eastman Chemicals) ("CAB"). The formulations were filled into size #3 gel cap shells. The specific details for the two different formulations produced using the GMP manufacturing processes of this Example 1d are disclosed below in Table 2d. The batch sizes were up to 500 g.

mixing bowl. The contents of the bowl were mixed at a planetary paddle speed of between 20 and 30 rpm and the disperser speed set between 650 and 850 rpm for a minimum of 10 minutes until the mixture was visually homogenous. The hydrocodone bitartrate API was added to the mixing bowl and mixed using a planetary paddle speed between 20 and 30 rpm and a disperser speed between 750 and 950 rpm for a minimum of 10 minutes. The viscosity enhancing agent (SiO$_2$) was added and mixed using the same mixing conditions for an additional 10 minutes.

The contents of the mixing bowl were homogenized using a Silverson L4RT Homogenizer with a square hole rotor stator at 6000 rpm for 13 to 17 minutes. Following homogenization, the contents of the mixing bowl were mixed using a planetary paddle speed between 20 and 30 rpm for 30 minutes under a vacuum (15 to 29 inches of mercury) to deaerate the mass. After breaking the vacuum, the pre-sieved network former (CAB) was added to the mixing bowl followed by the pre-sieved hydrophilic agent (HEC). The compounding mass was mixed using a planetary paddle speed between 25 and 45 rpm and a disperser speed of 200 rpm under vacuum (15-29 inches of mercury). During this final mixing step, the compounded mass was mixed for a minimum of 60 minutes and until no granules of CAB were observed.

The compounded mass was reheated in an oven prior to the filling operation. The compounded mass was filled into hard gelatin capsules and sealed using a Capsugel CFS-1000 and a 50% ethanol solution for sealing. The capsules were packaged into plastic bottles with child-resistant caps.

Example 2: Preparation of Formulations (Commercial-Scale Manufacturing Processes)

Two different commercial-scale manufacturing processes for the dosage forms of the present invention were developed and carried out as follows. The following raw materials were used to create the formulations: Oxycodone base, micronized ("OXY"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl TABLE 2d

| Formula # | HCB (mg) | SAIB (mg) | TA (mg) | CAB (mg) | IPM (mg) | HEC (mg) | SiO$_2$ (mg) | BHT (02 mg) | GEL (mg) | Total (mg) |
|---|---|---|---|---|---|---|---|---|---|---|
| HCB1 | 15.0 | 41.8 | 27.8 | 5.2 | 14.24 | 2.8 | 1.9 | 0.1 | 1.1 | 110.0 (mg) |
|  | 13.64 | 37.97 | 25.31 | 4.75 | 12.95 | 2.59 | 1.73 | 0.02 | 1.04 | (wt %) |
| HCB2 | 75.0 | 208.8 | 139.2 | 26.1 | 71.2 | 14.2 | 9.5 | 0.11 | 5.7 | 550.0 (mg) |
|  | 13.63 | 37.96 | 25.31 | 4.75 | 12.95 | 2.58 | 1.73 | 0.02 | 1.04 | (wt %) |

Figure 1G:
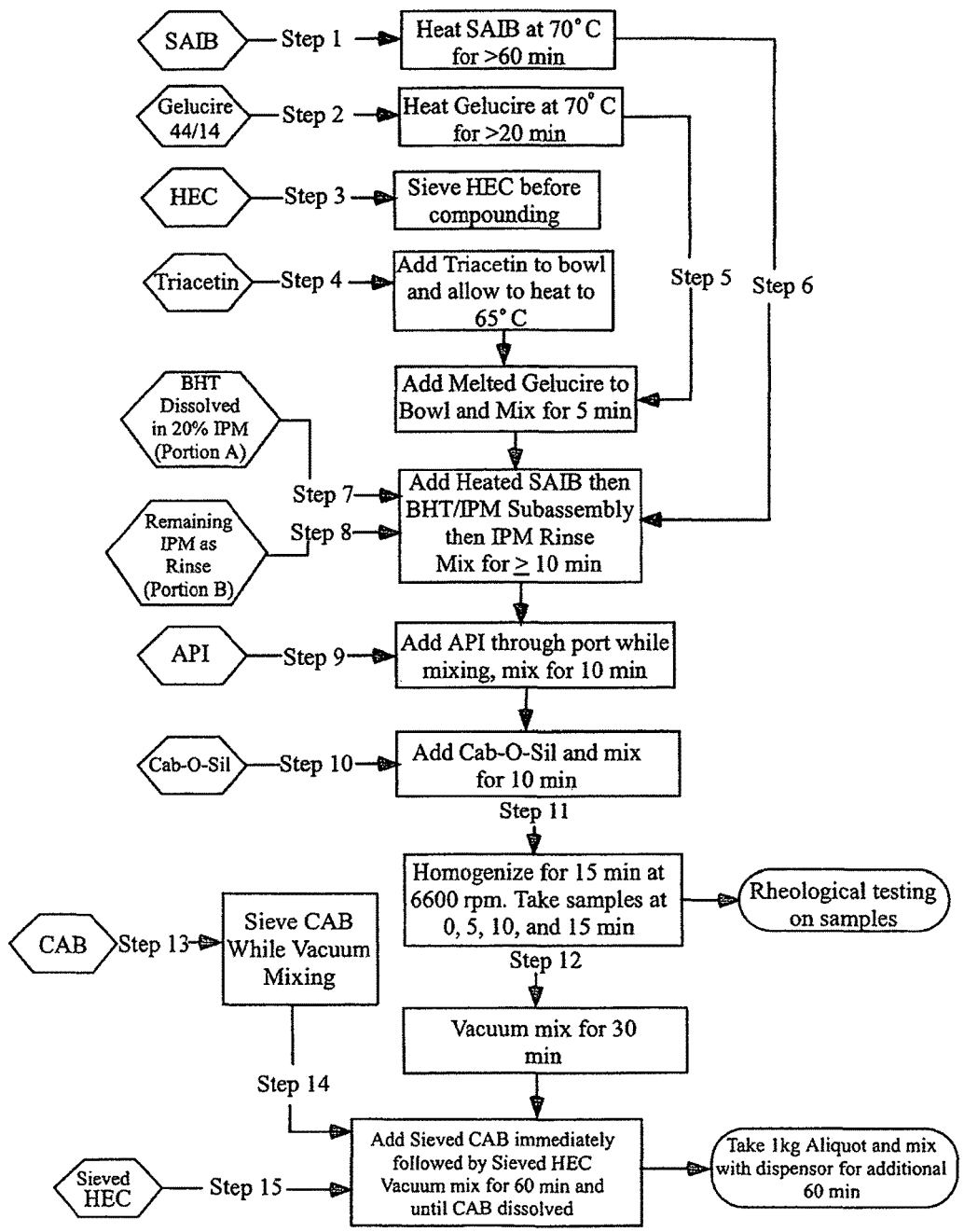

The flow chart for the instant GMP manufacturing process (Process Scheme 9) is depicted in FIG. 1G. The process was carried out as follows. Compounding was carried out using a Ross PDM-2 mixer fitted with a planetary paddle, side scraper, and high-speed disperser blade. The SAIB and a surfactant (Gelucire 44/14 (GEL)) were preheated in an oven at 70° C. The triacetin solvent (TA) was added to the jacketed mixing bowl and allowed to heat to the target processing temperature of 65° C. The melted GEL was removed from the oven and dispensed into the mixing bowl. The contents were allowed to mix for 5 minutes using a planetary paddle speed between 20 and 30 rpm. The heated SAIB was added to the mixing bowl, followed by addition of the stabilizing agent (BHT) dissolved in a portion of the IPM rheology modifier. The remaining IPM was used to rinse the IPM/BHT container and the rinse was added to the cellulose, NF ("HEC"); Sucrose Acetate Isobutyrate (Eastman Chemicals), ("SAIB"); Triacetin USP ("TA"); and Cellulose Acetate Butyrate, grade 381-20 BP, ethanol washed (Eastman Chemicals) ("CAB"). The specific details for the formulations produced using the commercial-scale manufacturing processes of this Example 2 are disclosed below in Table 3.

TABLE 3

| OXY (wt %) | SAIB (wt %) | TA (wt %) | CAB (wt %) | IPM (wt %) | HEC (wt %) | SiO$_2$ (wt %) | BHT (wt %) |
|---|---|---|---|---|---|---|---|
| 5.13 | 40.98 | 27.32 | 4.74 | 14.23 | 5.69 | 1.9 | 0.02 |

All of the raw materials were used as obtained from the various manufactures with the following exceptions. The oxycodone base raw material was found to have a variety of different particle sizes that could affect the final product uniformity. Accordingly, the oxycodone material was subjected to a jet milling process in order to micronize the solid material into a substantially homogenous particle size. The specific micronization process used is described in detail below. In addition, the CAB raw material was washed using ethanol (EtOH) and then dried in order to remove possible contaminants.

Figure 2:
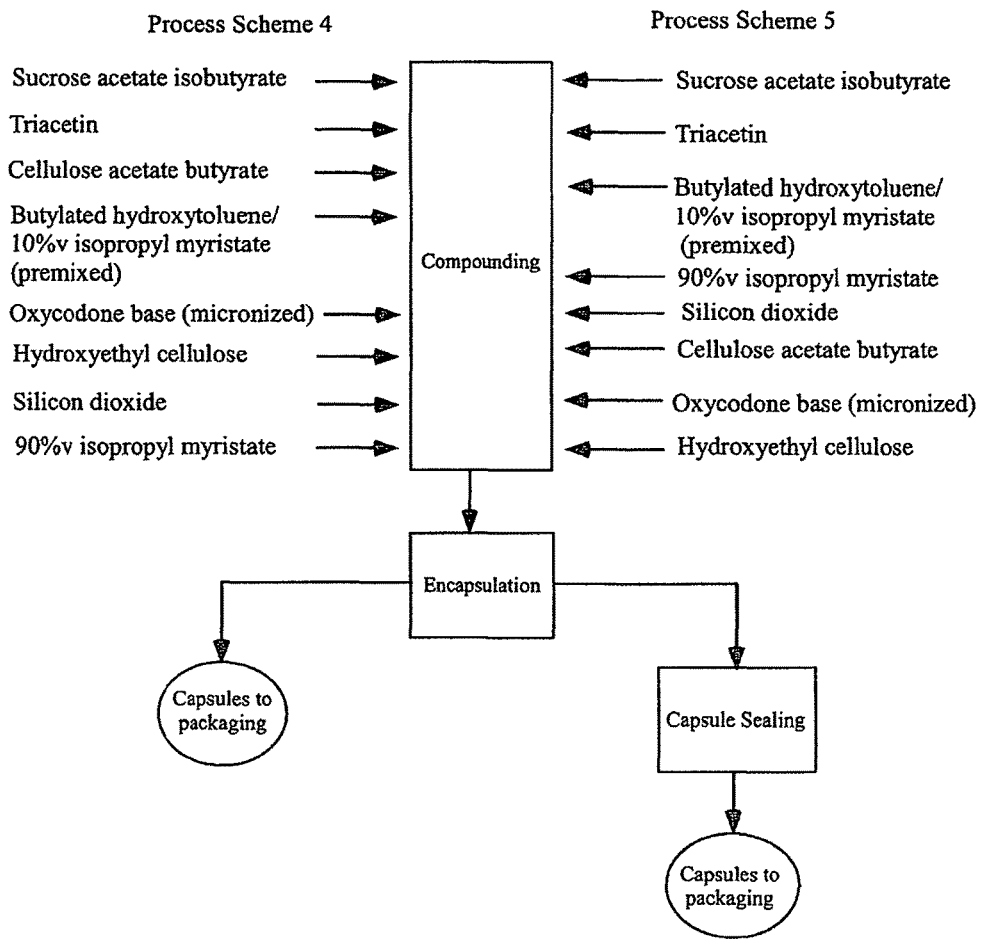
FIG. 2 depicts the commercial-scale manufacturing processes (Process Schemes 4-5) described in Example 2.

Two different commercial-scale manufacturing processes were developed for the dosage forms of the present invention. A schematic representation of each process (hereinafter Process Scheme 4 and Process Scheme 5, respectively) is provided in FIG. 2. In the first commercial process (Process Scheme 4), compounding was carried out at a 45 kg scale. In the second process (Process Scheme 5), compounding was carried out at 150 kg scale. The same materials were used in both processes but there were some differences in the methodology. One difference was the order in which ingredients were added during the manufacture in order to enhance mixing and efficiency during the compounding process. For example, in Process Scheme 5, the IPM and $SiO_2$ components were added earlier in the process and the CAB component was added later in the process to lower fluid viscosity during the first part of the compounding process. Another difference in the oral dosage forms produced by the processes was that the capsules filled from Process Scheme 4 were not sealed, while capsules filled from Process Scheme 5 were sealed using a liquid encapsulation microspray sealing (LEMS) process from Capsugel. Table 4 shows a manufacturing process and equipment comparison.

solution of SAIB in triacetin. Again, the mixture temperature was maintained at 50-60° C. In a third step, pre-sieved, cellulose acetate butyrate (CAB) was inducted into the vessel using high shear dispersion during the addition to prevent formation of agglomerates. The vessel contents were mixed with an anchor speed of 20-50 rpm, a rotor stator speed of 700-4500 rpm and a disperser speed of 700-3500 rpm until the CAB was completely dissolved and a clear liquid formulation was formed. After formation, the vessel contents were mixed for an additional thirty minutes with the same anchor, rotor stator and disperser speeds. In a fourth step, in a separate container, a solution was prepared containing butylated hydroxytoluene (BHT) and approximately 15% portion of isopropyl myristate (IPM). A 10% portion of the IPM may be set aside to be used as a rinse solvent later in the process. The remaining quantity of the IPM-BHT solution was subsequently added to the compounding vessel and mixed to achieve uniformity with an anchor speed of 20-50 rpm and disperser speed of 700-3500 rpm. After formation of a uniform formulation mixture, the vessel contents were mixed for an additional five minutes with the same anchor and disperser speeds. During the additional mixing, the stator was jogged as necessary at 700-1200 rpm. Again, the formulation mixture temperature was maintained at 50-60° C. In a fifth step, oxycodone (base) was inducted into the compounding vessel and mixed to achieve uniformity with an anchor speed of 20-50 rpm, disperser speed of 700-3500 rpm and a rotor stator speed of 800-4500 rpm. The formulation mixture temperature was maintained at 55-65° C. The vessel contents were mixed for a minimum of an additional two minutes with the same anchor, disperser and rotor stator speeds. In a sixth step, hydroxyethyl cellulose (HEC) was inducted into the vessel using high shear dispersion during the addition and mixed to

TABLE 4

| Process Description | Process Scheme 4 | Process Scheme 5 |
| --- | --- | --- |
| API Milling (micronization) | 8-20 kg scale<br>Spiral Jet Mill<br>Hosokawa Alpine model 50AS | 28-36 Kg scale<br>Spiral Jet Mill<br>Hosokawa Alpine Model 50AS |
| Compounding | 45 kg scale<br>Multishaft mixer including<br>low shear anchor agitator<br>high speed disperser<br>high shear rotor-stator<br>Charles Ross mixer model VMC 10 | 150 kg scale<br>Multishaft mixer including<br>low shear anchor agitator<br>high speed disperser<br>high shear rotor-stator<br>Charles Ross mixer model PVM 40 |
| Encapsulation | Hard gelatin capsule filling machine<br>Shionogi encapsulator model F-40 | Hard gelatin capsule filling machine<br>Zanasi encapsulator model 40E |
| Capsule Sealing | None - capsules were not sealed | Capsules sealed with LEMS technology<br>Capsugel sealing machine model LEMS30 |

Compounding for Process Scheme 4 was carried out using a Ross VMC-10 Mixer with SLIM. Accordingly, all references to a specific rpm numeric throughout this compounding process correspond to this model. In a first step, sucrose acetate isobutyrate (SAIB) was preheated to 50-65° C. and then added into a compounding vessel with an anchor speed of at 20-40 rpm. The temperature of the SAIB was maintained at 50-60° C. In a second step, triacetin (TA) was added into the compounding vessel and mixed at anchor speed of 20-40 rpm and a disperser speed of 700-2000 rpm. The vessel contents were mixed to achieve a uniform achieve a uniform dispersion with an anchor speed of 20-50 rpm, disperser speed of 700-3500 rpm and a rotor stator speed of 800-4500 rpm. The vessel contents were mixed for an additional two minutes with the same anchor, disperser and rotor stator speeds. Again, the formulation mixture temperature was maintained at 55-65° C. In a seventh step, colloidal silicon dioxide ($SiO_2$) was inducted into the vessel using high shear dispersion during the addition and mixed with an anchor speed of 20-50 rpm, disperser speed of 700-3500 rpm and a rotor stator speed of 800-4500 rpm. The vessel contents were mixed for a minimum of an additional two minutes with the same anchor, disperser and rotor stator speeds. Again, the formulation mixture temperature was maintained at 55-65° C. In an eighth step, IPM was inducted into the vessel and mixed with an anchor speed of 20-50 rpm, disperser speed of 700-2000 rpm and rotor stator speed of 1500-3000 rpm. The vessel contents were continuously mixed with anchor and maintained at 50-60° C. The final compounded formulation mass was de-aerated by vacuum and flushed with nitrogen at 4-5 psig for at least five minutes. The controlled-release formulation mass was filled into hard gelatin capsules to produce abuse-resistant oral dosage forms in accordance with the present invention, and then packaged into unit dose blisters or multidose plastic bottles with child-resistant closures for clinical supply.

Compounding for Process Scheme 5 was carried out with a Ross PVM-40 Mixer with SLIM. Accordingly, all references to a specific rpm numeric throughout the compounding procedure described below correspond to this model. In a first step, sucrose acetate isobutyrate (SAIB) was preheated to 50-65° C. and added to a compounding vessel. In a second step, triacetin was added to the compounding vessel. In a third step, a butylated hydroxytoluene/isopropyl myristate solution was prepared by dispensing a portion of isopropyl myristate (IPM) (balance of IPM is added in next step) into a separate stainless steel container. Butylated hydroxytoluene (BHT) was added to the container and the solution was mixed for at least ten minutes until the BHT was dissolved. The BHT/IPM solution was then added to the compounding vessel. In a fourth step, IPM was added to the compounding vessel and mixed to homogeneity with an anchor speed of 10-50 rpm and a disperser speed of 1-2550 rpm. The mixture temperature was maintained at 35-50° C. In a fifth step, colloidal silicon dioxide ($SiO_2$) was inducted into the compounding vessel and mixed to achieve uniform dispersion with an anchor speed of 10-50 rpm (e.g., 20 rpm), a disperser speed of 1-2550 rpm (e.g., 1000 rpm) and an rotor stator speed of 1-3600 rpm (e.g. 2500 rpm). Again the mixture temperature was maintained at 35-50° C. The vessel contents were mixed for an additional two to four minutes with the same anchor, disperser and rotor stator speeds. In a sixth step, cellulose acetate butyrate (CAB) was inducted into to the compounding vessel and mixed with an anchor speed of 10-50 rpm (e.g., 20 rpm), a disperser speed of 1-2550 rpm (e.g., 1500 rpm) and a rotor stator speed of 1-3600 rpm (e.g., 3000 rpm). The formulation mixture temperature was maintained at 40-60° C. The vessel contents were mixed for an additional two to four minutes with the same anchor, disperser and rotor stator speeds. In a seventh step, oxycodone (base) was inducted into the compounding vessel and mixed to achieve a uniform dispersion with an anchor speed of 10-50 rpm (e.g., 20 rpm), a disperser speed of 1-2550 rpm (e.g., 1500 rpm), and an speed of 1-3600 rpm (e.g., 3000 rpm). Again the controlled release formulation mixture temperature was maintained at 40-60° C. The vessel contents were mixed for an additional two to four minutes with the same anchor, disperser and rotor stator speeds. In an eighth step, hydroxyethyl cellulose (HEC) was inducted into the compounding vessel and mixed with an anchor speed of 10-50 rpm (e.g., 20 rpm), a disperser speed of 1-2550 rpm (e.g., 1500 rpm), and a rotor stator speed of 1-3600 rpm (e.g., 3000 rpm). Again the controlled release formulation mixture temperature was maintained at 40-60° C. The vessel contents were mixed for an additional two to four minutes with the same anchor, disperser and rotor stator speeds. The final compounded controlled release formulation mass was de-aerated by vacuum at no less than 14 mm Hg for no less than two hours with anchor speed of 10-50 rpm (e.g., 20 rpm) and dispersion speed of 1-2250 rpm (e.g., 1250 rpm). The compounded, controlled release formulation mass was filled into hard gelatin capsules to produce abuse-resistant oral dosage forms in accordance with the present invention. More particularly, the compounded, controlled release formulation mass was encapsulated using a Zanasi Liqui-Fill Encapsulator and sealed using a LEMS30 Capsule Sealer. Initially, the compounded mass is transferred from the Ross PVM-40 Mixer to a Zanasi Hopper. The transfer lines are heated with a heated hose controller to a temperature of 55-65° C. Then, a Zansai Liqui-Fill Encapsulator was readied by adjusting the Stroke Scale until the proper fill weight is obtained and the temperature of the compounded mass for filling is maintained at 60-65° C. Depending upon the size of the dosage form capsule, a variety of filling nozzles were designed with varying nozzle diameters (e.g., 1.2-2.0 mm) for use on the Encapsulator. For a 5 mg, 10 mg or 20 mg capsule dosage form, a 1.2 mm diameter nozzle is used. For a 30 mg or 40 mg capsule dosage form, a 1.5 mm diameter nozzle is used. Next, the filled capsule dosage forms are removed from the Zansai Liqui-Fill Encapsulator into a collection container and sealed using the LEMS30 Capsule Sealer (liquid encapsulation microspray sealing) from Capsugel and packaged into unit dose blisters or multidose plastic bottles with child-resistant closures.

In some cases, the oxycodone base used in Process Scheme 4 or Process Scheme 5 was micronized. Micronization of the oxycodone was conducted using a Hosokawa Alpine Spiral Jet Mill. In operation, a feed material comprising a non-micronized opioid is injected into a flat cylindrical grinding chamber, the chamber having nozzles arranged tangentially on a peripheral wall, in the presence of a propellant air pressure and grinding air pressure appropriate for providing the desired flow dynamics within the chamber needed to effect collision of the opioid particles with each other. An appropriate speed and pressure of the propellant air pressure (such as an injector air pressure of 6.8 Bar) and the grinding air pressure (such as 6.2 Bar) is applied such that a particle on particle collision and interaction with the chamber wall results. The injector gas pressure was always approximately 0.3 to 0.7 Bar higher than grinding pressure to obtain constant flow of oxycodone into the spiral jet mill. A micronized particle thus occurs, providing an opioid preparation having a reduced particle size, the particle size being less than about 10 The larger particles are held in the mill by centrifugal (mass) force, while the fine, micronized particles leave the mill in an air stream and are collected (drag force). One set of processing parameters that may be used in the methods for preparing a micronized opioid preparation within a jet gas mill, includes, a batch size of 4 kg; injector clearance default of +3 mm; a feed rate of 40 to 50 g/min; a grinding gas pressure of 6.8 Bar and an injector gas pressure of 6.2 Bar. Immediately following micronization, the micronized oxycodone is packaged in plastic bags with dessicant and then stored in plastic drums to preserve the integrity of the micronized particles. This is necessary to maintain stabilized micronized opioid particle preparations. The micronized opioids, particularly the salt forms such as oxycodone HCl or hydromorphone HCl, are hydroscopic. The immediate packaging with dessication is required to prevent agglomeration and/or fused particles. For example, the micronized oxydocone is placed into a labeled anti-static bag and secured with a cable or twist tie at the open end of the bag. The anti-static bag is placed into a poly bag with a layer of eight-unit, silica gel, printer, Natrasorb® S Tyvek® four-side seal bag desiccant separating the anti-static bag from the poly bag. The label on the anti-static bag is checked to ensure that it is visible through the poly bag and the poly bag is sealed at its open end. The poly bag is placed in a HDPE (high density polyethylene) drum with a layer of eight-unit, silica gel, printer, Natrasorb® S Tyvek® four-side seal bag desiccant separating the poly bag from the drum. A lid is placed on the open end of the drum and secured using a uniquely numbered security locking tag through a side lever-lock (SSL). Such dessicant packaged and stored micronized opioid preparations may be used in the manufacturing processes, including the compounding processes described herein.

Example 3: Analysis of Formulations (In Vitro Dissolution Testing Procedures)

In order to assess the controlled release performance of the dosage forms of the present invention, two in vitro dissolution test methods were developed as follows. The first dissolution method (Method 1) was based upon USP <711> Method A for delayed-release dosage forms and uses an USP dissolution apparatus Type 2 (without basket) with a two-stage media (an initial volume of 750 mL of 0.1N HCl acid as the dissolution medium, followed by adjustment to pH 6.8 by addition of 250 mL of sodium phosphate buffer after 2 hours). The two-stage media was selected to simulate the pH range over which a dosage form will release active agent during transit through the GI tract. Stainless steel coiled wire type 316 is used as a sinker to ensure that the dosage forms remain at the bottom of the dissolution vessel during release rate testing.

Figure 3:
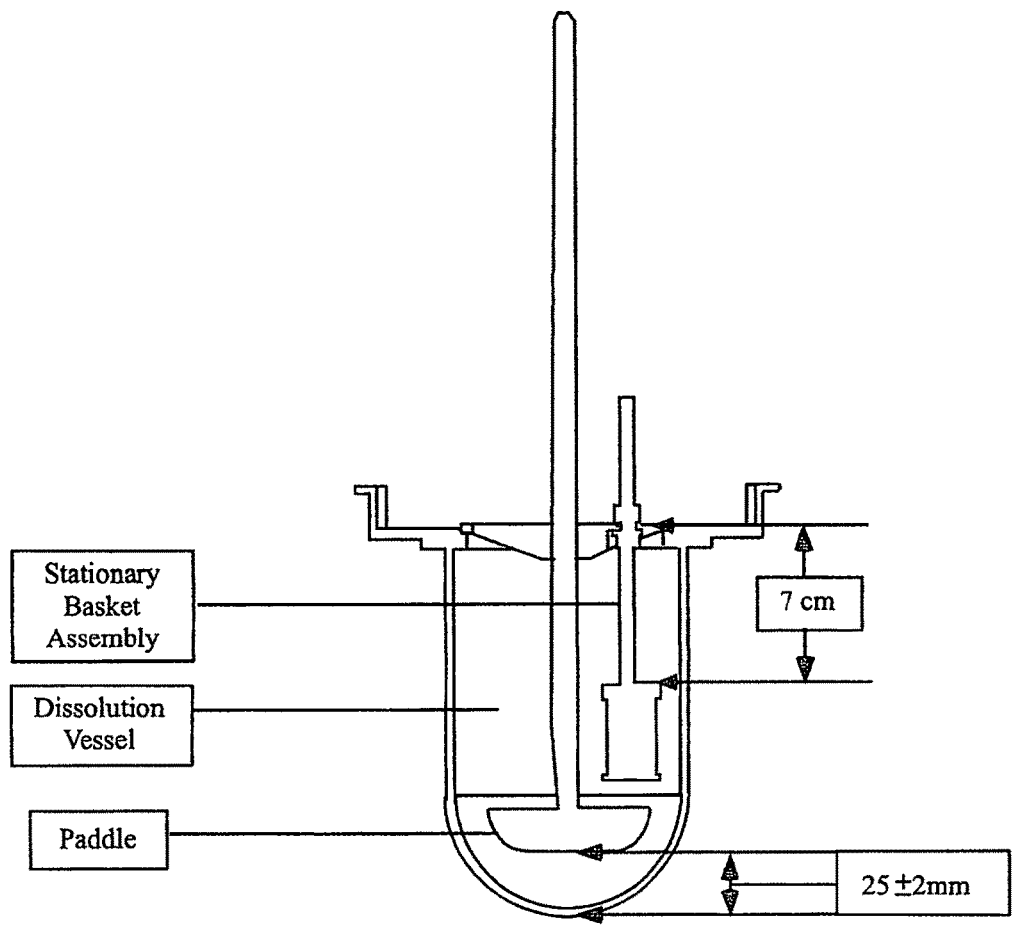
FIG. 3 is a pictorial representation of the modified dissolution vessel and paddle described in Example 3.

The second dissolution method (Method 2) was optimized to assess the controlled release performance of the controlled release dosage forms of the present invention having 5, 10, 20, 30 and 40 mg of the active agent. In this regard, the unique controlled release characteristics of the inventive dosage forms are such that standard dissolution methodology and apparatus may not bear a close relationship to the rate or extent of active agent release as observed in in vivo pharmacokinetic studies. This is due in large part to the use of very hydrophobic excipients in the inventive dosage forms (e.g., SAIB and IPM), resulting in compositions that result in a controlled release mass with low water permeability. Accordingly, this second method represents an enhancement of the earlier method (Method 1) to provide a better reflection of in vivo release. The new method uses the paddle configuration of an USP dissolution apparatus Type 2 with a stainless steel stationary basket assembly (type 316, 20-mesh basket with 20-mesh screen ceiling modification) attached to a modified conical low-loss evaporation cover on the dissolution vessel. These changes to the traditional apparatus were carried out in order to place the dosage form in the high shear flow zone of the USP dissolution apparatus, with an increased paddle speed to increase medium flow within the dissolution vessel. This new, fixed high-flow zone is located just above the rotating paddle. During testing, the dissolution media perfuses the stationary basket, facilitating release of the active agent from the full surface area of the dosage form and thus overcoming any surface boundary layer limitations that could result from placement of the dosage form at the bottom of the dissolution vessel. A pictorial representation of the modified dissolution vessel and paddle, with the stationary basket assembly is provided as FIG. 3. In addition to the stationary basket assembly, a screen ceiling inside the mesh basket was developed to prevent the dosage forms from floating within the basket.

Suitable stationary basket assemblies are commercially available and can be purchased from Varian as a kit. The kit contains a mesh basket (10, 20 or 40 mesh), which attaches to a basket shaft. A hole in the evaporation cover of the dissolution vessel allows the basket shaft to be secured to it. However, the evaporation covers provided with the kit are not ideal for use in an extended controlled release test. This is because the covers are flat and also contain a large cut out which allows them to be easily removed from the dissolution apparatus. Over the course of a 24-hour dissolution test, use of the covers provided with the kit would cause significant media loss due to evaporation. Evaporative media loss would ultimately lead to higher than expected release rate profiles. Previous dissolution studies with the dosage forms of the present invention have in fact given controlled release rate profiles well in excess of 100% release. An alternative to the kit evaporation cover was therefore developed.

The dissolution profiles using 20-Mesh Basket/20-Mesh Screen Ceiling and 40-Mesh Basket/without ceiling were determined to be the same. The 20-Mesh Baskets were chosen in order to maximize the hydrodynamic flow of dissolution media through the basket while minimizing leakage of the dosage form from the basket. The screen ceiling is used to confine the dosage form within the basket and improve assay variability.

In addition, Method 2 uses a single-phase dissolution medium (0.1N HCl with 0.5% (w/v) sodium dodecyl sulfate (SDS). The addition of the surfactant (SDS) to the dissolution medium improves the ability of the medium to wet the hydrophobic controlled release mass during testing.

Finally, a reverse phase HPLC method is used for determining the active agent concentration of the dosage form samples obtained from the dissolution testing methods of this Example 3. The mobile phase for the first dissolution method (Method 1) is prepared in two steps while the mobile phase for the second dissolution method (Method 2) is prepared in one step. A summary of the method parameters for Methods 1 and 2 is provided below as Table 5.

TABLE 5

| | Test Method | |
| --- | --- | --- |
| | Method 1 | Method 2 |
| Media | 750 mL 0.1N HCl (2 hours) 250 mL 0.2N Na Phosphate | 0.1N HCl/0.5% SDS (1000 mL) |
| Paddle Speed | 50 RPM | 100 RPM |
| Bath Temperature | 37° C. | 37° C. |
| Sample Containment | Coiled Sinker (Type 316 stainless steel) | Stationary Basket Assembly (20 Mesh with Ceiling) |
| Sample Timepoints | 0.25, 0.5, 1, 2, 3, 6, 10, 12, 18 and 24 hours | 0.25, 0.5, 1, 2, 3, 6, 10, 12, 18 and 24 hours |

TABLE 5-continued

| | Test Method | |
|---|---|---|
| | Method 1 | Method 2 |
| Mobile Phase | 65% SDS Buffer/35% CAN SDS Buffer (0.5% SDS/1% Acetic Acid/20% CAN) | 0.35% SDS/0.7% Acetic Acid/44% ACN/56% Water |
| HPLC Column | Waters XTerra C18, 5 µm, 4.6 × 150 mm | Waters XTerra C18, 5 µm, 4.6 × 150 mm |
| Flow Rate | 1.0 mL/min | 1.0 mL/min |
| Run Time | 8 min | 8 min |
| UV Detection | 240 nm | 240 nm |
| Injection Volume | 20 µL | 20 µL |
| Column Temperature | 40° C. | 40° C. |

Example 3a

The following in vitro dissolution test was carried out to characterize the in vitro release of abuse-resistant oxycodone oral dosage forms across a range of strengths (10 mg, 20 mg and 40 mg strengths).

The abuse-resistant oxycodone oral dosage forms used in this Example 3a were prepared using the following raw materials: Oxycodone base, micronized ("OXY"); Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); and Cellulose Acetate Butyrate, grade 381-20 BP, ethanol washed (Eastman Chemicals) ("CAB"). The formulations were produced using the commercial-scale manufacturing methods (Process Schemes 4 or 5 as described above) and then filled into size #00, #1 or #2 gel cap shells to produce 10, 20 and 40 mg dosage forms that were used as Test Capsules. The details of the formulations and the dosage forms containing the formulations of this Example 3a are disclosed below in Tables 6 and 7.

TABLE 6

| OXY (wt %) | SAIB (wt %) | TA (wt %) | CAB (wt %) | IPM (wt %) | HEC (wt %) | $SiO_2$ (wt %) | BHT (wt %) |
|---|---|---|---|---|---|---|---|
| 5.13 | 40.98 | 27.32 | 4.74 | 14.23 | 5.69 | 1.9 | 0.02 |

TABLE 7

| Capsule Size | OXY (mg) | SAIB (mg) | TA (mg) | CAB (mg) | IPM (mg) | HEC (mg) | $SiO_2$ (mg) | BHT (mg) | Total (mg) |
|---|---|---|---|---|---|---|---|---|---|
| size #2 | 10.0 | 79.9 | 53.3 | 9.2 | 27.7 | 11.1 | 3.7 | 0.04 | 195.0 |
| size #1 | 20.0 | 159.8 | 106.5 | 18.5 | 55.5 | 22.2 | 7.4 | 0.08 | 390.0 |
| size #00 | 40.0 | 319.6 | 213.1 | 37.0 | 111.0 | 44.4 | 14.8 | 0.16 | 780.0 |

Figure 4:
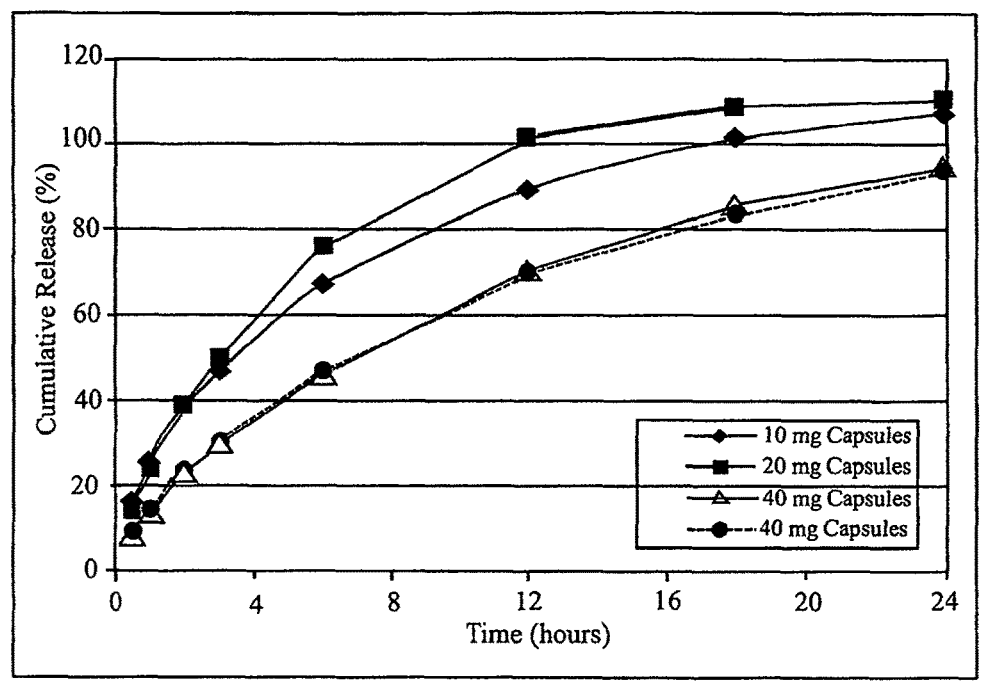

The dissolution study was carried out using the apparatus, reagents and methods of the Method 2 dissolution test described above, with the single exception that sample timepoints were at 0.5 hour, 1, 2, 3, 6, 12, 18 and 24 hour. Dissolution results were obtained on the following Test Capsules: two sets of eight 40 mg dosage forms (n=16); one set of eight 20 mg dosage forms (n=8); and one set of eight 10 mg dosage forms (n=8). The two sets of 40 mg dosage forms were tested using two different dissolution apparatus systems. The mean data from the four sets of Test Capsules are summarized below in Table 8. The release profiles from the Test Capsules are depicted in FIG. 4. As can be seen by these data, the two sets of 40 mg dosage forms had comparable release profiles. In addition, the 10 mg and 20 mg dosage forms exhibited faster release rates when compared to the 40 mg dosage forms. These results are consistent with the concept that relatively smaller capsules (dosage forms with larger surface to volume ratios) will generally provide faster release since the fraction of active agent at or near the dosage form surface increases with an increased surface to volume ratio.

TABLE 8

| Mean Cumulative Drug Released | | | | | | | | |
|---|---|---|---|---|---|---|---|---|
| 0.5 hr | 1 hr | 2 hr | 3 hr | 6 hr | 12 hr | 18 hr | 24 hr | |
| 40 mg Test Capsules (Apparatus 1) | | | | | | | | |
| 8% | 14% | 23% | 30% | 46% | 70% | 85% | 94% | Mean |
| 1 | 1 | 2 | 3 | 4 | 5 | 4 | 3 | Std Dev |
| 40 mg Test Capsules (Apparatus 2) | | | | | | | | |
| 9% | 14% | 23% | 30% | 47% | 69% | 83% | 93% | Mean |
| 1 | 2 | 3 | 3 | 5 | 6 | 6 | 5 | Std Dev |
| 20 mg Test Capsules | | | | | | | | |
| 14% | 24% | 39% | 50% | 76% | 101% | 108% | 110% | Mean |
| 2 | 2 | 3 | 4 | 5 | 4 | 2 | 2 | Std Dev |
| 10 mg Test Capsules | | | | | | | | |
| 16% | 25% | 38% | 47% | 67% | 89% | 101% | 107% | Mean |
| 2 | 4 | 8 | 10 | 14 | 12 | 7 | 3 | Std Dev |

Example 3b

The following in vitro dissolution test was carried out to: (a) characterize the in vitro release of abuse-resistant oxycodone oral dosage forms across a range of strengths (5 mg, 20 mg and 40 mg strengths) by multi-media dissolution testing; (b) demonstrate a dissolution profile similarity between dosage form product lots manufactured at two different manufacturing sites; and (c) demonstrate a dissolution profile similarity between two different dosage form product lots (5 mg and 40 mg dosage strengths) produced with different purity grades of the active agent (oxycodone).

The abuse-resistant oxycodone oral dosage forms used in this Example 3b were prepared using the following raw materials: Oxycodone base, micronized ("OXY"), grade 2 (specified to contain not more than 0.25% (w/w) 14-hydroxycodeinone (14-HC)) or grade 1 (specified to contain not more than 0.001% (w/w) 14-HC), both grades obtained from Noramco, Inc (Athens Ga.); Isopropyl Myristate, NF ("IPM"); Colloidal silicon dioxide (Cabosil®, Cabot Corp) ("$SiO_2$"); Butylated hydroxyl toluene, NF ("BHT");

Hydroxyethyl cellulose, NF ("HEC"); Sucrose Acetate Isobutyrate (Eastman Chemicals), ("SAIB"); Triacetin USP ("TA"); and Cellulose Acetate Butyrate, grade 381-20 BP, ethanol washed (Eastman Chemicals) ("CAB"). The formulations were produced using the commercial-scale manufacturing methods (Process Schemes 4 or 5 as described above) and then filled into size #00, #1 or #4 hard gelatin cap shells to produce 5, 20 and 40 mg dosage forms that were used as Test Capsules. The details of the formulations and the dosage forms containing the formulations of this Example 3b are disclosed below in Tables 9 and 10.

TABLE 9

| OXY (wt %) | SAIB (wt %) | TA (wt %) | CAB (wt %) | IPM (wt %) | HEC (wt %) | $SiO_2$ (wt %) | BHT (wt %) |
|---|---|---|---|---|---|---|---|
| 5.13 | 40.98 | 27.32 | 4.74 | 14.23 | 5.69 | 1.9 | 0.02 |

TABLE 10

| Capsule Size | OXY (mg) | SAIB (mg) | TA (mg) | CAB (mg) | IPM (mg) | HEC (mg) | $SiO_2$ (mg) | BHT (mg) | Total (mg) |
|---|---|---|---|---|---|---|---|---|---|
| size #4 | 5.0 | 40.0 | 26.6 | 4.6 | 13.9 | 5.5 | 1.9 | 0.02 | 97.5 |
| size #1 | 20.0 | 159.8 | 106.5 | 18.5 | 55.5 | 22.2 | 7.4 | 0.08 | 390.0 |
| size #00 | 40.0 | 319.6 | 213.1 | 37.0 | 111.0 | 44.4 | 14.8 | 0.16 | 780.0 |

Figure 5A:
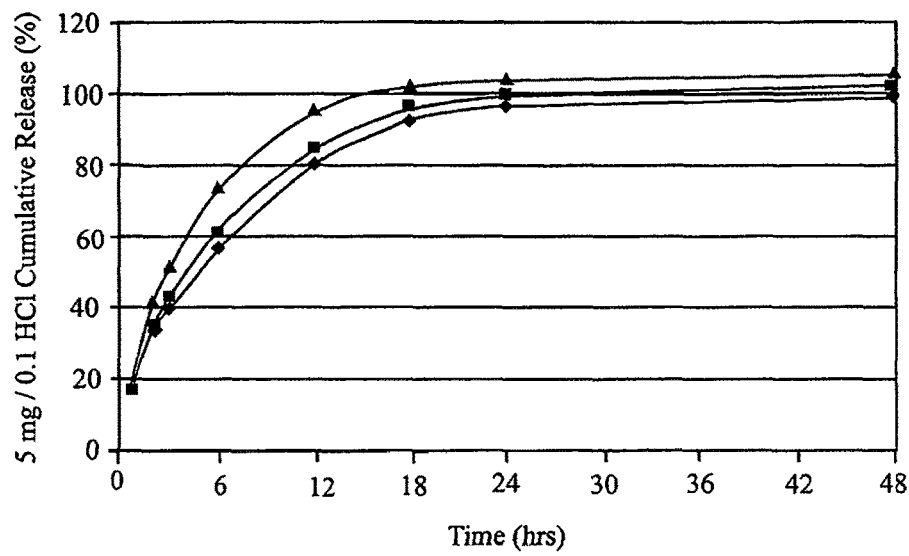
FIGS. 5A-5C show the results from the in vitro dissolution study of 5 mg strength Test Capsules as described in Example 3b.
Figure 5B:
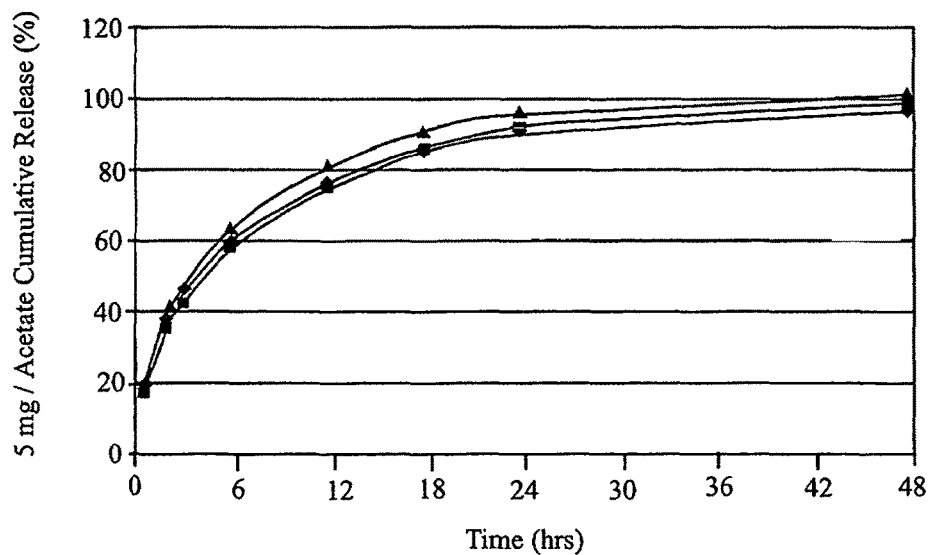
Figure 5C:
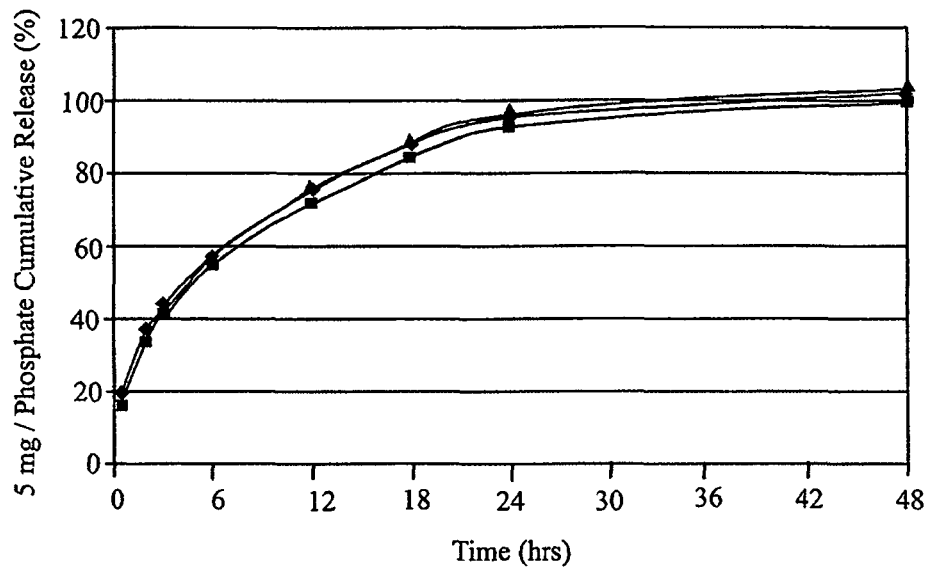
Figure 6A:
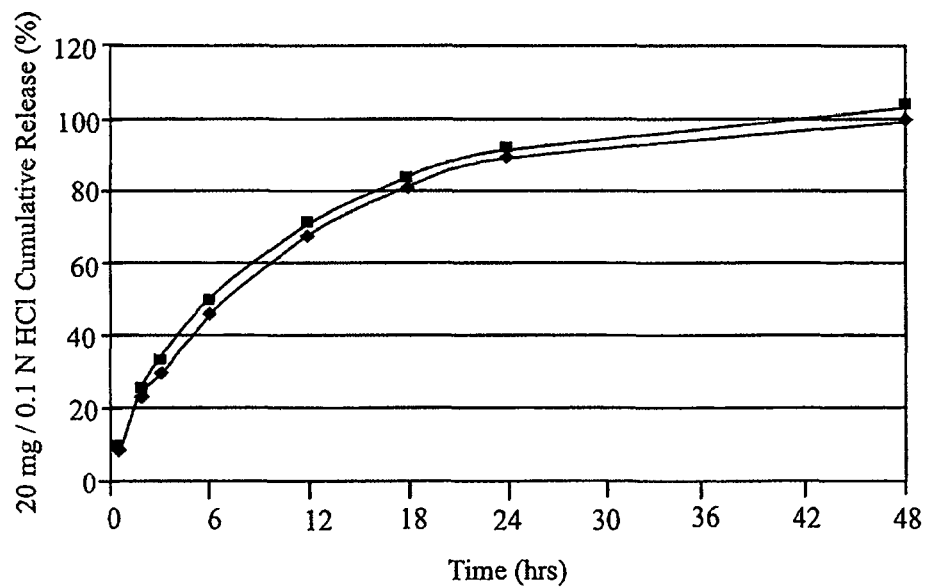
FIGS. 6A-6C show the results from the in vitro dissolution study of 20 mg strength Test Capsules as described in Example 3b.
Figure 6B:
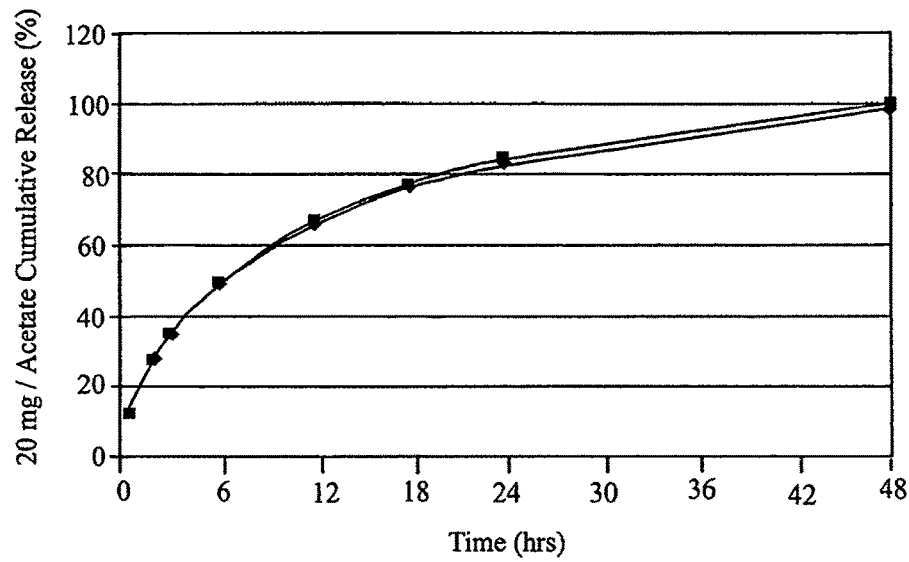
Figure 6C:
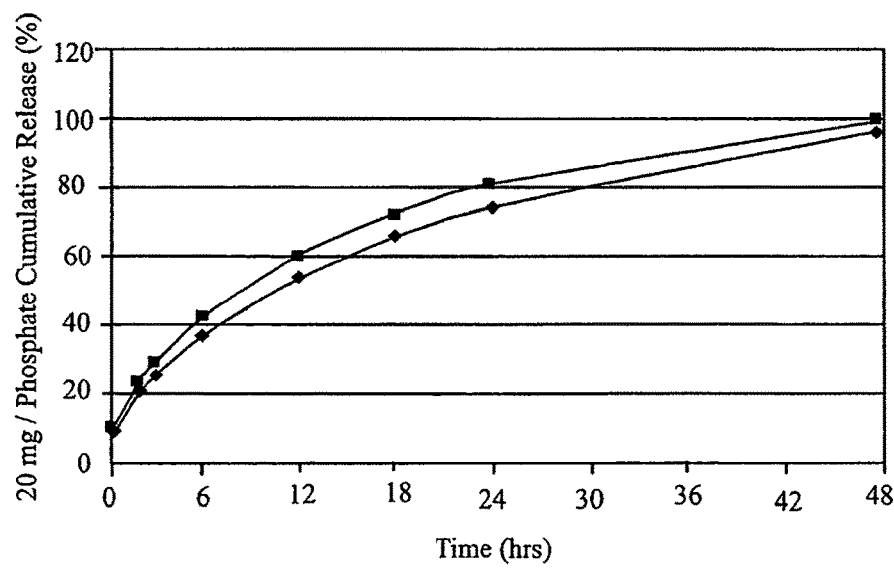
Figure 7A:
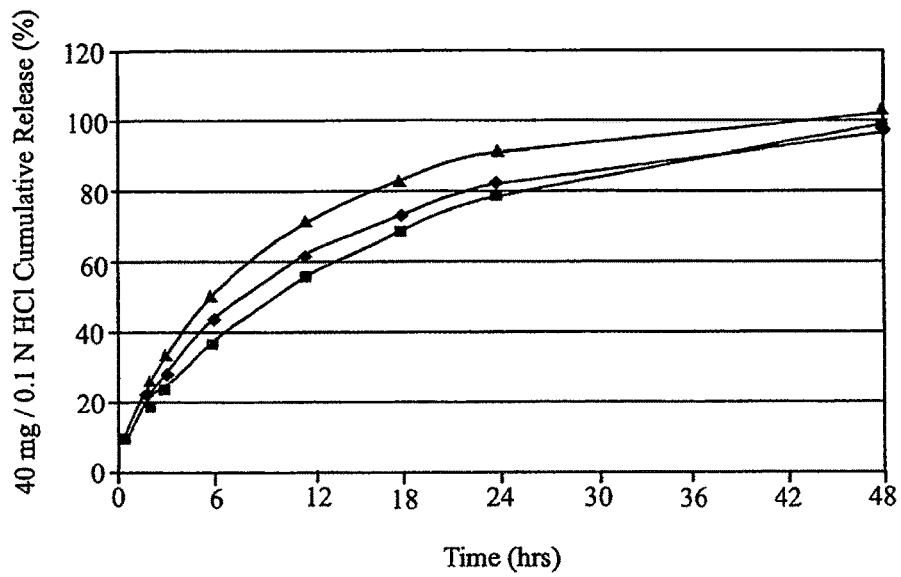
FIGS. 7A-7C show the results from the in vitro dissolution study of 40 mg strength Test Capsules as described in Example 3b.
Figure 7B:
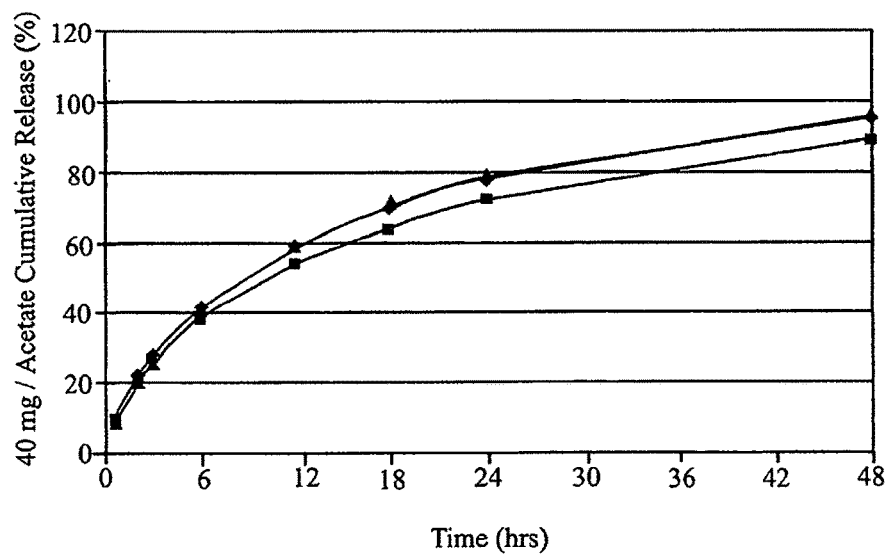
Figure 7C:
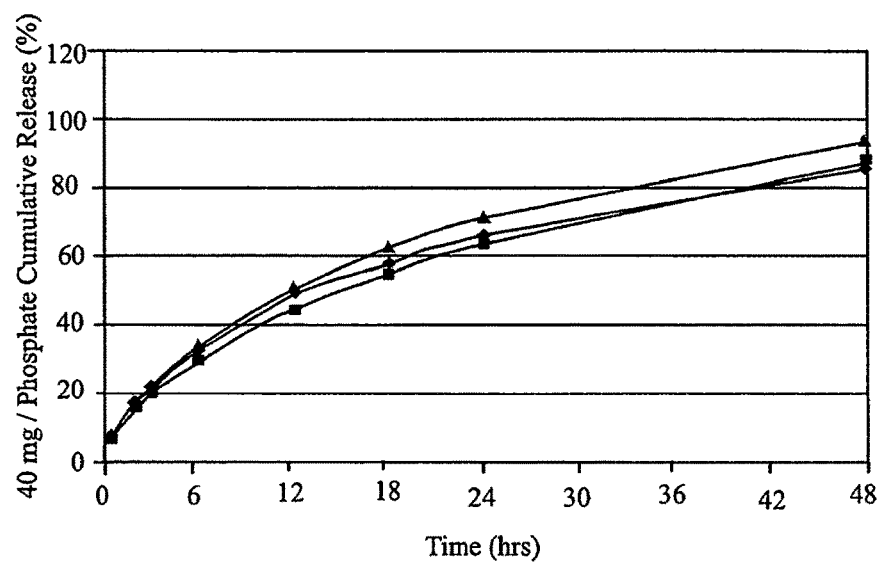

The dissolution study was carried out using the apparatus, reagents and methods of the Method 2 dissolution test described above, with the following exceptions: the sample timepoints were at 0.5 hour, 2, 3, 6, 12, 18, 24 and 48 hour. Dissolution results were obtained on the following Test Capsules: (Test 1, manufacturing site 1) twelve 40 mg dosage forms (n=12); twelve 20 mg dosage forms (n=8); and twelve 5 mg dosage forms (n=12); (Test 2, manufacturing site 2) twelve 40 mg dosage forms (n=12); twelve 20 mg dosage forms (n=8); and twelve 5 mg dosage forms (n=12); and (Test 3, high purity OXY) twelve 40 mg dosage forms (n=12); and twelve 5 mg dosage forms (n=12). The mean data obtained from Tests 1-3 are summarized below in Tables 11-13. The release profiles grouped together by common dosage strength and dissolution medium obtained from Tests 1-3 are depicted in FIGS. 5, 6 and 7.

TABLE 11

Mean Cumulative Drug Released

| 0.5 hr | 2 hr | 3 hr | 6 hr | 12 hr | 18 hr | 24 hr | 48 hr | |
|---|---|---|---|---|---|---|---|---|
| Test 1: 40 mg Test Capsules (0.1N HCl) | | | | | | | | |
| 8% | 21% | 27% | 42% | 61% | 73% | 82% | 98% | Mean |
| 1 | 3 | 4 | 6 | 8 | 8 | 8 | 4 | Std Dev |
| Test 1: 40 mg Test Capsules (Acetate Buffer) | | | | | | | | |
| 9% | 22% | 28% | 42% | 59% | 71% | 79% | 96% | Mean |
| 1 | 3 | 3 | 4 | 5 | 5 | 5 | 4 | Std Dev |
| Test 1: 40 mg Test Capsules (Phosphate Buffer) | | | | | | | | |
| 8% | 18% | 23% | 33% | 49% | 58% | 66% | 86% | Mean |
| 2 | 3 | 4 | 5 | 7 | 7 | 7 | 6 | Std Dev |
| Test 2: 40 mg Test Capsules (0.1N HCl) | | | | | | | | |
| 8% | 19% | 24% | 36% | 55% | 68% | 79% | 100% | Mean |
| 3 | 5 | 6 | 7 | 8 | 8 | 8 | 5 | Std Dev |
| Test 2: 40 mg Test Capsules (Acetate Buffer) | | | | | | | | |
| 9% | 21% | 26% | 38% | 54% | 64% | 72% | 90% | Mean |
| 2 | 4 | 4 | 4 | 5 | 5 | 6 | 4 | Std Dev |

TABLE 11-continued

Mean Cumulative Drug Released

| 0.5 hr | 2 hr | 3 hr | 6 hr | 12 hr | 18 hr | 24 hr | 48 hr | |
|---|---|---|---|---|---|---|---|---|
| Test 2: 40 mg Test Capsules (Phosphate Buffer) | | | | | | | | |
| 8% | 17% | 21% | 31% | 45% | 55% | 63% | 87% | Mean |
| 2 | 3 | 3 | 4 | 5 | 6 | 6 | 6 | Std Dev |
| Test 3: 40 mg Test Capsules (0.1N HCl) | | | | | | | | |
| 8% | 25% | 32% | 50% | 71% | 83% | 91% | 103% | Mean |
| 2 | 3 | 4 | 6 | 6 | 6 | 5 | 2 | Std Dev |
| Test 3: 40 mg Test Capsules (Acetate Buffer) | | | | | | | | |
| 7% | 20% | 26% | 40% | 59% | 71% | 80% | 97% | Mean |
| 1 | 2 | 3 | 4 | 6 | 6 | 5 | 3 | Std Dev |
| Test 3: 40 mg Test Capsules (Phosphate Buffer) | | | | | | | | |
| 8% | 18% | 23% | 34% | 50% | 62% | 72% | 93% | Mean |
| 2 | 4 | 5 | 6 | 7 | 8 | 8 | 6 | Std Dev |

TABLE 12

Mean Cumulative Drug Released

| 0.5 hr | 2 hr | 3 hr | 6 hr | 12 hr | 18 hr | 24 hr | 48 hr | |
|---|---|---|---|---|---|---|---|---|
| Test 1: 20 mg Test Capsules (0.1N HCl) | | | | | | | | |
| 9% | 23% | 30% | 46% | 68% | 81% | 89% | 99% | Mean |
| 1 | 2 | 3 | 4 | 6 | 6 | 4 | 1 | Std Dev |
| Test 1: 20 mg Test Capsules (Acetate Buffer) | | | | | | | | |
| 11% | 27% | 34% | 49% | 66% | 76% | 84% | 98% | Mean |
| 1 | 3 | 4 | 5 | 5 | 5 | 5 | 2 | Std Dev |
| Test 1: 20 mg Test Capsules (Phosphate Buffer) | | | | | | | | |
| 9% | 21% | 26% | 38% | 54% | 67% | 76% | 96% | Mean |
| 1 | 2 | 3 | 4 | 5 | 6 | 7 | 3 | Std Dev |
| Test 2: 20 mg Test Capsules (0.1N HCl) | | | | | | | | |
| 10% | 26% | 33% | 50% | 70% | 83% | 92% | 103% | Mean |
| 3 | 5 | 6 | 8 | 9 | 8 | 6 | 1 | Std Dev |
| Test 2: 20 mg Test Capsules (Acetate Buffer) | | | | | | | | |
| 11% | 27% | 34% | 49% | 66% | 77% | 84% | 100% | Mean |
| 2 | 4 | 5 | 6 | 6 | 5 | 5 | 3 | Std Dev |
| Test 2: 20 mg Test Capsules (Phosphate Buffer) | | | | | | | | |
| 10% | 23% | 29% | 42% | 61% | 73% | 81% | 99% | Mean |
| 2 | 3 | 4 | 5 | 6 | 6 | 5 | 3 | Std Dev |

TABLE 13

Mean Cumulative Drug Released

| 0.5 hr | 2 hr | 3 hr | 6 hr | 12 hr | 18 hr | 24 hr | 48 hr | |
|---|---|---|---|---|---|---|---|---|
| Test 1: 5 mg Test Capsules (0.1N HCl) | | | | | | | | |
| 17% | 34% | 41% | 57% | 81% | 93% | 97% | 99% | Mean |
| 2 | 4 | 4 | 6 | 7 | 3 | 2 | 2 | Std Dev |
| Test 1: 5 mg Test Capsules (Acetate Buffer) | | | | | | | | |
| 19% | 38% | 46% | 60% | 76% | 86% | 91% | 97% | Mean |
| 2 | 6 | 7 | 8 | 8 | 5 | 3 | 2 | Std Dev |
| Test 1: 5 mg Test Capsules (Phosphate Buffer) | | | | | | | | |
| 21% | 38% | 45% | 58% | 77% | 89% | 95% | 103% | Mean |
| 2 | 5 | 6 | 8 | 11 | 10 | 7 | 3 | Std Dev |
| Test 2: 5 mg Test Capsules (0.1N HCl) | | | | | | | | |
| 16% | 35% | 44% | 61% | 85% | 96% | 99% | 102% | Mean |
| 3 | 6 | 7 | 9 | 8 | 4 | 4 | 4 | Std Dev |

TABLE 13-continued

Mean Cumulative Drug Released

| 0.5 hr | 2 hr | 3 hr | 6 hr | 12 hr | 18 hr | 24 hr | 48 hr | |
|---|---|---|---|---|---|---|---|---|
| Test 2: 5 mg Test Capsules (Acetate Buffer) | | | | | | | | |
| 18% | 35% | 42% | 59% | 75% | 86% | 92% | 98% | Mean |
| 3 | 5 | 6 | 6 | 7 | 5 | 4 | 4 | Std Dev |
| Test 2: 5 mg Test Capsules (Phosphate Buffer) | | | | | | | | |
| 18% | 35% | 42% | 56% | 73% | 85% | 93% | 101% | Mean |
| 3 | 5 | 6 | 8 | 9 | 8 | 6 | 4 | Std Dev |
| Test 3: 5 mg Test Capsules (0.1N HCl) | | | | | | | | |
| 19% | 42% | 52% | 74% | 95% | 102% | 104% | 106% | Mean |
| 5 | 7 | 8 | 7 | 6 | 3 | 3 | 3 | Std Dev |
| Test 3: 5 mg Test Capsules (Acetate Buffer) | | | | | | | | |
| 19% | 39% | 47% | 63% | 81% | 91% | 96% | 101% | Mean |
| 3 | 4 | 5 | 7 | 7 | 4 | 2 | 2 | Std Dev |
| Test 3: 5 mg Test Capsules (Phosphate Buffer) | | | | | | | | |
| 18% | 36% | 43% | 58% | 77% | 89% | 97% | 104% | Mean |
| 3 | 6 | 7 | 9 | 9 | 7 | 4 | 3 | Std Dev |

As can be seen by these results, Test Capsules produced at three different active agent strengths (5 mg, 20 mg and 40 mg), and manufactured at two different scales and at two different sites demonstrate equivalent dissolution performance in three different aqueous buffer systems (pH 1, 4.5 and 6.8). In addition, Test Capsules produced at two different active agent strengths (5 mg and 40 mg) and using two different grades of the active agent demonstrated equivalent dissolution performance in the same buffer systems. Furthermore, cumulative release rates for a Test Capsule strengths and dissolution medium were generally highest in 0.1N HCl, slightly slower in acetate buffer, and slowest in phosphate buffer. This release performance was attributed to the relatively lower solubility of the active agent (oxycodone base) at pH 6.8 (the $pK_a$ of oxycodone base is 8.65).

Example 3c

The following in vitro dissolution test was carried out to characterize the in vitro release of abuse-resistant oxycodone oral dosage forms across a range of formulations. The abuse-resistant oxycodone oral dosage forms used in this Example 3c were prepared using the following raw materials: Oxycodone base, micronized ("OXY"); Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAM"); Triacetin USP ("TA"); Sodium Lauryl Sulfate ("SLS"); Labrafil M2125 CS ("LAB"); Gelucire 44/14 (Gattefosse) ("GEL"); and Cellulose Acetate Butyrate, grade 381-20 BP, ethanol washed (Eastman Chemicals) ("CAB"). The formulations were produced using the commercial-scale manufacturing methods (Process Schemes 4 or 5 as described above) and then filled into size #00 hard gelatin cap shells to produce 80 mg dosage forms that were used as Test Capsules. The details of the formulations and the dosage forms containing the formulations of this Example 3c are disclosed below in Table 14.

TABLE 14

| | OXY | SAIB | TA | CAB | IPM | HEC | $SiO_2$ | BHT | SLS | LAB | GEL | (Total) | |
|---|---|---|---|---|---|---|---|---|---|---|---|---|---|
| OXY1 | 80.0 | 281.4 | 208.4 | 42.0 | 112.0 | 42.0 | 14.0 | 0.2 | — | — | — | 780 | (mg) |
| | 10.26 | 36.08 | 26.72 | 5.38 | 14.36 | 5.38 | 1.79 | 0.02 | — | — | — | | (wt %) |
| OXY2 | 80.0 | 297.5 | 198.4 | 42.0 | 105.0 | 42.0 | 14.0 | 0.2 | 1.0 | — | — | 780 | (mg) |
| | 10.26 | 38.14 | 25.43 | 5.38 | 13.46 | 5.38 | 1.79 | 0.02 | 0.13 | — | — | | (wt %) |
| OXY3 | 80.0 | 285.5 | 190.3 | 42.0 | 105.0 | 42.0 | 14.0 | 0.2 | — | 21.0 | — | 780 | (mg) |
| | 10.26 | 36.60 | 24.40 | 5.38 | 13.46 | 5.38 | 1.79 | 0.02 | — | 2.69 | — | | (wt %) |
| OXY4 | 80.0 | 280.4 | 207.7 | 36.7 | 119.0 | 42.0 | 14.0 | 0.2 | — | — | — | 780 | (mg) |
| | 10.26 | 35.95 | 26.63 | 4.71 | 15.26 | 5.38 | 1.79 | 0.02 | — | — | — | | (wt %) |
| OXY5 | 80.0 | 281.0 | 200.8 | 42.0 | 119.0 | 42.0 | 14.0 | 0.2 | 1.0 | — | — | 780 | (mg) |
| | 10.26 | 36.03 | 25.74 | 5.38 | 15.26 | 5.38 | 1.79 | 0.02 | 0.13 | — | — | | (wt %) |
| OXY6 | 80.0 | 286.6 | 191.0 | 36.7 | 112.0 | 42.0 | 14.0 | 0.2 | — | 17.5 | — | 780 | (mg) |
| | 10.26 | 36.74 | 24.49 | 4.71 | 14.36 | 5.38 | 1.79 | 0.02 | — | 2.24 | — | | (wt %) |
| OXY7 | 80.0 | 284.4 | 210.7 | 42.0 | 112.0 | 42.0 | 15.8 | 0.2 | — | — | 14.0 | 780 | (mg) |
| | 10.26 | 36.46 | 27.01 | 5.38 | 14.36 | 2.69 | 2.02 | 0.02 | — | — | 1.79 | | (wt %) |
| OXY8 | 80.0 | 282.4 | 209.2 | 38.5 | 112.0 | 42.0 | 15.8 | 0.2 | — | — | — | 780 | (mg) |
| | 10.26 | 36.21 | 26.82 | 4.94 | 14.36 | 5.38 | 2.02 | 0.02 | — | — | — | | (wt %) |
| OXY9 | 80.0 | 285.9 | 204.3 | 38.5 | 112.0 | 42.0 | 15.8 | 0.2 | 1.4 | — | — | 780 | (mg) |
| | 10.26 | 36.66 | 26.19 | 4.94 | 14.36 | 5.38 | 2.02 | 0.02 | 0.18 | — | — | | (wt %) |

The dissolution study was carried out using the apparatus, reagents and methods of the Method 2 dissolution test described above, with the following exceptions: sample timepoints were at 0.5 hour, 1, 2, 3, 6, 10, 12, 18 and 24 hour. Dissolution results were obtained on the following Test Capsules: six (n=6) each of formulations OXY1-OXY9.

The mean dissolution data from the nine sets of Test Capsules are summarized below in Table 15.

TABLE 15

Mean Cumulative Drug Released

| 0.5 hr | 1 hr | 2 hr | 3 hr | 6 hr | 10 hr | 12 hr | 18 hr | 24 hr | |
|---|---|---|---|---|---|---|---|---|---|
| Formulation # OXY1 | | | | | | | | | |
| 7% | 12% | 20% | 27% | 45% | 62% | 69% | 83% | 91% | Mean |
| 1 | 2 | 4 | 4 | 6 | 5 | 5 | 4 | 4 | Std Dev |

TABLE 15-continued

Mean Cumulative Drug Released

| 0.5 hr | 1 hr | 2 hr | 3 hr | 6 hr | 10 hr | 12 hr | 18 hr | 24 hr | |
|---|---|---|---|---|---|---|---|---|---|
| Formulation # OXY2 | | | | | | | | | |
| 9% | 16% | 30% | 40% | 63% | 81% | 86% | 96% | 101% | Mean |
| 2 | 4 | 7 | 8 | 9 | 7 | 6 | 4 | 4 | Std Dev |
| Formulation # OXY3 | | | | | | | | | |
| 5% | 9% | 14% | 19% | 33% | 49% | 55% | 70% | 81% | Mean |
| 1 | 1 | 2 | 2 | 4 | 5 | 5 | 6 | 6 | Std Dev |
| Formulation # OXY4 | | | | | | | | | |
| 6% | 10% | 17% | 23% | 39% | 55% | 60% | 74% | 82% | Mean |
| 2 | 3 | 3 | 4 | 4 | 5 | 5 | 4 | 3 | Std Dev |

TABLE 15-continued

Mean Cumulative Drug Released

| 0.5 hr | 1 hr | 2 hr | 3 hr | 6 hr | 10 hr | 12 hr | 18 hr | 24 hr | |
|---|---|---|---|---|---|---|---|---|---|
| Formulation # OXY5 | | | | | | | | | |
| 7% | 13% | 24% | 31% | 49% | 66% | 72% | 84% | 91% | Mean |
| 1 | 4 | 8 | 9 | 10 | 10 | 9 | 6 | 4 | Std Dev |
| Formulation # OXY6 | | | | | | | | | |
| 6% | 10% | 17% | 22% | 39% | 57% | 63% | 79% | 88% | Mean |
| 2 | 2 | 4 | 5 | 9 | 10 | 10 | 8 | 6 | Std Dev |
| Formulation # OXY7 | | | | | | | | | |
| 9% | — | 28% | 37% | 55% | — | 77% | 91% | 98% | Mean |
| 1 | — | 2 | 2 | 3 | — | 3 | 2 | 1 | Std Dev |
| Formulation # OXY8 | | | | | | | | | |
| 6% | — | 17% | 23% | 39% | — | 63% | 80% | 91% | Mean |
| 2 | — | 3 | 4 | 6 | — | 7 | 6 | 4 | Std Dev |
| Formulation # OXY9 | | | | | | | | | |
| 8% | — | 26% | 35% | 53% | — | 75% | 89% | 97% | Mean |
| 0 | — | 1 | 1 | 1 | — | 1 | 0 | 1 | Std Dev |

Example 3d

The following in vitro dissolution test was carried out to characterize the in vitro release of abuse-resistant hydromorphone oral dosage forms across a range of strengths (8 mg and 16 mg strengths) and across a range of formulations.

The abuse-resistant hydromorphone oral dosage forms used in this Example 3d were prepared using the following raw materials: Hydromorphone HCl ("HMH"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Labrafil M2125 CS ("LAB"); and Cellulose Acetate Butyrate, grade 381-20 BP, ethanol washed (Eastman Chemicals) ("CAB"). The formulations were produced using the GMP manufacturing method of Example 1d above (Process Scheme 8) and then filled into either size #1 (HMH1) or #2 (HMH2-4) gel cap shells to produce 8 and 16 mg dosage forms that were used as Test Capsules. The details of the formulations and the dosage forms containing the formulations of this Example 3d are disclosed below in Table 16.

TABLE 16

| Formula # | HMH | SAIB | TA | CAB | IPM | HEC | SiO$_2$ | BHT | LAB | Total |
|---|---|---|---|---|---|---|---|---|---|---|
| HMH1 | 16.0 | 108.6 | 80.4 | 15.5 | 41.4 | 7.8 | 5.2 | 0.1 | — | 275.0 (mg) |
|  | 5.82 | 39.49 | 29.5 | 5.65 | 15.07 | 5.65 | 1.88 | 0.02 | — | (wt %) |
| HMH2 | 16.0 | 104.1 | 77.1 | 15.5 | 41.4 | 15.5 | 5.2 | 0.1 | — | 275.0 (mg) |
|  | 5.82 | 37.86 | 28.05 | 5.65 | 15.07 | 5.65 | 1.88 | 0.02 | — | (wt %) |
| HMH3 | 16.0 | 101.1 | 74.9 | 15.5 | 38.9 | 15.5 | 5.2 | 0.1 | 7.8 | 275.0 (mg) |
|  | 5.82 | 36.78 | 27.24 | 5.65 | 14.13 | 5.65 | 1.88 | 0.02 | 2.83 | (wt %) |
| HMH4 | 8.0 | 29.8 | 19.9 | 3.6 | 10.8 | 4.3 | 1.4 | 0.1 | 2.2 | 80.0 (mg) |
|  | 10.00 | 37.25 | 24.83 | 4.50 | 13.50 | 5.40 | 1.80 | 0.02 | 2.70 | (wt %) |

The dissolution study was carried out using the apparatus, reagents and methods of the Method 2 dissolution test described above, with the following exceptions: sample timepoints were at 0.5 hour, 1, 2, 3, 6, 10, 12, 18 and 24 hour. Dissolution results were obtained on the following Test Capsules: six (n=6) each of formulations HMH1-HMH4.

Figure 8:
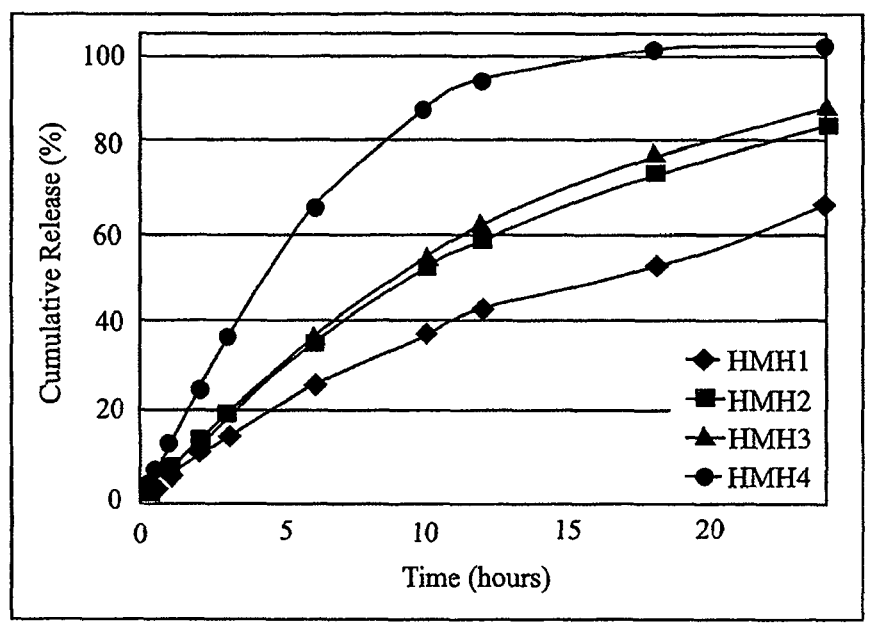
FIG. 8 shows the mean dissolution data results from the in vitro dissolution study of HMH Test Capsules as described in Example 3d.

The mean dissolution data from the four sets of Test Capsules are summarized below in Table 17. The dissolution release profiles of two formulations are depicted in FIG. 8.

TABLE 17

Mean Cumulative Drug Released

| 0.5 hr | 1 hr | 2 hr | 3 hr | 6 hr | 10 hr | 12 hr | 18 hr | 24 hr | |
|---|---|---|---|---|---|---|---|---|---|
| Formulation # HMH1 | | | | | | | | | |
| 2% | 5% | 10% | 14% | 25% | 37% | 42% | 52% | 66% | Mean |
| 1 | 2 | 3 | 4 | 6 | 8 | 8 | 7 | 7 | Std Dev |
| Formulation # HMH2 | | | | | | | | | |
| 3% | 6% | 13% | 19% | 35% | 52% | 58% | 73% | 84% | Mean |
| 1 | 1 | 3 | 4 | 6 | 7 | 7 | 7 | 7 | Std Dev |
| Formulation # HMH3 | | | | | | | | | |
| 3% | 6% | 12% | 19% | 36% | 54% | 61% | 77% | 88% | Mean |
| 1 | 2 | 3 | 5 | 8 | 10 | 9 | 8 | 6 | Std Dev |
| Formulation # HMH4 | | | | | | | | | |
| 6% | 12% | 24% | 36% | 65% | 87% | 94% | 101% | 102% | Mean |
| 1 | 2 | 4 | 7 | 10 | 9 | 8 | 4 | 3 | Std Dev |

Example 3e

The following in vitro dissolution test was carried out to characterize the in vitro release of abuse-resistant hydrocodone oral dosage forms across two different formulations.

The abuse-resistant hydrocodone oral dosage forms used in this Example 3e were prepared using the following raw materials: Hydrocodone Bitartrate ("HCB"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Gelucire 44/14 (Gattefosse) ("GEL"); and Cellulose Acetate Butyrate, grade 381-20 BP, ethanol washed (Eastman Chemicals) ("CAB"). The formulations were produced using the GMP manufacturing method of Example 1e above (Process Scheme 9) and then filled into size #3 gel cap shells to produce the dosage forms that were used as Test Capsules. The details of the formulations and the dosage forms containing the formulations of this Example 3e are disclosed below in Table 18.

TABLE 18

| Formula # | HCB (mg) | SAIB (mg) | TA (mg) | CAB (mg) | IPM (mg) | HEC (mg) | SiO$_2$ (mg) | BHT (02 mg) | GEL (mg) | Total (mg) |
|---|---|---|---|---|---|---|---|---|---|---|
| HCB1 | 15.0 | 41.8 | 27.8 | 5.2 | 14.24 | 2.8 | 1.9 | 0.1 | 1.1 | 110.0 (mg) |
|  | 13.64 | 37.97 | 25.31 | 4.75 | 12.95 | 2.59 | 1.73 | 0.02 | 1.04 | (wt %) |
| HCB2 | 75.0 | 208.8 | 139.2 | 26.1 | 71.2 | 14.2 | 9.5 | 0.11 | 5.7 | 550.0 (mg) |
|  | 13.63 | 37.96 | 25.31 | 4.75 | 12.95 | 2.58 | 1.73 | 0.02 | 1.04 | (wt %) |

Figure 9A:
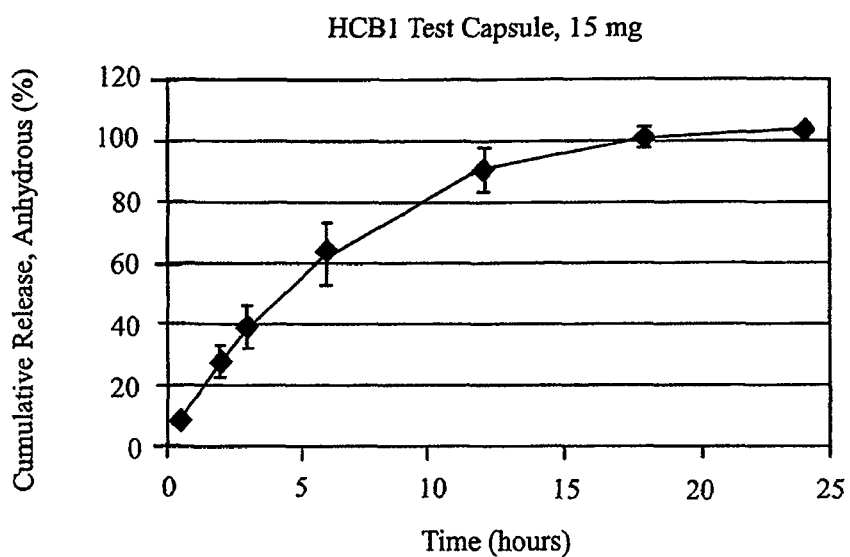
FIGS. 9A and 9B show the mean dissolution data results from the in vitro dissolution study of HCB1 and HCB2 Test Capsules as described in Example 3e.
Figure 9B:
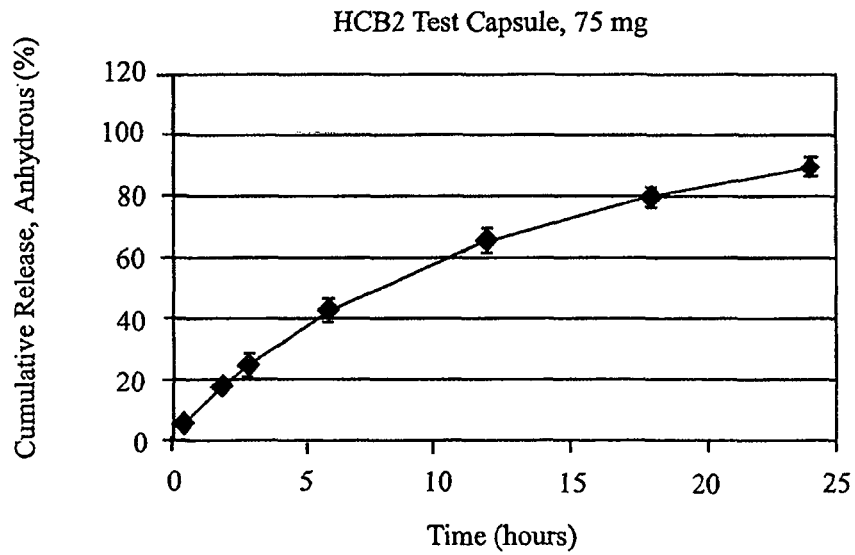

The dissolution study was carried out using the apparatus, reagents and methods of the Method 2 dissolution test described above, with the following exceptions: sample timepoints were at 0.5 hour, 2, 3, 6, 12, 18 and 24 hour. Dissolution results were obtained on the following Test Capsules: six (n=6) each of formulations HCB1 and HCB2. The mean dissolution data from the two sets of Test Capsules are summarized below in Table 19. The dissolution release profiles of formulations HCB1 and HCB2 are depicted in FIGS. 9A and 9B.

TABLE 19

Mean Cumulative Drug Released

| 0.5 hr | 2 hr | 3 hr | 6 hr | 12 hr | 18 hr | 24 hr | |
|---|---|---|---|---|---|---|---|
| Formulation # HCB1 | | | | | | | |
| 9% | 28% | 39% | 63% | 90% | 100% | 103% | Mean |
| 2 | 5 | 7 | 10 | 7 | 3 | 2 | Std Dev |
| Formulation # HCB2 | | | | | | | |
| 5% | 18% | 25% | 44% | 67% | 82% | 92% | Mean |
| 1 | 3 | 4 | 4 | 4 | 3 | 3 | Std Dev |

Example 3f

The following in vitro dissolution test was carried out to characterize the in vitro release of abuse-resistant oxymorphone oral dosage forms across several different formulations.

The abuse-resistant oxymorphone oral dosage forms used in this Example 3f were prepared using the following raw materials: oxymorphone HCl ("OMH"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); and Gelucire 44/14 (Gattefosse) ("GEL"). The formulations were produced using a lab-scale manufacturing process and then filled into size #1 gel capsules to produce the dosage forms that were used as Test Capsules. The details of the lab-scale manufacturing process are as follows. The SAIB and TA were mixed as a 1.5:1 stock solution. Temperature was maintained at 60° C.±5° C. throughout the process run. The SAIB/TA stock solution was mixed at 420 rpm for 15 minutes. The GEL was added and mixed into the compounding mix at 600 rpm for 15 minutes. An IPM/BHT solution and the remaining IPM were then added, and the resulting mixture was processed at 600 rpm for 15 minutes, after which the SiO$_2$ was added and mixed at 550 rpm for 20 minutes. Homogenization was then carried out at 9,600 rpm for 5 minutes. Pre-screened CAB was added to the compounding mixture, and mixed at 960 rpm for 5 minutes, then increased to 1,500 rpm for an additional 32 minutes to provide a placebo mixture. The OMH was added to pre-heated placebo mixture (60° C.±5° C.) and combined using a spatula, followed by homogenization at 9,600 rpm for 5 minutes to produce the final formulations. The details of the formulations and the dosage forms containing the formulations of this Example 3f are disclosed below in Table 20.

TABLE 20

|  | OMH | SAIB | TA | CAB | IPM | HEC | SiO$_2$ | BHT | GEL | (Total) | |
|---|---|---|---|---|---|---|---|---|---|---|---|
| OMH1 | 40.00 | 226.38 | 150.92 | 25.50 | 76.50 | 15.30 | 12.75 | 0.10 | 2.55 | 550 | (mg) |
|  | 7.27 | 41.16 | 27.44 | 4.64 | 13.91 | 2.78 | 2.32 | 0.02 | 0.46 |  | (wt %) |
| OMH2 | 40.00 | 214.14 | 142.76 | 25.50 | 76.50 | 35.70 | 7.65 | 0.10 | 7.65 | 550 | (mg) |
|  | 7.27 | 38.93 | 25.96 | 4.64 | 13.91 | 6.49 | 1.39 | 0.02 | 1.39 |  | (wt %) |
| OMH3 | 40.00 | 226.38 | 150.92 | 30.60 | 76.50 | 15.30 | 7.65 | 0.10 | 2.55 | 550 | (mg) |
|  | 7.27 | 41.16 | 27.44 | 5.56 | 13.91 | 2.78 | 1.39 | 0.02 | 0.46 |  | (wt %) |
| OMH4 | 40.00 | 214.14 | 142.76 | 25.50 | 76.50 | 35.70 | 12.75 | 0.10 | 2.55 | 550 | (mg) |
|  | 7.27 | 38.93 | 25.96 | 4.64 | 13.91 | 6.49 | 2.32 | 0.02 | 0.46 |  | (wt %) |

TABLE 20-continued

|       | OMH   | SAIB   | TA     | CAB   | IPM   | HEC   | SiO$_2$ | BHT  | GEL  | (Total) |
|-------|-------|--------|--------|-------|-------|-------|---------|------|------|---------|
| OMH5  | 40.00 | 208.02 | 138.68 | 30.60 | 76.50 | 35.70 | 12.75   | 0.10 | 7.65 | 550 (mg) |
|       | 7.27  | 37.82  | 25.21  | 5.56  | 13.91 | 6.49  | 2.32    | 0.02 | 1.39 | (wt %)  |
| OMH6  | 40.00 | 214.14 | 142.76 | 30.60 | 76.50 | 35.70 | 7.65    | 0.10 | 2.55 | 550 (mg) |
|       | 7.27  | 38.93  | 25.96  | 5.56  | 13.91 | 6.49  | 1.39    | 0.02 | 0.46 | (wt %)  |
| OMH7  | 40.00 | 220.26 | 146.84 | 30.60 | 76.50 | 15.30 | 12.75   | 0.10 | 7.65 | 550 (mg) |
|       | 7.27  | 40.05  | 26.70  | 5.56  | 13.91 | 2.78  | 2.32    | 0.02 | 1.39 | (wt %)  |
| OMH8  | 40.00 | 226.38 | 150.92 | 25.50 | 76.50 | 15.30 | 7.65    | 0.10 | 7.65 | 550 (mg) |
|       | 7.27  | 41.16  | 27.44  | 4.64  | 13.91 | 2.78  | 1.39    | 0.02 | 1.39 | (wt %)  |
| OMH9  | 40.00 | 218.73 | 145.82 | 28.05 | 76.50 | 25.50 | 10.20   | 0.10 | 5.10 | 550 (mg) |
|       | 7.27  | 39.77  | 26.51  | 5.10  | 13.91 | 4.64  | 1.85    | 0.02 | 0.93 | (wt %)  |
| OMH10 | 40.00 | 206.49 | 152.96 | 25.50 | 81.60 | 35.70 | 7.65    | 0.10 | —    | 550 (mg) |
|       | 7.27  | 37.54  | 27.81  | 4.64  | 14.84 | 6.49  | 1.39    | 0.02 | —    | (wt %)  |

Figure 10A:
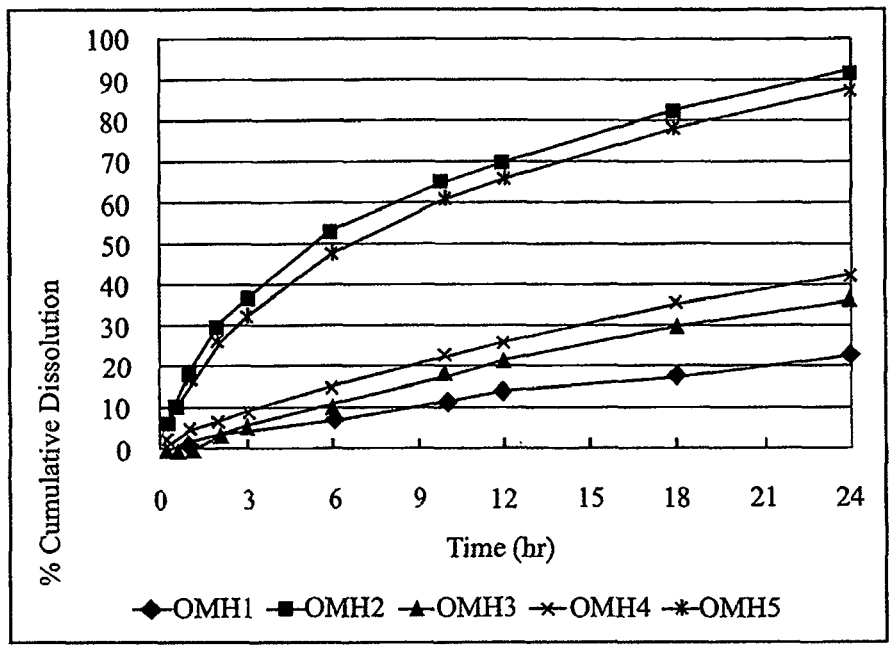
FIGS. 10A and 10B show the mean dissolution data results from the in vitro dissolution study of OMH1-OMH10 Test Capsules as described in Example 3f.
Figure 10B:
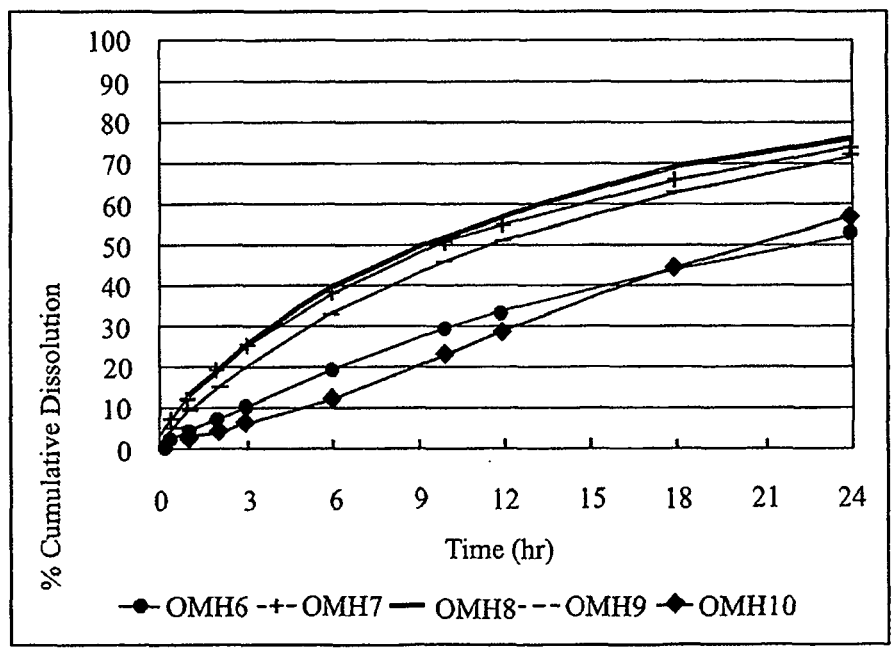

The dissolution study was carried out using the apparatus, reagents and methods of the Method 1 dissolution test described above, with the following exceptions: sample timepoints were at 0.5 hour, 1, 2, 3, 6, 10 12, 18 and 24 hour. Dissolution results were obtained on the following Test Capsules: four (n=4) each of formulations OMH1-OMH10. The mean dissolution data from the ten sets of Test Capsules are summarized below in Table 21 and depicted in FIGS. 10A and 10B.

TABLE 21

Mean Cumulative Drug Released

| 0.5 hr | 1 hr | 2 hr | 3 hr | 6 hr | 10 hr | 12 hr | 18 hr | 24 hr |   |
|---|---|---|---|---|---|---|---|---|---|
| Formulation # OMH1 |||||||||| |
| 0% | 2% | 4% | 5% | 8% | 12% | 14% | 18% | 23% | Mean |
| 0 | 2 | 1 | 1 | 1 | 0 | 1 | 1 | 1 | Std Dev |
| Formulation # OMH2 |||||||||| |
| 11% | 19% | 30% | 37% | 52% | 64% | 69% | 82% | 91% | Mean |
| 0 | 1 | 1 | 1 | 1 | 1 | 1 | 1 | 1 | Std Dev |
| Formulation # OMH3 |||||||||| |
| 0% | 1% | 4% | 6% | 11% | 18% | 21% | 30% | 36% | Mean |
| 0 | 2 | 1 | 1 | 2 | 2 | 3 | 3 | 3 | Std Dev |
| Formulation # OMH4 |||||||||| |
| 3% | 5% | 7% | 9% | 15% | 23% | 26% | 35% | 42% | Mean |
| 1 | 1 | 1 | 2 | 3 | 3 | 3 | 3 | 3 | Std Dev |
| Formulation # OMH5 |||||||||| |
| 11% | 17% | 27% | 33% | 48% | 61% | 66% | 78% | 87% | Mean |
| 1 | 1 | 1 | 1 | 0 | 1 | 1 | 1 | 2 | Std Dev |
| Formulation # OMH6 |||||||||| |
| 2% | 4% | 7% | 10% | 19% | 29% | 33% | 44% | 53% | Mean |
| 0 | 1 | 1 | 2 | 2 | 3 | 4 | 4 | 4 | Std Dev |
| Formulation # OMH7 |||||||||| |
| 7% | 11% | 19% | 25% | 38% | 51% | 55% | 66% | 74% | Mean |
| 1 | 1 | 1 | 1 | 2 | 2 | 3 | 3 | 3 | Std Dev |
| Formulation # OMH8 |||||||||| |
| 7% | 12% | 19% | 25% | 39% | 52% | 57% | 69% | 76% | Mean |
| 1 | 1 | 1 | 1 | 1 | 2 | 1 | 3 | 2 | Std Dev |
| Formulation # OMH9 |||||||||| |
| 5% | 9% | 15% | 20% | 33% | 46% | 51% | 63% | 72% | Mean |
| 1 | 2 | 3 | 4 | 6 | 6 | 7 | 5 | 5 | Std Dev |
| Formulation # OMH10 |||||||||| |
| 2% | 3% | 4% | 6% | 12% | 23% | 29% | 45% | 57% | Mean |
| 1 | 1 | 2 | 2 | 5 | 7 | 8 | 7 | 6 | Std Dev |

Example 3g

The following in vitro dissolution test was carried out to characterize the in vitro release of abuse-resistant amphetamine oral dosage forms across several different formulations.

The abuse-resistant amphetamine oral dosage forms used in this Example 3g were prepared using the following raw materials: d-Amphetamine Sulfate (Cambrex) ("AMP"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); Caprylocaproyl Polyoxyglycerides (Gattefosse) ("CPG"); Gelucire 50/13 (Gattefosse) ("GEL"); and Polyethylene Glycol 8000 (Dow Chemical) ("PEG 8000"). The formulations were produced using a GMP manufacturing process (Process Scheme 6 as described in Example 1a above) and then filled into size #1 gel capsules to produce the dosage forms that were used as Test Capsules. The details of the formulations and the dosage forms containing the formulations of this Example 3g are disclosed below in Tables 22 and 23.

TABLE 22

| | Formulation by Weight Percent (wt %) | | |
|---|---|---|---|
| Component | AMP1 | AMP2 | AMP3 |
| AMP | 7.50 | 5.45 | 5.45 |
| SAIB | 36.52 | 36.24 | 35.16 |
| TA | 27.05 | 26.85 | 26.04 |
| CAB | 4.86 | 4.96 | 4.96 |

TABLE 22-continued

| | Formulation by Weight Percent (wt %) | | |
|---|---|---|---|
| Component | AMP1 | AMP2 | AMP3 |
| IPM | 15.73 | 16.07 | 16.07 |
| HEC | 5.55 | 5.67 | 5.67 |
| SiO$_2$ | 1.85 | 1.89 | 1.89 |
| BHT | 0.02 | 0.02 | 0.02 |
| LAB | 0.93 | 0 | 0 |
| PEG 8000 | 0 | 2.84 | 0 |
| GEL | 0 | 0 | 4.73 |

TABLE 23

| | Formulation by Mass (mg) | | |
|---|---|---|---|
| Component | AMP1 | AMP2 | AMP3 |
| AMP | 15.00 | 14.99 | 14.99 |
| SAIB | 73.04 | 99.66 | 96.69 |
| TA | 54.10 | 73.84 | 71.61 |
| CAB | 9.72 | 13.64 | 13.64 |
| IPM | 31.46 | 44.19 | 44.19 |
| HEC | 11.10 | 15.93 | 15.59 |
| SiO$_2$ | 3.70 | 5.20 | 5.20 |
| BHT | 0.04 | 0.06 | 0.06 |
| LAB | 1.86 | 0 | 0 |
| PEG 8000 | 0 | 7.81 | 0 |
| GEL | 0 | 0 | 13.01 |
| Total | 200.02 | 275.32 | 274.98 |

Figure 11:
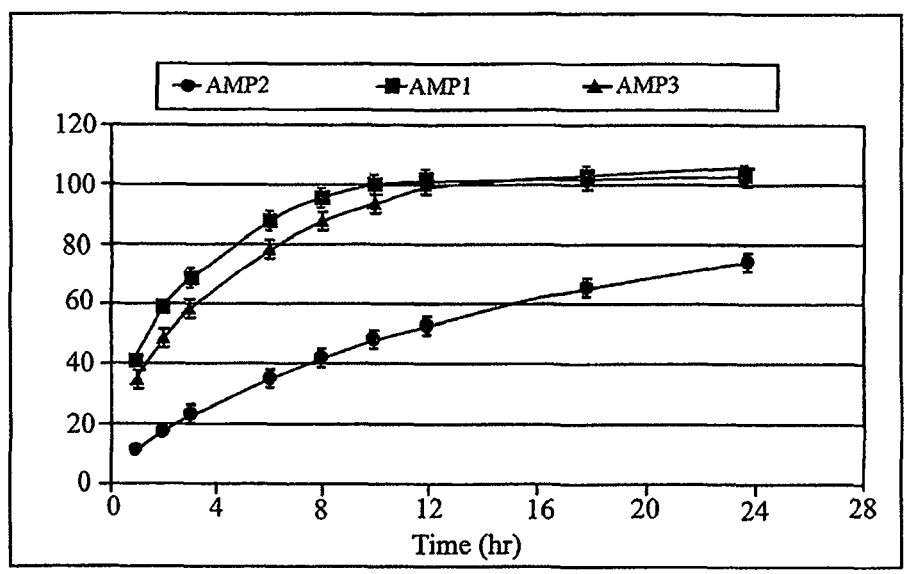
FIG. 11 shows the mean dissolution data results from the in vitro dissolution study of AMP1-AMP3 Test Capsules as described in Example 3g.

The dissolution study was carried out using the apparatus, reagents and methods of the Method 1 dissolution test described above, with the following exceptions: sample timepoints were at 1, 2, 3, 6, 8, 10 12, 18 and 24 hour. Dissolution results were obtained on the following Test Capsules: eight (n=8) each of formulations AMP1-AMP3. The mean dissolution data from the three sets of Test Capsules are summarized below in Table 24 and depicted in FIG. 11.

TABLE 24

| Mean Cumulative Drug Released | | | | | | | | | |
|---|---|---|---|---|---|---|---|---|---|
| 1 hr | 2 hr | 3 hr | 6 hr | 8 hr | 10 hr | 12 hr | 18 hr | 24 hr | |
| Formulation # AMP1 | | | | | | | | | |
| 41% 2 | 59% 3 | 69% 3 | 89% 2 | 97% 3 | 101% 2 | 103% 2 | 103% 2 | 104% 2 | Mean Std Dev |
| Formulation # AMP2 | | | | | | | | | |
| 11% 1 | 17% 2 | 22% 3 | 34% 3 | 42% 4 | 48% 4 | 53% 4 | 66% 3 | 75% 3 | Mean Std Dev |
| Formulation # AMP3 | | | | | | | | | |
| 34% 3 | 49% 3 | 59% 3 | 79% 3 | 88% 3 | 95% 2 | 100% 2 | 105% 1 | 106% 1 | Mean Std Dev |

Example 3h

The following in vitro dissolution test was carried out to characterize the in vitro release of abuse-resistant methylphenidate oral dosage forms across several different formulations.

The abuse-resistant methylphenidate oral dosage forms used in this Example 3h were prepared using the following raw materials: methylphenidate ("MPH"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAM"); Triacetin USP ("TA"); Cellulose Acetate Butyrate, grade 381-20 BP, ethanol washed (Eastman Chemicals) ("CAB"); Gelucire 50/13 (Gattefosse) ("GEL"); and Miglyol 812 ("MIG"). The formulations were produced using the manufacturing process (Process Scheme 6) as described in Example 1a above, and then filled into size #3 gelatin capsule shells to produce the dosage forms that were used as Test Capsules. The details of the formulations and the dosage forms containing the formulations of this Example 3h are disclosed below in Tables 25 and 26.

TABLE 25

| | Formulation by Weight Percent (wt %) | | | | | |
|---|---|---|---|---|---|---|
| Component | MPH1 40 mg | MPH2 48 mg | MPH3 48 mg | MPH4 48 mg | MPH5 48 mg | MPH6 48 mg |
| MPH | 20.00 | 20.00 | 20.00 | 20.00 | 20.00 | 20.00 |
| SAIB | 33.35 | 34.31 | 34.55 | 34.31 | 29.25 | 34.55 |
| TA | 22.23 | 22.87 | 23.03 | 22.87 | 20.89 | 23.03 |
| CAB | 4.80 | 5.20 | 6.40 | 5.21 | 5.58 | 6.42 |
| IPM | 13.60 | 12.80 | 12.80 | 12.80 | — | 12.80 |
| MIG | — | — | — | — | 16.0 | — |
| HEC | 0.00 | 2.40 | 0.00 | 2.40 | 4.80 | — |
| SiO$_2$ | 2.00 | 1.60 | 1.60 | 1.60 | 1.60 | 1.60 |
| BHT | 0.02 | 0.02 | 0.02 | 0.02 | 0.02 | 0.02 |
| GEL | 4.00 | 0.80 | 1.60 | 0.80 | 1.84 | 1.60 |

TABLE 26

| | Formulation by Mass (mg) | | | | | |
|---|---|---|---|---|---|---|
| Component | MPH1 40 mg | MPH2 48 mg | MPH3 48 mg | MPH4 48 mg | MPH5 48 mg | MPH6 48 mg |
| MPH | 40.00 | 48.00 | 48.00 | 48.00 | 48.00 | 48.00 |
| SAIB | 66.70 | 82.34 | 82.92 | 82.30 | 70.20 | 82.90 |
| TA | 44.46 | 54.89 | 55.27 | 54.90 | 50.10 | 55.30 |
| CAB | 9.60 | 12.48 | 15.36 | 12.50 | 13.40 | 15.40 |
| IPM | 27.20 | 30.72 | 30.72 | 30.70 | — | 30.70 |
| MIG | — | — | — | — | 38.40 | — |
| HEC | 0.00 | 5.76 | 0.00 | 5.80 | 11.50 | — |
| SiO$_2$ | 4.00 | 3.84 | 3.84 | 3.80 | 3.80 | 3.80 |
| BHT | 0.04 | 0.05 | 0.05 | 0.05 | 0.05 | 0.05 |
| GEL | 8.00 | 1.92 | 3.84 | 1.90 | 4.40 | 3.80 |
| Total | 200.00 | 240.00 | 240.00 | 240.00 | 240.00 | 240.00 |

Figure 12A:
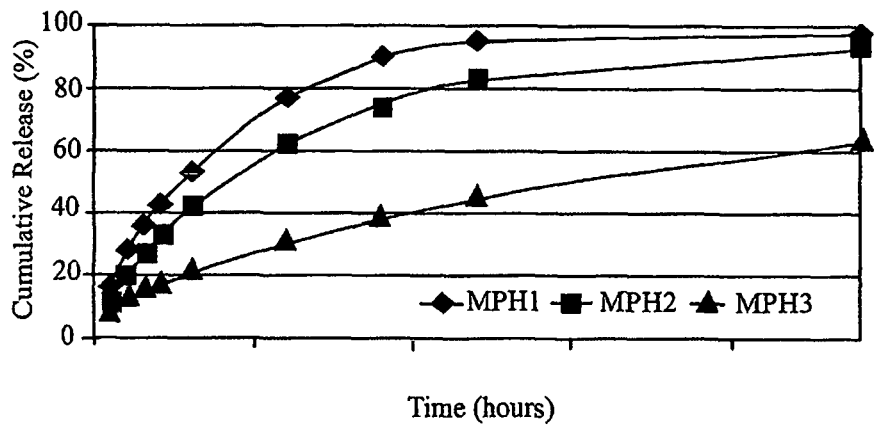
FIGS. 12A and 12B show the mean dissolution data results from the in vitro dissolution study of MPH1-MPH6 Test Capsules as described in Example 3h.
Figure 12B:
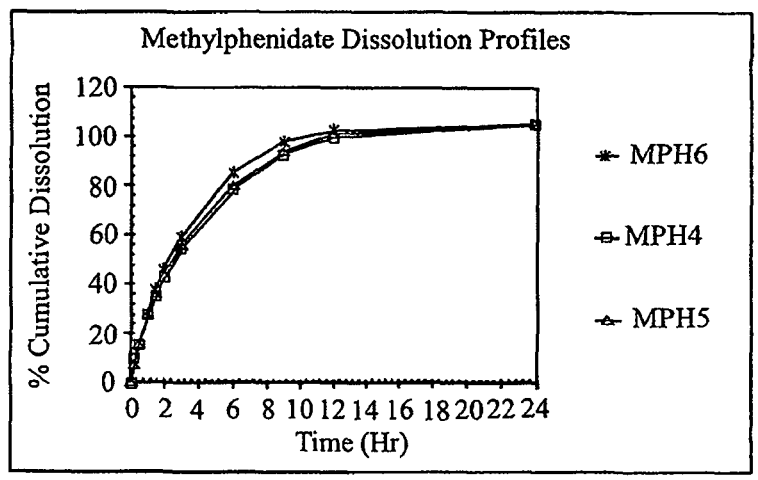

The dissolution study was carried out using the apparatus, reagents and methods of the Method 1 dissolution test described above, with the following exceptions: sample timepoints were at 0.5 hour, 1, 1.5, 2, 3, 6, 9, 12 and 24 hour. Dissolution results were obtained on the following Test Capsules: four (n=4) each of formulations MPH1 and MPH4-MPH6, and eight (n=8) each of formulations MPH2 and MPH3. The mean dissolution data from the six sets of Test Capsules are summarized below in Table 27, and depicted in FIGS. 12A and 12B.

TABLE 27

| Mean Cumulative Drug Released | | | | | | | | | |
|---|---|---|---|---|---|---|---|---|---|
| 0.5 hr | 1 hr | 1.5 hr | 2 hr | 3 hr | 6 hr | 9 hr | 12 hr | 24 hr | |
| Formulation # MPH1 | | | | | | | | | |
| 15.2% | 26.4% | 35.1% | 42.5% | 53.0% | 77.6% | 90.6% | 96.3% | 98.9% | Mean |
| 0.8 | 0.8 | 0.9 | 1.1 | 1.3 | 1.7 | 1.2 | 0.8 | 1.0 | SD |
| Formulation # MPH2 | | | | | | | | | |
| 11.1% | 19.27% | 26.4% | 32.5% | 42.0% | 62.1% | 74.5% | 83.1% | 94.5% | Mean |
| 1.3 | 2.0 | 2.8 | 3.5 | 4.8 | 6.2 | 5.9 | 5.7 | 7.0 | SD |
| Formulation # MPH3 | | | | | | | | | |
| 7.9% | 12.0% | 15.1% | 17.6% | 21.6% | 31.3% | 39.1% | 45.7% | 64.7% | Mean |
| 1.3 | 2.0 | 2.5 | 3.0 | 3.6 | 5.2 | 6.5 | 7.9 | 11.4 | SD |
| Formulation # MPH4 | | | | | | | | | |
| 15.3% | 27.5% | 34.8% | 42.3% | 54.0% | 78.0% | 92.5% | 99.5% | 104.3% | Mean |
| 1.7 | 3.1 | 2.2 | 1.9 | 2.2 | 1.4 | 1.9 | 1.3 | 1.3 | SD |
| Formulation # MPH5 | | | | | | | | | |
| 15.8% | 28.0% | 36.9% | 44.3% | 55.8% | 79.3% | 93.2% | 100.7% | 104.4% | Mean |
| 1.0 | 1.3 | 1.3 | 1.2 | 1.2 | 1.4 | 1.8 | 2.3 | 2.8 | SD |
| Formulation # MPH6 | | | | | | | | | |
| 14.9% | 27.6% | 37.5% | 45.7% | 58.5% | 84.9% | 97.6% | 101.7% | 104.3% | Mean |
| 1.0 | 1.4 | 1.9 | 2.3 | 3.2 | 4.0 | 2.0 | 1.0 | 0.4 | SD |

Example 4: Analysis of Formulations (In Vitro Extraction and Volatilization Testing Procedures)

In order to assess the abuse-resistance performance of the dosage forms of the present invention, the following in vitro extraction tests were developed. In particular, intentional abuse of controlled release pharmaceutical dosage forms will often times be carried out by simple extraction techniques that can separate most or all of the active agent from commercially available controlled release carrier systems using common household solvents. Accordingly, a panel of in vitro extraction tests was developed in order to assess the abuse-resistant performance of the dosage forms produced according to the instant invention.

Example 4a

In order to assess the abuse-resistance performance of dosage forms produced according to the present invention, a panel of tests to evaluate extraction of active agent from a dosage form into the following commonly available household solvents was developed as follows: vinegar (acetic acid), pH 2.5; cola soft drink, pH 2.5; baking soda solution (sodium bicarbonate), pH 8.2; 100 proof ethanol (50% v/v); and vegetable oil. The dosage forms of the present invention can be tested against this panel of common household solvents at both ambient or "room" temperature (25° C.) and with preheated extraction solvents (heated to 60° C.). In addition, exceptional stressing, such as the use of microwave and freeze-and-crush pretreatment of the dosage forms prior to extraction in the above-noted solvents can also be carried out.

The materials and apparatus used in the solvent extraction panel study of this Example 4a are as follows. Standard laboratory equipment includes a shaker (Jeio Tech Shaking Incubator, Model SI-600), hot water bath, hot plate, centrifuge, microwave oven, glass mortar and pestle, a 250 mL glass bottle with cap, and a filtering unit (0.2 µm nylon membrane). The solvent reagents used in the extraction panel study are prepared as follows: distilled water; 200 proof ethanol (Spectrum) mixed in equal parts distilled water to provide 100 proof ethanol solvent; distilled white vinegar 5% acidity (Heinz); cola soft drink (Coke Cola Classic); vegetable oil (Canola); baking soda (Arm & Hammer), saturated solution prepared by adding 527 g of baking soda to 2 L distilled water, mixed vigorously for approximately 1 hour, allowed to settle and then filtered the supernatant using the 0.2 µm nylon membrane. The pH of the Vinegar, cola soft drink and saturated baking soda solution are determined using a pH meter and recorded prior to extraction studies.

The test procedures used for all of the solvents except the vegetable oil solvent are as follows. 240 mL of each extraction solvent is placed into separate extraction bottles. A dosage form is then added (if the dosage form is a solid tablet, the form is crushed and then dropped into the solvent, if the dosage form is a liquid capsule, the capsule is cut to open the shell, and the liquid contents are squeezed from the capsule into the solvent, and then the empty shell is dropped into the solvent). Extraction is initiated on the shaker using a constant speed of 150 rpm. Samples (1 mL) are withdrawn at 5-, 20- and 60-minute time points. The samples are centrifuged at 10,000 rpm for 10 minutes, and about 0.5 mL of the supernatant is transferred into HPLC vials for analysis (HP Model 1200 or similar model). This extraction panel is then repeated wherein the extraction solutions are pre-warmed in a 60° C. water bath. The actual initial and final temperatures of the solvent solution are then taken.

The test procedures used for the vegetable oil solvent are as follows. 2 tablespoons of the oil is placed into an extraction bottle. A dosage form is then added (if the dosage form is a solid tablet, the form is crushed and then dropped into the solvent, if the dosage form is a liquid capsule, the capsule is cut to open the shell, and the liquid contents are squeezed from the capsule into the solvent, and then the empty shell is dropped into the solvent). Extraction is initiated on the shaker using a constant speed of 150 rpm. Samples (1 mL) are withdrawn at 5-, 15-, 30- and 60-minute time points. The samples are centrifuged at 10,000 rpm for 10 minutes, and about 0.5 mL of the supernatant is transferred into HPLC vials for analysis (HP Model 1200 or similar model).

For the exceptional stressing test (microwave, and freeze-and-crush pretreatment of the dosage forms prior to extraction in the above-noted solvents), the test procedures are as follows. For the microwave stress analysis, dosage forms are added to empty extraction bottles (if the dosage form is a solid tablet, it is crushed and then dropped into the bottle, if the dosage form is a liquid capsule, the capsule is cut to open the shell, and the liquid contents are squeezed from the capsule into the bottle). The extraction bottles (4 at a time) are then microwaved for 2 min with power level set at "High" (power=90). Upon removal from the microwave, the appearance of the dosage form is recorded. Next, either 240 mL of distilled water or 240 mL of the 100-proof ethanol solvent is added to the extraction bottle (to assess extraction into water or ethanol). Extraction is initiated on the shaker using a constant speed of 150 rpm. Samples (1 mL) are withdrawn at 5-, 20- and 60-minute time points. The samples are centrifuged at 10,000 rpm for 10 minutes, and about 0.5 mL of the supernatant is transferred into HPLC vials for analysis (HP Model 1200 or similar model). This extraction procedure is then repeated on untested dosage forms after they have been allowed to equilibrate to room temperature (~1.5 hr) after microwave treatment.

For the freeze-and-crush (physical and mechanical stress) analysis, dosage forms are stored in tact in a −80° C. freezer overnight (18 hrs). The test samples are then removed from the freezer and kept on dry ice until they are ready to be ground up. The frozen dosage forms are then placed into a freezer bag (about 9×12 cm) and crushed by pressing immediately in a glass mortar and pestle. Any excess (non-formulation containing) portion of the freezer bag is then removed to provide about a 9×9 cm test article that is quantitatively transferred (with the remaining freezer bag) into an extraction bottle. Next, either 240 mL of distilled water or 240 mL of the 100-proof ethanol solvent is added to the extraction bottle (to assess extraction into water or ethanol). Extraction is initiated on the shaker using a constant speed of 150 rpm. Samples (1 mL) are withdrawn at 5-, 20- and 60-minute time points. The samples are centrifuged at 10,000 rpm for 10 minutes, and about 0.5 mL of the supernatant is transferred into HPLC vials for analysis (HP Model 1200 or similar model).

In order to assess the abuse-resistance performance of a pharmaceutical dosage form produced according to the present invention in this Example 4a, the above-described extraction panel tests were carried out to assess a formulation produced according to Example 2 above. In particular, the following raw materials were used to create formulations for use in the extraction study: Oxycodone base, micronized ("OXY"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); and Cellulose Acetate Butyrate, grade 381-20 BP, ethanol washed (Eastman Chemicals) ("CAB"). The formulations were produced using the commercial-scale manufacturing Process Scheme 4 (as described above) and then filled into size 00 white opaque gel cap shells to produce 40 mg dosage forms that were used as Test Capsules. The details of the formulations of this Example 4a are disclosed below in Table 28.

TABLE 28

| OXY (wt %) | SAIB (wt %) | TA (wt %) | CAB (wt %) | IPM (wt %) | HEC (wt %) | SiO$_2$ (wt %) | BHT (wt %) |
|---|---|---|---|---|---|---|---|
| 5.13 | 40.98 | 27.32 | 4.74 | 14.23 | 5.69 | 1.9 | 0.02 |

As a Control, controlled release tablet dosage forms were sourced as OxyContin brand controlled release oxycodone tablets, 40 mg (Purdue Pharma, lot# W49E1, expiration date January 2009) and run in the same panel of tests. The pH of the cola soft drink, vinegar, and saturated baking soda solution at room temperature, prior to extraction, were found to be 2.49, 2.47 and 8.23, respectively.

Figure 13:
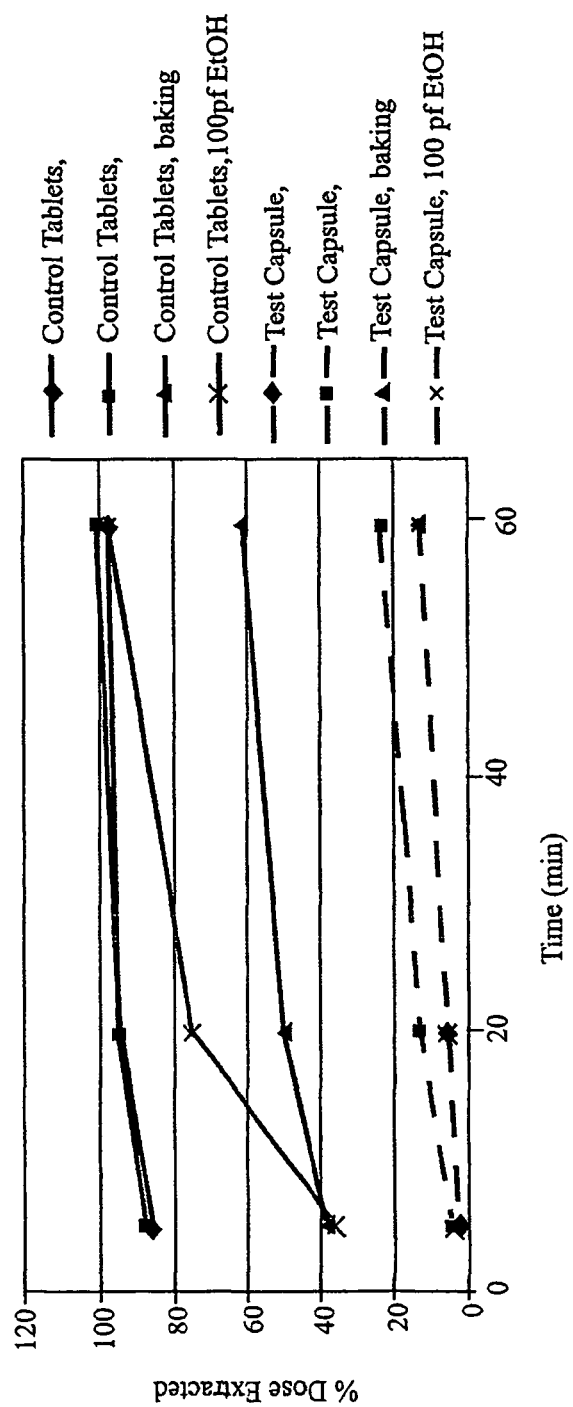

The overall kinetics of oxycodone extraction from the Test Capsules (produced according to the invention) and the Control (OxyContin) tablets in a panel of household solvents at ambient temperature (RT) is depicted in FIG. 13. As can be seen, the level of oxycodone released tails off for all groups after the 20-minute extraction point; however, the Control (OxyContin) tablets are prone to immediate release (ranging from 37 to 88%) compared to a range of just 1.4-3.3% for the Test Capsules at the 5-minute time point. With the sole exception of extraction in the saturated baking soda solvent, oxycodone extracted from the Control tablets was quantitative at the 60-minute extraction time point (100% extraction). Conversely, the amount of oxycodone extracted from the Test Capsules was only approximately 20% in the cola soft drink, and only 10% in other the solvents at the 60-minute extraction time point.

Figure 14:
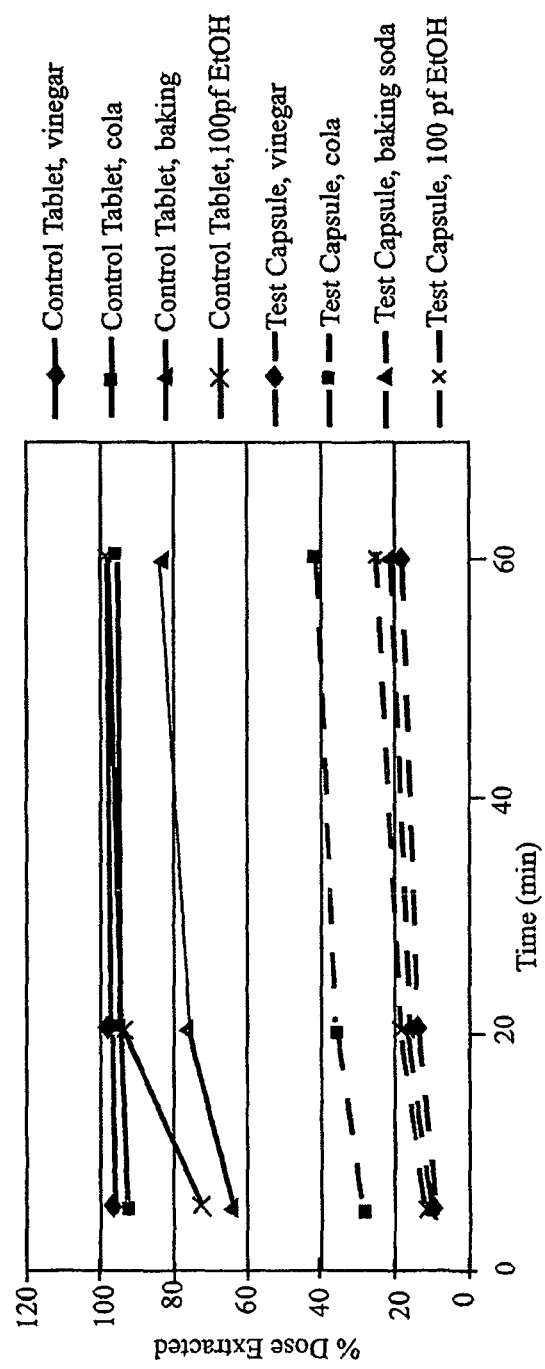

The overall kinetics of oxycodone extraction from the Test Capsules and the Control tablets in a panel of household solvents at elevated temperature (60° C.) is depicted in FIG. 14. The temperature of the solvents prior to extraction was measured at 62° C. prior to extraction, and 33° C. at the 60-minute extraction time point. As can be seen, the extraction of oxycodone again tails off for all groups after the 20-minute extraction point, and the Control tablets are prone to immediate release (from 64 to 96% compared to just 9-28% for the Test Capsules) at the 5-minute time point. In addition, in all solvents except the saturated baking soda solvent, oxycodone extraction from the Control tablets was quantitative at the 60-minute extraction time point (100% extraction). Conversely, the amount of oxycodone extracted from the Test Capsules was only approximately 42% in the cola soft drink, and only from 18 to 25% in other the solvents at the 60-minute extraction time point.

The numerical results of the extraction panel study of this Example 4a, including the results discussed above and depicted in FIGS. 13 and 14, are reported below in Table 29. As can be seen, formulations produced according to the present invention can be used to provide abuse-resistant oral pharmaceutical dosage forms that exhibit superior abuse-resistant performance across a panel of solvent extraction tests.

TABLE 29

| Stress Method | Extraction temp. | Extraction solvent | Test Capsule (% oxycodone extracted) 5 min | Test Capsule (% oxycodone extracted) 60 min | Control tablet (% oxycodone extracted) 5 min | Control tablet (% oxycodone extracted) 60 min |
|---|---|---|---|---|---|---|
| Mechanical Stress | RT | Water | 2.6 ± 0.8[1] | 13.5 ± 4.6 | — | — |
|  |  | 100-proof ethanol | 10.4 ± 5.9 | 32.0 ± 13.3 | — | — |
| Multiple Solvent Extraction Conditions | RT | Vinegar | 1.4 ± 0.5 | 11.4 ± 1.2 | 85.9 ± 0.8 | 96.6 ± 2.2 |
|  |  | Coke | 3.3 ± 2.3 | 21.8 ± 0.2 | 87.5 ± 2.7 | 98.7 ± 0.1 |
|  |  | Sat'd baking soda | 1.7 ± 0.1 | 10.7 ± 2.3 | 37.3 ± 1.0 | 59.5 ± 1.2 |
|  |  | 100-proof ethanol | 1.5 ± 0.1 | 10.3 ± 0.1 | 34.6 ± 3.3 | 96.9 ± 7.0 |
|  |  | vegetable oil | 2.52 | 3.37 | — | — |
|  | 62-33° C.[2] | Vinegar | 8.9 ± 2.3 | 18.1 ± 2.0 | 95.6 ± 2.2 | 97.3 ± 1.9 |
|  |  | Coke | 27.7 ± 1.6 | 42.2 ± 3.4 | 92.0 ± 2.1 | 96.0 ± 0.5 |
|  |  | Sat'd baking soda | 9.3 ± 2.7 | 20.8 ± 3.4 | 63.7 ± 0.8 | 84.1 ± 1.2 |
|  |  | 100-proof ethanol | 9.5 ± 1.0 | 25.2 ± 0.4 | 71.5 ± 17.7 | 98.5 ± 0.01 |
| Microwave | RT/ Immediate Extraction | Water | 7.8 ± 4.9 | 24.8 ± 9.5 | 75.5 ± 4.5 | 95.9 ± 1.4 |
|  |  | 100-proof ethanol | 14.6 ± 5.7 | 36.1 ± 8.1 | — | — |
|  | RT/ plus cool off | Water | 1.1 ± 0.1 | 14.0 ± 1.8 | — | — |
|  |  | 100-proof ethanol | 1.1 ± 0.5 | 17.8 ± 10.2 | — | — |

[1]average ± standard derivation
[2]initial and final temperature, respectively

In order to further assess the abuse-resistance performance of the dosage forms of the present invention, the following in vitro volatilization test was developed. In particular, intentional abuse of controlled release pharmaceutical dosage forms may alternatively be carried out by volatilization (smoking, or free-basing) techniques that can liberate active agent (in immediately active form) from commercially available controlled release carrier systems. Accordingly, a preliminary in vitro volatilization test was developed in order to assess: (1) whether oxycodone free base was more volatile than the salt (HCl) form; and (2) whether the abuse-resistant dosage forms produced according to the instant invention can prevent inhalation abuse through volatilization.

For the study, 40 mg of neat active agent (oxycodone in free base form, oxycodone in HCl salt form), 40 mg Test Capsules (produced as described above) and 40 mg SR Control (OxyContin brand controlled release oxycodone tablets) were weighed into individual petri dishes. Each petri dish was fitted with a watch glass as a cover, and the covered test dishes were placed on a hot plate (setting 10). After 30 seconds each watch glass was replaced with a fresh watch glass, and this step was repeated three times (to obtain 4 time points). Any residue deposited on the bottom side of the test watch glasses was carefully transferred with an Alpha Swab (TX 761) into 40/60 ethanol/.005M HCl solution, and the concentration of oxycodone solution was determined by HPLC. The observations taken during the test were as follows. The neat base form active agent (oxycodone free base form) vaporizes/sublimes upon heating, whereas there was extensive degradation and charring of the salt form active agent (oxycodone HCl), the Test Capsules, and the SR Control tablets. It was noted that vaporized drug (and solvents where present) escaped during each change of the watch glass, which may be at least partially responsible for the low recovery noted in the HPLC results below. In addition, the presence of solvents and other excipients in the Test Capsules made it difficult to volatilize the oxycodone active agent, and there was a particularly noxious smell noted when the Test Capsules were volatilized. The HPLC results obtained in this Example 4a are provided below in Table 30.

TABLE 30

| Test Sample | Time Point (minutes) | Oxycodone Collected (in mg) | % Recovery |
|---|---|---|---|
| oxycodone API (free base form) | 0.5 | 1.4730 |  |
|  | 1.0 | 7.2666 |  |
|  | 1.5 | 0.7356 |  |
|  | 2.0 | 0.7050 |  |
|  | (total): | 10.1802 | 24.0% |
| oxycodone API (HCl salt form) | 0.5 | 1.7202 |  |
|  | 1.0 | 0.4086 |  |
|  | 1.5 | 0.1236 |  |
|  | 2.0 | 0.0270 |  |
|  | (total): | 2.2794 | 5.7% |
| Test Capsule | 0.5 | 0.0048 |  |
|  | 1.0 | 0.1206 |  |
|  | 1.5 | 0.9732 |  |
|  | 2.0 | 1.1478 |  |
|  | (total): | 2.2464 | 5.6% |
| SR Control | 0.5 | 1.8144 |  |
|  | 1.0 | 3.0624 |  |
|  | 1.5 | 0.2928 |  |
|  | 2.0 | 0.084 |  |
|  | (total): | 5.2536 | 14.7% |

As can be seen from these results, the free base form of oxycodone (neat) volatilizes more readily than the neat HCl salt form. However, once sequestered within the controlled release system of the present invention, the oxycodone free base is volatilized to a much lower extent. Accordingly, although the current volatilization test procedure may not provide a quantitative measure, it is useful to provide relative measures of the degree to which a dosage form is subject to abuse using such techniques.

Example 4b

The following in vitro Abuse Resistance Evaluation was carried out to characterize the in vitro abuse resistance performance of dosage forms prepared according to the present invention: (a) following influence of physical, chemical or mechanical stress; and (b) via inhalation, wherein both sets of test procedures are compared to a commercially available product. More particularly, 3 different manufacturing lots of abuse-resistant oxycodone oral dosage 40 mg strength forms produced with different purity grades of the active agent (oxycodone) were used as the Test Capsules. OxyContin brand (oxycodone HCl controlled-release) Tablets, 40 mg strength (Lot W28A1, Purdue Pharma L.P.) were used as the commercial comparison.

The abuse-resistant oxycodone oral dosage forms used in this Example 4b were prepared using the following raw materials: Oxycodone base, micronized ("OXY"), grade 2 (specified to contain not more than 0.25% (w/w) 14-hydroxycodeinone (14-HC)) or grade 1 (specified to contain not more than 0.001% (w/w) 14-HC), both grades obtained from Noramco, Inc (Athens Ga.); Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); and Cellulose Acetate Butyrate, grade 381-20 BP, ethanol washed (Eastman Chemicals) ("CAB"). The formulations were produced using the commercial-scale manufacturing methods (Process Schemes 4 or 5 as described above) and then filled into size #00 hard gelatin cap shells to produce the 40 mg dosage forms that were used as Test Capsules. The details of the formulations and the dosage forms containing the formulations of this Example 4b are disclosed below in Table 31.

TABLE 31

| OXY | SAIB | TA | CAB | IPM | HEC | $SiO_2$ | BHT | (total) | |
|---|---|---|---|---|---|---|---|---|---|
| 5.13 | 40.98 | 27.32 | 4.74 | 14.23 | 5.69 | 1.9 | 0.02 | | (wt %) |
| 40.0 | 319.6 | 213.1 | 37.0 | 111.0 | 44.4 | 14.8 | 0.16 | 780.0 | (mg) |

The in vitro abuse resistance results were obtained on the following Test Capsules:

three 40 mg dosage forms (n=3), containing grade 2 oxycodone and selected as exhibiting the fastest dissolution rate from dissolution testing described in Example 3 above (OXY1); three 40 mg dosage forms (n=3), containing grade 2 oxycodone and selected as exhibiting the slowest dissolution rate from dissolution testing described in Example 3 above (OXY2); and three 40 mg dosage forms (n=3), containing grade 1 oxycodone (OXY3). The commercial comparison was against three 40 mg OxyContin (SR Control) tablets (n=3).

Figure 15:
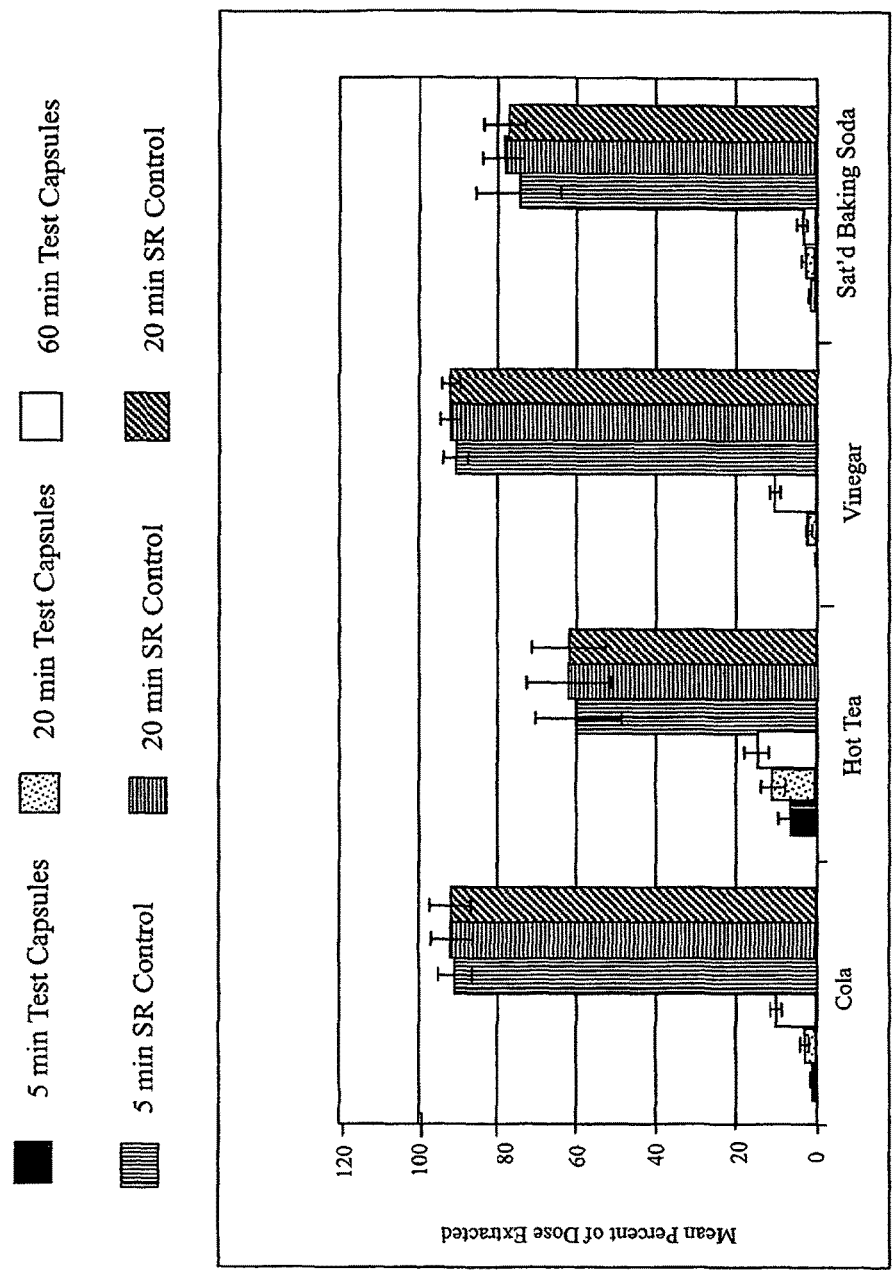
FIG. 15 shows the extraction results from Test Capsules compared against a SR Control in a panel of household solvents (vinegar, coal soft drink, hot tea and saturated baking soda solution) obtained in the in vitro abuse-resistance tests described in Example 4b.

The in vitro abuse resistance study was carried out substantially the same as in Example 4a above, using the same apparatus, reagents and methods described above, with any exceptions noted as follows. Initially, extraction of the oxycodone active agent from the Test Capsules and the SR Control tablets by four commercial beverages or common household liquids/preparations was assessed, where the four selected solvents were chosen based on their ubiquity and to span the acidic and alkaline pH range; i.e., vinegar (pH 2.5); cola soft drink (pH 2.4); hot tea (ranges pH 4.6-5.1, 65° C.-70° C.); and saturated baking soda in water (range pH 8.3-0.1). These selected solvents are readily accessible to potential abusers and constitute an assortment of non-toxic drinkable liquids that may be used to facilitate abuse. Test Capsules were cut open and squeezed to exude the liquid contents and assure intimate contact of test solvents with the controlled release matrix. The SR Control tablets were ground for 3 minutes with mortar and pestle to disrupt the controlled release matrix prior to placement in testing jars. The Test Capsules and treated SR Control tablets were placed into test jars containing 240 mL of each solvent. The closed jars were vigorously shaken at 100 rpm for 60 minutes, with shaking interrupted to withdraw samples at 5, 20 and 60 minutes. The solvent samples taken at each testing interval were centrifuged and assayed for oxycodone content by HPLC. The extraction results are provided in Tables 32 to 35 below, and in FIG. 15.

TABLE 32

Amount of Oxycodone Extracted in Vinegar (% of dose)

| | Time (min) | | |
|---|---|---|---|
| Sample ID | 5 | 20 | 60 |
| OXY1-a | 0 | 2 | 11 |
| OXY1-b | 0 | 2 | 10 |
| OXY1-c | 0 | 1 | 9 |
| OXY2-a | 0 | 1 | 8 |
| OXY2-b | 0 | 1 | 10 |
| OXY2-c | 1 | 2 | 12 |
| OXY3-a | 0 | 2 | 10 |
| OXY3-b | 0 | 2 | 9 |
| OXY3-c | 0 | 3 | 12 |
| SR Control-a | 87 | 89 | 89 |
| SR Control-b | 90 | 92 | 92 |
| SR Control-c | 93 | 94 | 94 |
| Mean (SD), Test Capsules | 0 (0.2) | 2 (0.6) | 10 (1.3) |
| Mean (SD), SR Control | 90 (3.0) | 92 (2.5) | 92 (2.5) |

TABLE 33

Amount of Oxycodone Extracted in Cola (% of dose)

| | Time (min) | | |
|---|---|---|---|
| Sample ID | 5 | 20 | 60 |
| OXY1-a | 1 | 3 | 10 |
| OXY1-b | 1 | 4 | 12 |
| OXY1-c | 1 | 2 | 11 |
| OXY2-a | 0 | 2 | 10 |
| OXY2-b | 1 | 2 | 8 |
| OXY2-c | 0 | 3 | 10 |
| OXY3-a | 1 | 2 | 10 |
| OXY3-b | 1 | 4 | 12 |
| OXY3-c | 2 | 6 | 12 |
| SR Control-a | 94 | 94 | 95 |
| SR Control-b | 86 | 86 | 86 |
| SR Control-c | 93 | 96 | 96 |
| Mean (SD), Test Capsules | 1 (0.6) | 3 (1.3) | 10 (1.4) |
| Mean (SD), SR Control | 91 (4.4) | 92 (5.3) | 92 (5.5) |

TABLE 34

Amount of Oxycodone Extracted in Hot Tea (% of dose)

|  | Time (min) | | |
|---|---|---|---|
| Sample ID | 5 | 20 | 60 |
| OXY1-a | 7 | 11 | 16 |
| OXY1-b | 4 | 8 | 11 |
| OXY1-c | 6 | 10 | 14 |
| OXY2-a | 11 | 16 | 19 |
| OXY2-b | 3 | 7 | 11 |
| OXY2-c | 3 | 7 | 11 |
| OXY3-a | 8 | 14 | 19 |
| OXY3-b | 6 | 10 | 14 |
| OXY3-c | 8 | 13 | 16 |
| SR Control-a | 48 | 51 | 53 |
| SR Control-b | 61 | 65 | 63 |
| SR Control-c | 70 | 71 | 71 |
| Mean (SD), Test Capsules | 6 (2.6) | 11 (3.2) | 15 (3.3) |
| Mean (SD), SR Control | 60 (11.1) | 62 (10.3) | 62 (9.0) |

TABLE 35

Amount of Oxycodone Extracted in Sat. Baking Soda (% of dose)

|  | Time (min) | | |
|---|---|---|---|
| Sample ID | 5 | 20 | 60 |
| OXY1-a | 1 | 2 | 4 |
| OXY1-b | 1 | 2 | 5 |
| OXY1-c | 1 | 2 | 5 |
| OXY2-a | 1 | 1 | 3 |
| OXY2-b | 0 | 1 | 2 |
| OXY2-c | 0 | 1 | 2 |
| OXY3-a | 1 | 1 | 3 |
| OXY3-b | 1 | 2 | 3 |
| OXY3-c | 1 | 2 | 3 |
| SR Control-a | 62 | 72 | 71 |
| SR Control-b | 80 | 81 | 81 |
| SR Control-c | 81 | 81 | 80 |
| Mean (SD), Test Capsules | 1 (0.5) | 2 (0.6) | 3 (1.1) |
| Mean (SD), SR Control | 74 (10.7) | 78 (5.2) | 77 (5.5) |

As can be seen by these solvent extraction results, the Test Capsules resisted extraction in all test solvents over the course of 60 minutes with agitation. After 5 minutes, 1% or less of the oxycodone was extracted from the Test Capsules in the cola, vinegar and saturated baking soda solution, as compared to 90% or greater from the SR Control tablets in cola and vinegar, and about 75% from the SR Control tablets in saturated baking soda solution. The greatest mean extraction 96% or 2.4 mg) of oxycodone from the Test Capsules at the 5 minute point occurred in hot tea. By comparison, extraction from the SR Control tablets in hot tea was ten fold higher (60%, or 24 mg). Extraction of oxycodone from the Test Capsules slightly increased in all solvents over the course of 60 minutes. In comparison, extraction from the SR Control tablets mostly occurred within 5 minutes and remained fairly constant for the remainder of the test, strongly suggesting dose dumping. The highest mean amount of oxycodone extracted from the Test Capsules (15%, or 6 mg) occurred after 60 minutes in hot tea.

Figure 16:
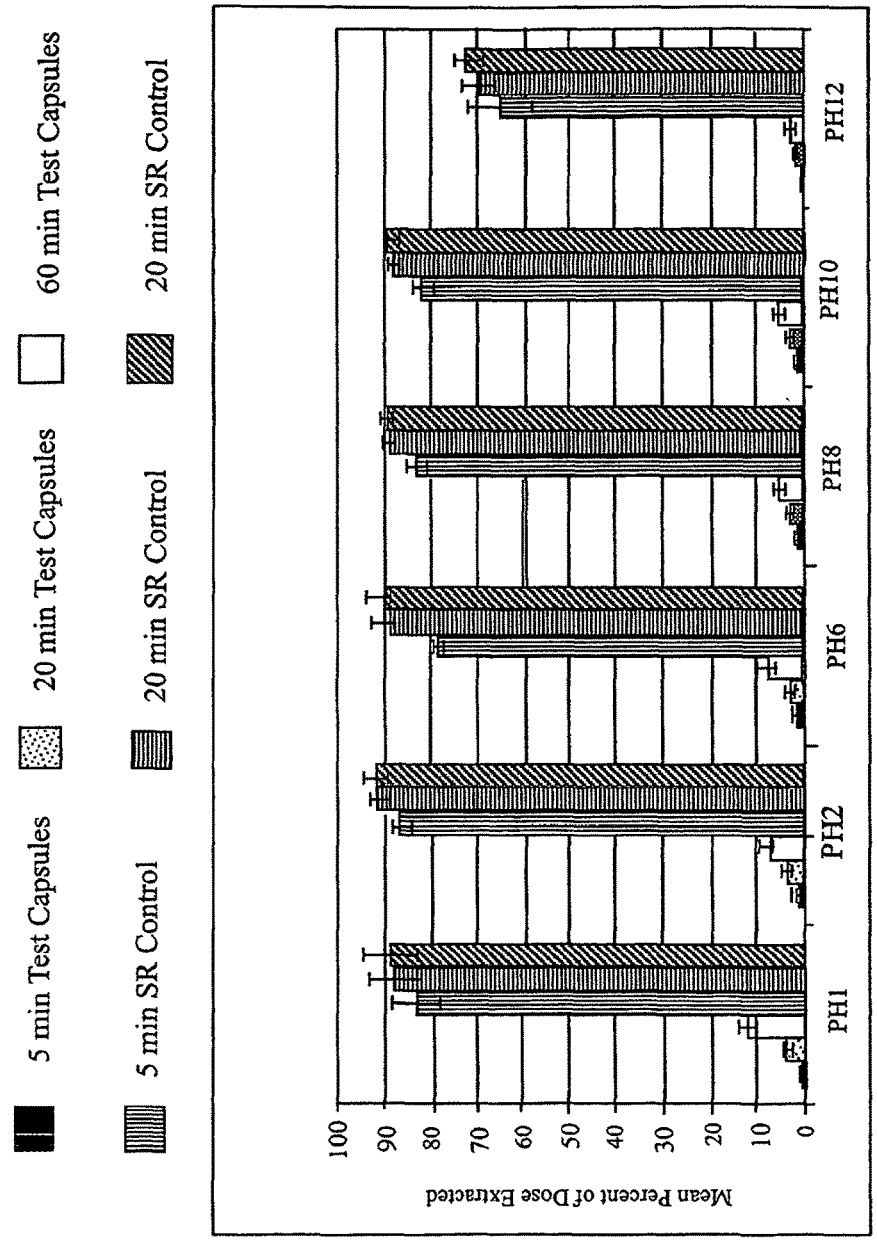
FIG. 16 shows the extraction results from Test Capsules compared against a SR Control in a panel of aqueous buffers (pH1-pH12) obtained in the in vitro abuse-resistance tests described in Example 4b.

Next, extraction of the oxycodone active agent from the Test Capsules and the SR Control tablets by each of six aqueous buffers over a range of pH 1-pH 12 was assessed. Specific buffer strengths were pH 1, pH 4, pH 6, pH 8, pH 10 and pH 12. The pH 1 buffer consisted of 0.1N HCl, the pH 4 buffer consisted of 5 mM acetate, and buffers of Ph 6, 10 and 12 consisted of 5 mM phosphate. Test Capsules were cut open and squeezed to exude the liquid contents and assure intimate contact of test solvents with the controlled release matrix. The SR Control tablets were ground for 3 minutes with mortar and pestle to disrupt the controlled release matrix prior to placement in testing jars. The Test Capsules and treated SR Control tablets were placed into test jars containing 240 mL of each buffer. The closed jars were vigorously shaken at 100 rpm for 60 minutes, with shaking interrupted to withdraw samples at 5, 20 and 60 minutes. The solvent samples taken at each testing interval were centrifuged and assayed for oxycodone content by HPLC. The extraction results are provided in Tables 36 to 41 below, and in FIG. 16.

TABLE 36

Amount of Oxycodone Extracted in Aq Buffer, pH 1 (% of dose)

|  | Time (min) | | |
|---|---|---|---|
| Sample ID | 5 | 20 | 60 |
| OXY1-a | 2 | 5 | 13 |
| OXY1-b | 1 | 3 | 12 |
| OXY1-c | 1 | 3 | 10 |
| OXY2-a | 1 | 4 | 13 |
| OXY2-b | 1 | 4 | 10 |
| OXY2-c | 1 | 3 | 10 |
| OXY3-a | 1 | 5 | 15 |
| OXY3-b | 1 | 4 | 14 |
| OXY3-c | 2 | 6 | 14 |
| SR Control-a | 89 | 93 | 94 |
| SR Control-b | 80 | 88 | 91 |
| SR Control-c | 81 | 82 | 83 |
| Mean (SD), Test Capsules | 1 (0.4) | 4 (0.9) | 12 (2.0) |
| Mean (SD), SR Control | 83 (4.9) | 88 (5.5) | 89 (5.7) |

TABLE 37

Amount of Oxycodone Extracted in Aq Buffer, pH 4 (% of dose)

|  | Time (min) | | |
|---|---|---|---|
| Sample ID | 5 | 20 | 60 |
| OXY1-a | 1 | 2 | 5 |
| OXY1-b | 2 | 4 | 9 |
| OXY1-c | 1 | 3 | 7 |
| OXY2-a | 1 | 3 | 7 |
| OXY2-b | 1 | 3 | 8 |
| OXY2-c | 2 | 2 | 7 |
| OXY3-a | 1 | 3 | 8 |
| OXY3-b | 1 | 2 | 6 |
| OXY3-c | 2 | 4 | 9 |
| SR Control-a | 85 | 94 | 95 |
| SR Control-b | 89 | 89 | 90 |
| SR Control-c | 85 | 90 | 91 |
| Mean (SD), Test Capsules | 1 (0.5) | 3 (0.7) | 7 (1.3) |
| Mean (SD), SR Control | 86 (2.3) | 91 (2.6) | 92 (2.6) |

TABLE 38

Amount of Oxycodone Extracted in Aq Buffer, pH 6 (% of dose)

|  | Time (min) | | |
|---|---|---|---|
| Sample ID | 5 | 20 | 60 |
| OXY1-a | 2 | 2 | 6 |
| OXY1-b | 0 | 2 | 4 |
| OXY1-c | 1 | 2 | 6 |
| OXY2-a | 1 | 3 | 7 |
| OXY2-b | 1 | 2 | 5 |
| OXY2-c | 1 | 2 | 6 |

TABLE 38-continued

Amount of Oxycodone Extracted in Aq Buffer, pH 6 (% of dose)

| Sample ID | Time (min) 5 | 20 | 60 |
|---|---|---|---|
| OXY3-a | 1 | 2 | 6 |
| OXY3-b | 2 | 5 | 12 |
| OXY3-c | 1 | 3 | 10 |
| SR Control-a | 78 | 91 | 91 |
| SR Control-b | 79 | 85 | 85 |
| SR Control-c | 80 | 91 | 93 |
| Mean (SD), Test Capsules | 1 (0.6) | 3 (1.0) | 7 (2.4) |
| Mean (SD), SR Control | 79 (1.0) | 89 (3.5) | 90 (4.2) |

TABLE 39

Amount of Oxycodone Extracted in Aq Buffer, pH 8 (% of dose)

| Sample ID | Time (min) 5 | 20 | 60 |
|---|---|---|---|
| OXY1-a | 1 | 2 | 4 |
| OXY1-b | 1 | 2 | 4 |
| OXY1-c | 1 | 2 | 4 |
| OXY2-a | 2 | 3 | 5 |
| OXY2-b | 1 | 2 | 5 |
| OXY2-c | 1 | 3 | 7 |
| OXY3-a | 1 | 3 | 6 |
| OXY3-b | 1 | 2 | 4 |
| OXY3-c | 1 | 3 | 7 |
| SR Control-a | 91 | 91 | 92 |
| SR Control-b | 86 | 89 | 89 |
| SR Control-c | 90 | 91 | 91 |
| Mean (SD), Test Capsules | 1 (0.5) | 2 (0.6) | 5 (1.2) |
| Mean (SD), SR Control | 89 (2.6) | 90 (1.2) | 91 (1.5) |

TABLE 40

Amount of Oxycodone Extracted in Aq Buffer, pH 10 (% of dose)

| Sample ID | Time (min) 5 | 20 | 60 |
|---|---|---|---|
| OXY1-a | 1 | 1 | 4 |
| OXY1-b | 1 | 2 | 5 |
| OXY1-c | 1 | 3 | 6 |
| OXY2-a | 0 | 1 | 4 |
| OXY2-b | 0 | 2 | 4 |
| OXY2-c | 0 | 2 | 4 |
| OXY3-a | 0 | 2 | 4 |
| OXY3-b | 0 | 2 | 5 |
| OXY3-c | 1 | 2 | 5 |
| SR Control-a | 82 | 87 | 88 |
| SR Control-b | 83 | 88 | 89 |
| SR Control-c | 80 | 88 | 88 |
| Mean (SD), Test Capsules | 0 (0.5) | 2 (0.5) | 4 (0.8) |
| Mean (SD), SR Control | 82 (1.5) | 88 (0.6) | 88 (0.6) |

TABLE 41

Amount of Oxycodone Extracted in Aq Buffer, pH 12 (% of dose)

| Sample ID | Time (min) 5 | 20 | 60 |
|---|---|---|---|
| OXY1-a | 0 | 1 | 3 |
| OXY1-b | 0 | 1 | 3 |
| OXY1-c | 0 | 1 | 3 |
| OXY2-a | 1 | 2 | 4 |
| OXY2-b | 0 | 1 | 3 |
| OXY2-c | 0 | 1 | 3 |
| OXY3-a | 0 | 1 | 3 |
| OXY3-b | 0 | 1 | 4 |
| OXY3-c | 0 | 1 | 3 |
| SR Control-a | 65 | 70 | 71 |
| SR Control-b | 71 | 73 | 75 |
| SR Control-c | 57 | 65 | 69 |
| Mean (SD), Test Capsules | 0 (0.3) | 1 (0.2) | 3 (0.4) |
| Mean (SD), SR Control | 64 (7.0) | 69 (4.0) | 72 (3.1) |

As can be seen by these buffer extraction results, all Test Capsules were resistant to extraction of oxycodone in all buffers over the course of 60 minutes with agitation. After five minutes, 1% or less of the oxycodone active agent was extracted in pH 1-12 aqueous buffers as contrasted with 64% or greater from the SR Control tablets. The amount of oxycodone extracted from the Test Capsules was seen to decrease with increasing pH. The greatest mean oxycodone extraction form the Test Capsules was 12% (4.8 mg) in pH 1 buffer after 60 minutes, as compared with 89% mean oxycodone extraction (35.6 mg) from the SR Control comparison. Finally, whereas extraction of oxycodone from the Test Capsules in all buffers increased slightly with time, virtually complete dose dumping of oxycodone from the SR Control tablets occurred within the first 5 minutes (83% or 33.2 mg) and remained fairly constant for the remainder of the test.

Figure 17:
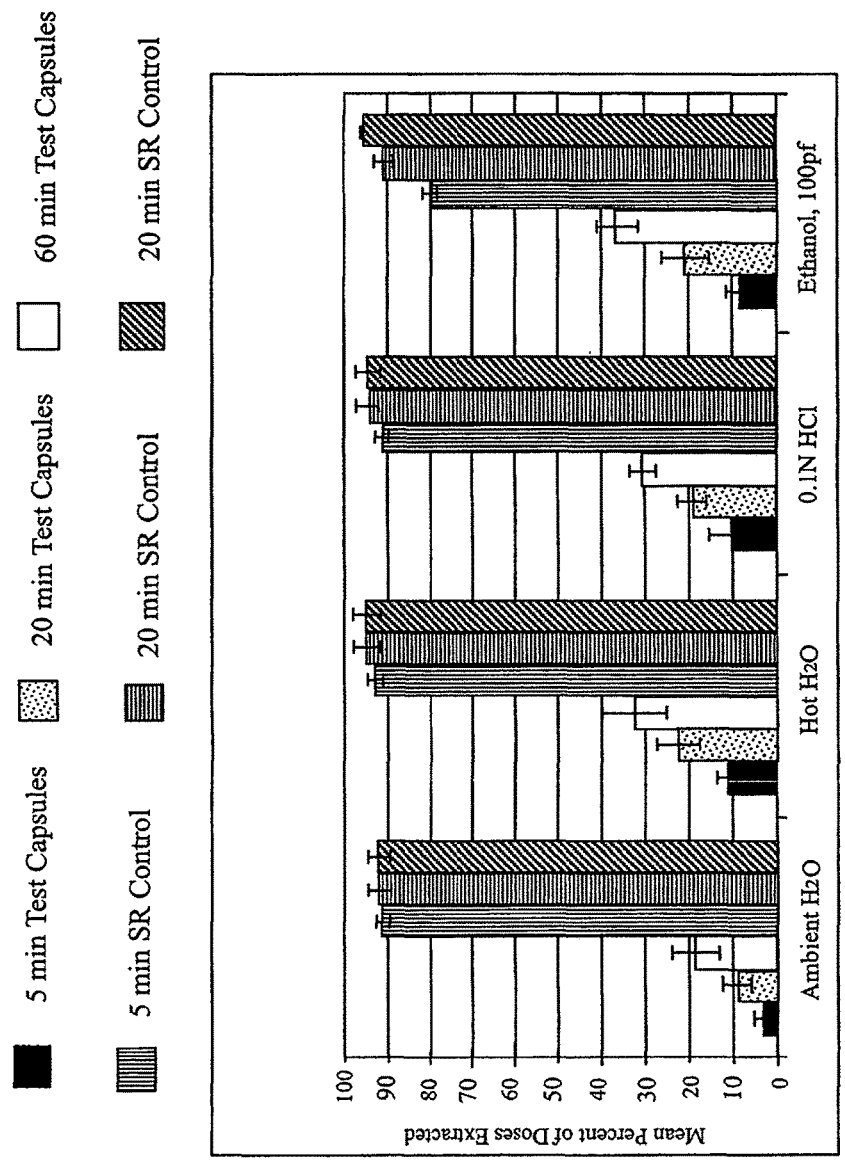
FIG. 17 shows the extraction results from physically disrupted Test Capsules compared against a physically disrupted SR Control and then extracted in a panel of household solvents (hot and cold water, strong acid and 100 proof ethanol) obtained in the in vitro abuse-resistance tests described in Example 4b.

Continuing with the study, extraction of the oxycodone active agent from the Test Capsules and the SR Control tablets following physical disruption was determined. In particular, the Test Capsules were chilled in dry ice for 16 to 20.5 hours to promote any tendency for freezing or brittleness of the formulation. Each chilled capsule was then placed immediately within the fold of a plastic film and ground in a mortar and pestle for 3 minutes. Enclosing the capsule within the folds of plastic film during grinding prevented loss of test material due to the tendency for product residue to stick to the mortar and pestle. Each SR Control tablet was also crushed and ground in a mortar and pestle. Three extraction solvents including water heated to 60-70° C. and at ambient (25° C.) temperature, 0.1N HCl, and 100 proof ethanol were used for the extraction solvents. The physically disrupted samples were placed into testing jars containing 240 mL of the various solvents. The closed jars were vigorously shaken at 100 rpm for 60 minutes, with shaking interrupted to withdraw samples at 5, 20 and 60 minutes. The solvent samples taken at each testing interval were centrifuged and assayed for oxycodone content by HPLC. The extraction results are provided in Tables 42 to 45 below, and in FIG. 17.

TABLE 42

Amount of Oxycodone Extracted in Water, 25° C. (% of dose)

| Sample ID | Time (min) 5 | 20 | 60 |
|---|---|---|---|
| OXY1-a | 1 | 7 | 17 |
| OXY1-b | 2 | 7 | 15 |

TABLE 42-continued

Amount of Oxycodone Extracted in Water, 25° C. (% of dose)

| Sample ID | Time (min) | | |
|---|---|---|---|
| | 5 | 20 | 60 |
| OXY1-c | 1 | 8 | 17 |
| OXY2-a | 6 | 12 | 22 |
| OXY2-b | 6 | 11 | 21 |
| OXY2-c | 7 | 15 | 27 |
| OXY3-a | 2 | 8 | 18 |
| OXY3-b | 3 | 8 | 16 |
| OXY3-c | 1 | 4 | 8 |
| SR Control-a | 90 | 92 | 92 |
| SR Control-b | 87 | 87 | 88 |
| SR Control-c | 87 | 88 | 88 |
| Mean (SD), Test Capsules | 3 (2.4) | 9 (3.3) | 18 (5.2) |
| Mean (SD), SR Control | 88 (1.7) | 89 (2.6) | 89 (2.3) |

TABLE 43

Amount of Oxycodone Extracted in Water, 60-70° C. (% of dose)

| Sample ID | Time (min) | | |
|---|---|---|---|
| | 5 | 20 | 60 |
| OXY1-a | 9 | 25 | 36 |
| OXY1-b | 11 | 19 | 26 |
| OXY1-c | 12 | 31 | 45 |
| OXY2-a | 13 | 22 | 30 |
| OXY2-b | 15 | 27 | 38 |
| OXY2-c | 12 | 22 | 32 |
| OXY3-a | 7 | 18 | 28 |
| OXY3-b | 10 | 19 | 26 |
| OXY3-c | 9 | 17 | 23 |
| SR Control-a | 90 | 94 | 94 |
| SR Control-b | 92 | 93 | 92 |
| SR Control-c | 88 | 88 | 88 |
| Mean (SD), Test Capsules | 11 (2.3) | 22 (4.7) | 32 (7.0) |
| Mean (SD), SR Control | 90 (2.) | 92 (3.2) | 91 (3.1) |

TABLE 44

Amount of Oxycodone Extracted in 0.1N HCl (% of dose)

| Sample ID | Time (min) | | |
|---|---|---|---|
| | 5 | 20 | 60 |
| OXY1-a | 4 | 14 | 27 |
| OXY1-b | 4 | 16 | 27 |
| OXY1-c | 2 | 15 | 27 |
| OXY2-a | 18 | 22 | 32 |
| OXY2-b | 16 | 22 | 31 |
| OXY2-c | 13 | 18 | 27 |
| OXY3-a | 11 | 21 | 34 |
| OXY3-b | 9 | 19 | 31 |
| OXY3-c | 10 | 20 | 32 |
| SR Control-a | 88 | 92 | 89 |
| SR Control-b | 93 | 94 | 94 |
| SR Control-c | 84 | 89 | 92 |
| Mean (SD), Test Capsules | 10 (5.6) | 19 (3.2) | 30 (2.9) |
| Mean (SD), SR Control | 88 (4.5) | 92 (2.5) | 92 (2.5) |

TABLE 45

Amount of Oxycodone Extracted in 100 Proof Ethanol (% of dose)

| Sample ID | Time (min) | | |
|---|---|---|---|
| | 5 | 20 | 60 |
| OXY1-a | 8 | 18 | 33 |
| OXY1-b | 7 | 9 | 30 |
| OXY1-c | 13 | 19 | 29 |
| OXY2-a | 9 | 26 | 42 |
| OXY2-b | 10 | 27 | 42 |
| OXY2-c | 9 | 23 | 37 |
| OXY3-a | 4 | 22 | 36 |
| OXY3-b | 4 | 19 | 32 |
| OXY3-c | 9 | 21 | 35 |
| SR Control-a | 79 | 87 | 93 |
| SR Control-b | 82 | 90 | 93 |
| SR Control-c | 72 | 86 | 93 |
| Mean (SD), Test Capsules | 8 (3.0) | 20 (5.2) | 35 (4.5) |
| Mean (SD), SR Control | 78 (5.1) | 88 (2.1) | 93 (0.0) |

During testing it was note that the Test Capsules maintain their fluid characteristics even at temperatures as low as those employed in this test. Although the gelatin capsule shell fractures as a result of the crushing and grinding, the formulations from the capsules remain as a high viscosity liquid. It is thus believed that the formulations of the present invention are not susceptible to techniques that may be used to crush or grind traditional controlled release dosage forms. As can be seen by the solvent extraction results, the Test Capsules resisted rapid release of oxycodone even after chilling, crushing, grinding and exposure to an extraction solvent. The amount of extracted oxycodone after 60 minutes ranged from 18% in water to 35% in the 100 proof ethanol solution. Cumulative extraction was seen to gradually increase with time in all extraction solvents, with no evidence of rapid release or dose dumping. These data thus suggest that the instant abuse-resistant dosage forms strongly resist extraction of the active ingredient (oxycodone) even after aggressive physical disruption. Furthermore, the sticky liquid mass that is obtained was found difficult to handle. In contrast, crushing and grinding the SR Control tablets in this test clearly results in a compromise of its solid controlled release matrix. In this regard, from 70 to 90% of the oxycodone dose was extracted in each of the extraction solvents after only 5 minutes, with slight increases thereafter.

Next, extraction of oxycodone from the test capsules and the SR Control tablets using canola oil was assessed. Intimate contact of the extraction oil with the Test Capsule formulations was ensured by cutting open the capsules and squeezing the contents into the oil. Each SR Control tablet was crushed and ground in a mortar and pestle for 3 minutes. The contents of the Test Capsules and the processed SR Control tablets were placed in 10 mL of canola oil. This volume of oil was selected since routine ingestion of a larger amount of oil would have a laxative effect and therefore was considered impractical. The closed jars were vigorously shaken at 100 rpm for 60 minutes, with shaking interrupted to withdraw samples at 30 and 60 minutes. The solvent samples taken at each testing interval were centrifuged and assayed for oxycodone content by HPLC. The results of the study showed that neither the Test Capsules nor the SR Control tablets demonstrated extraction into vegetable oil since not more than 1% of oxycodone was extracted from either dosage form. These data suggest that canola oil is not a good solvent for oxycodone base or oxycodone HCl, and such a test is likely inconclusive for dosage forms containing this active agent.

Figure 18:
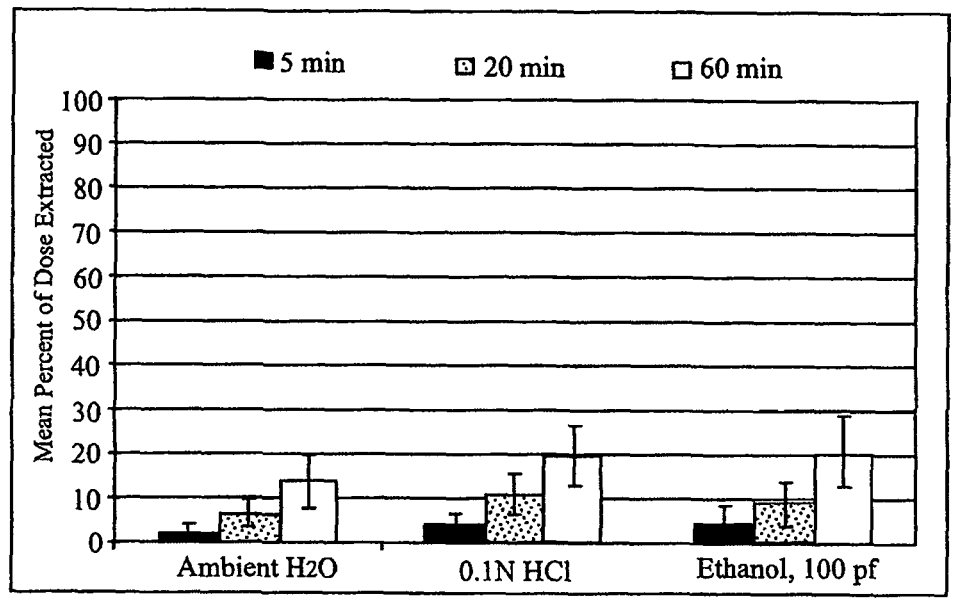
FIG. 18 shows the extraction results from microwaved Test Capsules compared against a SR Control and then extracted in a panel of household solvents (water, strong acid and 100 proof ethanol) obtained in the in vitro abuse-resistance tests described in Example 4b.

Continuing with the study, extraction of oxycodone from the Test Capsules following heating by microwave radiation was determined. Each Test Capsule was heated in a sample jar for 2 minutes at high power setting (1250 watts) in a household microwave oven. Microwave heating caused the liquid contained within the Test Capsules to melt thought the gelatin capsule, and in many cases, the heated liquid mass also caused the capsule to explode. A volume of 240 mL of the following test liquids was then added to each test jar: water (25° C.), 0.1N HCl, and 100 proof alcohol solution. The closed jars were vigorously shaken at 100 rpm for 60 minutes, with shaking interrupted to withdraw samples at 5, 20 and 60 minutes. The solvent samples taken at each testing interval were centrifuged and assayed for oxycodone content by HPLC. The extraction results are provided in Tables 46 to 48 below, and in FIG. 18.

TABLE 46

Amount of Oxycodone Extracted in Water after Microwaving (% of dose)

| Sample ID | Time (min) | | |
|---|---|---|---|
| | 5 | 20 | 60 |
| OXY1-a | 3 | 6 | 12 |
| OXY1-b | 8 | 14 | 29 |
| OXY1-c | 1 | 5 | 10 |
| OXY2-a | 2 | 6 | 12 |
| OXY2-b | 0 | 3 | 9 |
| OXY2-c | 1 | 7 | 12 |
| OXY3-a | 1 | 6 | 12 |
| OXY3-b | 2 | 7 | 15 |
| OXY3-c | 3 | 7 | 15 |
| Mean (SD), Test Capsules | 2 (2.2) | 7 (3.0) | 14 (5.9) |

TABLE 47

Amount of Oxycodone Extracted in 100 Proof Ethanol after Microwaving (% of dose)

| Sample ID | Time (min) | | |
|---|---|---|---|
| | 5 | 20 | 60 |
| OXY1-a | 2 | 8 | 11 |
| OXY1-b | 4 | 4 | 19 |
| OXY1-c | 5 | 11 | 24 |
| OXY2-a | 4 | 13 | 26 |
| OXY2-b | 6 | 8 | 26 |
| OXY2-c | 1 | 3 | 8 |
| OXY3-a | 2 | 7 | 17 |
| OXY3-b | 15 | 19 | 35 |
| OXY3-c | 2 | 7 | 16 |
| Mean (SD), Test Capsules | 4 (4.2) | 9 (4.8) | 20 (8.3) |

TABLE 48

Amount of Oxycodone Extracted in 0.1N HCl after Microwaving (% of dose)

| Sample ID | Time (min) | | |
|---|---|---|---|
| | 5 | 20 | 60 |
| OXY1-a | 3 | 6 | 13 |
| OXY1-b | 6 | 17 | 28 |
| OXY1-c | 6 | 13 | 26 |
| OXY2-a | 1 | 8 | 18 |
| OXY2-b | 4 | 8 | 12 |
| OXY2-c | 1 | 4 | 10 |
| OXY3-a | 8 | 16 | 27 |

TABLE 48-continued

Amount of Oxycodone Extracted in 0.1N HCl after Microwaving (% of dose)

| Sample ID | Time (min) | | |
|---|---|---|---|
| | 5 | 20 | 60 |
| OXY3-b | 7 | 15 | 23 |
| OXY3-c | 4 | 12 | 21 |
| Mean (SD), Test Capsules | 4 (2.6) | 11 (4.6) | 20 (6.9) |

As can be seen by these extraction results, only 4% (1.6 mg) or less of the oxycodone dose was extracted from the microwaved Test Capsules after 5 minutes of extraction in each of the extraction liquids. After 60 minutes, only about 14-10% of the oxycodone dose was extracted in any test liquid. These data show that the Test Capsules resist rapid extraction or dose dumping of the active agent (oxycodone) in common household liquids even following extreme thermal stress.

Example 4c

The following in vitro Injection Abuse Resistance Evaluation was carried out to characterize the ability of abuse-resistant formulations prepared according to the present invention to resist injection-based forms of abuse. In this regard, the characteristics of an injectable suspension are defined as syringeability and injectability. Syringeability pertains to the ability of a suspension to be drawn into an empty syringe through a hypodermic needle, while injectability address the ability of a suspension to be pushed from a pre-filled syringe through a hypodermic needle. Both characteristics depend upon the viscosity and physical characteristics of a test formulation.

For the test, placebo (no active agent) formulations were evaluated for syringeability and injectability to assess resistance to abuse by injection. The placebo formulations used in this Example 4c were prepared using the following raw materials: Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAM"); Triacetin USP ("TA"); and Cellulose Acetate Butyrate, grade 381-20 BP, ethanol washed (Eastman Chemicals) ("CAB"). The placebo formulations were produced using the commercial-scale manufacturing methods (Process Schemes 4 or 5 as described above) and filled into gelatin capsule shells (size #00) to produce Test Capsules. The details of the placebo formulation used in this Example 4c are disclosed below in Table 49.

TABLE 49

| SAIB | TA | CAB | IPM | HEC | $SiO_2$ | BHT | (total) | |
|---|---|---|---|---|---|---|---|---|
| 43.19 | 28.80 | 5.0 | 15.0 | 6.0 | 2.0 | 0.02 | | (wt %) |
| 319.6 | 213.1 | 37.0 | 111.0 | 44.4 | 14.8 | 0.16 | 740.0 | (mg) |

The test equipment and apparatus used in this study included syringe barrel (Becton Dickinson (B-D) 3 mL Disposable Syringe with Leur-Lok Tip; hypodermic needles (B-D (305136) PrecisionGlide Needle 27G1.25; B-D (305125) PrecisionGlide Needle 25G1; B-D (305190) PrecisionGlide Needle IV 1.5, 21G; B-D (305185) Precision-Glide Needle Fill 1.5, 18G); and an Instron 5542 Load Frame, controlled by BLUEHILL software.

Initially, syringeability was assessed in two ways: first by attempting to draw the placebo formulation from a Test Capsule by piercing the capsule shell with the hypodermic needle and attempting to draw the formulation into the syringe; and second, by attempting to squeeze the formulation from a cut capsule into the posterior end of a syringe barrel (i.e., with the plunger removed). The syringeability analysis was conducted using placebo formulations equilibrated at room temperature (25° C.). Both of these techniques represent practices that may be employed by a drug abuser. Any placebo formulation mass successfully drawn or filled into the syringe was quantified and recorded.

Injectability was evaluated using the Instron Load Frame instrument to push the plunger of a pre-loaded syringe in an attempt to deliver the placebo formulation. The force required for successful injection of the placebo formulation or the force at which failure occurred was recorded by the instrument. The single-use syringe barrels were filled with approximately 1 g of the placebo formulation (range 0.64 to 1.14 g). Entrapped air was removed by application of vacuum while depressing the plunger to minimize variability in the injectability analysis. Testing was performed on two sets of placebo formulations that were equilibrated to either 25° C. or 37° C. Needles with gauge sizes of 18, 21, 25 and 27 were joined by a Luer-Lok fitting to the pre-loaded syringe barrel. Three different crosshead speeds (i.e., plunger depression rates) were evaluated for each needle gauge. Crosshead speeds of 150 mm/min, 550 mm/min, and 950 mm/min were selected based upon documented typical injection rates for parenteral administration. Three samples were tested at each set of conditions.

The results of this abuse-resistance test were as follows. Syringeability: it was not possible to draw the placebo formulation into the syringe using the largest bore needle (18 gauge) due to the high viscosity and thixotropy of the formulation. As a result, evaluation using smaller bore needles (21, 25 and 27 gauge) were not performed. Placebo formulation at room temperature was squeezed from an opened capsule into the posterior end of a tarred syringe barrel. The weights successfully transferred into each of five syringes was recorded. A mean weight of 0.42 g (range 0.22-0.50 g, mean of 54%, range 28-64%) was transferred from the Test Capsules. Accordingly, syringeability was not achieved for any gauge needle in the study. In this regard, the high viscosity and sticky character of the placebo formulation prevented quantitative transfer of capsule contents into the syringe barrel.

Injectability of the placebo formulations at room temperature was only achieved using an 18 gauge needle at the slowest crosshead speed of 150 mm/min. At 37° C., the formulation is less viscous and injectability was achieved with all three samples using the 18 gauge needle at a speed of 150 mm/min, and with two of the three samples using an 18 gauge needle at a speed of 550 mm/min. Either load failures of mechanical failures occurred at both test temperatures, and at all three crosshead speeds with the 21, 25 and 27 gauge needles.

The following information was considered in interpreting the outcome of each test. Single use disposable syringes are rated to withstand an internal barrel pressure of 45 $lb_f/in^2$ for 30 seconds (corresponding to a pressure exerted on the plunger rod of 18.2 N). For 3 mL (ID=0.34 in.) disposable syringe barrels, 1 $lb_f$ applied to the plunger rod generates 11.0 $lb_f/in^2$ within the syringe barrel. The mean pinch force (Palmer Pinch) exerted by healthy males is 23 to 23.4 $lb_f$.

The following failure modes were used to assess injectability in this study. Overall failure of the test was concluded upon failure of at least one sample with a triplicate test set. A Plunger Barrel failure occurs when excessive internal pressure causes the syringe barrel to flex, resulting in fluid bypassing the plunger stopper. This event is determined by observing the sample, or is evidenced by a declining load force profile in the Instron tracing. A Leur-Lok Coupling Failure occurs when excessive internal pressure causes the needle to separate from the syringe barrel. This failure event is determined by observing incomplete sample delivery from the syringe, or is evidenced by a precipitous drop in the load force profile in the Instron tracing. An Excessive Force failure occurs when the force required to successfully deliver fluid from the syringe exceeds 23.4 $lb_f$ (104 N), the average (Palmer) pinch force of a healthy male. This event is evident from the Instron tracing.

Successful injection of placebo formulation required comparable performance of all three test samples. The criterion for success was at least 80% delivery of the initial pre-filled mass. In addition, the Instron tracing should display a consistent profile of force applied during plunger travel. Even in cases where the force profile remained consistent during the test and resulted in delivery of placebo mass from the syringe, a force greater than 62N was required to achieve delivery. This magnitude of force generates a barrel pressure of 153 $lb_f/in^2$, which is 340% of the pressure rated by the manufacturer.

These results of both the syringeability and injectability evaluations demonstrate the improbability of delivering an abuse-resistant controlled release formulation prepared according to the invention using common hypodermic needles such as those available to drug abusers. This is thought to be due to a combination of limitations of suitable syringe pressures, limitations of human strength and the highly viscous nature of the instant formulations.

Example 4d

The following in vitro Inhalation Abuse Resistance Evaluation was carried out to characterize the ability of abuse-resistant formulations prepared according to the present invention to resist inhalation-based forms of abuse. More particularly, 2 different manufacturing lots of abuse-resistant oxycodone oral dosage 40 mg strength forms produced with different purity grades of the active agent (oxycodone) were used as the Test Capsules. OxyContin brand (oxycodone HCl controlled-release) Tablets, 40 mg strength (Lot W28A1, Purdue Pharma L.P.), (SR Control) were used as the commercial comparison.

The abuse-resistant oxycodone oral dosage forms used in this Example 4d were prepared using the following raw materials: Oxycodone base, micronized ("OXY"), grade 2 (specified to contain not more than 0.25% (w/w) 14-hydroxycodeinone (14-HC)) or grade 1 (specified to contain not more than 0.001% (w/w) 14-HC), both grades obtained from Noramco, Inc (Athens Ga.); Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); and Cellulose Acetate Butyrate, grade 381-20 BP, ethanol washed (Eastman Chemicals) ("CAB"). The formulations were produced using the commercial-scale manufacturing methods (Process Schemes 4 or 5 as described above) and then filled into size #00 hard gelatin cap shells to produce the 40 mg dosage forms that were used as Test Capsules. The details of the formulations and the dosage forms containing the formulations of this Example 4d are disclosed below in Table 50.

TABLE 50

| OXY | SAIB | TA | CAB | IPM | HEC | SiO$_2$ | BHT | (total) | |
|---|---|---|---|---|---|---|---|---|---|
| 5.13 | 40.98 | 27.32 | 4.74 | 14.23 | 5.69 | 1.9 | 0.02 | | (wt %) |
| 40.0 | 319.6 | 213.1 | 37.0 | 111.0 | 44.4 | 14.8 | 0.16 | 780.0 | (mg) |

The in vitro Inhalation Abuse Resistance Evaluation used the following Test Capsules: three 40 mg dosage forms (n=3), containing grade 2 oxycodone (OXY1); three 40 mg dosage forms (n=3), containing grade 1 oxycodone (OXY2). The commercial comparison was against three 40 mg SR Control tablets (n=3).

A volatilization study was conducted to evaluate the potential for abuse of the Test Capsules by inhalation. Initially, thermal gravimetric analysis was used to measure the weight loss of oxycodone base and oxycodone HCl in order to determine the correct temperature to conduct the volatilization study. Oxycodone base was subjected to increasing temperature conditions (30 to 350° C.) at a ramping rate of 20° C./min. Vaporization occurred above 200° C. and was complete at 310° C. Vaporization of oxycodone HCl (28 to 400° C.) was analogous to that of the free base up to approximately 300° C. after which significant decomposition of the salt form occurred. Based on these observations, a temperature of 280° C. was selected for this study. This temperature is above the melting point of oxycodone (to ensure adequate drug vaporization) and below 300° C. (to limit decomposition of the salt form). A maximum exposure time of 10 minutes was selected based on pre-test observations that little additional oxycodone was recovered beyond that time point.

Figure 19:
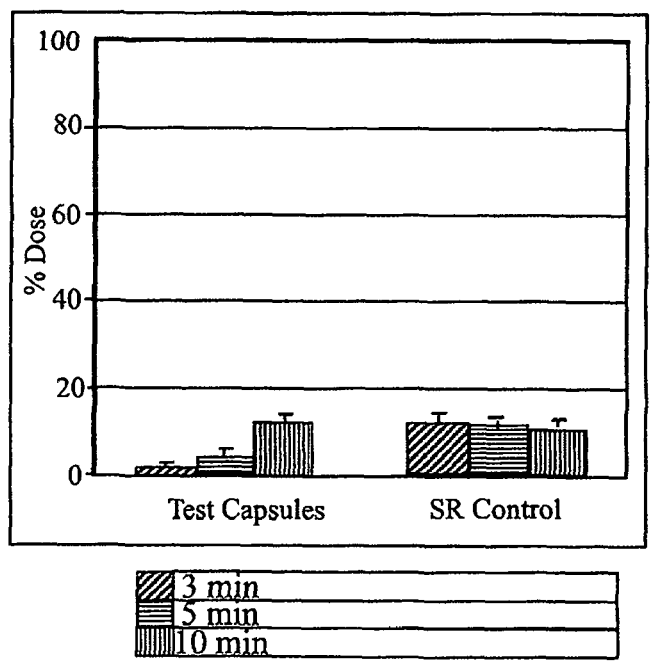
FIG. 19 shows the volatilization results from Test Capsules against a SR Control obtained in the in vitro abuse-resistance test described in Example 4d.
Figure 20:
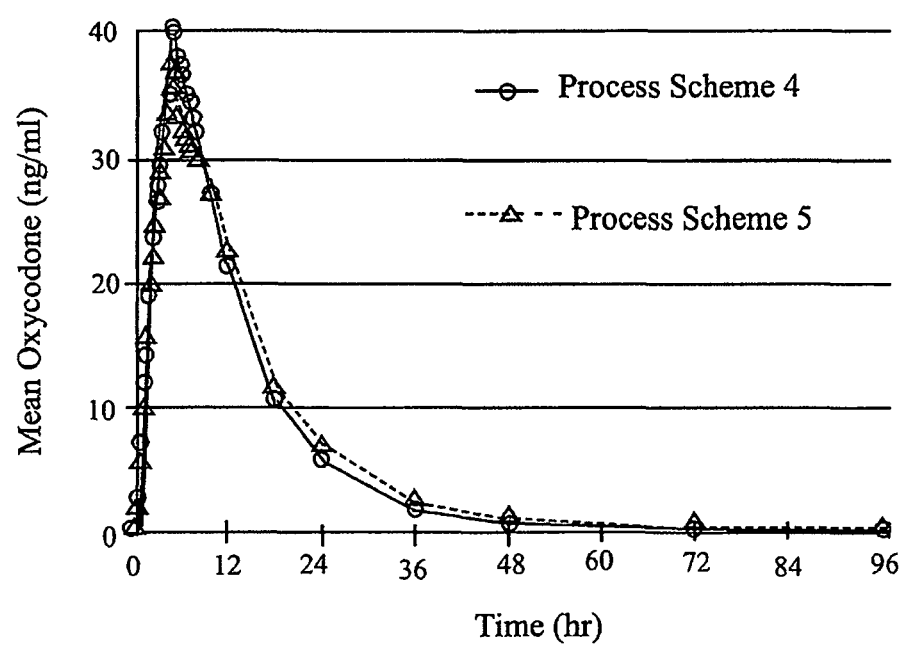

A volatilization system was designed to control the temperature applied to the test samples. The system was constructed from an aluminum block, with temperature monitoring thermocouple, mounted to a hot plate. Each aluminum block contains four holes for positioning of glass sample dishes. Each sample dish was capped with a pre-chilled aluminum cover that held a frozen gel pack on top to facilitate condensation of volatilized oxycodone. Three dishes contained test samples in each trial, while the fourth served as a blank control. The two lots of Test Capsules and the single lot of SR Control tablets were evaluated in triplicate. Each Test Capsule was cut open and the liquid contents squeezed into a sample dish, and each SR Control tablet was ground with a mortar and pestle and then transferred to a sample dish. The aluminum block was stabilized at 280° C. prior to initiating the study. The covers were swabbed for oxycodone at 3, 5 and 10 minutes, and the samples were analyzed using HPLC. The results of the volatilization study were as follows: average oxycodone recoveries following volatilization at 280° C. (data in the form of mean oxycodone recovered with standard deviation (SD), reported as a % of initial dose): Test Capsules=2% (0.8) at 3 minutes; 4% (2.1) at 5 minutes; and 12% (2.1) at 10 minutes. SR Control tablets=12% (2) at 3 minutes; 11% (2) at 5 minutes; and 10% (2) at 10 minutes. These data are depicted in FIG. 19.

As can be seen by these results, volatilization of three SR Control tablets at 280° C. for 3 minutes resulted in an average oxycodone release of 12% of total drug mass; while volatilization of six Test Capsules tablets at 280° C. for 3 minutes only resulted in an average oxycodone release of 2% of total drug mass. However, after 10 minutes, an approximately equal amount of oxycodone had volatilized from each formulation (10% compared with 12% release). Observations during the testing noted that vaporization of oxycodone from the Test Capsules was accompanied by liberation of smoke which is likely to be unpleasant (based upon volatilization of placebo Test Capsule formulations that resulted in generation of pungent, acrid white smoke that was found to irritate the respiratory tract and throat when inhaled). Vaporization of oxycodone from the SR Control tablets exhibited significant charring. The low level of oxycodone liberated from the Test Capsules upon initial heating in this volatilization study, accompanied by the generation of an unpleasant smoke suggest that the abuse-resistant dosage forms of the present invention are likely to discourage abuse by inhalation.

Example 4e

The following in vitro Abuse Resistance Evaluation was carried out to characterize the in vitro abuse resistance performance of oxycodone oral dosage forms prepared according to the present invention. More particularly, abuse-resistant oxycodone oral dosage forms across a range of formulations were assessed for resistance to extraction in an ethanol solution. The abuse-resistant oxycodone oral dosage forms used in this Example 4e were prepared using the following raw materials: Oxycodone base, micronized ("OXY"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAM"); Triacetin USP ("TA"); Sodium Lauryl Sulfate ("SLS"); Labrafil M2125 CS ("LAB"); Gelucire 44/14 (Gattefosse) ("GEL"); and Cellulose Acetate Butyrate, grade 381-20 BP, ethanol washed (Eastman Chemicals) ("CAB"). The formulations were produced using the commercial-scale manufacturing methods (Process Schemes 4 or 5 as described above) and then filled into size #00 hard gelatin cap shells to produce 80 mg dosage forms that were used as Test Capsules. The details of the formulations and the dosage forms containing the formulations of this Example 4e are disclosed below in Table 51.

TABLE 51

| | OXY | SAIB | TA | CAB | IPM | HEC | SiO$_2$ | BHT | SLS | LAB | GEL | (Total) | |
|---|---|---|---|---|---|---|---|---|---|---|---|---|---|
| OXY1 | 80.0 | 281.4 | 208.4 | 42.0 | 112.0 | 42.0 | 14.0 | 0.2 | — | — | — | 780 | (mg) |
| | 10.26 | 36.08 | 26.72 | 5.38 | 14.36 | 5.38 | 1.79 | 0.02 | — | — | — | | (wt %) |
| OXY2 | 80.0 | 297.5 | 198.4 | 42.0 | 105.0 | 42.0 | 14.0 | 0.2 | 1.0 | — | — | 780 | (mg) |
| | 10.26 | 38.14 | 25.43 | 5.38 | 13.46 | 5.38 | 1.79 | 0.02 | 0.13 | — | — | | (wt %) |
| OXY3 | 80.0 | 285.5 | 190.3 | 42.0 | 105.0 | 42.0 | 14.0 | 0.2 | — | 21.0 | — | 780 | (mg) |
| | 10.26 | 36.60 | 24.40 | 5.38 | 13.46 | 5.38 | 1.79 | 0.02 | — | 2.69 | — | | (wt %) |

TABLE 51-continued

|  | OXY | SAIB | TA | CAB | IPM | HEC | SiO$_2$ | BHT | SLS | LAB | GEL | (Total) |  |
|---|---|---|---|---|---|---|---|---|---|---|---|---|---|
| OXY4 | 80.0 | 280.4 | 207.7 | 36.7 | 119.0 | 42.0 | 14.0 | 0.2 | — | — | — | 780 | (mg) |
|  | 10.26 | 35.95 | 26.63 | 4.71 | 15.26 | 5.38 | 1.79 | 0.02 | — | — | — |  | (wt %) |
| OXY5 | 80.0 | 281.0 | 200.8 | 42.0 | 119.0 | 42.0 | 14.0 | 0.2 | 1.0 | — | — | 780 | (mg) |
|  | 10.26 | 36.03 | 25.74 | 5.38 | 15.26 | 5.38 | 1.79 | 0.02 | 0.13 | — | — |  | (wt %) |
| OXY6 | 80.0 | 286.6 | 191.0 | 36.7 | 112.0 | 42.0 | 14.0 | 0.2 | — | 17.5 | — | 780 | (mg) |
|  | 10.26 | 36.74 | 24.49 | 4.71 | 14.36 | 5.38 | 1.79 | 0.02 | — | 2.24 | — |  | (wt %) |
| OXY7 | 80.0 | 284.4 | 210.7 | 42.0 | 112.0 | 21.0 | 15.8 | 0.2 | — | — | 14.0 | 780 | (mg) |
|  | 10.26 | 36.46 | 27.01 | 5.38 | 14.36 | 2.69 | 2.02 | 0.02 | — | — | 1.79 |  | (wt %) |
| OXY8 | 80.0 | 282.4 | 209.2 | 38.5 | 112.0 | 42.0 | 15.8 | 0.2 | — | — | — | 780 | (mg) |
|  | 10.26 | 36.21 | 26.82 | 4.94 | 14.36 | 5.38 | 2.02 | 0.02 | — | — | — |  | (wt %) |
| OXY9 | 80.0 | 285.9 | 204.3 | 38.5 | 112.0 | 42.0 | 15.8 | 0.2 | 1.4 | — | — | 780 | (mg) |
|  | 10.26 | 36.66 | 26.19 | 4.94 | 14.36 | 5.38 | 2.02 | 0.02 | 0.18 | — | — |  | (wt %) |

The in vitro Abuse Resistance Evaluation used the following Test Capsules: six (n=6) each of formulations OXY1-OXY9.

The ethanol solution extraction study was carried out substantially the same as in Example 4a above, using the same apparatus, reagents and methods described above, with the following exceptions: the extraction solution was 60 mL of 80 proof ethanol (40%); and sampling was conducted at time=0.5 hour, 1, 2 and 3 hours. The results of the extraction study are provided below in Table 52.

TABLE 52

| | Amount of Oxycodone Extracted in 80 Proof Ethanol (% of dose) Time (hr.) | | | |
|---|---|---|---|---|
| | 0.5 | 1 | 2 | 3 |
| OXY1 | | | | |
| Mean | 7 | 16 | 25 | 32 |
| Std Dev. | 1 | 4 | 6 | 8 |
| OXY2 | | | | |
| Mean | 8 | 18 | 28 | 35 |
| Std Dev. | 2 | 3 | 4 | 5 |
| OXY3 | | | | |
| Mean | 8 | 14 | 21 | 27 |
| Std Dev. | 2 | 2 | 5 | 6 |
| OXY4 | | | | |
| Mean | 12 | 18 | 26 | 32 |
| Std Dev. | 1 | 2 | 3 | 3 |
| OXY5 | | | | |
| Mean | 11 | 16 | 24 | 30 |
| Std Dev. | 2 | 3 | 3 | 4 |
| OXY6 | | | | |
| Mean | 8 | 11 | 14 | 17 |
| Std Dev. | 1 | 1 | 1 | 2 |
| OXY7 | | | | |
| Mean | 9 | 15 | — | 30 |
| Std Dev. | 1 | 2 | — | 2 |

TABLE 52-continued

| | Amount of Oxycodone Extracted in 80 Proof Ethanol (% of dose) Time (hr.) | | | |
|---|---|---|---|---|
| | 0.5 | 1 | 2 | 3 |
| OXY8 | | | | |
| Mean | 12 | 18 | — | 32 |
| Std Dev. | 1 | 2 | — | 3 |
| OXY9 | | | | |
| Mean | 12 | 18 | — | 33 |
| | 1 | 2 | — | 3 |

Example 4f

The following in vitro Abuse Resistance Evaluation was carried out to characterize the in vitro abuse resistance performance of hydromorphone oral dosage forms prepared according to the present invention. More particularly, abuse-resistant hydromorphone oral dosage forms across a range of strengths (8 mg and 16 mg strengths) and across a range of formulations were assessed for resistance to extraction in an ethanol solution. The abuse-resistant hydromorphone oral dosage forms used in this Example 4f were prepared using the following raw materials: Hydromorphone HCl ("HMH"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Labrafil M2125 CS ("LAB"); and Cellulose Acetate Butyrate, grade 381-20 BP, ethanol washed (Eastman Chemicals) ("CAB"). The formulations were produced using the GMP manufacturing method of Example 1d above (Process Scheme 8) and then filled into either size #1 (HMH1) or #2 (HMH2-4) gel cap shells to produce 8 and 16 mg dosage forms that were used as Test Capsules. The details of the formulations used in this Example 4f are disclosed below in Table 53.

TABLE 53

| Formula: | HMH | SAIB | TA | CAB | IPM | HEC | SiO$_2$ | BHT | LAB | Total | |
|---|---|---|---|---|---|---|---|---|---|---|---|
| HMH1 | 16.0 | 108.6 | 80.4 | 15.5 | 41.4 | 7.8 | 5.2 | 0.1 | — | 275.0 | (mg) |
|  | 5.82 | 39.49 | 29.5 | 5.65 | 15.07 | 5.65 | 1.88 | 0.02 | — |  | (wt %) |
| HMH2 | 16.0 | 104.1 | 77.1 | 15.5 | 41.4 | 15.5 | 5.2 | 0.1 | — | 275.0 | (mg) |
|  | 5.82 | 37.86 | 28.05 | 5.65 | 15.07 | 5.65 | 1.88 | 0.02 | — |  | (wt %) |
| HMH3 | 16.0 | 101.1 | 74.9 | 15.5 | 38.9 | 15.5 | 5.2 | 0.1 | 7.8 | 275.0 | (mg) |
|  | 5.82 | 36.78 | 27.24 | 5.65 | 14.13 | 5.65 | 1.88 | 0.02 | 2.83 |  | (wt %) |

TABLE 53-continued

| Formula: | HMH | SAIB | TA | CAB | IPM | HEC | SiO₂ | BHT | LAB | Total | |
|---|---|---|---|---|---|---|---|---|---|---|---|
| HMH4 | 8.0 | 29.8 | 19.9 | 3.6 | 10.8 | 4.3 | 1.4 | 0.1 | 2.2 | 80.0 | (mg) |
|  | 10.00 | 37.25 | 24.83 | 4.50 | 13.50 | 5.40 | 1.80 | 0.02 | 2.70 |  | (wt %) |

The in vitro Abuse Resistance Evaluation used the following Test Capsules: six 16 mg dosage forms, formulation HMH1 (n=6); six 16 mg dosage forms, formulation HMH2 (n=6); six 16 mg dosage forms, formulation HMH3 (n=6); and six 8 mg dosage forms, formulation HMH4 (n=6).

The ethanol solution extraction study was carried out substantially the same as in Example 4a above, using the same apparatus, reagents and methods described above, with the following exceptions: the extraction solution was 60 mL of 80 proof ethanol (40%); and sampling was conducted at time=0.5 hour, 1, 2 and 3 hours. The results of the extraction study are provided below in Table 54.

TABLE 54

| | Amount of Hydromorphone Extracted in 80 Proof Ethanol (% of dose) Time (hr.) | | | |
|---|---|---|---|---|
| | 0.5 | 1 | 2 | 3 |
| | HMH1 | | | |
| Mean | 3 | 5 | 8 | 10 |
| Std Dev. | 0 | 1 | 1 | 1 |
| | HMH2 | | | |
| Mean | 7 | 12 | 18 | 22 |
| Std Dev. | 0 | 1 | 3 | 4 |
| | HMH3 | | | |
| Mean | 6 | 9 | 14 | 20 |
| Std Dev. | 2 | 1 | 2 | 2 |
| | HMH4 | | | |
| Mean | 9 | 13 | 20 | 27 |
| Std Dev. | 1 | 2 | 4 | 6 |

Example 4g

The following in vitro Abuse Resistance Evaluation was carried out to characterize the in vitro abuse resistance performance of hydrocodone oral dosage forms prepared according to the present invention. More particularly, abuse-resistant hydrocodone oral dosage forms across a range of strengths (15 mg and 75 mg strengths) and across a range of formulations were assessed for resistance to extraction in an ethanol solution. The abuse-resistant hydrocodone oral dosage forms used in this Example 4g were prepared using the following raw materials: Hydrocodone Bitartrate ("HCB"); Isopropyl Myristate, NF ("IPM"); Colloidal silicon dioxide (Cabosil®, Cabot Corp) ("SiO₂"); Butylated hydroxyl toluene, NF ("BHT"); Hydroxyethyl cellulose, NF ("HEC"); Sucrose Acetate Isobutyrate (Eastman Chemicals), ("SAM"); Triacetin USP ("TA"); Gelucire 44/14 (Gattefosse) ("GEL"); and Cellulose Acetate Butyrate, grade 381-20 BP, ethanol washed (Eastman Chemicals) ("CAB"). The formulations were produced using the GMP manufacturing method of Example 1e above (Process Scheme 9) and then filled into size #3 gel cap shells to produce the dosage forms that were used as Test Capsules. The details of the formulations and the dosage forms containing the formulations of this Example 4g are disclosed below in Table 55.

TABLE 55

| Formula # | HCB (mg) | SAIB (mg) | TA (mg) | CAB (mg) | IPM (mg) | HEC (mg) | SiO₂ (mg) | BHT (02 mg) | GEL (mg) | Total (mg) | |
|---|---|---|---|---|---|---|---|---|---|---|---|
| HCB1 | 15.0 | 41.8 | 27.8 | 5.2 | 14.24 | 2.8 | 1.9 | 0.1 | 1.1 | 110.0 | (mg) |
|  | 13.64 | 37.97 | 25.31 | 4.75 | 12.95 | 2.59 | 1.73 | 0.02 | 1.04 |  | (wt %) |
| HCB2 | 75.0 | 208.8 | 139.2 | 26.1 | 71.2 | 14.2 | 9.5 | 0.11 | 5.7 | 550.0 | (mg) |
|  | 13.63 | 37.96 | 25.31 | 4.75 | 12.95 | 2.58 | 1.73 | 0.02 | 1.04 |  | (wt %) |

The in vitro Abuse Resistance Evaluation used the following Test Capsules: six 15 mg dosage forms, formulation HCB1 (n=6); and six 75 mg dosage forms, formulation HCB2 (n=6).

The ethanol solution extraction study was carried out substantially the same as in Example 4a above, using the same apparatus, reagents and methods described above, with the following exceptions: the extraction solution was 60 mL of 80 proof ethanol (40%); and sampling was conducted at time=0.5 hour, 1 and 3 hours. The results of the extraction study are provided below in Table 56.

TABLE 56

| | Amount of Hydrocodone Extracted in 80 Proof Ethanol (% of dose) Time (hr.) | | |
|---|---|---|---|
| | 0.5 | 1 | 3 |
| | HCB1 | | |
| Mean | 9 | 12 | 20 |
| Std Dev. | 1 | 1 | 2 |
| | HCB2 | | |
| Mean | 3 | 5 | 12 |
| Std Dev. | 1 | 2 | 2 |

Example 4h

The following in vitro Abuse Resistance Evaluation was carried out to characterize the in vitro abuse resistance performance of oxymorphone oral dosage forms prepared according to the present invention. More particularly, abuse-resistant oxymorphone oral dosage forms across a range of formulations were assessed for resistance to extraction in an ethanol solution. The abuse-resistant oxymorphone oral dosage forms used in this Example 4h were prepared using the following raw materials: oxymorphone HCl ("OMH"); Isopropyl Myristate, NF ("IPM"); Colloidal silicon dioxide (Cabosil®, Cabot Corp) ("SiO₂"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); and Gelucire 44/14 (Gattefosse) ("GEL"). The formulations were produced using the lab-scale manufacturing process described in Example 3f above and then filled into size #1 gel capsules to produce the dosage forms that were used as Test Capsules. The details of the formulations and the dosage forms containing the formulations of this Example 4h are disclosed below in Table 57.

TABLE 57

|  | OMH | SAIB | TA | CAB | IPM | HEC | SiO₂ | BHT | GEL | (Total) |  |
|---|---|---|---|---|---|---|---|---|---|---|---|
| OMH1 | 40.00 | 226.38 | 150.92 | 25.50 | 76.50 | 15.30 | 12.75 | 0.10 | 2.55 | 550 | (mg) |
|  | 7.27 | 41.16 | 27.44 | 4.64 | 13.91 | 2.78 | 2.32 | 0.02 | 0.46 |  | (wt %) |
| OMH2 | 40.00 | 214.14 | 142.76 | 25.50 | 76.50 | 35.70 | 7.65 | 0.10 | 7.65 | 550 | (mg) |
|  | 7.27 | 38.93 | 25.96 | 4.64 | 13.91 | 6.49 | 1.39 | 0.02 | 1.39 |  | (wt %) |
| OMH3 | 40.00 | 226.38 | 150.92 | 30.60 | 76.50 | 15.30 | 7.65 | 0.10 | 2.55 | 550 | (mg) |
|  | 7.27 | 41.16 | 27.44 | 5.56 | 13.91 | 2.78 | 1.39 | 0.02 | 0.46 |  | (wt %) |
| OMH4 | 40.00 | 214.14 | 142.76 | 25.50 | 76.50 | 35.70 | 12.75 | 0.10 | 2.55 | 550 | (mg) |
|  | 7.27 | 38.93 | 25.96 | 4.64 | 13.91 | 6.49 | 2.32 | 0.02 | 0.46 |  | (wt %) |
| OMH5 | 40.00 | 208.02 | 138.68 | 30.60 | 76.50 | 35.70 | 12.75 | 0.10 | 7.65 | 550 | (mg) |
|  | 7.27 | 37.82 | 25.21 | 5.56 | 13.91 | 6.49 | 2.32 | 0.02 | 1.39 |  | (wt %) |
| OMH6 | 40.00 | 214.14 | 142.76 | 30.60 | 76.50 | 35.70 | 7.65 | 0.10 | 2.55 | 550 | (mg) |
|  | 7.27 | 38.93 | 25.96 | 5.56 | 13.91 | 6.49 | 1.39 | 0.02 | 0.46 |  | (wt %) |
| OMH7 | 40.00 | 220.26 | 146.84 | 30.60 | 76.50 | 15.30 | 12.75 | 0.10 | 7.65 | 550 | (mg) |
|  | 7.27 | 40.05 | 26.70 | 5.56 | 13.91 | 2.78 | 2.32 | 0.02 | 1.39 |  | (wt %) |
| OMH8 | 40.00 | 226.38 | 150.92 | 25.50 | 76.50 | 15.30 | 7.65 | 0.10 | 7.65 | 550 | (mg) |
|  | 7.27 | 41.16 | 27.44 | 4.64 | 13.91 | 2.78 | 1.39 | 0.02 | 1.39 |  | (wt %) |
| OMH9 | 40.00 | 218.73 | 145.82 | 28.05 | 76.50 | 25.50 | 10.20 | 0.10 | 5.10 | 550 | (mg) |
|  | 7.27 | 39.77 | 26.51 | 5.10 | 13.91 | 4.64 | 1.85 | 0.02 | 0.93 |  | (wt %) |
| OMH10 | 40.00 | 206.49 | 152.96 | 25.50 | 81.60 | 35.70 | 7.65 | 0.10 | — | 550 | (mg) |
|  | 7.27 | 37.54 | 27.81 | 4.64 | 14.84 | 6.49 | 1.39 | 0.02 | — |  | (wt %) |

The in vitro Abuse Resistance Evaluation used the following Test Capsules: three each (n=3) of formulations OMH1-OMH10.

The ethanol solution extraction study was carried out substantially the same as in Example 4a above, using the same apparatus, reagents and methods described above, with the following exceptions: the extraction solution was 60 mL of 80 proof ethanol (40%); and sampling was conducted at time=0.5 hour, 1 and 3 hours. The results of the extraction study are provided below in Table 58.

TABLE 58

| | Amount of Oxymorphone Extracted in 80 Proof Ethanol (% of dose) Time (hr.) | | |
|---|---|---|---|
| | 0.5 | 1 | 3 |
| OMH1 | | | |
| Mean | 2 | 3 | 8 |
| Std Dev. | 1 | 1 | 1 |
| OMH2 | | | |
| Mean | 10 | 17 | 40 |
| Std Dev. | 1 | 2 | 5 |
| OMH3 | | | |
| Mean | 3 | 4 | 14 |
| Std Dev. | 1 | 2 | 2 |
| OMH4 | | | |
| Mean | 3 | 5 | 13 |
| Std Dev. | 1 | 1 | 3 |
| OMH5 | | | |
| Mean | 5 | 9 | 24 |
| Std Dev. | 0 | 0 | 2 |
| OMH6 | | | |
| Mean | 2 | 4 | 10 |
| Std Dev. | 0 | 0 | 1 |
| OMH7 | | | |
| Mean | 5 | 8 | 15 |
| Std Dev. | 1 | 1 | 1 |
| OMH8 | | | |
| Mean | 10 | 14 | 27 |
| Std Dev. | 2 | 2 | 4 |
| OMH9 | | | |
| Mean | 4 | 5 | 10 |
| Std Dev. | 1 | 1 | 1 |
| OMH10 | | | |
| Mean | 6 | 11 | 24 |
| Std Dev. | 4 | 6 | 9 |

Example 4i

The following in vitro Abuse Resistance Evaluation was carried out to characterize the in vitro abuse resistance performance of amphetamine oral dosage forms prepared according to the present invention. More particularly, abuse-resistant amphetamine oral dosage forms across a range of formulations were assessed for resistance to extraction in an ethanol solution. The abuse-resistant amphetamine oral dosage forms used in this Example 4i were prepared using the following raw materials: d-Amphetamine Sulfate (Cambrex) ("AMP"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); Caprylocaproyl Polyoxyglycerides (Gattefosse) ("CPG"); Gelucire 50/13 (Gattefosse) ("GEL"); and Polyethylene Glycol 8000 (Dow Chemical) ("PEG 8000"). The formulations were produced using a GMP manufacturing process (Process Scheme 6 as described in Example 1a above) and then filled into size #1 gel capsules to produce the dosage forms that were used as Test Capsules. The details of the formulations and the dosage forms containing the formulations of this Example 4i are disclosed below in Tables 59 and 60.

TABLE 59

| | Formulation by Weight Percent (wt %) | | |
|---|---|---|---|
| Component | AMP1 | AMP2 | AMP3 |
| AMP | 7.50 | 5.45 | 5.45 |
| SAIB | 36.52 | 36.24 | 35.16 |
| TA | 27.05 | 26.85 | 26.04 |
| CAB | 4.86 | 4.96 | 4.96 |
| IPM | 15.73 | 16.07 | 16.07 |
| HEC | 5.55 | 5.67 | 5.67 |
| SiO$_2$ | 1.85 | 1.89 | 1.89 |
| BHT | 0.02 | 0.02 | 0.02 |
| LAB | 0.93 | 0 | 0 |
| PEG 8000 | 0 | 2.84 | 0 |
| GEL | 0 | 0 | 4.73 |

TABLE 60

| | Formulation by Mass (mg) | | |
|---|---|---|---|
| Component | AMP1 | AMP2 | AMP3 |
| AMP | 15.00 | 14.99 | 14.99 |
| SAIB | 73.04 | 99.66 | 96.69 |
| TA | 54.10 | 73.84 | 71.61 |
| CAB | 9.72 | 13.64 | 13.64 |
| IPM | 31.46 | 44.19 | 44.19 |
| HEC | 11.10 | 15.93 | 15.59 |
| SiO$_2$ | 3.70 | 5.20 | 5.20 |
| BHT | 0.04 | 0.06 | 0.06 |
| LAB | 1.86 | 0 | 0 |
| PEG 8000 | 0 | 7.81 | 0 |
| GEL | 0 | 0 | 13.01 |
| Total | 200.02 | 275.32 | 274.98 |

The in vitro Abuse Resistance Evaluation used the following Test Capsules: three (n=3) each of formulations AMP1-AMP3.

The ethanol solution extraction study was carried out substantially the same as in Example 4a above, using the same apparatus, reagents and methods described above, with the following exceptions: the extraction solution was 60 mL of 80 proof ethanol (40%); and sampling was conducted at time=0.5 hour and 3 hours. The results of the extraction study are provided below in Table 61.

TABLE 61

| | Amount of Amphetamine Extracted in 80 Proof Ethanol (% of dose) | |
|---|---|---|
| | Time (hr.) | |
| | 0.5 | 3 |
| AMP1 | | |
| Mean | 23 | 59 |
| Std Dev. | 2 | 4 |
| AMP2 | | |
| Mean | 8 | 27 |
| Std Dev. | 0 | 2 |
| AMP3 | | |
| Mean | 12 | 39 |
| Std Dev. | 0 | 2 |

Example 4j

The following in vitro Abuse Resistance Evaluation was carried out to characterize the in vitro abuse resistance performance of methylphenidate oral dosage forms prepared according to the present invention. More particularly, abuse-resistant methylphenidate oral dosage forms across a range of formulations were assessed for resistance to extraction in an ethanol solution. The abuse-resistant methylphenidate oral dosage forms used in this Example 4j were prepared using the following raw materials: methylphenidate ("MPH"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); Gelucire 50/13 (Gattefosse) ("GEL"); and Miglyol 812 ("MIG"). The formulations were produced using the manufacturing process (Process Scheme 6) as described in Example 1a above, and then filled into size #3 gelatin capsule shells to produce the dosage forms that were used as Test Capsules. The details of the formulations and the dosage forms containing the formulations of this Example 4j are disclosed below in Tables 62 and 63.

TABLE 62

| | Formulation by Weight Percent (wt %) | | | | | |
|---|---|---|---|---|---|---|
| Component | MPH1 40 mg | MPH2 48 mg | MPH3 48 mg | MPH4 48 mg | MPH5 48 mg | MPH6 48 mg |
| MPH | 20.00 | 20.00 | 20.00 | 20.00 | 20.00 | 20.00 |
| SAIB | 33.35 | 34.31 | 34.55 | 34.31 | 29.25 | 34.55 |
| TA | 22.23 | 22.87 | 23.03 | 22.87 | 20.89 | 23.03 |
| CAB | 4.80 | 5.20 | 6.40 | 5.21 | 5.58 | 6.42 |
| IPM | 13.60 | 12.80 | 12.80 | 12.80 | — | 12.80 |
| MIG | — | — | — | — | 16.0 | — |
| HEC | 0.00 | 2.40 | 0.00 | 2.40 | 4.80 | — |
| SiO$_2$ | 2.00 | 1.60 | 1.60 | 1.60 | 1.60 | 1.60 |
| BHT | 0.02 | 0.02 | 0.02 | 0.02 | 0.02 | 0.02 |
| GEL | 4.00 | 0.80 | 1.60 | 0.80 | 1.84 | 1.60 |

TABLE 63

| Component | MPH1 40 mg | MPH2 48 mg | MPH3 48 mg | MPH4 48 mg | MPH5 48 mg | MPH6 48 mg |
|---|---|---|---|---|---|---|
| | Formulation by Mass (mg) | | | | | |
| MPH | 40.00 | 48.00 | 48.00 | 48.00 | 48.00 | 48.00 |
| SAIB | 66.70 | 82.34 | 82.92 | 82.30 | 70.20 | 82.90 |
| TA | 44.46 | 54.89 | 55.27 | 54.90 | 50.10 | 55.30 |
| CAB | 9.60 | 12.48 | 15.36 | 12.50 | 13.40 | 15.40 |
| IPM | 27.20 | 30.72 | 30.72 | 30.70 | — | 30.70 |
| MIG | — | — | — | — | 38.40 | — |
| HEC | 0.00 | 5.76 | 0.00 | 5.80 | 11.50 | — |
| $SiO_2$ | 4.00 | 3.84 | 3.84 | 3.80 | 3.80 | 3.80 |
| BHT | 0.04 | 0.05 | 0.05 | 0.05 | 0.05 | 0.05 |
| GEL | 8.00 | 1.92 | 3.84 | 1.90 | 4.40 | 3.80 |
| Total | 200.00 | 240.00 | 240.00 | 240.00 | 240.00 | 240.00 |

The in vitro Abuse Resistance Evaluation used the following Test Capsules: three (n=3) each of formulations MPH1-MPH6.

The ethanol solution extraction study was carried out substantially the same as in Example 4a above, using the same apparatus, reagents and methods described above, with the following exceptions: the extraction solution was 60 mL of 80 proof ethanol (40%); and sampling was conducted at time=0.5 hr and 3 hours. The results of the extraction study are provided below in Table 64.

TABLE 64

| | Amount of Methylphenidate Extracted in 80 Proof Ethanol (% of dose) Time (hr.) | |
|---|---|---|
| | 0.5 | 3 |
| MPH1 | | |
| Mean | 18.4 | 63.0 |
| Std Dev. | 0.9 | 0.9 |
| MPH2 | | |
| Mean | 7.2 | 25.7 |
| Std Dev. | 0.5 | 1.7 |
| MPH3 | | |
| Mean | 6.1 | 22.9 |
| Std Dev. | 0.6 | 1.3 |
| MPH4 | | |
| Mean | 10 | 32 |
| Std Dev. | 1 | 3 |
| MPH5 | | |
| Mean | 10 | 40 |
| Std Dev. | 1 | 2 |
| MPH6 | | |
| Mean | 11 | 43 |
| Std Dev. | 2 | 4 |

Example 5: Analysis of Formulations (Formulation Viscosity Testing Procedures)

In order to assess the viscosity of formulations prepared in accordance with the present invention, the following viscosity tests were developed. Both standard and dynamic viscosity measurements may be obtained using these tests. The viscosity testing apparatus used in the methods described in this Example 5 are Brookfield Digital Rheometers. The two specific models used are the following: JPII, Model HBDV-III+CP with a programmable/digital Controller Model 9112; and JPI, Model LVDV-III+CP, with an Immersion Circulator Model 1122S. For both rheometer models the CPE Spindle 52 was used. For Dynamic Rheology, the dynamic rheology of the formulations can be measured using an Anton Paar Physica MCR301 rheometer (Anton Paar USA, Ashland, Va.) that is equipped with temperature and oscillatory strain control modules.

Sample formulations can be presented in two different formats for the viscosity testing methods, either as bulk formulation or as single dosage forms (e.g., gelatin capsules). For bulk formulation testing, 0.5 mL of the formulation is injected directly into the rheometer cup. When testing dosage forms, two gelatin capsules are needed for each measurement. The gelatin capsules are opened using a razor blade and a clean cutting surface. The contents are then squeezed out and placed in the rheometer cup.

Typical temperature conditions for the viscosity testing methods are 37° C. for most single point measurements, and 30° C., 40° C., 50° C., and 60° C. for temperature profiles. For each sample two different shear rates measured: $1^{st}$—low shear, an rpm setting is selected to provide a torque value between 10-15%; and $2^{nd}$—high shear, an rpm setting is selected to give a torque value between 20-90%

Data collection of the viscosity measurements is carried out using standard techniques. For example, the Brookfield Digital Rheometer data report screen automatically displays the rotational speed, spindle number, torque value (%), and the viscosity for manual recording.

Finally, complex viscosity of formulation samples can be measured using varying oscillatory strain in the linear viscoelastic regime. Here, the intrinsic complex viscosity of a sample formulation at rest can be obtained based on a mathematical curve fit of empirical data points. The advantage of the dynamic oscillatory experiment is that it probes the sample formulation material without destroying the material's microstructure.

Example 6: In Vitro/In Vivo Correlation (IVIVC) Analysis of Formulations

The concept of in vitro/in vivo correlation (IVIVC) determination for an oral extended (controlled, sustained) release dosage forms is a well-known tool used by pharmaceutical scientists, allowing for the prediction of expected bioavailability and other pharmacological performance characteristics from in vitro dissolution profile characteristics. Information and guidance regarding IVIVC determination can be found on the US FDA website and in other pharmacological reference sites. In order to assess and characterize the abuse-resistant dosage forms prepared in accordance with the present invention, the following IVIVC analyses were carried out.

Example 6a

The following IVIVC analysis was used to establish the correlation between the in vitro controlled release profile of candidate formulations obtained using the second dissolution method (Method 2) described above in Example 3 (that was optimized to assess the controlled release performance of the controlled release dosage forms of the present invention) and the in vivo blood concentration data obtained in the pharmacokinetic human clinical trails described herein below via developing a transformation function according to FDA Guideline for Extended Release (ER) dosage forms.

More particularly, a predictive mathematical model describing the relationship between the rate or extent of active agent dissolution observed in the in vitro dissolution testing described in Example 3 above, and the actual in vivo pharmacokinetic performance observed (measured plasma drug concentration or amount of active agent absorbed upon administration to human subjects, for example in Examples 7 and 8 below) was developed for an abuse-resistant oxycodone oral dosage form prepared in accordance with the present invention. In particular, the following raw materials were used to create formulations for use in the studies: Oxycodone base, micronized ("OXY"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); and Cellulose Acetate Butyrate, grade 381-20 BP, ethanol washed (Eastman Chemicals) ("CAB"). The formulations were filled into gel caps to provide suitable dosage forms (Test Capsules).

Ideally, plasma concentrations of oxycodone after administration of the Test Capsules would have been obtained in one crossover study in one panel of volunteers. However, as the data were obtained from different studies, all pharmacokinetic, deconvolution, and convolution analyses were done using the mean plasma concentration data from the respective studies. The Test Capsule in vitro data were fit to the Weibull function, $$\% \text{ Dissolved} = 100\% \times \left(1 - e^{-\left(\frac{t}{\tau}\right)^\beta}\right)$$

where $\tau$ is the time required for 62.5% of the dose to dissolve and $\beta$ is the slope parameter, which was the simplest model that was consistent with the dissolution for the extremes in data for slow and fast dissoluting lots.

The mean plasma concentration-time data were consistent with a two-compartment model with first-order absorption and elimination. The model was parameterized in terms of the absorption rate constant, K01, the elimination rate constant, K10, the distribution rate constants, K12 and K21, and the volume of the central compartment (Compartment 1), Vc/F, □ where F is the bioavailability.

The parameters are derived from the secondary parameters, with the parameters "A" and "B" normalized to dose. The mean oxycodone plasma concentration-time data for the Test Capsule lots were deconvoluted using the parameters estimated from the solution to obtain estimates of the in vivo release rates.

This analysis indicated that dissolution profiles for the Test Capsule lots that have a value of T in the Weibull function ranging from 6 to 14 h should provide equivalent in vivo plasma concentration-time profiles. Although the dissolution profile appears to slow over time, there is no apparent effect on in vivo bioavailability. In particular, the observed values of T in the Weibull function (taken over the course of more than a year) were 6.09±0.12; 10.1±0.08; 12.8±0.19; 11.6±0.11; and 14.1±0.21.

Example 6b

The following analysis was used to establish the correlation between the in vitro controlled release profile of d-amphetamine from candidate abuse-resistant formulations, and in vivo blood concentration data obtained in a pharmacokinetic human clinical trial described herein below, via developing a transformation between the cumulative percent of dose input into the systemic circulation in vivo (cumulative input) and the cumulative percent of dose released in vitro (cumulative release).

Given human plasma concentration-time profiles of d-amphetamine derived from oral dosing of abuse-resistant formulations prepared in accordance with the present invention, cumulative input profiles can be obtained through deconvolution. This necessitates having the unit impulse response function (UIR), which can be derived from a compartmental pharmacokinetic analysis of human concentration-time data following intravenous bolus dosing of d-amphetamine. Such data were obtained from the open literature:

$$\text{UIR} = (Ae^{+\alpha t} + Be^{-\beta t})/\text{Dose}_{iv}$$

where A=98.3±6.01, B=28.2±0.56, α=9.65±0.64, and β=6.31×10$^{-2}$±3.78×10$^{-3}$.

Deconvolution of the mean plasma profiles for three abuse-resistant amphetamine oral dosage forms was done in WinNonLin 5.2 (Pharsight Corp., Mountain View, Calif.) to give values of the cumulative percent of dose absorbed in vivo. Values of the cumulative percent of dose released in vitro were measured using the second dissolution method at the same times as the human concentration-time profiles. By plotting release in vitro against input in vivo, a transformation could be found by least squares fitting of cubic polynomials. For example, $$y = ax^3 - bx^2 + cx + d$$

where y is % release in vitro, x is % input in vivo, and a=2×10$^{-4}$, b=2.54×10$^{-2}$, c=1.53 and d=36. Other functional forms providing a good fit could be found. Having such a transformation, one can calculate the in vitro release profile required to produce a desired concentration-time profile in vivo.

In addition, by inverting the transformation, either analytically or numerically, one can calculate input in vivo from release in vitro, and then convolve the input with the UIR to predict the human concentration-time profile for d-amphetamine obtained from a particular in vitro release profile.

Example 7: In Vivo Analysis of Formulations (Human Clinical Trials, Pharmacokinetic Studies)

In order to assess the in vivo controlled release performance of abuse-resistant oxycodone oral dosage forms prepared in accordance with the present invention, the following human clinical trails were carried out. In all studies described below, plasma samples were analyzed for oxycodone, noroxycodone, and oxymorphone by CEDRA Corporation using a validated LC-MS-MS procedure. The method was validated for a range of 0.250 to 125 ng/mL for oxycodone, 0.500 to 250 ng/mL for noroxycodone and 0.0500 to 25.0 ng/mL for oxymorphone. Data were analyzed by noncompartmental methods in WinNonlin. Concentration-time data that were below the limit of quantification (BLQ) were treated as zero (0.00 ng/mL) in the data summarization and descriptive statistics. In the pharmacokinetic analyses, BLQ concentrations were treated as zero from time-zero up to the time at which the first quantifiable concentration was observed; embedded and/or terminal BLQ concentrations were treated as "missing".

The abuse-resistant oxycodone oral dosage forms used in the studies were prepared using the following raw materials: Oxycodone base, micronized ("OXY"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); and Cellulose Acetate Butyrate, grade 381-20 BP, ethanol washed (Eastman Chemicals) ("CAB"). The formulations were produced using the commercial-scale manufacturing methods (Process Schemes 4 or 5 as described above) and then filled into size 00 white opaque gel cap shells to produce 5, 10, 20, 30 and 40 mg dosage forms that were used as Test Capsules. The details of the formulations and the dosage forms containing the formulations used in the studies of Examples 7a-7f are disclosed below in Tables 65 and 66.

TABLE 65

| OXY (wt %) | SAIB (wt %) | TA (wt %) | CAB (wt %) | IPM (wt %) | HEC (wt %) | SiO$_2$ (wt %) | BHT (wt %) |
|---|---|---|---|---|---|---|---|
| 5.13 | 40.98 | 27.32 | 4.74 | 14.23 | 5.69 | 1.9 | 0.02 |

TABLE 66

| Capsule Strength | OXY (mg) | SAIB (mg) | TA (mg) | CAB (mg) | IPM (mg) | HEC (mg) | SiO$_2$ (mg) | BHT (mg) | Total (mg) |
|---|---|---|---|---|---|---|---|---|---|
| 5 mg | 5.0 | 40.0 | 26.6 | 4.6 | 13.9 | 5.5 | 1.8 | 0.02 | 97.5 |
| 10 mg | 10.0 | 79.9 | 53.3 | 9.2 | 27.7 | 11.1 | 3.7 | 0.04 | 195.0 |
| 20 mg | 20.0 | 159.8 | 106.5 | 18.5 | 55.5 | 22.2 | 7.4 | 0.08 | 390.0 |
| 30 mg | 30.0 | 239.7 | 159.8 | 27.8 | 83.2 | 33.3 | 11.1 | 0.12 | 585.0 |
| 40 mg | 40.0 | 319.6 | 213.1 | 37.0 | 111.0 | 44.4 | 14.8 | 0.16 | 780.0 |

Example 7a

The following human clinical trial study was a single-center, two-way crossover registration PK study to demonstrate the bioequivalence of two abuse-resistant oxycodone formulations prepared in accordance with the present invention and used for clinical trial supplies, that is, formulations produced using Process Scheme 4 method (see Example 2) versus formulations made using the Process Scheme 5 method (see Example 2). This study was conducted in 48 healthy adult male and female volunteers (fed state). The formulations were provided as 40 mg dosage form Test Capsules and prepared as discussed above. A single dose of each of the two formulations was administered separated by 96 hours. Subjects were administered naltrexone blockade to prevent opioid-related adverse events.

Mean linear plasma concentration-time curves of oxycodone in the study are shown in FIG. 19. The $C_{max}$ and $T_{max}$ values, based on mean oxycodone plasma concentration-time values, are presented below in Table 67, while the mean (SD) oxycodone PK parameters from noncompartmental analysis of individual data in the study are presented below in Table 68.

TABLE 67

| Parameter | Mfr. Process Scheme 4 (40 mg Oxycodone) | Mfr. Process Scheme 5 (40 mg Oxycodone) |
|---|---|---|
| $T_{max}$ (hr) | 4.67 | 4.67 |
| $C_{max}$ (ng/mL) | 39.7 | 37.5 |

TABLE 68

| | Mfr. Process Scheme 4 (40 mg Oxycodone) | | Mfr. Process Scheme 5 (40 mg Oxycodone) | |
|---|---|---|---|---|
| Parameter | Mean | (SD) | Mean | (SD) |
| $T_{max}$ (hr) | 5.34 | (2.19) | 5.76 | (2.72) |
| $C_{max}$ (ng/mL) | 46.4 | (14.4) | 45.0 | (17.8) |
| $AUC_{last}$ (hr * ng/mL) | 533.6 | (168.5) | 545.8 | (161.2) |
| $AUC_{inf}$ (hr * ng/mL) | 540.4 | (169.6) | 561.2 | (162.0) |

As can be seen from the data, a statistical analysis of the log-transformed $C_{max}$ and AUC parameters demonstrated that the formulations manufactured by Process Schemes 4 and 5 were bioequivalent.

Example 7b

Figure 21:
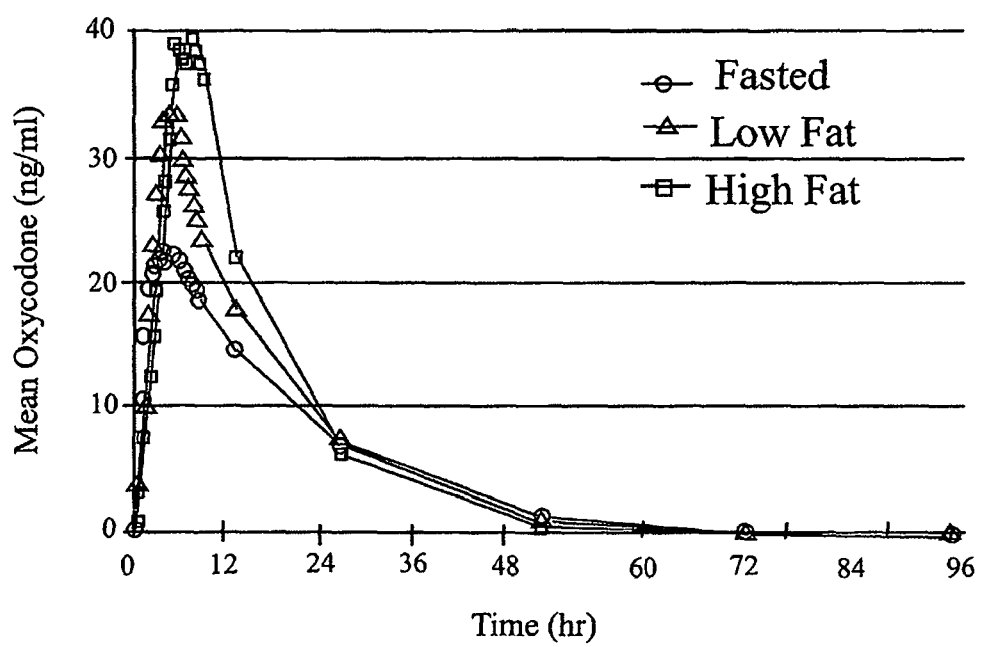
FIG. 21 depicts the mean linear plasma concentration-time curves of active agent in the clinical trial study described in Example 7b.

This next human clinical trial study was a single-center, three-way crossover, food effect, PK study to determine the rate and extent of absorption of 40 mg oxycodone base in abuse-resistant oral dosage forms when administered in a fasted state, after consumption of a low fat meal, and after consumption of a high fat meal. This study was conducted in 48 healthy, adult male and female volunteers. Subjects were administered naltrexone blockade to prevent opioid-related adverse events. Forty-six subjects received all three doses of study dosage forms. Mean linear and semi-logarithmic oxycodone plasma concentration-time curves from the study are shown in FIG. 21.

The $C_{max}$ and $T_{max}$ values, based on mean oxycodone plasma concentration-time values, are presented below in Table 69, and mean oxycodone PK parameters from noncompartmental analysis of individual data in the study are presented below in Table 70.

TABLE 69

| Parameter | 40 mg OXY (Fasted) | 40 mg OXY (Low Fat Breakfast) | 40 mg OXY (High Fat Breakfast) |
|---|---|---|---|
| $T_{max}$ (hr) | 3.33 | 4.67 | 6.50 |
| $C_{max}$ (ng/mL) | 22.2 | 33.5 | 38.6 |

TABLE 70

| | 40 mg OXY (Fasted) | | 40 mg OXY (Low Fat Breakfast) | | 40 mg OXY (High Fat Breakfast) | |
|---|---|---|---|---|---|---|
| Parameter | Mean | (SD) | Mean | (SD) | Mean | (SD) |
| $T_{max}$ (hr) | 3.99 | (1.80) | 4.10 | (1.24) | 5.72 | (2.03) |
| $C_{max}$ (ng/mL) | 25.8 | (10.3) | 38.7 | (16.2) | 50.6 | (24.4) |
| $AUC_{0-t}$ (hr*ng/mL) | 429.3 | (162.1) | 499.0 | (173.0) | 549.0 | (178.9) |
| $AUC_{inf}$ (hr*ng/mL) | 515.5 | (129.6) | 545.2 | (170.2) | 602.1 | (148.9) |

Log-transformed parameters were calculated for maximum exposure ($C_{max}$) and total exposure ($AUC_{last}$ and $AUC_{inf}$) and used in the statistical analysis. The 90% confidence intervals for the treatment ratios (test-to-reference) of the three parameters using the log-transformed data and the two one-sided t-tests procedure indicated that oxycodone exposure parameters for either low fat or high fat fed conditions were not within the 80-125% limits of the fasted condition. Therefore, food has a significant effect on both the rate and extent of absorption of oxycodone from the study abuse-resistant oral dosage forms; oral bioavailability is increased under fed conditions relative to administration of dosage forms in the fasted state. There was no significant difference in the extent of exposure resulting from either the low or high fed breakfast.

Example 7c

Figure 22:
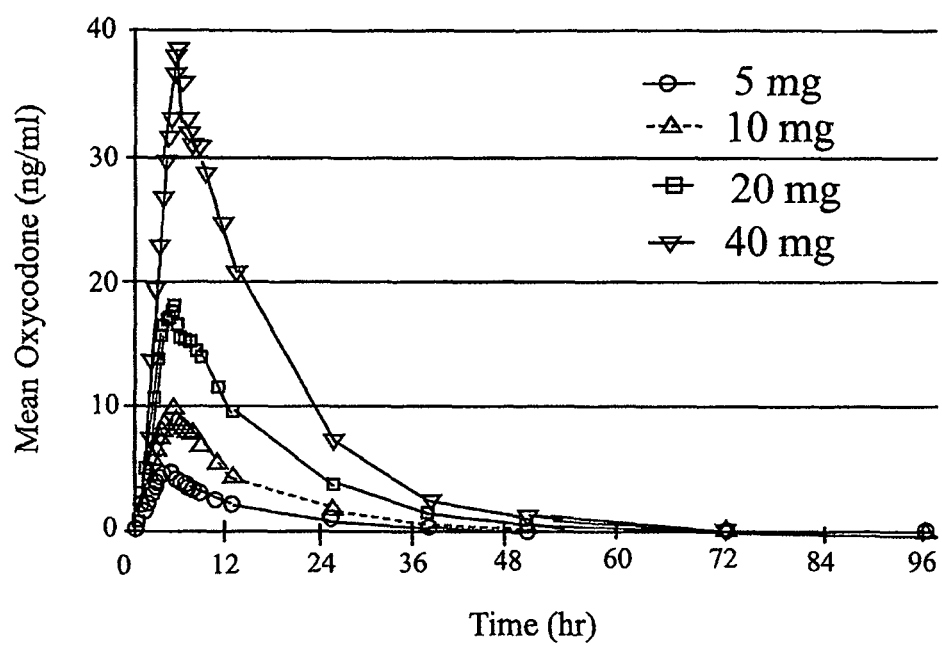
FIG. 22 shows the mean linear plasma concentration-time curves of active agent in the clinical trial study described in Example 7c.
Figure 23:
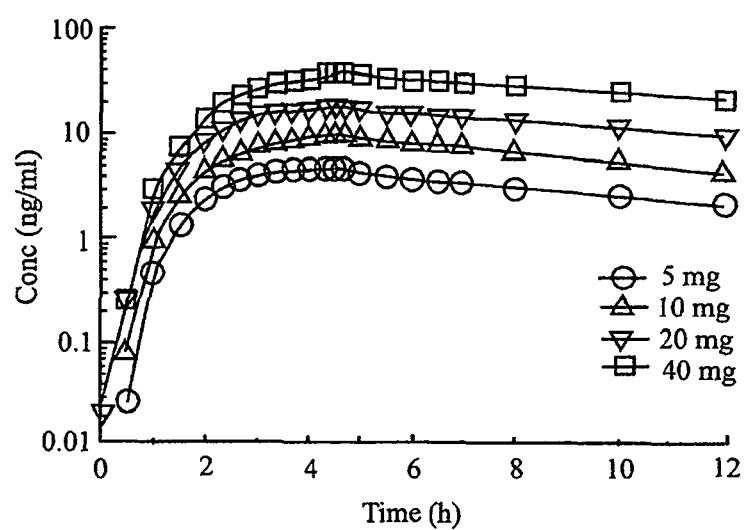
FIG. 23 shows the results from the dose proportionality test of Test Capsules containing oxycodone at dosage strengths 5, 10, 20 and 40 mg as obtained in the clinical trial study described in Example 7c.

The following human clinical trial study was a single-center, four-way crossover PK study to demonstrate the dose proportionality of 5, 10, 20, and 40 mg abuse-resistant oral dosage forms produced according to the present invention and administered under single dose conditions. This study was conducted in 48 healthy adult male and female volunteers (fed state). Subjects were administered naltrexone blockade to prevent opioid-related adverse events. Forty-six subjects received all four doses of study dosage forms. The mean linear and semi-logarithmic oxycodone plasma concentration-time curves obtained in the study are shown in FIG. 22. The $C_{max}$ and $T_{max}$ values from this Example 7c study, based on mean oxycodone plasma concentration-time values, are presented below in Table 71. The mean oxycodone PK parameters from noncompartmental analysis of individual data in this Example 7c study are presented in Table 72 and depicted in FIG. 23. As can be seen, the statistical analysis indicated the study dosage forms are dose proportional over the entire range of doses.

TABLE 71

| Parameter | 5 mg OXY | 10 mg OXY | 20 mg OXY | 40 mg OXY |
|---|---|---|---|---|
| $T_{max}$ (hr) | 4.33 | 4.67 | 4.50 | 4.67 |
| $C_{max}$ (ng/mL) | 4.60 | 9.59 | 18.2 | 39.0 |

TABLE 72

| Parameter | 5 mg OXY | | 10 mg OXY | | 20 mg OXY | | 40 mg OXY | |
|---|---|---|---|---|---|---|---|---|
| | Mean | (SD) | Mean | (SD) | Mean | (SD) | Mean | (SD) |
| $T_{max}$ (hr) | 3.92 | (1.08) | 4.06 | (1.09) | 5.11 | (2.08) | 5.49 | (2.55) |
| $C_{max}$ (ng/mL) | 5.16 | (1.45) | 10.9 | (4.17) | 21.3 | (8.45) | 47.5 | (23.7) |
| $AUC_{last}$ (hr*ng/mL) | 58.90 | (17.09) | 125.4 | (38.82) | 264.3 | (75.58) | 546.4 | (166.4) |
| $AUC_{inf}$ (hr*ng/mL) | 74.19 | (15.78) | 143.0 | (38.04) | 292.5 | (72.58) | 577.9 | (162.3) |

Example 7d

The following human clinical trial study was a single-center, steady state PK study in which subjects received 30 minutes after the start of a standardized breakfast study abuse-resistant oral dosage forms (Test Capsules containing oxycodone free base, 40 mg, "OXY") BID for 5 days. Subjects were administered naltrexone blockade to prevent opioid-related adverse events. Thirty-six subjects were enrolled in this study, 22 males and 14 females. Two females and one male did not complete the study; 33 subjects were enrolled in the PK analysis.

The $C_{max}$ and $T_{max}$ values from this Example 7d study, based on mean oxycodone plasma concentration-time values, are presented below in Table 73 and mean oxycodone PK parameters from noncompartmental analysis of individual data in this study are presented below in Table 74.

TABLE 73

| Parameter | Day 1 | Day 5 |
|---|---|---|
| $T_{max}$ (hr) | 4.75 | 4.50 |
| $C_{max}$ ng/mL) | 38.5 | 58.7 |

TABLE 74

| | Day 1 OXY Capsules, 40 mg | | | | Day 5 OXY Capsules, 40 mg | | | |
|---|---|---|---|---|---|---|---|---|
| Parameter | n | Mean | SD | CV % | n | Mean | SD | CV % |
| $T_{max}$ (hr) | 33 | 5.51 | 2.11 | 38.29 | 33 | 4.34 | 1.47 | 33.79 |
| $C_{max}$ (ng/mL) | 33 | 44.6 | 17.8 | 39.90 | 33 | 64.4 | 26.3 | 40.77 |

TABLE 74-continued

| | Day 1 OXY Capsules, 40 mg | | | | Day 5 OXY Capsules, 40 mg | | | |
|---|---|---|---|---|---|---|---|---|
| Parameter | n | Mean | SD | CV % | n | Mean | SD | CV % |
| $T_{min}$ (hr) | . | . | . | . | 33 | 9.15 | 4.98 | 54.43 |
| $C_{min}$ (ng/mL) | . | . | . | . | 33 | 25.6 | 7.10 | 27.71 |
| $AUC_{0-\tau}$ (hr*ng/mL) | . | . | . | . | 33 | 510.2 | 156.6 | 30.70 |
| $AUC_{0-12}$ (hr*ng/mL) | 33 | 307.9 | 108.8 | 35.35 | . | . | . | . |
| $AUC_{0-24}$ (hr*ng/mL) | . | . | . | . | 33 | 738.5 | 212.1 | 28.72 |
| $AUC_{0-36}$ (hr*ng/mL) | . | . | . | . | 32 | 833.4 | 234.0 | 28.07 |
| $AUC_{0-48}$ (hr*ng/mL) | . | . | . | . | 32 | 868.1 | 240.9 | 27.75 |
| $AUC_{last}$ (hr*ng/mL) | 33 | 307.9 | 108.9 | 35.36 | 33 | 887.2 | 261.0 | 29.42 |
| $AUC_{inf}$ (hr*ng/mL) | . | . | . | . | 30 | 908.5 | 256.7 | 28.26 |
| $AUC_{Extrap}$ (%) | . | . | . | . | 30 | 1.41 | 1.75 | 124.47 |
| $\lambda_z$ (hr$^{-1}$) | . | . | . | . | 30 | 0.0790 | 0.0368 | 46.56 |
| $T_{1/2}$ (hr) | . | . | . | . | 30 | 11.28 | 6.27 | 55.56 |
| $T_{last}$ (hr) | 33 | 12.00 | 0.02 | 0.13 | 33 | 68.73 | 30.04 | 43.71 |
| $C_{last}$ (ng/mL) | 33 | 20.0 | 5.31 | 26.61 | 33 | 0.821 | 0.641 | 78.15 |
| Fluctuation (%) | . | . | . | . | 33 | 87.91 | 33.30 | 37.88 |
| Accumulation[1] | . | . | . | . | 33 | 1.75 | 0.48 | 27.55 |

Note:
Full precision data used in pharmacokinetic analysis.
[1] Accumulation = $AUC_{0-\tau}$ (Day 5)/$AUC_{0-12}$ (Day 1).

In this study, a significant gender effect was observed for $C_{max}$ and $T_{max}$ of oxycodone at steady state. However, a small number of females completed the study relative to the number of males that completed the study. An ANOVA found that the power for the study was low. A replacement steady state study is thus described below in Example 7e. Based upon a comparison of the trough (pre-dose) plasma concentrations after the first dose of the study dosage forms on Study Days 1, 2, 3, 4, and 5, steady-state concentrations of oxycodone were, on average, achieved on Day 2. After the administration of the 40 mg study dosage forms every 12 hours for five consecutive days, there was a significant increase in peak and overall systemic exposure to oxycodone, noroxycodone, and oxymorphone relative to exposure after the first dose. Based on log-transformed $AUC_{0-12}$ values in the current study, percent ratios (Day 5/Day 1) were 168.46% for oxycodone, 306.24% for noroxycodone, and 192.33% for oxymorphone. Based on $AUC_{0-\tau}$ (Day 5)/$AUC_{0-12}$ (Day 1) ratios for individual subjects, there is a 1.75-fold increase in oxycodone exposure during a dosing regiment of the 40 mg study dosage forms every 12 hours over 5 consecutive days. The accumulation ratios for noroxycodone and oxymorphone are 3.22 and 2.00, respectively.

Example 7e

The following human clinical study was a single-center, steady state PK study in which subjects received the study abuse-resistant oral dosage forms (capsules containing oxycodone free base, 30 mg, "OXY Test Capsules" or OXY) administered BID. Subjects were administered naltrexone blockade to prevent opioid-related adverse events. In addition, subjects received a meal prior to each dose of the study Test Capsules (OXY). 48 subjects were enrolled in this study, 28 males and 20 females. Three subjects did not complete the study and three other subjects experienced emesis; with the final result being that 42 subjects completed the PK analysis (25 males and 17 females).

The $C_{max}$ and $T_{max}$ values from subjects (pooled male and female) receiving the Test Capsules (OXY), based on mean oxycodone plasma concentration-time values, are presented below in Table 75 and mean oxycodone PK parameters from noncompartmental analysis of individual data are presented below in Table 76.

TABLE 75

| Parameter | Day 1 | Day 5 | Day 5 (Male) | Day 5 (Female) |
|---|---|---|---|---|
| $T_{max}$ (hr) | 4.50 | 4.75 | 4.75 | 4.75 |
| $C_{max}$ (ng/mL) | 27.2 | 43.9 | 39.0 | 51.1 |

TABLE 76

| | Day 1 OXY Test Capsules | | | | Day 5 OXY Test Capsules | | | |
|---|---|---|---|---|---|---|---|---|
| Parameter | n | Mean | SD | CV % | n | Mean | SD | CV % |
| $T_{max}$ (hr) | 42 | 5.04 | 1.69 | 33.44 | 42 | 4.11 | 1.22 | 29.61 |
| $C_{max}$ (ng/mL) | 42 | 31.6 | 11.3 | 35.89 | 42 | 49.6 | 17.8 | 35.96 |
| $C_{min}$ (ng/mL) | . | . | . | . | 42 | 19.2 | 7.37 | 38.36 |
| $AUC_{0-\tau}$ (hr*ng/mL) | 42 | 218.2 | 63.91 | 29.9 | 42 | 378.7 | 116.0 | 30.62 |
| $AUC_{0-12}$ (hr*ng/mL) | 42 | 218.2 | 63.91 | 29.9 | 42 | 378.7 | 116.0 | 30.62 |
| $AUC_{last}$ (hr*ng/mL) | . | . | . | . | 42 | 661.9 | 222.8 | 33.66 |
| $AUC_{inf}$ (hr*ng/mL) | . | . | . | . | 39 | 686.3 | 223.0 | 32.49 |
| $T_{1/2}$ (hr) | . | . | . | . | 39 | 12.37 | 9.35 | 75.64 |
| $C_{last}$ (ng/mL) | 42 | 15.7 | 6.09 | 38.78 | 42 | 0.650 | 0.422 | 65.00 |
| Fluctuation (%) | . | . | . | . | 42 | 97.21 | 31.95 | 32.87 |

Based upon a comparison of the trough (pre-dose) plasma concentrations after the first dose of the study Test Capsules on Study Days 1, 2, 3, 4, and 5, steady-state concentrations of oxycodone were, on average, achieved on Day 2. After the administration of the 30 mg Test Capsules every 12 hours for five consecutive days, there was a significant increase in peak and overall systemic exposure to oxycodone, noroxycodone, and oxymorphone relative to exposure after the first dose.

As a further analysis, an investigation into a possible effect of gender on the pharmacokinetic profile of the Test Capsules following a single dose of the Test Capsules, and a steady-state multiple dosing regimen of the Test Capsules administered BID for 5 days. The pharmacokinetic parameters of oxycodone after a single dose of the Test Capsules are reported below in Table 77, and the pharmacokinetic parameters of oxycodone on day 5 after multiple dose administration of the Test Capsules are reported below in Table 78. The mean data for the male and female test groups from this gender analysis are reported above in Table 75.

TABLE 77

| Parameter | Day 1 Male OXY Test Capsules | | | | Day 1 Female OXY Test Capsules | | | |
|---|---|---|---|---|---|---|---|---|
| | n | Mean | SD | CV % | n | Mean | SD | CV % |
| $T_{max}$ (hr) | 25 | 4.87 | 1.85 | 38.02 | 17 | 5.30 | 1.43 | 26.89 |
| $C_{max}$ (ng/mL) | 25 | 26.8 | 8.63 | 32.18 | 17 | 38.6 | 11.4 | 29.61 |
| $AUC_{0-\tau}$ (hr*ng/mL) | 25 | 196.0 | 56.27 | 28.71 | 17 | 250.9 | 61.75 | 24.61 |
| $AUC_{last}$ (hr*ng/mL) | 25 | 196.0 | 56.27 | 28.71 | 17 | 251.0 | 61.70 | 24.58 |
| $C_{last}$ (ng/mL) | 25 | 14.2 | 5.36 | 37.62 | 17 | 17.9 | 6.61 | 36.96 |

TABLE 78

| Parameter | Day 5 Male OXY Test Capsules | | | | Day 5 Female OXY Test Capsules | | | |
|---|---|---|---|---|---|---|---|---|
| | n | Mean | SD | CV % | n | Mean | SD | CV % |
| $T_{max}$ (hr) | 25 | 4.01 | 1.26 | 31.30 | 17 | 4.25 | 1.18 | 27.75 |
| $C_{max}$ (ng/mL) | 25 | 44.3 | 12.8 | 28.82 | 17 | 57.5 | 21.5 | 37.38 |
| $AUC_{0-\tau}$ (hr * ng/mL) | 25 | 358.0 | 101.6 | 28.38 | 17 | 409.3 | 131.6 | 32.15 |
| $AUC_{last}$ (hr * ng/mL) | 25 | 636.0 | 206.9 | 32.50 | 17 | 698.9 | 246.0 | 35.19 |
| $AUC_{inf}$ (hr * ng/mL) | 23 | 664.4 | 204.6 | 30.79 | 16 | 717.8 | 250.6 | 34.91 |
| $C_{min}$ (ng/mL) | 25 | 18.6 | 7.14 | 38.31 | 17 | 20.1 | 7.84 | 39.08 |
| Fluctuation (%) | 25 | 87.80 | 25.56 | 29.12 | 17 | 111.05 | 35.97 | 32.39 |

As can be seen by these gender results, peak oxycodone concentrations for males were lower and occurred at earlier times relative to the maximum oxycodone concentrations for females. The higher oxycodone plasma concentrations observed for females were also reflected in the AUC values.

Example 7f

The following human clinical study was a multicenter, randomized, double-blind, placebo-controlled, phase III study in patients with moderate to severe chronic pain due to osteoarthritis of the hip or knee. The study evaluated the efficacy and safety of abuse-resistant oral dosage forms (capsules containing oxycodone base and prepared according to the present invention) relative to placebo over a 12-week double-blind treatment period.

The study abuse-resistant oral dosage forms used in the studies were prepared using the following raw materials: Oxycodone base, micronized ("OXY"); Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAM"); Triacetin USP ("TA"); and Cellulose Acetate Butyrate, grade 381-20 BP, ethanol washed (Eastman Chemicals) ("CAB"). The formulations were produced using the commercial-scale manufacturing methods (Process Schemes 4 or 5 as described above) and then filled into size 00 white opaque gel cap shells to produce 5, 10, 20, 30 and 40 mg dosage forms that were used as Test Capsules. The details of the formulations of this Example 7f are disclosed below in Tables 79 and 80.

TABLE 79

| OXY (wt %) | SAIB (wt %) | TA (wt %) | CAB (wt %) | IPM (wt %) | HEC (wt %) | $SiO_2$ (wt %) | BHT (wt %) |
|---|---|---|---|---|---|---|---|
| 5.13 | 40.98 | 27.32 | 4.74 | 14.23 | 5.69 | 1.9 | 0.02 |

TABLE 80

| Capsule Strength | OXY (mg) | SAIB (mg) | TA (mg) | CAB (mg) | IPM (mg) | HEC (mg) | $SiO_2$ (mg) | BHT (mg) | Total (mg) |
|---|---|---|---|---|---|---|---|---|---|
| 5 mg | 5.0 | 40.0 | 26.6 | 4.6 | 13.9 | 5.5 | 1.8 | 0.02 | 97.5 |
| 10 mg | 10.0 | 79.9 | 53.3 | 9.2 | 27.7 | 11.1 | 3.7 | 0.04 | 195.0 |
| 20 mg | 20.0 | 159.8 | 106.5 | 18.5 | 55.5 | 22.2 | 7.4 | 0.08 | 390.0 |
| 30 mg | 30.0 | 239.7 | 159.8 | 27.8 | 83.2 | 33.3 | 11.1 | 0.12 | 585.0 |
| 40 mg | 40.0 | 319.6 | 213.1 | 37.0 | 111.0 | 44.4 | 14.8 | 0.16 | 780.0 |

For the study, patients meeting eligibility criteria entered a 2-week open-label titration phase in which all patients were administered the study abuse-resistant oral dosage form 5 mg BID titrated up to 20 mg BID. Patients able to tolerate the study abuse-resistant oral dosage form 20 mg BID were randomized in a 1:1 ratio to receive the study abuse-resistant oral dosage form BID or placebo BID. A total of 558 patients were enrolled into the open-label titration phase of the study and a total of 412 patients were randomized. Dose adjustments were allowed during the first four weeks of the double-blind treatment period.

A patient entered the two week open-label titration period if the mean value of the diary pain intensity score (PI) over the last 2 days of the washout period (Baseline PI) is 5; if IVRS diary compliance was 75%; and, if the patient continued to meet all inclusion/exclusion criteria. Patients were titrated from the study abuse-resistant oral dosage form 5 mg BID to 20 mg BID over these 2 weeks.

At the end of the open-label titration period, a patient was enrolled in the double-blind placebo-controlled study if the patient was able to tolerate the study abuse-resistant oral dosage form 20 mg BID (no unacceptable adverse events) and if IVRS diary compliance was ≥75%. A total of 412 patients were randomized in a 1:1 ratio to receive the study abuse-resistant oral dosage form BID or placebo. Randomization was stratified by both baseline PI (<7.5 vs. ≥7.5) and by the average PI over the last 2 days of the open-label titration period (<5 vs. ≥5). The patients were thus divided into two groups as follows: Group A, 200 patients received the study abuse-resistant oral dosage form BID in a double-blind treatment period of 12 weeks; and Group B, 200 patients received placebo BID in a double-blind treatment period of 12 weeks. During the first four weeks of the double-blind treatment period, patients were titrated (up or down) to analgesic effect. At the conclusion of four weeks, the dose was fixed for an additional 8 weeks.

The primary endpoint for the clinical trial of this Example 7f was a decrease in pain intensity (AUC) between the study abuse-resistant oral dosage forms (Test Capsules) dosed BID and Placebo dosed BID during the twelve week treatment period. Subjects that received Test Capsules BID demonstrated a statistically significant decrease in their pain intensity-AUC as compared to the subjects that received Placebo BID and thus the study met its primary endpoint that was prospectively defined (p=0.007). The primary endpoint results (Pain Intensity-AUC for the 12 week double-blind period for the analysis population:intent to treat population are reported below in Table 81.

TABLE 81

|  | PLACEBO BID (N = 207) | TEST CAPSULES BID (N = 203) | TOTAL (N = 410) |
| --- | --- | --- | --- |
| AREA UNDER CURVE (AUC) |  |  |  |
| MEAN (SD) | −30.4(140.38) | −54.9(122.44) | −42.5(132.21) |
| MEDIAN | −1.5 | −27.1 | −9.8 |
| MINIMUM, MAXIMUM | −501.8, 370.7 | −683.3, 382.8 | −683.3, 382.8 |
| N | 205 | 201 | 406 |
| MODEL P-VALUES |  |  |  |
| TREATMENT [1] | 0.007 |  |  |
| PRE-RANDOMIZATION PI [1] | <0.001 |  |  |

With regard to the above-noted results in Table 81, the Intent to Treat Population were all randomized patients who took any study medicament and have at least one post-randomization Pain Intensity measurement. In addition, the Area Under the Curve (AUC) was calculated by the Linear Trapezodial Method using change from pre-randomization pain intensity scores. The p-values reported above were from ANCOVA Model including treatment as the main effect and pre-randomization pain intensity as a covariate.

Secondary endpoints for the clinical trial included: pain intensity (change in pain intensity by week), quality of analgesia, global assessment, Short Form 12 Question Health Survey (SF-12) and Western Ontario and MacMaster Universities Osteoarthritis Index (WOMAC). For the pain intensity results, the group that received the Test Capsules BID had consistently lower pain intensity scores at each week during the twelve-week clinical trial as compared to the group that received the Placebo BID (p=0.024 at week twelve). For quality of analgesia, the group that received Test Capsules BID showed a consistent and greater improvement in the quality of analgesia at each week during the twelve-week clinical trial as compared to the group that received the Placebo BID (p=0.004 at week twelve). For global assessment, the group that received Test Capsules BID showed a consistently better global assessment at each week during the twelve week clinical trial as compared to the group that received the Placebo BID (p=0.007 at week twelve). For SF-12, the group that received Test Capsules BID had a higher value for the physical component score of the SF-12 (p=0.003 at week twelve) and for the mental component score of the SF-12 (p=0.055 at week twelve) as compared to the group administered Placebo BID, wherein higher values correspond to better health or functioning. For the stiffness and physical function subscales of the WOMAC, although the values were lower in the group administered Test Capsules BID as compared to the group administered Placebo BID, as expected, the differences were not significant (stiffness subscale p=0.366 at week twelve and physical function subscale p=0.221 at week twelve). For the pain subscale of the WOMAC, the values (% change from baseline to week twelve) were significantly lower in the group administered Test Capsules BID as compared to the group administered Placebo BID (p=0.023 at week twelve), wherein lower values correspond to better health or functioning. No drug-related safety issues were noted in this study.

Example 7g

This human clinical trial study was a single-center, randomized, open-label, phase I study to assess the safety and pharmacokinetics of three different high-dose (80 mg strength) abuse-resistant oxycodone formulations, and to assess the performance of these against two lower strength (40 mg) abuse-resistant oxycodone dosage forms that used in the studies of Examples 7a-7f above (collectively, the OXY Test Capsules).

The abuse-resistant oxycodone oral dosage forms used in this Example 7g were prepared using the following raw materials: Oxycodone base, micronized ("OXY"); Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Sodium Lauryl Sulfate ("SLS"); Labrafil M2125 CS ("LAB"); and Cellulose Acetate Butyrate, grade 381-20 BP, ethanol washed (Eastman Chemicals) ("CAB"). The formulations were produced using the commercial-scale manufacturing methods (Process Schemes 4 or 5 as described above) and then filled into size #00 hard gelatin cap shells to produce 80 mg dosage forms that were used as Test Capsules. The details of the formulations are disclosed below in Table 82.

TABLE 82

|  | OXY | SAIB | TA | CAB | IPM | HEC | $SiO_2$ | BHT | SLS | LAB | (Total) |
| --- | --- | --- | --- | --- | --- | --- | --- | --- | --- | --- | --- |
| OXY1 | 80.0 | 281.4 | 208.4 | 42.0 | 112.0 | 42.0 | 14.0 | 0.2 | — | — | 780 (mg) |
|  | 10.26 | 36.08 | 26.72 | 5.38 | 14.36 | 5.38 | 1.79 | 0.02 | — | — | (wt %) |

TABLE 82-continued

|  | OXY | SAIB | TA | CAB | IPM | HEC | SiO$_2$ | BHT | SLS | LAB | (Total) |  |
|---|---|---|---|---|---|---|---|---|---|---|---|---|
| OXY2 | 80.0 | 297.5 | 198.4 | 42.0 | 105.0 | 42.0 | 14.0 | 0.2 | 1.0 | — | 780 | (mg) |
|  | 10.26 | 38.14 | 25.43 | 5.38 | 13.46 | 5.38 | 1.79 | 0.02 | 0.13 | — |  | (wt %) |
| OXY3 | 80.0 | 285.5 | 190.3 | 42.0 | 105.0 | 42.0 | 14.0 | 0.2 | — | 21.0 | 780 | (mg) |
|  | 10.26 | 36.60 | 24.40 | 5.38 | 13.46 | 5.38 | 1.79 | 0.02 | — | 2.69 |  | (wt %) |
| OXY10 | 40.0 | 319.6 | 213.1 | 37.0 | 111.0 | 44.4 | 14.8 | 0.16 | — | — | 780 | (mg) |
|  | 5.13 | 40.98 | 27.32 | 4.74 | 14.23 | 5.69 | 1.9 | 0.02 | — | — |  | (wt %) |

All four treatments received dosing after an overnight fast of at least 10 hours, followed by thirty minutes after the start of a standard breakfast (8 ounces orange juice, two fried eggs, and two slices of toast with butter and preserve). Dosing days were separated by a washout period of 3 days. All subjects were administered naltrexone blockade to prevent opioid-related adverse events. Sixteen (16) healthy male subjects enrolled in the study, and 15 completed the four treatment periods of the study. Plasma samples were analyzed for oxycodone using a validated LC-MS-MS procedure.

The results of a pharmacokinetic analysis of the study results from this Example 7g are presented below in Table 83. In addition, the oral bioavailability of oxycodone for the three 80 mg OXY Test Capsules relative to the 2×40 mg Test Capsules is presented in Table 84 below.

TABLE 83

| Parameter | OXY1 Test Capsules | OXY2 Test Capsules | OXY3 Test Capsules | OXY10 Test Capsules (2 × 40 mg) |
|---|---|---|---|---|
| $T_{max}$ (hr) | 4.66 ± 1.67 | 4.68 ± 1.16 | 4.35 ± 1.80 | 4.38 ± 1.04 |
| $C_{max}$ (ng/mL) | 61.7 ± 17.3 | 47.5 ± 13.5 | 52.7 ± 27.9 | 87.4 ± 28.8 |
| $AUC_{last}$ (hr * ng/mL) | 903.6 ± 242.6 | 838.3 ± 220.2 | 834.7 ± 331.5 | 1001 ± 213.8 |
| $AUC_{inf}$ (hr * ng/mL) | 905.5 ± 245.5 | 855.3 ± 218.7 | 872.6 ± 343.1 | 1028 ± 216.3 |

TABLE 84

| Treatment | $C_{max}$ Ratio (%) | $AUC_{last}$ Ratio (%) | $AUC_{inf}$ Ratio (%) |
|---|---|---|---|
| OXB1 vs. OXB10 (2 × 40 mg) | 70.59 | 90.27 | 88.08 |
| OXB2 vs. OXB10 (2 × 40 mg) | 54.35 | 83.75 | 83.20 |
| OXB3 vs. OXB10 (2 × 40 mg) | 60.30 | 83.39 | 84.88 |

As can be seen by these results, the pharmacokinetic profiles for the three different high-strength Test Capsule formulations (OXY1-OXY3) were comparable with peak oxycodone concentrations observed at 4.35 to 4.68 hours. The mean $C_{max}$ values for the three high-strength Test Capsule formulations were 29% to 46% lower than the mean $C_{max}$ after administration of the 2×40 mg Test Capsule (OXY10). Likewise, overall systemic exposure to oxycodone after administration of the three 80 mg Test Capsule formulations (OXY1-OXY3) was lower (10% to 17%) than after administration of the 2×40 mg Test Capsule (OXY10). Finally, the relative bioavailability based upon the $AUC_{last}$ of the three 80 mg Test Capsule formulations (OXY1-OXY3) was very good (>80%), ranging from 83.39% to 90.27%.

Example 7h

This human clinical trial study was a single-center, randomized, open-label, phase I study to assess the safety and pharmacokinetics of three different high-dose (80 mg strength) abuse-resistant oxycodone formulations, and to assess the performance of these against two lower strength (40 mg) abuse-resistant oxycodone dosage forms that used in the studies of Examples 7a-7f above (collectively, the OXY Test Capsules).

The abuse-resistant oxycodone oral dosage forms used in this Example 7h were prepared using the following raw materials: Oxycodone base, micronized ("OXY"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Sodium Lauryl Sulfate ("SLS"); Labrafil M2125 CS ("LAB"); and Cellulose Acetate Butyrate, grade 381-20 BP, ethanol washed (Eastman Chemicals) ("CAB"). The formulations were produced using the commercial-scale manufacturing methods (Process Schemes 4 or 5 as described above) and then filled into size #00 hard gelatin cap shells to produce 80 mg dosage forms that were used as Test Capsules. The details of the formulations are disclosed below in Table 85.

TABLE 85

|  | OXY | SAIB | TA | CAB | IPM | HEC | SiO$_2$ | BHT | SLS | LAB | (Total) |  |
|---|---|---|---|---|---|---|---|---|---|---|---|---|
| OXY4 | 80.0 | 280.4 | 207.7 | 36.7 | 119.0 | 42.0 | 14.0 | 0.2 | — | — | 780 | (mg) |
|  | 10.26 | 35.95 | 26.63 | 4.71 | 15.26 | 5.38 | 1.79 | 0.02 | — | — |  | (wt %) |
| OXY5 | 80.0 | 281.0 | 200.8 | 42.0 | 119.0 | 42.0 | 14.0 | 0.2 | 1.0 | — | 780 | (mg) |
|  | 10.26 | 36.03 | 25.74 | 5.38 | 15.26 | 5.38 | 1.79 | 0.02 | 0.13 | — |  | (wt %) |
| OXY6 | 80.0 | 286.6 | 191.0 | 36.7 | 112.0 | 42.0 | 14.0 | 0.2 | — | 17.5 | 780 | (mg) |
|  | 10.26 | 36.74 | 24.49 | 4.71 | 14.36 | 5.38 | 1.79 | 0.02 | — | 2.24 |  | (wt %) |

TABLE 85-continued

| | OXY | SAIB | TA | CAB | IPM | HEC | SiO$_2$ | BHT | SLS | LAB | (Total) | |
|---|---|---|---|---|---|---|---|---|---|---|---|---|
| OXY10 | 40.0 | 319.6 | 213.1 | 37.0 | 111.0 | 44.4 | 14.8 | 0.16 | — | — | 780 | (mg) |
| | 5.13 | 40.98 | 27.32 | 4.74 | 14.23 | 5.69 | 1.9 | 0.02 | — | — | | (wt %) |

All four treatments received dosing after an overnight fast of at least 10 hours, followed by thirty minutes after the start of a standard breakfast (8 ounces orange juice, two fried eggs, and two slices of toast with butter and preserve). Dosing days were separated by a washout period of 3 days. All subjects were administered naltrexone blockade to prevent opioid-related adverse events. Sixteen (16) healthy male subjects enrolled in the study, and completed the four treatment periods of the study. Plasma samples were analyzed for oxycodone using a validated LC-MS-MS procedure.

The results of a pharmacokinetic analysis of the study results from this Example 7h are presented below in Table 86. In addition, the oral bioavailability of oxycodone for the three 80 mg OXY Test Capsules relative to the 2×40 mg Test Capsules is presented in Table 87 below.

TABLE 86

| Parameter | OXY4 Test Capsules | OXY5 Test Capsules | OXY6 Test Capsules | OXY10 Test Capsules (2 × 40 mg) |
|---|---|---|---|---|
| $T_{max}$ (hr) | 4.44 ± 1.72 | 4.47 ± 2.38 | 4.55 ± 1.52 | 4.22 ± 1.16 |
| $C_{max}$ (ng/mL) | 75.5 ± 28.7 | 65.7 ± 27.7 | 69.9 ± 20.8 | 91.0 ± 30.5 |
| $AUC_{last}$ (hr * ng/mL) | 1020 ± 340.9 | 954.0 ± 315.0 | 1023 ± 296.4 | 966.2 ± 267.6 |
| $AUC_{inf}$ (hr * ng/mL) | 1069 ± 415.7 | 964.8 ± 319.6 | 1037 ± 301.6 | 981.4 ± 264.0 |

TABLE 87

| Treatment | $C_{max}$ Ratio (%) | $AUC_{last}$ Ratio (%) | $AUC_{inf}$ Ratio (%) |
|---|---|---|---|
| OXB4 vs. OXB10 (2 × 40 mg) | 82.97 | 105.57 | 108.93 |
| OXB5 vs. OXB10 (2 × 40 mg) | 72.20 | 98.74 | 98.31 |
| OXB6 vs. OXB10 (2 × 40 mg) | 76.81 | 105.88 | 105.67 |

As can be seen by these results, the pharmacokinetic profiles for the three different high-strength Test Capsule formulations (OXY4-OXY6) were comparable with peak oxycodone concentrations observed at 4.44 to 4.55 hours. The mean $C_{max}$ values for the three high-strength Test Capsule formulations were 17% to 28% lower than the mean $C_{max}$ after administration of the 2×40 mg Test Capsule (OXY10). However, overall systemic exposure to oxycodone after administration of the three 80 mg Test Capsule formulations (OXY4-OXY6) was comparable to that after administration of the 2×40 mg Test Capsule (OXY10). Finally, the relative bioavailability based upon the $AUC_{last}$ of the three 80 mg Test Capsule formulations (OXY4-OXY6) was nearly complete, ranging from 98.74% to 105.88%.

Example 8: In Vivo Abuse Resistance Evaluation of Formulations

Human drug-liking studies have demonstrated that reward increases with the rate of rise in drug blood levels; wherein the faster influx of drug into the blood provides a better rush or high. Savage et al. (2008) *Addict Sci Clin Pract* 4(2):4-25; Marsch et al. (2001) *J Pharmacol Exp Ther* 2001 299(3): 1056-1065. A study to determine which properties of prescription opioids make them more attractive for the purposes of abuse supported the speed of onset as a key factor. Butler et al. (2006) *Harm Reduct J* 2006 3:5.

Prescription drug abusers manipulate sustained-release ("SR") opioid formulations to dose dump (rapidly release) the active agent and increase the rate of rise to achieve the desired high. Common methods of SR opioid abuse are chewing, crushing and extracting and then orally ingesting, snorting or injecting the opioid active agent to achieve a high. In experienced casual abusers may chew or crush SR opioids and mix the manipulated drug with alcohol. As casual abusers generally have no drug tolerance, dose dumping of the opioid active agent poses a significant health risk and may even lead to accidental and potentially fatal overdose.

In order to investigate the extent of dose dumping that occurs after physical manipulation of the currently available SR formulation of oxycodone (OxyContin, hereinafter the "SR Control")), the following phase I study was conducted in five healthy male volunteers. The lowest SR Control dose (10 mg) was chosen to optimize safety for the volunteers. The SR Control tablets were crushed using a mortar and pestle, and the manipulated dosage forms were administered to volunteers with water or 40 proof alcohol and compared against SR Control tablets swallowed whole and to a 10 mg dose of an immediate release formulation of oxycodone (Roxycodone, 2×5 mg).

The results of the study are provided below in Table 88, and depicted in FIG. 24.

TABLE 88

| Parameter | SR Control 10 mg Whole Mean (Std Dev) | Oxycodone IR 2 × 5 mg Whole Mean (Std Dev) |
|---|---|---|
| $T_{max}$ (hr) | 1.91 (0.90) | 1.35 (0.95) |
| $C_{max}$ (ng/mL) | 6.82 (1.26) | 18.9 (4.86) |

| Parameter | SR Control 10 mg Crushed/Water Mean (Std Dev) | SR Control 10 mg Crushed/Alcohol Mean (Std Dev) |
|---|---|---|
| $T_{max}$ (hr) | 0.90 (0.22) | 0.95 (0.41) |
| $C_{max}$ (ng/mL) | 21.8 (5.84) | 21.0 (8.24) |

Figure 24:
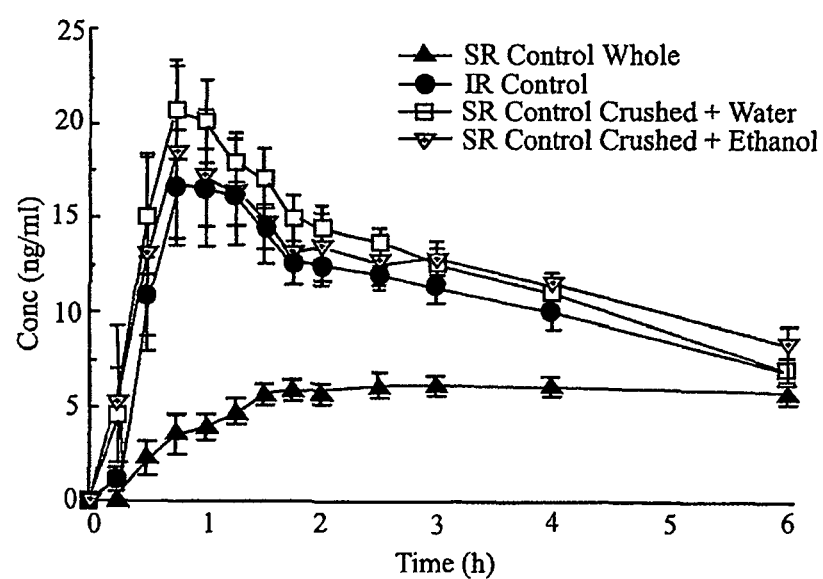
FIGS. 24 and 25 show the results of the in vivo abuse-resistance test comparing a SR Control tablet containing 10 mg oxycodone against an immediate release oxycodone dosage form as described in Example 8.
Figure 25:
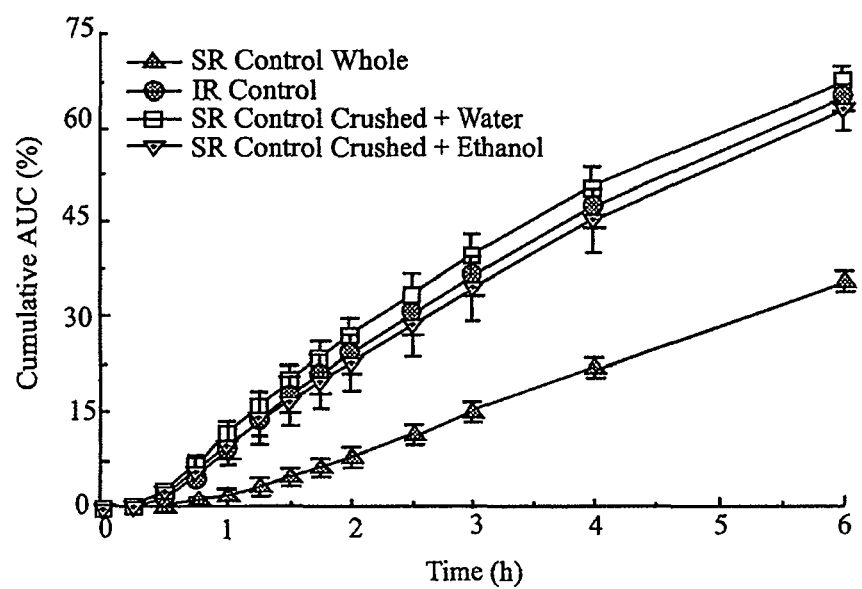

As can be seen by these results, crushing the SR Control tablets and ingesting with water or alcohol significantly increased both the rate and extent of absorption of oxycodone (see FIG. 24). In particular, the $C_{max}$ increased from 6.82 ng/mL to 21.8 and 21.0 ng/mL for the SR Control with water or alcohol, respectively. This $C_{max}$ was very similar to that obtained with the oxycodone IR tablets (18.9 ng/mL). Similarly, $T_{max}$ decreased from 1.91 hours to 0.90 and 0.95 after crushing with water or alcohol, respectively. These $T_{max}$ values were shorter than the $T_{max}$ obtained with the IR tablets (1.35 hour).

The total AUC is a pharmacological metric that represents the total amount of active agent absorbed. The AUC to a specific time, i.e., the cumulative AUC, represents the amount of active agent absorbed to that time, and allows one to assess the rate of increase in exposure. This automatically corrects for differences in bioavailability and allows a true comparison among treatments and/or formulations. The rapid rate of absorption and the loss of controlled-release mechanism after physical manipulation of the SR Control tablets are evident from FIG. 24 which shows that the rate of absorption is significantly increased.

An Abuse Quotient, or AQ, can be used as a method to express the attractiveness for abuse of a formulation/dosage form. Webster LR (2007) *Emerging opioid formulations: abuse deterrent or abuse resistant?* [Internet] Available from: http:www.emergingsolutionsinpain.com/opencms/esp/commentaries/index.html. The AQ takes into account the observation that increasing $C_{max}$ and decreasing $T_{max}$ increases the attractiveness of a particular dosage form for abuse. Represented as a formula, $AQ=C_{max}/T_{max}$. In the instant study, the AQ was 3.57 for the SR Control taken intact and 14.0 for the immediate release tablets. After crushing the SR Control with water or ethanol, the AQ for the SR Control increased to 24.2 and 22.2, respectively, suggesting that the attractiveness of the SR Control for abuse was greatly increased after physical manipulation. AQ is a dose dependent metric as $C_{max}$ varies with dose. For ease of comparison of this initial study with subsequent in vivo abuse resistance evaluations of the abuse-resistant dosage forms of the present invention with dose levels of 40 mg, the equivalent AQ after dose adjustment would be 14.3 of the SR Control (40 mg) taken intact and 56.0 for the immediate release (40 mg). After crushing the SR Control with water or alcohol, the dose adjusted AQ would increase to 96.8 and 88.8, respectively.

Accordingly, four Phase I In Vivo Abuse Resistance Evaluation studies were conducted to challenge abuse-resistant dosage forms of the present invention using physical and chemical manipulation in order to attempt to include dose dumping or immediate-release effect. Since food effect studies with the relevant dosage forms indicated that administration with food significantly increase the rate and the extent of absorption of oxycodone from the abuse-resistant dosage forms, all PK studies described in this Example 8 administered the Test Capsules with food, while reference oxycodone IR oral solution was administered under fasting conditions as a benchmark for the most rapid absorption of oxycodone. Subjects in all PK studies were pretreated with naltrexone to minimize opioid-related side effects.

In all of the In Vivo Abuse Resistance Evaluation studies described below, plasma samples were analyzed for oxycodone, noroxycodone, and oxymorphone by CEDRA Corporation using a validated LC-MS-MS procedure. The method was validated for a range of 0.250 to 125 ng/mL for oxycodone, 0.500 to 250 ng/mL for noroxycodone and 0.0500 to 25.0 ng/mL for oxymorphone. Data were analyzed by noncompartmental methods in WinNonlin. Concentration-time data that were below the limit of quantification (BLQ) were treated as zero (0.00 ng/mL) in the data summarization and descriptive statistics. In the pharmacokinetic analyses, BLQ concentrations were treated as zero from time-zero up to the time at which the first quantifiable concentration was observed; embedded and/or terminal BLQ concentrations were treated as "missing".

The abuse-resistant oxycodone oral dosage forms used in the studies were prepared using the following raw materials: Oxycodone base, micronized ("OXY"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); and Cellulose Acetate Butyrate, grade 381-20 BP, ethanol washed (Eastman Chemicals) ("CAB"). The formulations were produced using the commercial-scale manufacturing methods (Process Schemes 4 or 5 as described above) and then filled into size 00 white opaque gel cap shells to produce 5, 10, 20, 30 and 40 mg dosage forms that were used as the OXY Test Capsules. The details of the formulations and the dosage forms containing the formulations of this Example 8 are disclosed below in Tables 89 and 90.

TABLE 89

| OXY (wt %) | SAIB (wt %) | TA (wt %) | CAB (wt %) | IPM (wt %) | HEC (wt %) | SiO$_2$ (wt %) | BHT (wt %) |
|---|---|---|---|---|---|---|---|
| 5.13 | 40.98 | 27.32 | 4.74 | 14.23 | 5.69 | 1.9 | 0.02 |

TABLE 90

| Capsule Strength | OXY (mg) | SAIB (mg) | TA (mg) | CAB (mg) | IPM (mg) | HEC (mg) | SiO$_2$ (mg) | BHT (mg) | Total (mg) |
|---|---|---|---|---|---|---|---|---|---|
| 5 mg | 5.0 | 40.0 | 26.6 | 4.6 | 13.9 | 5.5 | 1.8 | 0.02 | 97.5 |
| 10 mg | 10.0 | 79.9 | 53.3 | 9.2 | 27.7 | 11.1 | 3.7 | 0.04 | 195.0 |
| 20 mg | 20.0 | 159.8 | 106.5 | 18.5 | 55.5 | 22.2 | 7.4 | 0.08 | 390.0 |
| 30 mg | 30.0 | 239.7 | 159.8 | 27.8 | 83.2 | 33.3 | 11.1 | 0.12 | 585.0 |
| 40 mg | 40.0 | 319.6 | 213.1 | 37.0 | 111.0 | 44.4 | 14.8 | 0.16 | 780.0 |

Example 8a

The following In Vivo Abuse Resistance Evaluation study was a single-center, four-way crossover PK study to assess the effect of physical disruption of the controlled release carrier system on the release of the oxycodone active agent from abuse-resistant oral dosage forms produced according to the present invention. The study dosage forms (capsules containing oxycodone free base, 40 mg) ("OXY" Test Capsules) were administered (fed state) intact or crushed with alcohol. For comparison, oxycodone sustained release (SR) tablets (OxyContin brand sustained release Oxycodone tablets, 40 mg, Purdue Pharma), "SR Control" were administered (fasting state) intact or crushed with alcohol, as well as 40 mg oral solution of oxycodone HCl as a comparator of an immediate release ("IR Control") (fasting state) in order to represent a "worst-case scenario". Subjects were administered naltrexone blockade to prevent opioid-related adverse events. Fifty subjects were enrolled in this study, 27 males and 23 females. One male did not complete the study and another male experienced emesis within 12 hours of dosing; 48 subjects were included in the PK analysis.

Figure 26:
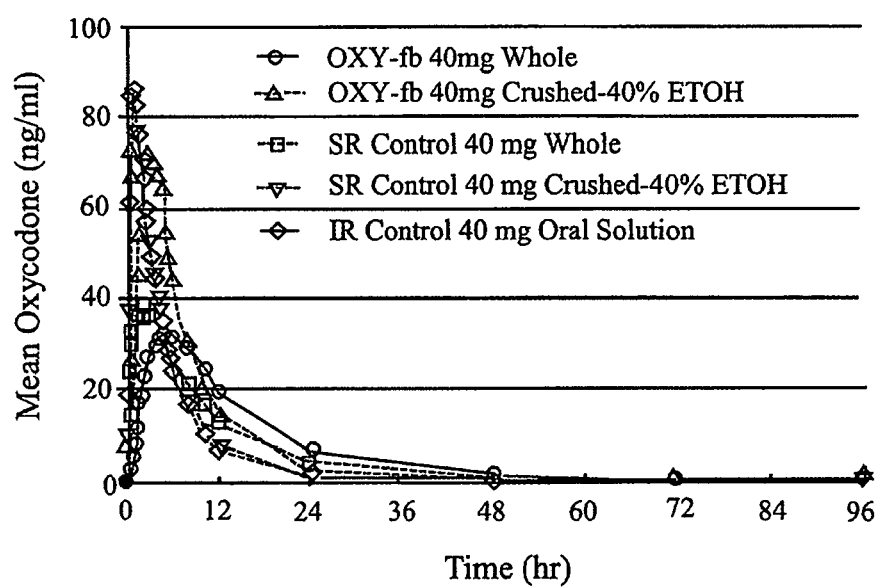
FIG. 26 depicts the mean linear plasma concentration-time curves of active agent in the clinical trial study described in Example 8.

The mean linear and semi-logarithmic oxycodone plasma concentration-time curves obtained in this Example 8a study are depicted in FIG. 26. The $C_{max}$ and $T_{max}$ values, based on mean oxycodone plasma concentration-time values, are presented below in Table 91, and mean oxycodone PK parameters from noncompartmental analysis of individual data obtained in the Example 8a study are presented below in Table 92.

TABLE 91

| Parameter | OXY 40 mg Capsule-Whole | OXY 40 mg Capsule-Crushed | SR Control 40 mg Tablet-Whole | SR Control 40 mg Tablet-Crushed | IR Control 40 mg Oral Solution |
|---|---|---|---|---|---|
| $T_{max}$ (hr) | 4.50 | 3.00 | 2.00 | 1.50 | 1.00 |
| $C_{max}$ ng/mL) | 36.8 | 71.3 | 38.4 | 76.7 | 86.0 |

TABLE 92

| Parameter | Treatment A: OXY (40 mg Capsule-Whole) | | | | Treatment B: OXY (40 mg Capsule-Crushed) | | | |
|---|---|---|---|---|---|---|---|---|
| | n | Mean | SD | CV % | n | Mean | SD | CV % |
| $T_{max}$ (hr) | 39 | 5.15 | 2.24 | 43.46 | 40 | 2.97 | 0.97 | 32.51 |
| $C_{max}$ (ng/mL) | 39 | 43.8 | 18.4 | 41.98 | 40 | 78.8 | 10.5 | 13.30 |
| $AUC_{0-2}$ (hr * ng/mL) | 39 | 13.15 | 9.533 | 72.51 | 40 | 54.88 | 25.13 | 45.78 |
| $AUC_{0-4}$ (hr * ng/mL) | 39 | 64.62 | 35.87 | 55.51 | 40 | 192.0 | 34.06 | 17.74 |
| $AUC_{0-6}$ (hr * ng/mL) | 39 | 132.2 | 52.80 | 39.93 | 40 | 303.6 | 41.73 | 13.74 |
| $AUC_{0-12}$ (hr * ng/mL) | 39 | 289.5 | 76.69 | 26.49 | 40 | 461.6 | 69.02 | 14.95 |
| $AUC_{0-24}$ (hr * ng/mL) | 39 | 443.7 | 108.0 | 24.35 | 40 | 557.4 | 96.09 | 17.24 |
| $AUC_{0-48}$ (hr * ng/mL) | 30 | 555.6 | 133.8 | 24.08 | 12 | 665.3 | 103.7 | 15.59 |
| $AUC_{last}$ (hr * ng/mL) | 39 | 534.6 | 143.6 | 26.85 | 40 | 569.7 | 109.7 | 19.26 |
| $AUC_{inf}$ (hr * ng/mL) | 27 | 585.8 | 143.5 | 24.49 | 9 | 677.6 | 96.07 | 14.18 |
| $AUC_{Extrap}$ (%) | 27 | 1.79 | 1.73 | 96.25 | 9 | 0.48 | 0.16 | 34.12 |
| $\lambda_z$ (hr$^{-1}$) | 27 | 0.0804 | 0.0215 | 26.77 | 9 | 0.1081 | 0.0082 | 7.55 |
| $T_{1/2}$ (hr) | 27 | 9.30 | 2.80 | 30.13 | 9 | 6.45 | 0.53 | 8.18 |
| $T_{last}$ (hr) | 39 | 50.46 | 18.91 | 37.47 | 40 | 31.80 | 12.61 | 39.67 |
| $C_{last}$ (ng/mL) | 39 | 1.57 | 2.19 | 140.07 | 40 | 1.41 | 0.943 | 67.01 |
| Parameter | Treatment C: SR Control (40 mg Tablet-Whole) | | | | Treatment D: SR Control (40 mg Tablet-Crushed) | | | |
| | n | Mean | SD | CV % | n | Mean | SD | CV % |
| $T_{max}$ (hr) | 40 | 2.09 | 0.97 | 46.55 | 39 | 1.48 | 0.66 | 44.38 |
| $C_{max}$ (ng/mL) | 40 | 42.3 | 9.82 | 23.20 | 39 | 88.4 | 27.4 | 30.97 |
| $AUC_{0-2}$ (hr * ng/mL) | 40 | 50.30 | 12.55 | 24.95 | 39 | 109.1 | 39.61 | 36.31 |
| $AUC_{0-4}$ (hr * ng/mL) | 40 | 123.0 | 26.47 | 21.52 | 39 | 215.8 | 63.13 | 29.26 |
| $AUC_{0-6}$ (hr * ng/mL) | 40 | 185.2 | 39.97 | 21.58 | 39 | 281.4 | 75.94 | 26.98 |
| $AUC_{0-12}$ (hr * ng/mL) | 40 | 300.3 | 67.32 | 22.42 | 39 | 372.5 | 102.6 | 27.55 |
| $AUC_{0-24}$ (hr * ng/mL) | 39 | 398.5 | 96.38 | 24.19 | 39 | 423.7 | 123.5 | 29.14 |
| $AUC_{0-48}$ (hr * ng/mL) | 16 | 507.8 | 122.2 | 24.06 | 2 | 619.3 | 197.6 | 31.90 |
| $AUC_{last}$ (hr * ng/mL) | 40 | 422.5 | 117.8 | 27.89 | 39 | 425.2 | 126.1 | 29.65 |
| $AUC_{inf}$ (hr * ng/mL) | 16 | 512.4 | 122.0 | 23.81 | 2 | 621.9 | 197.4 | 31.75 |
| $AUC_{Extrap}$ (%) | 16 | 0.85 | 0.50 | 58.88 | 2 | 0.43 | 0.17 | 38.58 |
| $\lambda_z$ (hr$^{-1}$) | 16 | 0.0995 | 0.0144 | 14.43 | 2 | 0.1022 | 0.0103 | 10.08 |
| $T_{1/2}$ (hr) | 16 | 7.12 | 1.13 | 15.86 | 2 | 6.81 | 0.69 | 10.08 |
| $T_{last}$ (hr) | 40 | 33.90 | 13.55 | 39.98 | 39 | 25.24 | 5.36 | 21.24 |
| $C_{last}$ (ng/mL) | 40 | 2.23 | 2.33 | 104.51 | 39 | 0.951 | 0.587 | 61.78 |

TABLE 92-continued

| Parameter | Treatment E: IR Control (40 mg Oral Solution) | | | |
|---|---|---|---|---|
| | n | Mean | SD | CV % |
| $T_{max}$ (hr) | 40 | 0.97 | 0.25 | 25.60 |
| $C_{max}$ (ng/mL) | 40 | 91.6 | 26.3 | 28.67 |
| $AUC_{0-2}$ (hr * ng/mL) | 40 | 128.3 | 34.84 | 27.15 |
| $AUC_{0-4}$ (hr * ng/mL) | 40 | 230.5 | 55.93 | 24.26 |
| $AUC_{0-6}$ (hr * ng/mL) | 40 | 291.9 | 70.74 | 24.24 |
| $AUC_{0-12}$ (hr * ng/mL) | 40 | 374.7 | 95.82 | 25.57 |
| $AUC_{0-24}$ (hr * ng/mL) | 40 | 419.6 | 112.8 | 26.89 |
| $AUC_{0-48}$ (hr * ng/mL) | 40 | 425.7 | 116.2 | 27.30 |
| $AUC_{last}$ (hr * ng/mL) | 40 | 421.3 | 114.9 | 27.28 |
| $AUC_{inf}$ (hr * ng/mL) | 40 | 426.4 | 116.9 | 27.42 |
| $AUC_{Extrap}$ (%) | 40 | 1.16 | 0.58 | 49.56 |
| $\lambda_z$ (hr$^{-1}$) | 40 | 0.1765 | 0.0311 | 17.62 |
| $T_{1/2}$ (hr) | 40 | 4.08 | 1.03 | 25.36 |
| $T_{last}$ (hr) | 40 | 25.50 | 8.67 | 34.00 |
| $C_{last}$ (ng/mL) | 40 | 0.883 | 0.563 | 63.78 |

As can be seen from these results, the following comparisons and conclusions can be drawn.

1. Treatment A vs. B:

(OXY Test Capsule 40 mg capsule (whole) vs. OXY Test Capsule 40 mg capsule (crushed), extracted with 40% ethanol). The 90% confidence interval for comparing the maximum exposure, based on $\ln(C_{max})$, was outside the required 80% to 125% limits for oxycodone. The $C_{max}$ values of the crushed Test Capsules were nearly twice as that of the intact Test Capsules and the time to reach the maximum concentration ($T_{max}$) was earlier with the crushed Test Capsules (2.97 hours vs. 5.15 hours). The 90% confidence intervals for comparing total systemic exposure, based on $\ln(AUC_{last})$ and $\ln(AUC_{inf})$, were within the accepted 80% to 125% limits for oxycodone. The 90% confidence intervals for comparing the earlier systemic exposure, $\ln(AUC_{0-2})$, $\ln(AUC_{0-4})$, $\ln(AUC_{0-6})$, and $\ln(AUC_{0-12})$, and a later exposure $\ln(AUC_{0-24})$ were outside the 80% to 125% limits for oxycodone. However, $\ln(AUC_{0-48})$ was within the 80% to 125% limits.

2. Treatment D vs. E:

(SR Control (OxyContin) 40 mg tablet (crushed, extracted with 40% ethanol) vs. IR Control (Oxycodone HCl) oral solution 40 mg). The 90% confidence interval for comparing the maximum exposure of the SR Control, based on $\ln(C_{max})$, was within the required 80% to 125% limits for the IR Control (oxycodone). The 90% confidence interval for comparing total systemic exposure, based on $\ln(AUC_{last})$, was within the accepted 80% to 125% limits for the IR Control. The 90% confidence intervals for comparing the earlier systemic exposure, $\ln(AUC_{0-4})$, $\ln(AUC_{0-6})$, and $\ln(AUC_{0-12})$, and the later systemic exposure $\ln(AUC_{0-24})$ were also within the 80% to 125% limits for the IR Control.

3. Treatment B Vs. E:

(OXY Test Capsules 40 mg capsule (crushed, extracted with 40% ethanol) vs. IR Control (Oxycodone HCl) oral solution 40 mg). The 90% confidence interval for comparing the maximum exposure of the crushed Test Capsules, based on $\ln(C_{max})$, was within the required 80% to 125% limits for the IR Control. The time to reach the maximum concentration ($T_{max}$) took longer with the crushed Test Capsules than with the IR Control (2.97 hours vs. 0.97 hours). The 90% confidence intervals for comparing total systemic exposure, based on $\ln(AUC_{last})$ and $\ln(AUC_{inf})$, were outside the accepted 80% to 125% limits for the IR Control. The 90% confidence intervals for comparing the earlier systemic exposure, $\ln(AUC_{0-2})$, $\ln(AUC_{0-4})$, and $\ln(AUC_{0-12})$, and the later systemic exposures $\ln(AUC_{0-24})$ and $\ln(AUC_{0-48})$ were also outside the 80% to 125% limits for the IR Control.

4. Treatment B Vs. D:

(OXY Test Capsules 40 mg capsule (crushed, extracted with 40% ethanol) vs. SR Control 40 mg tablet (crushed, extracted with 40% ethanol). The 90% confidence interval for comparing the maximum exposure of both the OXY Test Capsules and the SR Control, based on $\ln(C_{max})$, was within the required 80% to 125% limits for the IR Control. However, the time to reach the maximum concentration ($T_{max}$) took twice as long with the crushed Test Capsules than with the SR Control (2.97 hours vs. 1.48 hours). The 90% confidence intervals for comparing total systemic exposure, based on $\ln(AUC_{last})$ were outside the accepted 80% to 125% limits for the IR Control. The 90% confidence intervals for both test compositions comparing the earlier systemic exposure, $\ln(AUC_{0-2})$, $\ln(AUC_{0-4})$, and $\ln(AUC_{0-6})$ were within the required 80% to 125% limits. However the intermediate values of systemic exposure, $\ln(AUC_{0-12})$ and the later systemic exposure $\ln(AUC_{0-24})$ were outside the required 80% to 125% limits for both compositions.

5. Treatment C vs. D:

(SR Control 40 mg tablet (whole) vs. SR Control 40 mg tablet (crushed, extracted with 40% ethanol)). The 90% confidence interval for comparing the maximum exposure, based on $\ln(C_{max})$, was outside the required 80% to 125% limits for the IR Control. The time to reach the maximum concentration ($T_{max}$) was slightly longer with the intact SR Control tablet versus the SR Control crushed tablet (2.09 hours vs. 1.48 hours). The 90% confidence intervals for comparing the later systemic exposure, $\ln(AUC_{0-24})$ and the total systemic exposure, based on ln(AUC$_{last}$), were within the accepted 80% to 125% limits. The 90% confidence intervals for comparing the earlier systemic exposure, ln(AUC$_{0-2}$), ln(AUC$_{0-4}$), and ln(AUC$_{0-6}$) and intermediate values of systemic exposure, ln(AUC$_{0-12}$) were outside the 80% to 125% limits.

Figure 27:
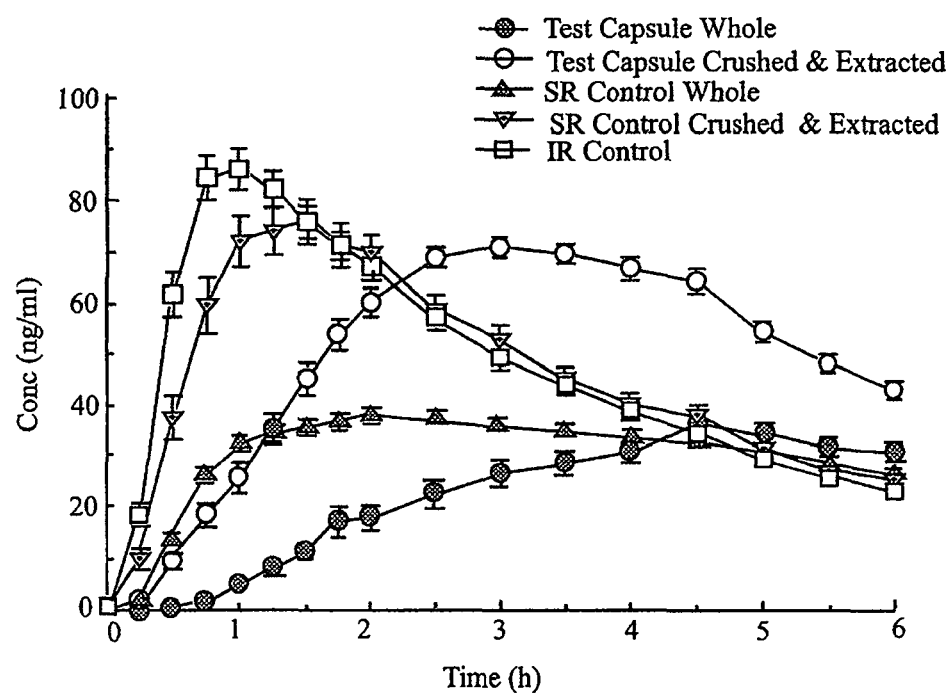
Figure 28:
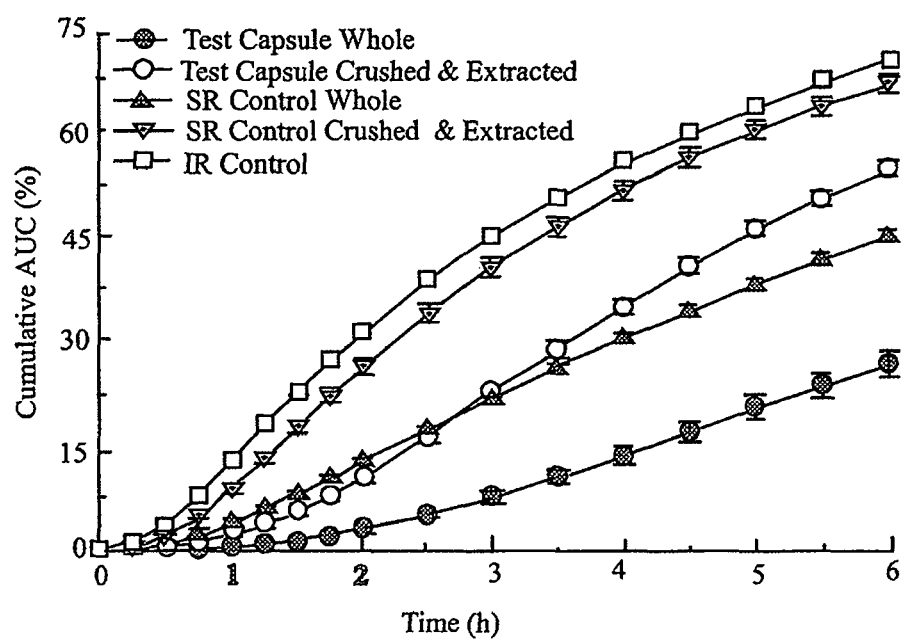

Furthermore, the cumulative AUC of oxycodone (0-6 hours) after oral administration of single doses of 40 mg OXY Test Capsules (whole or crushed and extracted with 40% ethanol) and 40 mg SR Control tablets swallowed whole or crushed and extracted with 40% ethanol, and a single 40 mg oxycodone solution IR Control are depicted in FIG. 27. As can be seen by reference to this figure, and the above tabulated PK results, the C$_{max}$ of the OXY Test Capsules increased from 43.8±18.4 ng/mL to 78.8±10.5 ng/mL and the T$_{max}$ decreased from 5.15±2.24 h to 2.97±0.97 h. However, crushing and extracting the OXY Test Capsules with 40% ethanol did not affect the extent of total absorption, and regardless of the means used to manipulate the instant abuse-resistant dosage forms, absorption was 3-fold slower that after administration of the IR Control (mean T$_{max}$ was 0.97±0.25 h). The rate of absorption and peak exposure to oxycodone after the OXY Test Capsules were crushed and extracted with 40% ethanol were also lower than those for the SR Control tablets (T$_{max}$ was 1.48 while C$_{max}$ was 88.4 ng/mL). It was noted that at 1 hour post administration, oxycodone plasma concentrations after the OXY Test Capsules were crushed and extracted with 40% ethanol were lower than those after the SR Control was taken intact. The cumulative percent of the total area under the oxycodone plasma concentration vs. time results are depicted in FIG. 28 for each of the study dosage forms. As can be seen, FIG. 28 shows that based upon the cumulative percent of total AUC, the rate of exposure for OXY Test Capsules after crushing and extraction (40% ethanol) remains substantially lower than that for both the SR Control tablets after crushing and extraction and the IR Control solution, with a particularly pronounced difference during the initial hours after administration.

Finally, the AQ calculations for this Example 8A study were as follows: OXY Test Capsules (intact), AQ=8.5 and OXY Test Capsules (crushed and extracted), AQ=26.5; SR Control (intact), AQ=20.2, SR Control (crushed and extracted), AQ=59.7; and IR Control, AQ=94.3.

Example 8b

The following In Vivo Abuse Resistance Evaluation studies were single-center, three-way crossover PK studies to determine the release rate of oxycodone after dissolving the study abuse-resistant oral dosage forms (capsules containing oxycodone free base, 40 mg, "OXY" Test Capsules) in the buccal cavity of healthy volunteers. The 40 mg study dosage forms were administered (fed state) and allowed to dissolve in the buccal cavity for 10 minutes to compare with 40 mg study dosage forms administered (fed state) intact, and a 40 mg oral solution of immediate release (IR) oxycodone HCl ("IR Control") (fasting state) in order to represent a "worst-case scenario". Subjects were administered naltrexone blockade to prevent opioid-related adverse events. A total of 48 healthy adult male and female volunteers were enrolled. Forty-two (42) of the 48 subjects enrolled in the first study completed the study (3 subjects experienced emesis within 12 hours of dosing and 3 subjects did not complete required treatments; and all 6 were thus excluded from the PK analysis). Forty-four (44) of the 48 subjects enrolled in the second study completed the study; however, 2 subjects who completed the study experienced emesis with 12 hours of dosing and were therefore excluded from the PK analysis).

Figure 29:
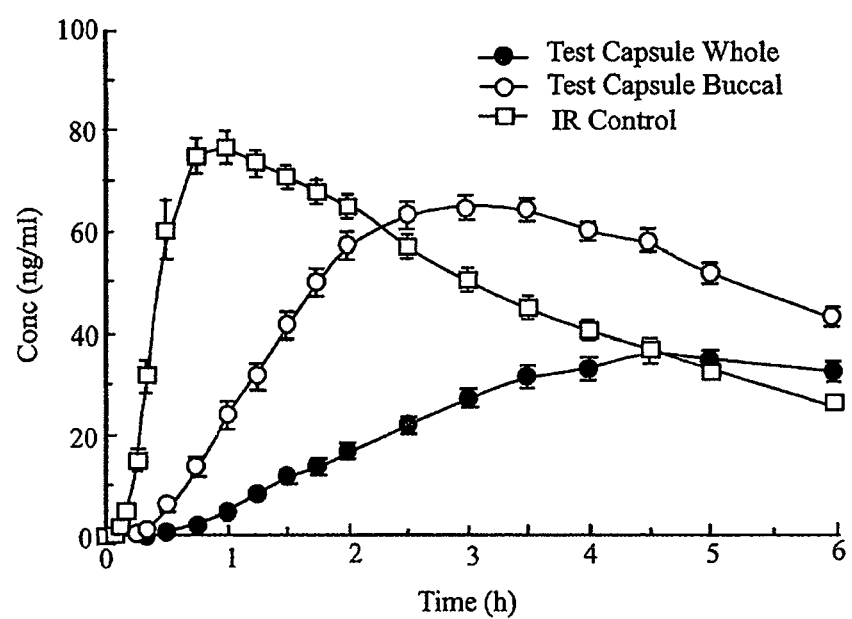
FIG. 29 shows the results of the in vivo abuse-resistance test of 40 mg Test Capsules containing oxycodone after being held in the buccal cavity as described in Example 8b.

Mean oxycodone plasma concentrations (0-6 hours) obtained from the first Example 8b in vivo abuse resistance study are depicted in FIG. 29. The C$_{max}$ and T$_{max}$ values from the first and second Example 8b studies, based on mean oxycodone plasma concentration-time values, are presented below in Tables 93 and 94, respectively.

TABLE 93

| Parameter | OXY Test Capsule Whole | OXY Test Capsule Dissolved in Buccal Cavity | IR Control |
|---|---|---|---|
| T$_{max}$ (hr) | 4.50 | 3.00 | 1.00 |
| C$_{max}$ (ng/mL) | 36.2 | 64.6 | 76.6 |

TABLE 94

| Parameter | OXY Test Capsule Whole Mean (Std Dev) | OXY Test Capsule Dissolved in Buccal Cavity Mean (Std Dev) | IR Control Mean (Std Dev) |
|---|---|---|---|
| T$_{max}$ (hr) | 5.61 (2.32) | 2.89 (0.79) | 1.15 (0.62) |
| C$_{max}$ (ng/mL) | 41.80 (16.30) | 71.10 (14.20) | 86.70 (30.80) |
| AUC$_{0-2}$ (hr * ng/mL) | 12.12 (8.49) | 48.44 (22.49) | 116.80 (31.32) |
| AUC$_{last}$ (hr * ng/mL) | 547.60 (226.90) | 596.20 (177.20) | 434.10 (148.40) |

As can be seen by these results, holding the OXY Test Capsules in the buccal cavity for 10 minutes did not result in rapid transmucosal absorption of oxycodone as indicated by the lack of difference in mean plasma concentrations during the very early sampling time points between buccal and whole treatments. In addition, the total extent of exposure to oxycodone was not affected by holding the OXY Test Capsules in the buccal cavity.

The AQ for the OXY Test Capsules administered intact in this study was 7.5, while the AQ for OXY Test Capsules after holding in the buccal cavity was 24.6. However, the AQ for the IR Control was much greater (75.4), suggesting that the attractiveness of the instant abuse-resistant dosage forms was much less than abuse of an oral solution of oxycodone.

Example 8c

The following In Vivo Abuse Resistance Evaluation study was a single-center, randomized crossover study to assess the effect of rigorous mastication on the rate and extent of absorption of 40 mg oxycodone base in abuse-resistant oral dosage forms in comparison with the same dosage forms swallowed whole (both under fed conditions) and an oxycodone immediate release solution under fasted conditions. A total of 48 healthy subjects (29 males, 19 females) were enrolled in the study. Subjects were administered naltrexone blockade to block opioid-related effects. Four subjects (2 each male and female) did not complete the study, and a total of 44 subjects were thus included in the PK analysis.

Figure 30:
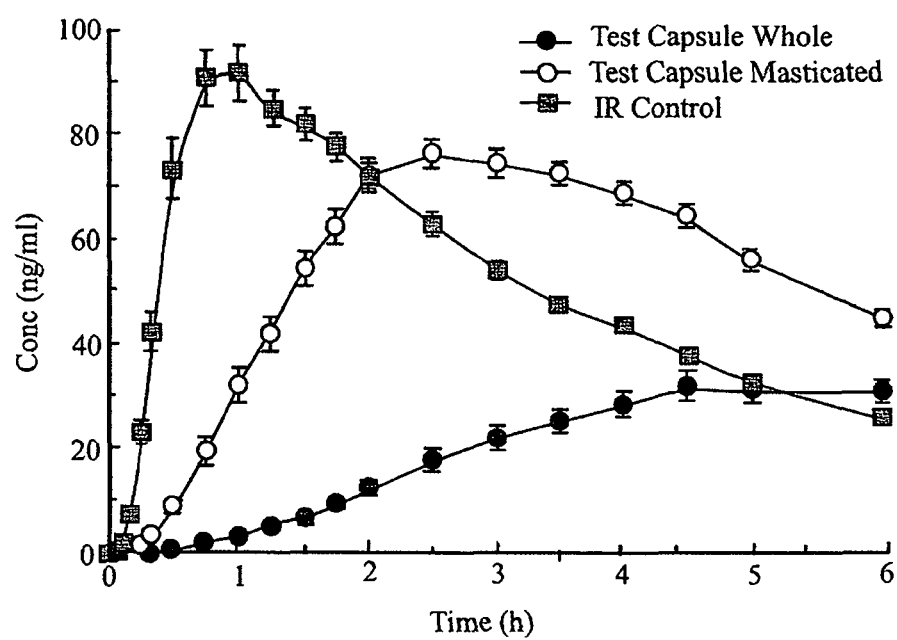
FIG. 30 shows the results of the in vivo abuse-resistance test of 40 mg Test Capsules containing oxycodone taken either whole or after vigorous mastication as described in Example 8.

The PK results from this Example 8c study are reported below in Table 95. In addition, the cumulative percent (mean) of the total area under the oxycodone plasma concentration vs. time curve data are depicted in FIG. 30.

TABLE 95

| Parameter | OXY Test Capsule Whole Mean (Std Dev) | OXY Test Capsule Chewed Mean (Std Dev) | IR Control Mean (Std Dev) |
|---|---|---|---|
| $T_{max}$ (hr) | 5.52 (1.83) | 2.67 (0.78) | 1.07 (0.46) |
| $C_{max}$ (ng/mL) | 40.50 (18.80) | 82.30 (16.70) | 102.00 (33.40) |
| $AUC_{0-2}$ (hr * ng/mL) | 8.32 (5.75) | 64.09 (27.94) | 138.80 (40.12) |
| $AUC_{last}$ (hr * ng/mL) | 512.50 (118.30) | 596.80 (134.40) | 455.80 (113.60) |

As can be seen, vigorous mastication (chewing) of the OXY Test Capsules increased the mean $C_{max}$ from 40.5 ng/mL to 82.3 ng/mL. However, relative to the IR Control oral solution, the $C_{max}$ for the chewed Test Capsules was significantly lower and occurred at a significantly later time. The mean $T_{max}$ for the chewed OXY Test Capsules decreased from 5.52 hours to 2.67 hours, as compared to 1.07 for the IR Control oral solution. The total extent of absorption was not affected by chewing the OXY Test Capsules. These data indicate that chewing (a common form of abuse) of the abuse-resistant dosage forms of the present invention did not defeat the controlled release mechanism of the formulations, as evident from the lack of dose dumping and plasma concentration profiles that retained a broad plateau.

Finally, the AQ for the Test Capsules (intact) was 7.3, whereas the AQ for the chewed Test Capsules was 30.8. However, the AQ for the comparator oral solution was 95.3.

Example 8d

The following In Vivo Abuse Resistance Evaluation study was a single-center, four-way crossover PK study to determine the rate and extent of absorption of 40 mg oxycodone base in abuse-resistant oral dosage forms when co-administered with 240 mL of 4% ethanol, 20% ethanol and 40% ethanol in comparison to 240 mL of water (fed state). A total of 37 healthy adult male and female volunteers received at least one dose of the study dosage forms. Subjects were administered naltrexone blockade to block opioid-related effects. Because of the large quantities of alcohol administered, a large percentage of subjects experienced emesis. Approximately 25% of subjects vomited after receiving 20% ethanol and 38% of subjects vomited after receiving 40% ethanol. Pharmacokinetic blood sampling for a given treatment period was discontinued after emesis. After the second treatment period of the study, it was decided not to allow any additional female subjects to receive the study dosage forms with 40% ethanol, since all female subjects receiving this treatment had vomited. Therefore, data for the 40% ethanol treatment is only available for 18 subjects.

In this study, the total volume of liquid given with administration of the study dosage form was 480 mL, compared to 240 mL in previous (Phase I) studies. It appears that in the absence of alcohol, the relatively large volume of water resulted in the physiological response of rapid stomach emptying as evidenced by the shorter $T_{max}$ relative to that seen in the previous studies.

Figure 31:
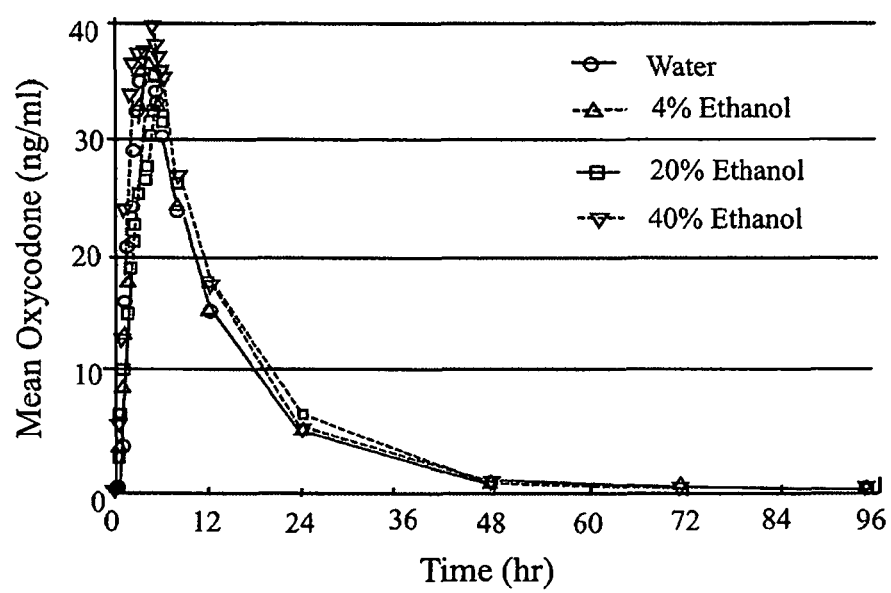
FIG. 31 depicts the mean linear plasma concentration-time curves of active agent in the in vivo abuse-resistance study described in Example 8d.

The mean linear and semi-logarithmic oxycodone plasma concentration-time curves from the study in this Example 8d are shown in FIG. 31. The $C_{max}$ and $T_{max}$ values, based on mean oxycodone plasma concentration-time values, are presented below in Table 96, mean oxycodone PK parameters from noncompartmental analysis of individual data from the study in this Example 8d are presented below in Table 97.

TABLE 96

| Parameter | 40 mg OXY (w/ water) | 40 mg OXY (w/4% EtOH) | 40 mg OXY (w/20% EtOH) | 40 mg OXY (w/40% EtOH) |
|---|---|---|---|---|
| $T_{max}$ (hr) | 3.33 | 4.67 | 4.67 | 4.67 |
| $C_{max}$ (ng/mL) | 36.8 | 37.7 | 32.8 | 39.9 |

TABLE 97

| Parameter | 40 mg OXY (w/water) Mean (SD) | 40 mg OXY (w/4% EtOH) Mean (SD) | 40 mg OXY (w/20% EtOH) Mean (SD) | 40 mg OXY (w/40% EtOH) Mean (SD) |
|---|---|---|---|---|
| $T_{max}$ (hr) | 4.02 (1.29) | 4.37 (1.79) | 5.14 (1.55) | 4.13 (1.95) |
| $C_{max}$ (ng/mL) | 45.3 (23.1) | 45.0 (20.6) | 39.0 (16.1) | 49.7 (27.2) |
| $AUC_{last}$ (hr * ng/mL) | 471.3 (154.6) | 471.8 (147.5) | 496.3 (153.6) | 537.7 (191.5) |
| $AUC_{inf}$ (hr * ng/mL) | 513.8 (156.5) | 516.0 (144.1) | 542.5 (144.6) | 585.3 (184.3) |

In the statistical analysis for this Example 8d, the ratios of co-ingestion with alcohol to co-ingestion with water were calculated for maximum exposure ($C_{max}$) and total exposure ($AUC_{last}$), and these data are shown below in Table 98. As can be seen, there was no significant effect from the co-ingestion of alcohol on the maximum exposure and extent of oxycodone absorption from abuse-resistant oral dosage forms of the present invention.

TABLE 98

| Parameter | Coadministration w/ 4% EtOH | Coadministration w/ 20% EtOH | Coadministration w/ 40% EtOH |
|---|---|---|---|
| $C_{max}$ Ratio* | 0.99 | 0.86 | 1.10 |
| AUC Ratio* | 1.00 | 1.05 | 1.14 |

Figure 32:
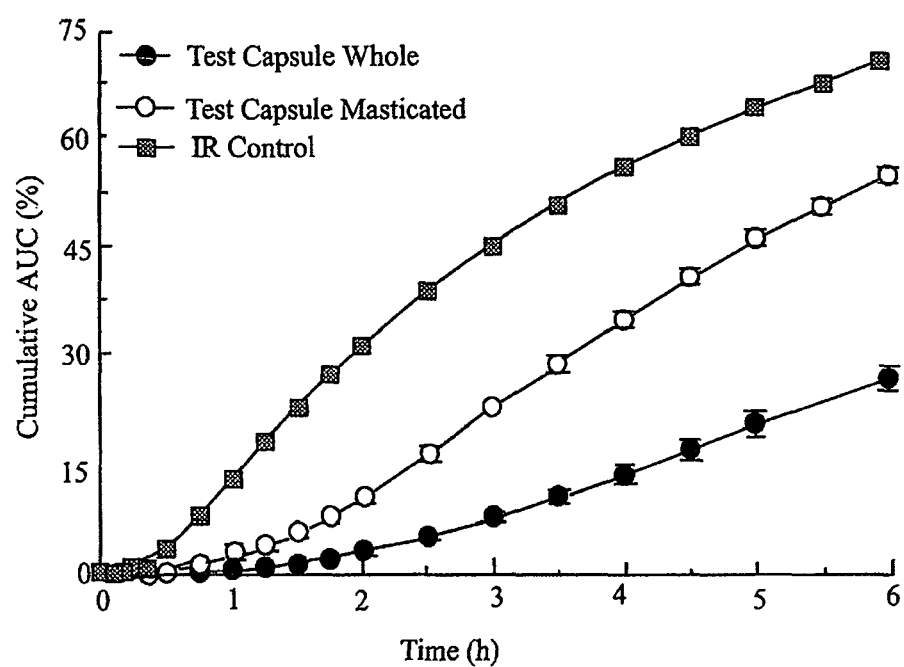
FIG. 32 shows the mean plasma concentration of oxocodone (0-6 hour) after ingestion of 40 mg Test Capsules containing oxycodone when taken with water, or with 4%, 20% or 40% ethanol as described in Example 8d.

*Ratio of average values when co-ingested with alcohol compared to co-ingested with water The cumulative AUC of oxcodone (0-6 h) after administration of a single 40 mg OXY Test Capsule with water, 4% EtOH, 20% EtOH and 40% EtOH data are depicted in FIG. 32. As can be seen, the mean plasma concentration profiles across all treatment groups were similar and displayed a typical controlled release pattern, indicating that there was no dose dumping as a result of co-ingestion with the various strengths of alcohol. In addition, comparison of $C_{max}$ and $AUC_{last}$ between each ethanol treatment and water demonstrated no effect (4% EtOH), a small decrease in $C_{max}$ (20% EtOH) and a 10% increase in $C_{max}$ with only the highest alcohol strength tested (40% EtOH).

Example 9: In Vivo Analysis of Formulations (Human Clinical Trails, Pharmacokinetic Studies)

In order to assess the in vivo controlled release performance of abuse-resistant hydromorphone oral dosage forms prepared in accordance with the present invention, the following human clinical trails were carried out. In the studies described below, plasma samples were analyzed for hydromorphone using a validated LC-MS-MS procedure.

Example 9a

The abuse-resistant hydromorphone oral dosage forms used in this study were prepared using the following raw materials: Hydromorphone HCl, ("HMH"); Isopropyl Myristate, NF (IPM); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); and Cellulose Acetate Butyrate, grade 381-20 BP, ethanol washed (Eastman Chemicals) ("CAB"). The formulations were produced using the commercial-scale manufacturing methods (Process Schemes 4 or 5 as described above) and then filled into size 00 white opaque gel cap shells to produce 16 mg dosage forms that were used as Test Capsules. The details of the HMH Test Capsule formulations of this Example 9a are disclosed below in Table 99.

TABLE 99

| HMH HCl (wt %) | SAIB (wt %) | TA (wt %) | CAB (wt %) | IPM (wt %) | HEC (wt %) | SiO$_2$ (wt %) | BHT (wt %) |
|---|---|---|---|---|---|---|---|
| 5.82 | 39.49 | 29.25 | 5.65 | 15.07 | 2.83 | 1.88 | 0.02 |

This human clinical trial study was a single-center food effect, PK study to determine the rate and extent of absorption of hydromorphone from 16 mg strength abuse-resistant oral dosage forms when administered in a fasted state and after consumption of a meal. The comparison was against an 8 mg single dose of Dilaudid brand hydromorphone HCl oral solution administered in a fasting state. The study was conducted in healthy, adult male and female volunteers. There were 12 subjects in each study group (fed and fasted). Subjects were administered naltrexone blockade to prevent opioid-related adverse events. The fed group were administered a "standard" meal that consisted of 8 oz orange juice, two fried eggs, and two slices of toast with butter and preserve.

The mean PK results from this Example 9a study are presented below in Table 100. The results from the pharmacokinetic analysis are reported below in Table 101.

TABLE 100

| Parameter | HMH Test Capsules (Fasted) | HMH Test Capsules (Fed) | IR Control (Fasted) |
|---|---|---|---|
| T$_{max}$ (hr) | 4 | 6 | 0.5 |
| C$_{max}$ (ng/mL) | 1.52 ± 1.62 | 1.23 ± 1.13 | 9.17 ± 2.69 |
|  | 43.04 ± 22.80 | 52.63 ± 21.34 |  |

TABLE 101

| Parameter | HMH Test Capsules (Fasted) | HMH Test Capsules (Fed) | IR Control (Fasted) |
|---|---|---|---|
| T$_{max}$ (hr) | 9.13 ± 8.31 | 11.6 ± 9.60 | 0.67 ± 0.31 |
| C$_{max}$ (ng/mL) | 1.7 ± 1.60 | 1.99 ± 1.29 | 10.5 ± 2.27 |
| AUC$_{last}$ (hr * ng/mL) | 33.28 ± 18.24 | 40.81 ± 21.52 | 43.67 ± 7.81 |
| AUC$_{inf}$ (hr * ng/mL) | 39.84 ± 27.17 | 51.24 ± 22.10 | 46.76 ± 6.53 |

As can be seen by these results, food has an effect on both the rate and extent of absorption of hydromorphone from the study abuse-resistant oral dosage forms, where oral bioavailability is increased under fed conditions relative to administration of dosage forms in the fasted state.

Example 9b

The abuse-resistant hydromorphone oral dosage forms used in this Example 9b were prepared using the following raw materials: Hydromorphone HCl ("HMH"); Isopropyl Myristate, NF ("IPM"); Colloidal silicon dioxide (Cabosil®, Cabot Corp) ("SiO$_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Labrafil M2125 CS ("LAB"); and Cellulose Acetate Butyrate, grade 381-20 BP, ethanol washed (Eastman Chemicals) ("CAB"). The formulations were produced using the GMP manufacturing method of Example 1d above (Process Scheme 8) and then filled into size #2 gel cap shells to produce 8 and 16 mg dosage forms that were used as the HMH Test Capsules. The details of the formulations and the dosage forms containing the formulations of this Example 9b are disclosed below in Table 102.

TABLE 102

| Formula # | HMH | SAIB | TA | CAB | IPM | HEC | SiO$_2$ | BHT | LAB | Total |
|---|---|---|---|---|---|---|---|---|---|---|
| HMH1 | 16.0 | 104.1 | 77.1 | 15.5 | 41.4 | 15.5 | 5.2 | 0.1 | — | 275.0 (mg) |
|  | 5.82 | 37.86 | 28.05 | 5.65 | 15.07 | 5.65 | 1.88 | 0.02 | — | (wt %) |
| HMH2 | 16.0 | 101.1 | 74.9 | 15.5 | 38.9 | 15.5 | 5.2 | 0.1 | 7.8 | 275.0 (mg) |
|  | 5.82 | 36.78 | 27.24 | 5.65 | 14.13 | 5.65 | 1.88 | 0.02 | 2.83 | (wt %) |
| HMH3 | 8.0 | 29.8 | 19.9 | 3.6 | 10.8 | 4.3 | 1.4 | 0.1 | 2.2 | 80.0 (mg) |
|  | 10.00 | 37.25 | 24.83 | 4.50 | 13.50 | 5.40 | 1.80 | 0.02 | 2.70 | (wt %) |

This human clinical trial study was a single-center, randomized crossover study to evaluate the pharmacokinetic profile of three different HMH formulations (two QD, one BID) of HMH Test Capsules HMH1-HMH3 against the profile of an IR Control (Dilaudid) oral solution administered QID (every 6 hours). There were 15 healthy male subjects in each study group. One subject dropped out from the IR Control group, so PK results were obtained from 14 subjects for that group only. Subjects were administered naltrexone blockade to prevent opioid-related adverse events. Plasma samples were analyzed for hydromorphone using a validated LC-MS-MS procedure. The results from a pharmacokinetic analysis in this study 9b are reported below in Table 103.

TABLE 103

| Parameter | HMH1 Test Capsules | HMH2 Test Capsules | HMH3 Test Capsules | IR Control (Fasted) |
|---|---|---|---|---|
| $T_{max}$ (hr) | 6.40 ± 4.31 | 5.41 ± 2.38 | 12.13 ± 6.45 | 11.51 ± 7.23 |
| $C_{max}$ (ng/mL) | 2.48 ± 0.87 | 3.14 ± 1.89 | 3.76 ± 0.94 | 6.45 ± 0.99 |
| $AUC_{last}$ (hr * ng/mL) | 44.16 ± 20.81 | 53.78 ± 22.01 | 74.13 ± 17.93 | 91.95 ± 20.23 |
| $AUC_{inf}$ (hr * ng/mL) | 46.94 ± 22.59 | 59.39 ± 27.16 | 76.45 ± 20.07 | 96.20 ± 21.09 |

Example 10: In Vivo Analysis of Formulations (Human Clinical Trails, Pharmacokinetic Studies)

In order to assess the in vivo controlled release performance of abuse-resistant hydrocodone oral dosage forms prepared in accordance with the present invention, the following human clinical trail was carried out.

The abuse-resistant hydrocodone oral dosage form used in this Example 10 was prepared using the following raw materials: Hydrocodone Bitartrate ("HCB"); Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Gelucire 44/14 (Gattefosse) ("GEL"); and Cellulose Acetate Butyrate, grade 381-20 BP, ethanol washed (Eastman Chemicals) ("CAB"). The formulations were produced using the GMP manufacturing method of Example 1e above (Process Scheme 9) and then filled into size #3 gel cap shells to produce the dosage forms that were used as Test Capsules. The details of the formulation are disclosed below in Table 104.

TABLE 104

| Formula # | HCB (mg) | SAIB (mg) | TA (mg) | CAB (mg) | IPM (mg) | HEC (mg) | $SiO_2$ (mg) | BHT (02 mg) | GEL (mg) | Total (mg) |
|---|---|---|---|---|---|---|---|---|---|---|
| HCB1 | 15.0 | 41.8 | 27.8 | 5.2 | 14.24 | 2.8 | 1.9 | 0.1 | 1.1 | 110.0 (mg) |
|  | 13.64 | 37.97 | 25.31 | 4.75 | 12.95 | 2.59 | 1.73 | 0.02 | 1.04 | (wt %) |

This human clinical trial study was a single-center, randomized, active-controlled crossover study to evaluate the pharmacokinetic profile, as well as describe the effect of food on the rate and extent of absorption of hydrocodone from 15 mg strength abuse-resistant oral dosage forms produced according to the present invention. Subjects were randomly assigned to one of three treatment groups. The fed treatment group received treatments after an overnight fast of at least 8 hours, followed by thirty minutes after the start of a standard breakfast (8 ounces orange juice, two fried eggs, and two slices of toast with butter and preserve). The two fasted groups received treatments after an overnight fast of at least 8 hours. All subjects were administered naltrexone blockade to prevent opioid-related adverse events. The active control was a 30 mL dose of Lortab Elixir (hydrocodone bitartrate/acetaminophen 7.5 mg/500 mg per 15 mL), "IR Control". Twenty four (24) healthy male subjects entered the study, and the PK analysis was conducted on 22 subjects that completed the study. The plasma samples were analyzed for hydrocodone using a validated LC-MS-MS procedure.

The results from a pharmacokinetic analysis in this Example 10b study are reported below in Table 105.

TABLE 105

| Parameter | HCB Test Capsules (Fed) | HCB Test Capsules (Fasted) | IR Control (Fasted) |
|---|---|---|---|
| $T_{max}$ (hr) | 7.64 ± 2.51 | 8.37 ± 4.27 | 1.53 ± 0.66 |
| $C_{max}$ (ng/mL) | 10.1 ± 5.65 | 6.62 ± 1.97 | 37.1 ± 9.53 |
| $AUC_{0-12}$ (hr * ng/mL) | 68.98 ± 28.65 | 57.13 ± 18.43 | 212.1 ± 46.63 |
| $AUC_{last}$ (hr * ng/mL) | 178.7 ± 69.53 | 159.0 ± 63.53 | 259.0 ± 56.77 |
| $T_{1/2}$ (hr) | 14.84 ± 8.09 | 21.11 ± 8.31 | 5.18 ± 0.65 |

As can be seen by these results, the mean rate and extent of hydrocodone exposure after administration of the HCB Test Capsules increased under fed conditions relative to fasting conditions. The rate of exposure and peak of exposure after administration of the HCB Test Capsules was not as high as that seen with the oral hydrocodone elixir (IR Control).

Example 11: In Vivo Analysis of Formulations (Human Clinical Trails, Pharmacokinetic Studies)

In order to assess the in vivo controlled release performance of abuse-resistant amphetamine oral dosage forms prepared in accordance with the present invention, the following human clinical trail was carried out.

The abuse-resistant amphetamine oral dosage forms used in this Example 11 study were prepared using the following raw materials: d-Amphetamine Sulfate (Cambrex) ("AMP"); Isopropyl Myristate, NF ("IPM"); Colloidal silicon dioxide (Cabosil®, Cabot Corp) ("$SiO_2$"); Butylated hydroxyl toluene, NF ("BHT"); Hydroxyethyl cellulose, NF ("HEC"); Sucrose Acetate Isobutyrate (Eastman Chemicals), ("SAIB"); Triacetin USP ("TA"); Cellulose Acetate Butyrate, grade 381-20 BP, ethanol washed (Eastman Chemicals) ("CAB"); Caprylocaproyl Polyoxyglycerides (Gattefosse) ("CPG"); Gelucire 50/13 (Gattefosse) ("GEL"); and Polyethylene Glycol 8000 (Dow Chemical) ("PEG 8000"). The formulations were produced using a GMP manufacturing process (Process Scheme 6 as described in Example 1a above) and then filled into size #1 gel capsules to produce the dosage forms that were used as the AMP Test Capsules. The details of the formulations are disclosed below in Tables 106 and 107.

TABLE 106

| Component | Formulation by Weight Percent (wt %) | | |
|---|---|---|---|
| | AMP1 | AMP2 | AMP3 |
| AMP | 7.50 | 5.45 | 5.45 |
| SAIB | 36.52 | 36.24 | 35.16 |
| TA | 27.05 | 26.85 | 26.04 |
| CAB | 4.86 | 4.96 | 4.96 |
| IPM | 15.73 | 16.07 | 16.07 |
| HEC | 5.55 | 5.67 | 5.67 |
| $SiO_2$ | 1.85 | 1.89 | 1.89 |
| BHT | 0.02 | 0.02 | 0.02 |
| LAB | 0.93 | 0 | 0 |
| PEG 8000 | 0 | 2.84 | 0 |
| GEL | 0 | 0 | 4.73 |

TABLE 107

| Component | Formulation by Mass (mg) | | |
|---|---|---|---|
| | AMP1 | AMP2 | AMP3 |
| AMP | 15.00 | 14.99 | 14.99 |
| SAIB | 73.04 | 99.66 | 96.69 |
| TA | 54.10 | 73.84 | 71.61 |
| CAB | 9.72 | 13.64 | 13.64 |
| IPM | 31.46 | 44.19 | 44.19 |
| HEC | 11.10 | 15.93 | 15.59 |
| $SiO_2$ | 3.70 | 5.20 | 5.20 |
| BHT | 0.04 | 0.06 | 0.06 |
| LAB | 1.86 | 0 | 0 |
| PEG 8000 | 0 | 7.81 | 0 |
| GEL | 0 | 0 | 13.01 |
| Total | 200.02 | 275.32 | 274.98 |

This human clinical trial study was a single-center, randomized, open-label, phase I study to assess the safety and pharmacokinetics of three abuse-resistant amphetamine formulations, and to assess the performance of these Test Capsules against commercially available reference 15 mg strength controlled release d-amphetamine sulfate tablets (Dexedrine), hereinafter (SR Control) in healthy adult male and female volunteers under fed conditions. The study was conducted in 12 evaluable healthy subjects. Subjects were administered a single dose of each of the four test formulations separated by a minimum of seven days. A standard 4×4 Latin square design was used to assign subjects to treatments. Amphetamine levels were measured in plasma samples using a validated LC-MS-MS procedure.

Figure 33:
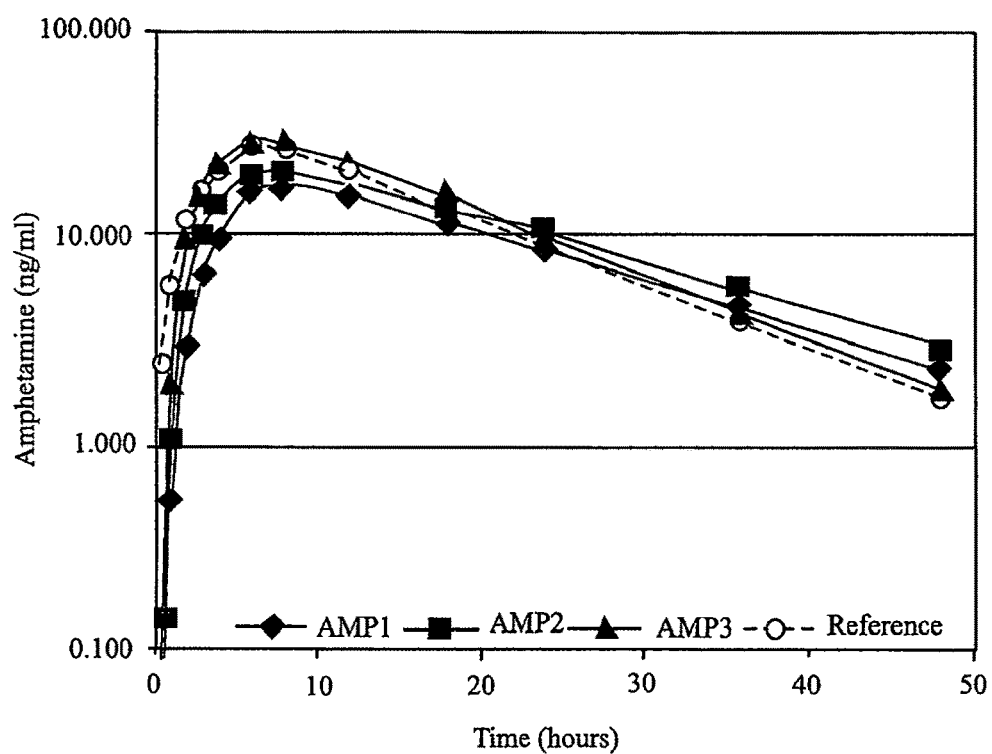
FIG. 33 shows the mean linear plasma concentration-time curve of amphetamine from Test Capsules administered in the clinical trial study described in Example 11.

The results of the study are depicted in FIG. 33, where the mean plasma concentration-time curves of amphetamine are shown. In addition, the mean pharmacokinetic values, based on plasma concentration-time values, are presented below in Table 108.

TABLE 108

| | AMP1 Test Capsules | AMP2 Test Capsules | AMP3 Test Capsules | Reference Product |
|---|---|---|---|---|
| N | 14 | 15 | 13 | 15 |
| $C_{max}$ (ng/mL) | 18.1 ± 8.2 | 21.1 ± 4.8 | 29.4 ± 5.8 | 27.8 ± 7.9 |
| $t_{max}$ (hour) | 9.4 ± 2.0 | 7.6 ± 1.5 | 6.6 ± 1.7 | 6.3 ± 1.0 |
| Half Life (hour) | 12.8 ± 6.9 | 12 ± 3.8 | 9.7 ± 1.9 | 9.6 ± 1.3 |
| $AUCt_i$ (hr * ng/mL) | 394.3 ± 164.2 | 474.6 ± 92.5 | 547.5 ± 114.4 | 509.4 ± 103.6 |
| $AUC_i$ (hr * ng/mL) | 447.7 ± 164.2 | 527.0 ± 119.9 | 575.3 ± 126.3 | 533.4 ± 113.7 |
| Relative Bioavailability | 83.7 ± 25.4 | 99.0 ± 17.8 | 109.0 ± 13.6 | |

For all PK profiles, an absorption phase lasting approximately 6-7 hours was evident. This was followed by a distribution phase and an elimination phase. Although all of the test formulations delivered the same dose of amphetamine, it is noteworthy that the AMP1 Test Capsules displayed the lowest mean profile of all four test formulations, and displayed a greater individual variation in amphetamine concentration.

The time course of concentration changes was very similar across the 4 treatment groups. Near peak concentrations occur at approximately 6 hours for all treatment groups, with maintenance of those near peak concentrations for approximately another 24 hours. This profile was consistent between individuals. There was a tendency for the formulation with the lowest $C_{max}$ (AMP1 Test Capsules) to display a delayed $T_{max}$. The mean terminal elimination half-life remained consistent regardless of the formulation administered.

Calculation of the relative bioavailability of AMP Test Capsules compared to a single dose of the 15 mg amphetamine commercial product revealed that the AMP2 and AMP3 Test Capsules had similar relative bioavailabilities. The relative bioavailability of each of the AMP Test Capsules compared to the SR Control was as follows:

AMP1 (n=14): 83.7±25.4
AMP2 (n=14): 99.0±17.8
AMP3 (n=13): 109.0±13.6.

Although this study was not designed to assess the bioequivalence of the AMP Test Capsule formulations, bioequivalence intervals were constructed for the ln-transformed ratios of $AUC_t$ (Table 109), $AUC_i$ (Table 110), and $C_{max}$ (Table 111).

TABLE 109

| $Ln(AUC_t)$ | LSM | LSM SE | Geometric Mean | test-ref difference | Difference SE | Difference DF | CI90 lower | CI90 upper |
|---|---|---|---|---|---|---|---|---|
| SR Control | 6.23 | 0.06 | 505.6 | | | | | |
| AMP1 | 5.91 | 0.06 | 368.9 | −0.32 | 0.07 | 35.00 | 64.9 | 82.0 |
| AMP2 | 6.16 | 0.06 | 473.8 | −0.07 | 0.07 | 35.00 | 83.3 | 105.4 |
| AMP3 | 6.32 | 0.07 | 555.3 | 0.09 | 0.07 | 35.00 | 97.3 | 124.0 |

LSM = Least Square Means
SE = Standard Error
D-F = Degrees of Freedom
CI90 lower = lower range of the 90% confidence interval
CI90 upper = upper range of the 90% confidence interval

TABLE 110

| $Ln(AUC_i)$ formulation | LSM | LSM SE | Geometric Mean | test-ref difference | Difference SE | Difference DF | CI90 lower | CI90 upper |
|---|---|---|---|---|---|---|---|---|
| SR Control | 6.2711 | 0.068 | 529.0489 | | | | | |
| AMP1 | 6.0315 | 0.0701 | 416.3577 | −0.2395 | 0.0732 | 35 | 69.55 | 89.06 |
| AMP2 | 6.2616 | 0.067 | 524.0704 | −0.0095 | 0.0736 | 35 | 87.48 | 112.17 |
| AMP3 | 6.3717 | 0.0732 | 585.0422 | 0.1006 | 0.0758 | 35 | 97.28 | 125.71 |

LSM = Least Square Means
SE = Standard Error
D-F = Degrees of Freedom
CI90 lower = lower range of the 90% confidence interval
CI90 upper = upper range of the 90% confidence interval

TABLE 111

| $Ln(C_{max})$ formulation | LSM | LSM SE | Geometric Mean | test-ref difference | Difference SE | Difference DF | CI90 lower | CI90 upper |
|---|---|---|---|---|---|---|---|---|
| SR Control | 3.3005 | 0.0735 | 27.127 | | | | | |
| AMP1 | 2.7883 | 0.0767 | 16.2536 | −0.5122 | 0.0941 | 35 | 51.11 | 70.24 |
| AMP2 | 3.0212 | 0.0721 | 20.5151 | −0.2794 | 0.0946 | 35 | 64.45 | 88.74 |
| AMP3 | 3.371 | 0.0814 | 29.1071 | 0.0705 | 0.0975 | 35 | 90.99 | 126.53 |

LSM = Least Square Means
SE = Standard Error
D-F = Degrees of Freedom
CI90 lower = lower range of the 90% confidence interval
CI90 upper = upper range of the 90% confidence interval The embodiments disclosed herein are exemplary only, and are not meant to limit the invention, which should be interpreted solely in light of the claims.

We claim:

1. A method for treating pain in a subject, the method comprising:
    orally administering a pharmaceutical dosage form to the subject, the pharmaceutical dosage form comprising a mixture comprising:
        oxycodone, either in free base form or a pharmaceutically acceptable salt form thereof,
        about 30 wt % to about 60 wt % of sucrose acetate isobutyrate,
        about 0.1 wt % to about 40 wt % of triacetin,
        about 0.1 wt % to about 20 wt % of a cellulose acetate butyrate, and
        about 0.1 wt % to about 10 wt % of hydroxyethylcellulose.
2. The method of claim 1, wherein the mixture further comprises a surfactant.
3. The method of claim 1, wherein the mixture further comprises a viscosity enhancing agent.
4. The method of claim 3, wherein the viscosity enhancing agent comprises a stiffening agent.
5. The method of claim 3, wherein the viscosity enhancing agent comprises a $SiO_2$.
6. The method of claim 1, wherein the mixture further comprises a hydrophobic solvent.
7. The method of claim 1, wherein the oxycodone is in the form of a pharmaceutically acceptable salt.
8. The method of claim 1, wherein the oxycodone is in the form of a free base.
9. The method of claim 1, wherein the oxycodone is present in the mixture in an amount ranging from about 1.3 wt % to about 35 wt %.
10. The method of claim 1, wherein the cellulose acetate butyrate has a number average molecular weight ranging from 66,000 to 83,000.
11. The method of claim 1, wherein the hydroxyethylcellulose is present in an amount ranging from about 3 wt % to about 10 wt %.
12. The method of claim 1, wherein the mixture further comprises a rheology modifier.
13. The method of claim 1, wherein the mixture further comprises a rheology modifier selected from isopropyl myristate, caprylic/capric triglyceride, ethyl oleate, triethyl citrate, dimethyl phthalate, and benzyl benzoate.
14. The method of claim 1, wherein the mixture further comprises isopropyl myristate.
15. The method of claim 1, wherein the mixture further comprises a rheology modifier present in an amount ranging from about 0.1 wt % to about 20 wt %.
16. The method of claim 1, wherein the mixture further comprises saturated polyglycolized glyceride.
17. The method of claim 1, wherein the mixture further comprises saturated polyglycolized glyceride present in an amount ranging from about 0.01 wt % to about 5 wt %.
18. The method of claim 1, wherein the mixture comprises a suspension.
19. The method of claim 1, wherein the mixture is encapsulated within a capsule.
20. The method of claim 19, wherein the capsule comprises gelatin, hydroxyethylcellulose, or hydroxypropylmethylcellulose.

* * * * *